US011230737B2

(12) United States Patent
Schmitt et al.

(10) Patent No.: US 11,230,737 B2
(45) Date of Patent: Jan. 25, 2022

(54) METHODS FOR ASSESSING THE TREATMENT RESPONSE OF TNBC PATIENTS TO NEO-ADJUVANT CHEMOTHERAPY BY ANALYSING CPG METHYLATION

(71) Applicant: THERAWIS DIAGNOSTICS GMBH, Munich (DE)

(72) Inventors: Manfred Schmitt, Munich (DE); Olaf G. Wilhelm, Munich (DE); Rudolf Napieralski, Munich (DE)

(73) Assignee: THERAWIS DIAGNOSTICS GMBH

( * ) Notice: Subject to any disclaimer, the term of this patent is extended or adjusted under 35 U.S.C. 154(b) by 202 days.

(21) Appl. No.: 16/076,775

(22) PCT Filed: Feb. 10, 2017

(86) PCT No.: PCT/EP2017/053070

§ 371 (c)(1),
(2) Date: Aug. 9, 2018

(87) PCT Pub. No.: WO2017/137601

PCT Pub. Date: Aug. 17, 2017

(65) Prior Publication Data

US 2019/0323084 A1 Oct. 24, 2019

(30) Foreign Application Priority Data

Feb. 11, 2016 (EP) .................................... 16155279

(51) Int. Cl.
*C12Q 1/68* (2018.01)
*C12P 19/34* (2006.01)
*C12Q 1/6886* (2018.01)

(52) U.S. Cl.
CPC ..... *C12Q 1/6886* (2013.01); *C12Q 2600/106* (2013.01); *C12Q 2600/154* (2013.01); *C12Q 2600/158* (2013.01)

(58) Field of Classification Search
CPC ............ C12Q 1/6886; C12Q 2600/106; C12Q 2600/154
See application file for complete search history.

(56) References Cited

U.S. PATENT DOCUMENTS

2020/0181712 A1* 6/2020 Schmitt ................ C12Q 1/6806

FOREIGN PATENT DOCUMENTS

| | | |
|---|---|---|
| EP | 1 561 821 | 8/2005 |
| WO | 2007/039128 | 4/2007 |
| WO | 2015/169857 | 11/2015 |

OTHER PUBLICATIONS

Maier, S. et al. European Journal of Cancer, 43, pp. 1679-1686. (Year: 2007).*
Göbel, G. et al. "Prognostic significance of methylated RASSF1A and PITX2 genes in blood—and bone marrow plasma of breast cancer patients" Breast Cancer Res Treat (2011) 130:109-117 (Year: 2011).*
Gil, E.Y. et al. "Promoter methylation of RASSF1A modulates the effect of the microtubule-targeting agent docetaxel in breast cancer" International Journal of Oncology, 41: 611-620 (Year: 2012).*
Lenz, G. et al. "Promoter methylation and expression of DNA repair genes hMLH1 and MGMT in acute myeloid leukemia" Ann Hematol (2004) 83: 628-633 (Year: 2004).*
Costello, J.F. et al. "Graded Methylation in the Promoter and Body of the 06-Methylguanine DNA Methyltransferase (MGMT) Gene Correlates with MGMT Expression in Human Glioma Cells" The Journal of Biological Chemistry, vol. 269, No. 25, Issue of Jun. 24, p. 17228-17237 (Year: 1994).*
Hoshikawa, Y. et al. "Hypoxia induces different genes in the lungs of rats compared with mice" Physiol Genomics 12: 209-219 (Year: 2003).*
The International Search Report (ISR) with Written Opinion for PCT/EP2017/053070 dated Apr. 7, 2017, pp. 1-15.
Hartman, Oliver et al. "DNA Methylation Markers Predict Outcome in Node-Positive, Estrogen Receptor-Positive Breast Cancer with Adjuvant Anthracycline-Based Chemotherapy" Clinical Cancer Research (2009) vol. 15(1), pp. 315-323.
Harbeck, Nadia et al. "Multicenter Study Using Paraffin-EInbedded Tumor Tissue Testing PITX2 DNA Methylation as a Marker for Outcome Prediction in Tamoxifen-Treated, Node-Negative Breast Cancer Patients" Journal of Clinical Oncology (2008) vol. 26(31), pp. 5036-5042.
Eads et al., Cancer Research, 2001; vol. 61:3410-3418.
Eads et al., Nucleic Acids Res, Apr. 15, 2000;28(8):E32.

* cited by examiner

*Primary Examiner* — Stephen T Kapushoc
(74) *Attorney, Agent, or Firm* — McDonnell Boehnen Hulbert & Berghoff LLP

(57) ABSTRACT

The present invention relates to methods for predicting the efficacy of anthracycline-based neo-adjuvant chemotherapy in triple-negative breast cancer. This is achieved by determining epigenetic changes within the PITX2 gene. Detection of the methylation state of Cp G sites in a genomic sequence of PITX2 allows an estimate of the response or failure of an individual breast cancer patient to neo-adjuvant therapy.

12 Claims, 7 Drawing Sheets

Figure 1:
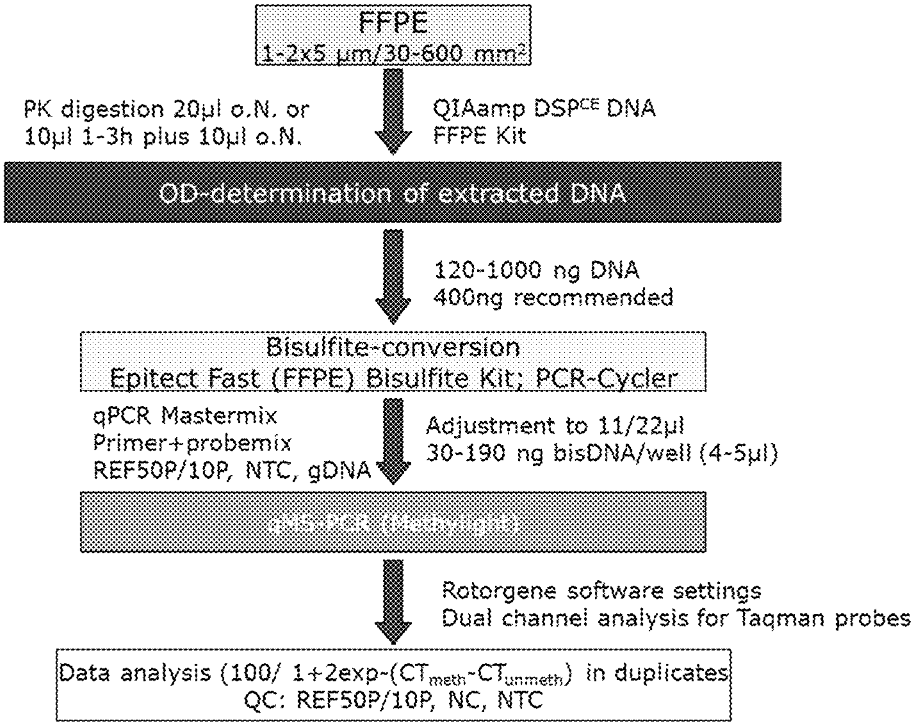

Specification includes a Sequence Listing.

METHODS FOR ASSESSING THE TREATMENT RESPONSE OF TNBC PATIENTS TO NEO-ADJUVANT CHEMOTHERAPY BY ANALYSING CPG METHYLATION

CROSS-REFERENCE TO RELATED APPLICATION

This application is a U.S. national phase of International Application No. PCT/EP2017/053070, filed on Feb. 10, 2017, which claims priority to European Patent Application No. 16155279.9, filed Feb. 11, 2016, both of which are incorporated by reference herein in their entirety.

FIELD OF THE INVENTION

The present invention relates to the field of pharmacogenomics and in particular to assessing the response of a patient afflicted with triple-negative breast cancer (TNBC) to anthracycline-based neo-adjuvant chemotherapy (NAC) by analysing CpG methylation of the paired-like homeodomain 2 (PITX2) gene. Depending on the result of the analysis, a decision can be made between anthracycline-based therapy and non-anthracycline-based treatment prior to NAC, thereby optimizing the treatment plan for each patient individually.

BACKGROUND OF THE INVENTION

Breast cancer is the most common malignancy in women with more than 464,000 new cases diagnosed in 2012 in Europe (source: Cancer Research UK) and with about 75,000 new cases per year in Germany (source: WHO IACR report 2014). Breast cancers are staged according to their size, location and occurrence of metastasis. Methods of treatment include the use of surgery, radiation therapy, chemotherapy and endocrine therapy, which are also used as adjuvant therapies to surgery.

Approximately 70,000 (15%) patients will suffer from so-called triple-negative breast cancer (TNBC). TNBC is characterized by the absence of estrogen-receptor, progesterone-receptor and HER2 overexpression/amplification. This specific breast cancer indication belongs to the high-risk group of patients according to the St. Gallen classification with very poor prognosis and clinical outcome. The poor outcome is also attributable to the fact that these patients cannot be treated by endocrine or HER2-targeted therapy.

In contrast to other types of breast cancer, TNBC is treated in the neo-adjuvant setting. Neo-adjuvant treatment schedule is characterized by core biopsy taken from the breast to affirm the histological diagnosis followed by neo-adjuvant chemotherapy (NAC). Thereafter, patients will undergo breast surgery. Pathological examination of the whole resected breast tumor lesion will reveal whether invasive tumor is still present or not. If no invasive tumor is present, this result is classified as pathological complete remission (pCR). pCR has been acknowledged as a validated surrogate efficacy endpoint for overall survival (OS), yet, only ~ 30-50% of the TNBC patients will show pCR after neo-adjuvant chemotherapy. While TNBC patients with pCR have a good prognosis and do not need further systemic treatment, patients without pCR might benefit from further adjuvant systemic therapy.

Since there is only one chance for a patient to undergo neo-adjuvant therapy, it is of utmost importance to choose the best care for the patient, which includes the therapy regimen with the highest probability of response in terms of pCR after neo-adjuvant treatment and to search for strategies for the prediction of chemotherapy response prior to NAC. In order to optimize the selection of treatment options, a rapid, specific and sensitive method for the assessment of a therapy response is of crucial importance.

The use of predictive biomarkers is becoming increasingly relevant in cancer therapy as it allows for better identification of patients who will respond positively to the therapy, and of patients not responding. In breast cancer, predictive markers can determine the benefits of chemotherapy, endocrine therapy, and other types of therapy, such as immunotherapy (Characiejus. Anticancer Res. 2011; 31:639; Duffy. Clin Chem. 2005; 51:494; van de Vijver. Virchows Arch. 2014; 464:283). There are many advantages to utilizing a predictive marker in cancer therapy. Predictive biomarkers can help to improve patient selection and can guide physicians to optimize the treatment plan for each patient individually including better patient management, minimizing unnecessary suffering from drug side effects, reducing loss of precious time whilst determining whether a therapy will provide any benefit, and a reduction in costs for both the patient and the health insurance systems.

Alterations of DNA-methylation in the promoter region of genes is an early and frequent change in cancer, including breast cancer.

More than 65 years ago Mandel and Metais described for the first time their observation of the presence of extracellular nucleic acids in humans (Mandel P, Metais P. Les acides nucleiques du plasma sanguin chez l'homme. C.R. Acad. Sci. Paris 142, 241-243. 1948) and more than four decades later it could be clearly demonstrated that tumor-associated genetic alterations can be found in cell-free nucleic acids isolated from plasma, serum and other body fluids (Fleischhacker M, Schmidt B. (2007) Circulating nucleic acids (CNAs) and cancer—a survey. Biochim Biophys Acta 1775: 181-232; Jung K, Fleischhacker M, Rabien A. (2010) Cell-free DNA in the blood as a solid tumor biomarker-a critical appraisal of the literature. Clin Chim Acta 411: 1611-1624). This includes epigenetic alterations observed in different forms of malignant tumors. A hallmark of mammalian chromatin is DNA methylation and it is known that cytosine methylation in the context of a CpG dinucleotide plays a role in the regulation of development and is important in basic biological processes like embryogenesis and cell differentiation (Smith Z D, Meissner A. (2013) DNA methylation: roles in mammalian development. Nat Rev Genet 14: 204-220; Gibney E R, Nolan C M. (2010) Epigenetics and gene expression. Heredity (Edinb) 105: 4-13). As such, methylation not only regulates gene transcription, but also plays a role in maintaining genome stability, imprinting and X-chromosome inactivation. Epigenetic alterations in oncogenes and tumor suppressor genes are of key importance in the development of cancer (Suva M L, Riggi N, Bernstein B E. (2013) Epigenetic reprogramming in cancer. Science 339: 1567-1570).The ubiquity of such epigenetic changes in cancer events through DNA-methylation has led to a variety of innovative diagnostic and therapeutic strategies; the most recent technical advances have shown the great potential of DNA-methylation markers as valuable tools for decision making in the treatment of cancer patients (Stefansson and Esteller. Am J Pathol. 2013; 183:1052).

Although several genes altered by DNA-methylation have been associated with response to adjuvant therapy in breast cancer patients in small exploratory studies, currently, no predictive DNA-methylation test for breast cancer is commercially available. This is remarkable since, in contrast to RNA and proteins, DNA is a very stable biological material that can be extracted from the same clinical tissue samples that are subjected to analysis by the pathologist for clinical-routine malignancy diagnostics.

PITX2 has been identified as a result of a European transnational cooperation within the FP6 framework program and the PathoBiology Group of the EORTC (European Organization for Research and Treatment of Cancer). The PITX2 (paired-like homeodomain 2) gene encodes a member of the RIEG/PITX homeobox family, which is in the bicoid class of homeodomain proteins. PITX2 controls cell proliferation in a tissue-specific manner and is involved in morphogenesis. During embryonic development, it exerts a role in the expansion of muscle progenitors and plays a role in the proper localization of asymmetric organs such as the heart and stomach. As transcription factor, PITX2 is strongly involved in developmental processes and functions as a main executor of transcriptional regulation of developmental target genes by interacting with other proteins like HDAC1/3 and P300. PITX2 itself mediates target gene activation/inactivation for many signaling pathways like Estrogen receptor pathway, WNT/ß-catenin and TGF-beta pathway, regulating and being regulated by many second messengers of these pathways, which are distinctively active in different breast cancer subtypes.

Measurement of DNA-methylation in the promoter region of PITX2 was reported to estimate the potential response or failure of an individual breast cancer patient to systemic chemo- or endocrine therapy (Harbeck. J Clin Oncol. 2008; 26:5036; Nimmrich. Breast Cancer Res Treat. 2008; 111: 429).

Methods for prognosis and/or for prediction of the outcome of estrogen-treatment in patients suffering from hormone receptor positive breast cancer by determining the expression level of PITX2 or the genetic or epigenetic modifications of the genomic DNA associated with the gene PITX2 were also described in EP 1 561 821, EP 1 554 407, EP 1 561 821, and EP 2 157 191.

Recent data in non-metastasized breast cancer patients further suggested that PITX2 DNA-methylation state may predict the response to adjuvant anthracycline-based chemotherapy. Specifically, in WO 2007/039128 the increase of methylation of PITX2 was used as a predictive marker for the outcome of an adjuvant anthracycline treatment in a variety of cell proliferative disorders including breast cancer.

Thus, at present, increased methylation of the PITX2 gen was described as potential marker for the prediction of the outcome of endocrine therapy in hormone receptor positive breast cancer and anthracycline-based therapy of various cell proliferative orders in the adjuvant setting, e.g. following surgery only.

The present inventors now for the first time found that determination of the expression of the PITX2 gene and/or a genomic sequence thereof is also useful for predicting the outcome of chemotherapy of TNBC patients in the neo-adjuvant setting. The principle is to use the methylation state of tumor DNA from the breast cancer marker PITX2 that is obtained from biopsy-tissue obtained during routinely performed diagnostic biopsy as an indicator for the clinical outcome. While PITX2 hypermethylation was reported to lead to worse prognosis in estrogen receptor positive breast cancer patients (Harbeck. J Clin Oncol. 2008; 26:5036; Maier. EJC. 2007; 43:1679-1686), it was surprisingly found by the present inventors that in TNBC patients hypomethylation of the PITX2 gene is indicative of a poor clinical outcome in terms of pathological complete remission (pCR).

Several neo-adjuvant chemotherapy (NAC)-regimens are currently being used for the treatment of TNBC.

While anthracycline/taxane combinations (herein referred to anthracycline-based chemotherapy) have shown pCR rates of 28-41% recent data also emphasize a benefit for treatment of TNBC patients with carboplatinum containing therapy regimens owing to their unique genetic properties.

Surprisingly, the present inventors found that DNA methylation state in the PITX2 gene, and, specifically, PITX2 hypomethylation could specifically predict a poor outcome of anthracycline-based neo-adjuvant chemotherapy in patients diagnosed with triple-negative breast cancer (TNBC). This is essential because there is only one chance for a patient to undergo neo-adjuvant therapy, and the prediction of response with respect to pCR will, for the first time, help to recommend anthracycline- versus non-anthracycline-based therapy.

The present invention thus meets the long felt need to provide a rapid, specific and sensitive method for predicting the response of TNBC patients to anthracycline-based treatment prior to NAC, which allows to select those TNBC patients benefiting from such therapy. Since treatment regimens in neo-adjuvant chemotherapy not only differ with regard to efficacy, but often with regard to toxicity, said method will also encourage TNBC patients likely to respond to stay on a rationally selected therapy, despite possible toxic side effects.

SUMMARY OF THE INVENTION

In a first aspect, the present invention relates to a method for predicting the outcome of neo-adjuvant chemotherapy of a subject afflicted with triple-negative breast cancer (TNBC) comprising the steps:

a) providing a biological sample from the subject, b) determining the expression or methylation state of the gene and/or genomic sequence of PITX2 and/or regulatory sequences thereof within said sample; and c) determining therefrom the outcome of a treatment of said subject.

In an embodiment of the first aspect, the method further comprises step d) wherein a suitable treatment regimen for the subject is determined.

In a further embodiment of the method according to the first aspect, the neo-adjuvant chemotherapy is anthracycline-based.

In a further embodiment of said method determining the expression or methylation state of the gene and/or genomic sequence of PITX2 and/or regulatory sequences thereof within said sample in step b) is accomplished by analysis of genomic DNA isolated from the biological sample. Said expression may be determined by determining the methylation state of one or more CpG sites within said gene and/or genomic sequence and/or regulatory regions thereof or by determining the amount of mRNA encoding PITX2 and/or the amount of PITX2 protein. The methylation state of one or more CpG sites may be determined by converting, in said genomic DNA, or a fragment thereof, cytosine unmethylated in the 5-position to uracil or to another base that is detectably dissimilar to cytosine in terms of hybridization properties (i.e. that does not hybridize to guanine), preferably by bisulfite conversion.

In a further embodiment of the method according to the first aspect, the sample in step a) is selected from the group consisting of body fluids such as nipple aspirate, blood, serum, plasma, cells, cell lines, blood cells, tissue, tissue biopsies, preferably breast tissue biopsies and all possible combinations thereof, preferably wherein said sample is provided in in a state selected from the group consisting of natural, frozen, lyophilized, preserved, embedded, paraffin embedded, and all possible combinations thereof, more preferably wherein the sample is a paraffin-embedded tissue sample or an anticoagulated blood sample.

In a further embodiment the method according to the first aspect comprises contacting genomic DNA isolated from a biological sample obtained from the subject with at least one reagent, or a series of reagents that distinguishes between methylated and non-methylated CpG dinucleotides within at least one target region of the genomic DNA, preferably wherein the target region comprises, or hybridizes under stringent conditions to a sequence of at least 16 contiguous nucleotides of the PITX2 gene and/or regulatory regions thereof, wherein said contiguous nucleotides comprise at least one CpG dinucleotide sequence, and whereby predicting the outcome of anthracycline treatment of cell proliferative disorders is at least in part, afforded.

In a further embodiment of said method, PITX2 hypomethylation is indicative for a poor clinical outcome. Said hypomethylation may be a degree of methylation of the target DNA of up to 95%, up to 90%, up to 80%, up to 70%, up to 60%, up to 50%, up to 40%, up to 30%, up to 20%, or up to 10% lower than a degree of methylation of a control.

In a further embodiment of said method, said hypomethylation may be a percent methylation ratio (PMR) of the target DNA of less than 5% PMR, less than 4% PMR, less than 3% PMR, less than 2% PMR, or less than 1% PMR.

In a further embodiment of the method of the first aspect, step d) may comprise determining neoadjuvant chemotherapy as a suitable treatment regimen for a subject exhibiting a percent methylation ratio (PMR) value of >1% PMR, or a percent methylation ratio (PMR) value of >2% PMR. Preferably, said neo-adjuvant chemotherapy is anthracycline-based chemotherapy.

In a further embodiment of the method according to the first aspect, an endpoint of the clinical outcome is pathological complete remission (pCR).

In a second aspect, the present invention relates to a method for predicting the outcome of neo-adjuvant chemotherapy in a subject afflicted with triple-negative breast cancer (TNBC), comprising:

a) isolating genomic DNA from a biological sample of the subject;

b) converting, in said genomic DNA, or a fragment thereof, cytosine unmethylated in the 5-position to uracil or to another base that is detectably dissimilar to cytosine in terms of hybridization properties;

c) amplifying a region of the converted genomic DNA, or of the converted fragment thereof, using at least two primers, wherein said region comprises at least 16 contiguous nucleotides of the PITX2 gene and/or regulatory regions thereof, wherein said contiguous nucleotides comprise at least one CpG dinucleotide sequence;

d) detecting the presence or absence of, or the quantity of DNA amplified in step c);

e) determining, based on the presence or absence of, or on the quantity of said amplificate, the methylation state of the gene and/or genomic sequence of PITX2; and f) predicting from said methylation state the outcome of the neo-adjuvant treatment.

In an embodiment of the second aspect, the method further comprises step g) wherein a suitable treatment regimen for the subject is determined.

In a further embodiment of the method according to the second aspect, the neo-adjuvant chemotherapy is anthracycline-based.

In an embodiment of the method according to the second aspect, at least two primers used in step c) each comprise a contiguous sequence of at least 16 nucleotides in length that is complementary to, or hybridizes under moderately stringent or stringent conditions to a sequence selected from the group consisting of SEQ ID NO: 1 to SEQ ID NO: 30 and complements thereof.

In a further embodiment of said method, the neo-adjuvant treatment is an anthracycline-based chemotherapy.

In a yet further embodiment of said method, PITX2 hypomethylation is indicative for a poor clinical outcome. Said hypomethylation may be a degree of methylation of the target DNA of up to 95%, up to 90%, up to 80%, up to 70%, up to 60%, up to 50%, up to 40%, up to 30%, up to 20%, or up to 10% lower than a degree of methylation of a control.

In a yet further embodiment of said method, said hypomethylation may be a percent methylation ratio (PMR) of the target DNA of less than 5% PMR, less than 4% PMR, less than 3% PMR, less than 2% PMR, or less than 1% PMR.

In a further embodiment of the method of the second aspect, step g) may comprise determining neoadjuvant chemotherapy as a suitable treatment regimen for a subject exhibiting a percent methylation ratio (PMR) value of >1% PMR, or a percent methylation ratio (PMR) value of >2% PMR. Preferably, said neo-adjuvant chemotherapy is anthracycline-based chemotherapy.

In a further embodiment of the method according to the second aspect, the sample in step a) is selected from the group consisting of body fluids such as nipple aspirate, blood, serum, plasma, cells, cell lines, blood cells, tissue, tissue biopsies, in particular breast tissue biopsies and all possible combinations thereof, preferably wherein said sample is provided in in a state selected from the group consisting of natural, frozen, lyophilized, preserved, embedded, paraffin embedded, and all possible combinations thereof, more preferably wherein the sample is a paraffin-embedded tissue sample or an anticoagulated blood sample.

In a further embodiment of the method according to the second aspect, an endpoint of the clinical outcome is pathological complete remission (pCR).

FIGURES

FIG. 1: Schematic representation of the workflow established to assess the DNA-methylation status of the PITX2 promoter gene extracted from formalin-fixed and paraffin-embedded (FFPE) breast tumor tissue, hereinafter referred to as "PITX2-Test" (see Example 3).

Figure 2:
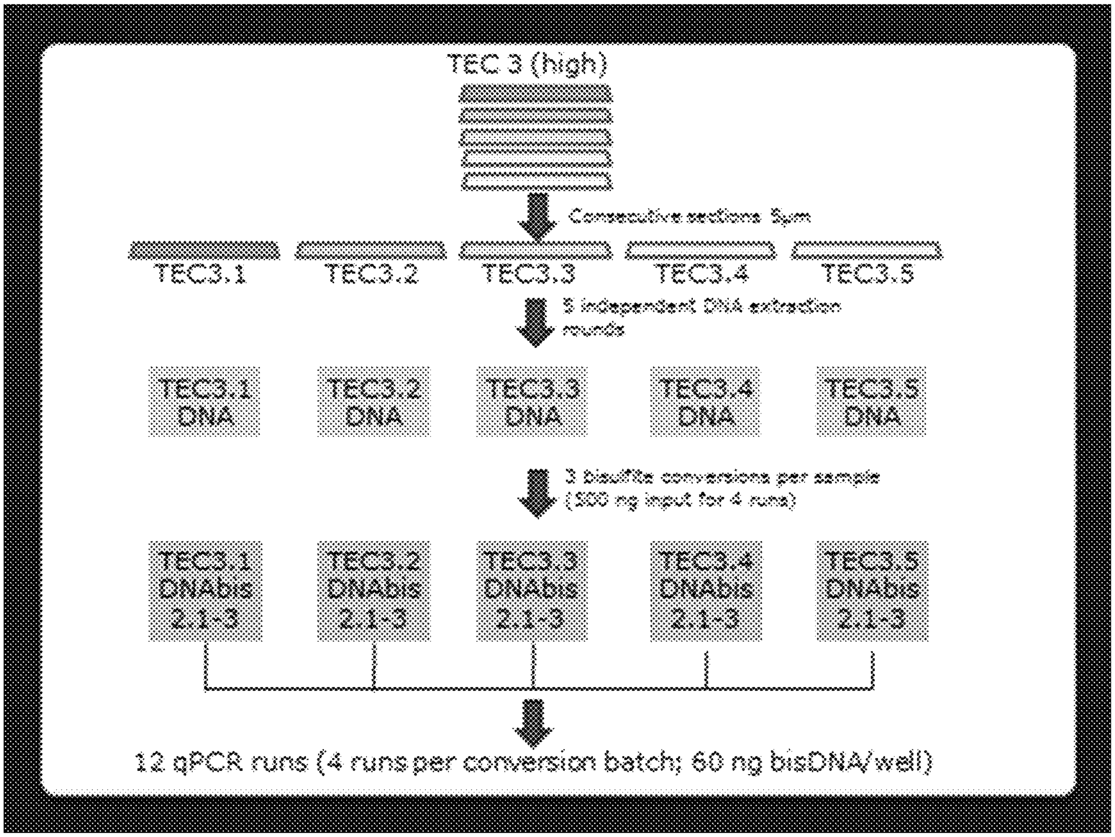

FIG. 2: Schematic representation of the workflow of determining PMR value variations (heterogeneity) between consecutive tumor tissue sections and reproducibility of PMR values in 12 independent qPCR runs (see Example 4).

Figure 3:
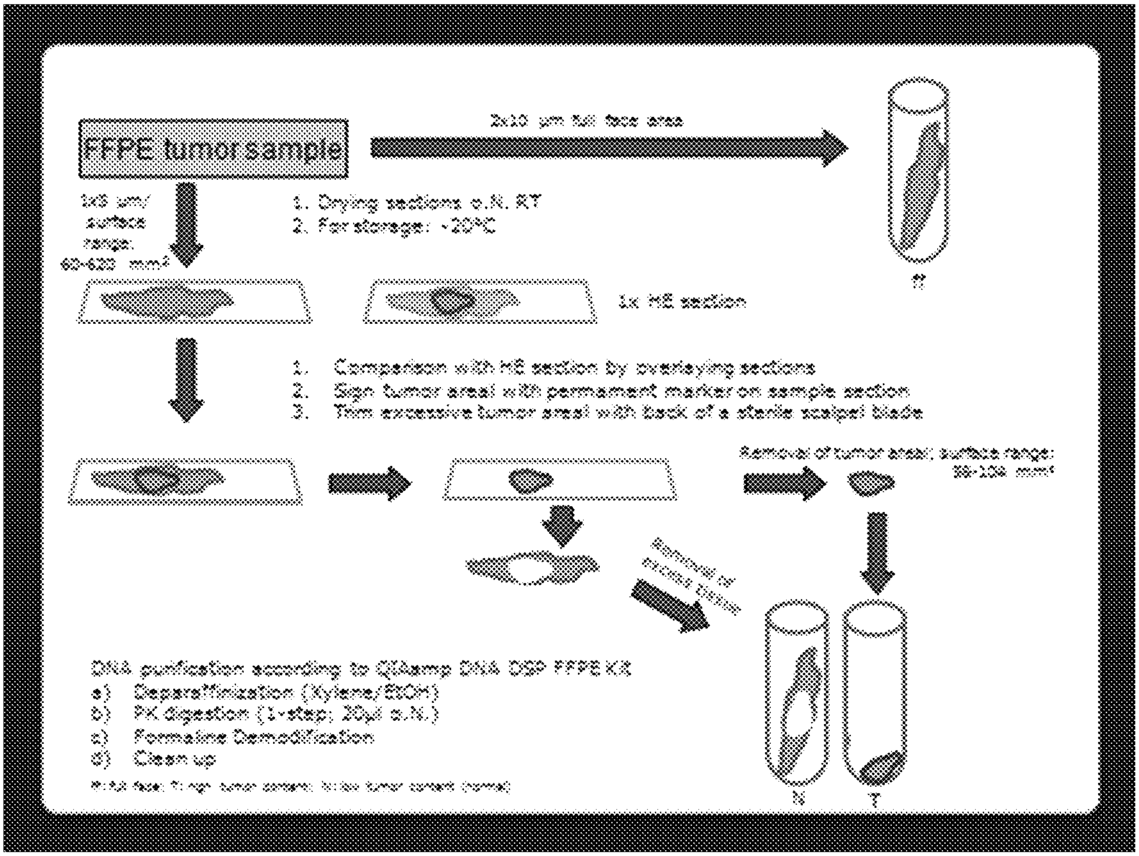

FIG. 3: Schematic representation of the workflow to obtain macro-dissected tumor areas (see Example 5).

Figure 4:
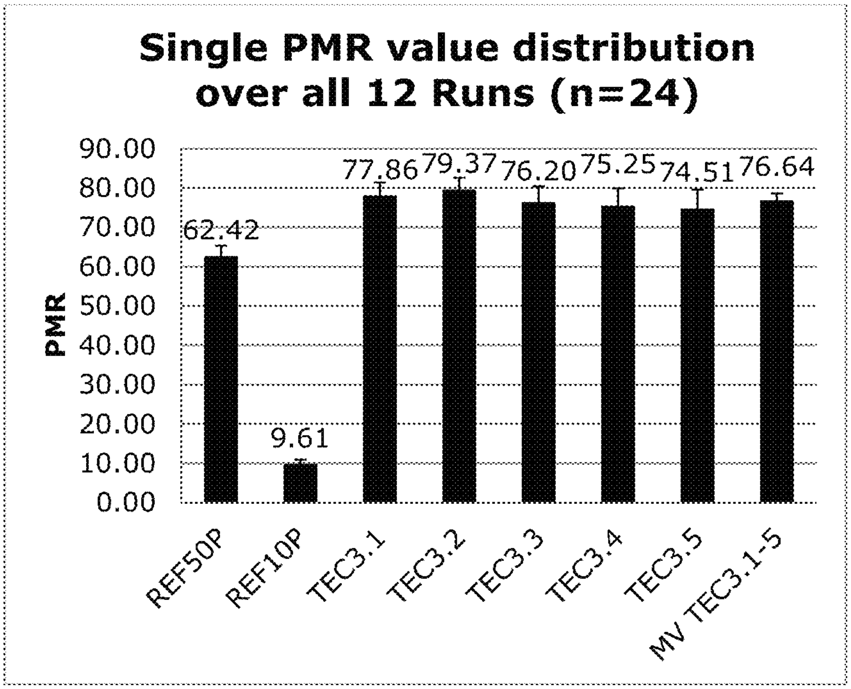

FIG. 4: Percent methylation ratio (PMR) value variations (heterogeneity) between consecutive tumour tissue sections. REF50P/10P: Reference Plasmid mixtures (meth:unmeth 1:1 and 1:9).

Figure 5:
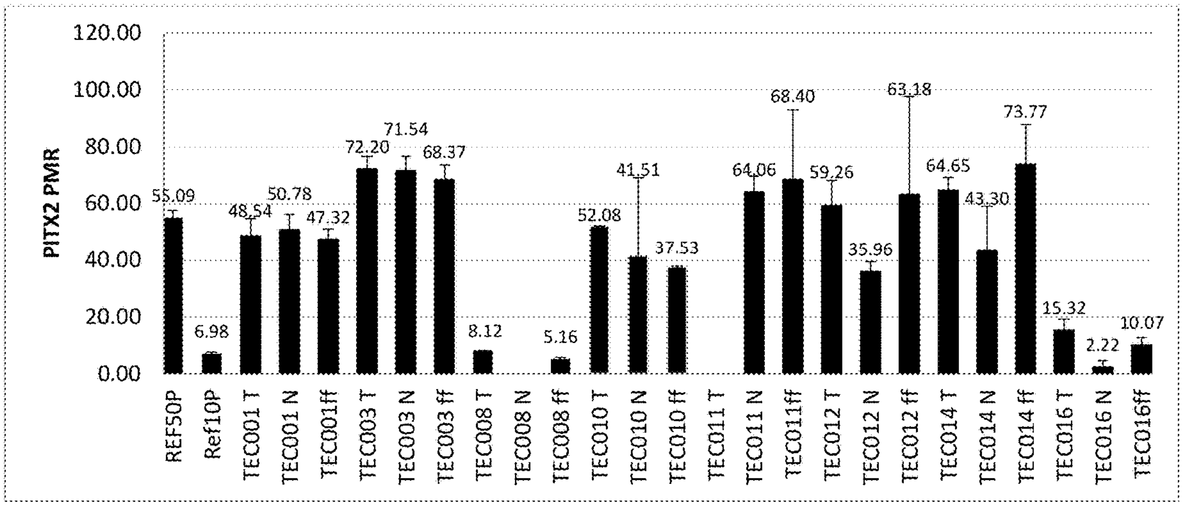

FIG. 5: Mean values of the PMR analyses for macro-dissected tissue areas with high (T) or low (N) tumor cell content as compared to full-face FFPE tumor tissue sections (ff). REF50P/10P: Reference Plasmid mixtures.

Figure 6:
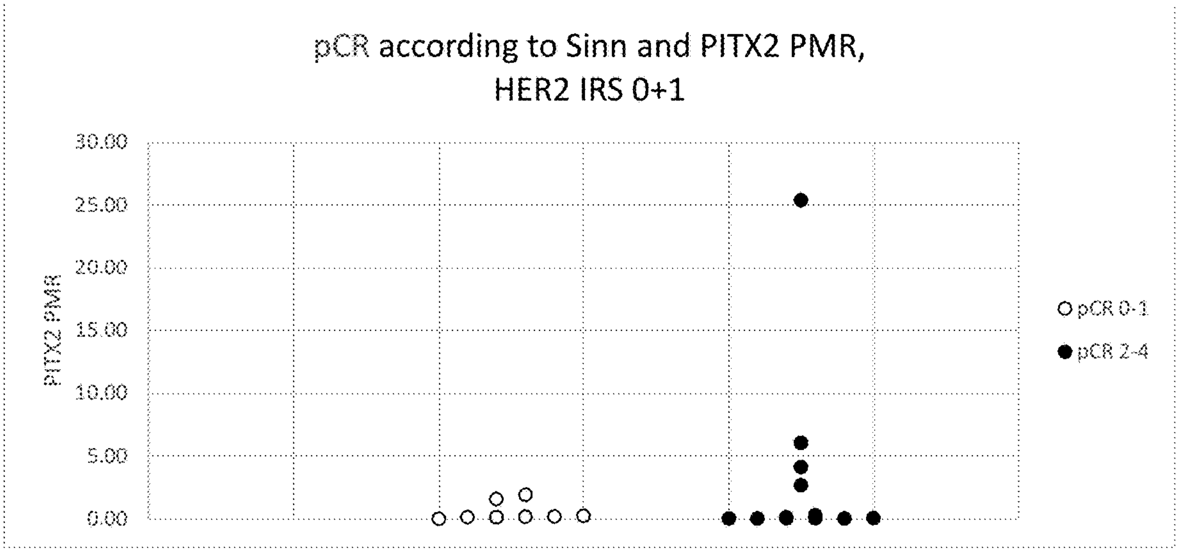

FIG. 6: PITX2 DNA methylation status (PMR %) in TNBC FFPE tumor tissue sections was correlated with pathological complete remission (pCR) according to Sinn et al. Two independent experimental runs were performed and mean values for both experiments were taken. TNBC patients included pCR 2-4 according to Sinn et al.

Figure 7:
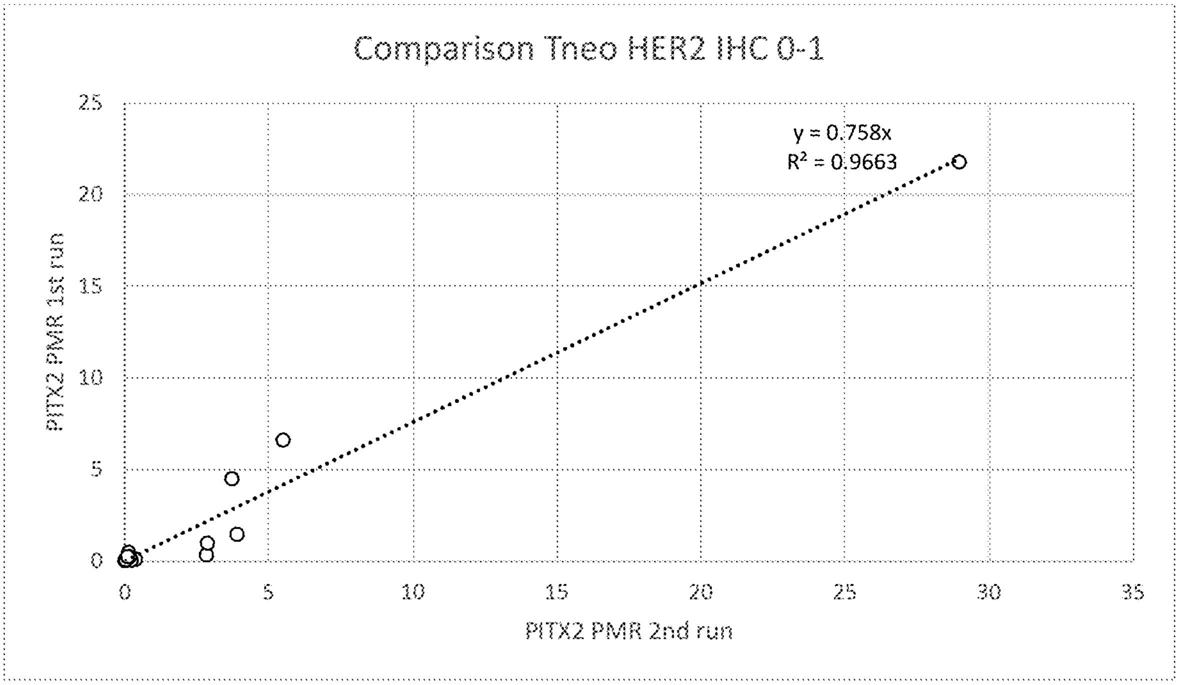

FIG. 7: Correlation of results of the two independent qPCR runs. HER2: Human epidermal growth factor receptor 2; IHC: Immunoreactive score (IRS) 0-3. 0=no protein expression; 1=low protein expression; 2=moderate protein expression; 3=high protein expression. Score 2 only qualifies for targeted therapy if FISH HER2 gene amplification test is positive.

DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

DETAILED DESCRIPTION OF THE INVENTION

Characterization of a cancer in terms of predicting treatment outcome enables the physician to make an informed decision as to a therapeutic regimen with appropriate risk and benefit tradeoffs to the patient.

Accordingly, the present invention provides methods for predicting the outcome of neo-adjuvant chemotherapy of a subject afflicted with triple-negative breast cancer (TNBC).

Subject

The term "subject" as used herein refers to an individual, such as a human, a non-human primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. The term does not denote a particular age or sex. In a particular meaning, the subject is a mammal. In a preferred meaning, the subject is a human.

Outcome

The term "predicting the outcome of neo-adjuvant chemotherapy" as used herein refers to the expected outcome of the cancer disease in response to said treatment and generally relates to the assessment of its state of development, progression, or of its regression, and/or the prognosis of the course of the cancer in the future. The prediction of the treatment effect can be done using any assessment criterion used in oncology and known to the person skilled in the art. Generally, the effect of the treatment can be assessed by determining the tumor size and/or the number of cancer cells. As will be understood by persons skilled in the art, such assessment normally may not be correct for 100% of the patients, although it preferably is correct. The term, however, requires that a correct prediction can be made for a statistically significant part of the subjects. Whether a part is statistically significant can be determined easily by the person skilled in the art using several well-known statistical evaluation tools, for example, determination of confidence intervals, determination of p values, Student's t-test, Mann-Whitney test, etc. Details are provided in Dowdy and Wearden, Statistics for Research, John Wiley & Sons, New York 1983. The preferred confidence intervals are at least 50%, at least 60%, at least 70%, at least 80%, at least 90%, at least 95%. The p values are preferably 0.05, 0.01, or 0.005.

Pathological Complete Remission (pCR)

In a preferred embodiment of the present invention, an endpoint of the clinical outcome is pathological complete remission (pCR). Pathological examination of the whole resected breast tumor lesion will reveal whether invasive tumor is still present or not. More specifically, pCR is defined as absence of residual invasive cancer by histological evaluation (hematoxylin-eosin staining) of the complete resected breast specimen and all sampled regional lymph nodes, following completion of neo-adjuvant systemic therapy (i.e. ypT0/Tis ypN0 in the current AJCC staging system). If no invasive tumor is present, this result is classified as pathological complete remission (pCR). pCR is an accepted endpoint by the EMA and FDA (Guidance for Industry, Pathological Complete Response in Neoadjuvant Treatment of High-Risk Early-Stage Breast Cancer: Use as an Endpoint to Support Accelerated Approval. U.S. Department of Health and Human Services Food and Drug Administration Center for Drug Evaluation and Research (CDER), October 2014 Clinical/Medical).

Pathological complete remission (pCR) may be classified into four different stages according to Sinn et al. (Sinn H P, Schmid H, Junkermann H, Huober J, Leppien G, Kaufmann M, Bastert G, Otto H F. *Histologic regression of breast*

*cancer after primary* (*neoadjuvant*) *chemotherapy*. Geburtshilfe Frauenheilkd. 1994 October; 54(10):552-8), as depicted in Table 1 below:

TABLE 1

Classification of pCR according to Sinn et al.

| pCR according to Sinn: | Response to neoadjuvant chemotherapy: |
|---|---|
| Sinn 0-1 | no response |
| Sinn 2 | largely tumor free |
| Sinn 3 | tumor-free but in situ carcinoma present |
| Sinn 4 | pathological complete remission (no invasive tumor present, no carcinoma in situ present and no invasive tumor cells present in axillary lymph nodes |

pCR has been acknowledged as a validated surrogate efficacy endpoint for overall survival (OS), yet, only ~30-50% of the TNBC patients will show pCR after neo-adjuvant chemotherapy (NAC). While TNBC patients with pCR have a good prognosis and do not need further systemic treatment, patients without pCR might benefit from further adjuvant systemic therapy.

Triple-Negative Breast Cancer (TNBC)

The terms "triple-negative breast cancer" and "TNBC" as used herein refer to any breast cancer that does not express or overexpress the genes for estrogen receptor (ER), progesterone receptor (PR) or HER2 according to clinical guidelines stated in the American society of clinical oncologists for immunohistochemical assessment of ER/PR and HER2 expression state and clinical guidelines for TNBC (Oakman C1, Viale G, Di Leo A.; Management of triple negative breast cancer. Breast. 2010 October; 19(5):312-21).

The above-defined lack of gene expression or overexpression means that the growth of the cancer is not supported by the hormones estrogen and progesterone, nor by the presence of too many HER2 receptors. Therefore, triple-negative breast cancer does not respond to hormonal therapy (such as tamoxifen or aromatase inhibitors) or therapies that target HER2 receptors, such as Herceptin (chemical name: trastuzumab). Also for this reason, this specific breast cancer indication belongs to the high-risk group of patients according to the St. Gallen classification with very poor prognosis and clinical outcome. However, other medicines can be used to treat triple-negative breast cancer. In contrast to other types of breast cancer, TNBC is treated by neo-adjuvant chemotherapy.

Neo-Adjuvant Chemotherapy (NAC)

In the context of the present invention, the term "neo-adjuvant chemotherapy" or "NAC" refers to a treatment given as a first step to shrink a tumor before the main treatment, which is usually surgery, is given. Examples of neoadjuvant therapy include chemotherapy, radiation therapy, and hormone therapy. It is a type of induction therapy.

In the present context, said neo-adjuvant chemotherapy preferably is anthracycline-based. Anthracyclines are a large group of compounds synthesized by different *Streptomyces* species. They possess antibiotic activity and have cytotoxic effects on eukaryotic cells. All anthracyclines have a tetrahydronaphthacenedione ring structure attached by a glycosidic linkage to a sugar molecule, structural diversity of anthracyclines is generated by modifications of the backbone including a large number of different side chains. Anthracyclines have excellent antineoplastic activity in metastatic, neoadjuvant, and adjuvant settings and are used in the treatment of various haematopoietic and solid tumours. Although their mechanism of chemotherapeutic action is unclear it involves noncovalent DNA intercalation, formation of covalent DNA adducts, topoisomerase II (topo II) poisoning, and free radical effects on cellular membranes and DNA.

In the present context, anthracycline-based neo-adjuvant chemotherapy preferably comprises administering at least one anthracycline, which may be selected from the group consisting of mitoxantrone, doxorubicin, aclarubicin, daunorubicin, epirubicin, idarubicin and combinations thereof.

In an embodiment, anthracycline-based neo-adjuvant chemotherapy comprises administering to a subject at least one anthracycline selected from the above-mentioned group in combination with a platinum compound, which may be selected from cisplatin, carboplatin, oxaliplatin, satraplatin, picoplatin, nedaplatin, triplatin, lipoplatin, and combinations thereof. Typically, the at least one anthracycline and the platinum compound are administered to the subject in a sequential manner.

In a preferred embodiment, the subject receives anthracycline-based neo-adjuvant chemotherapy over a time period of 24 weeks. Within this time period the subject may receive four cycles of anthracycline-treatment followed by 12 weeks of treatment with carboplatin.

However, the clinical utility of anthracyclines are limited due to acute and chronic toxicities, particularly cardiotoxicity, myelosuppression, nausea and vomiting, and alopecia. Heart failure following anthracycline therapy is a major clinical problem in cancer treatment. The establishment of predictors of the anthracycline treatment outcome would allow the identification and exclusion of individuals who would not benefit from said treatment, and thus to increase the safety of anthracycline treatment. Furthermore by determining which patients would benefit from anthracycline treatment, but wherein said predicted outcome is sub-optimal patients can be recommended for further chemotherapeutic or other treatments.

This is particularly essential in the treatment of TNBC because there is only one chance for a patient to undergo neo-adjuvant therapy. The prediction of response with respect to pCR after neo-adjuvant therapy would help to recommend anthracycline- versus non-anthracycline-based therapy.

Accordingly, there is a long felt need in the art for determining which patients afflicted with TNBC will benefit from anthracycline-based treatment in the neoadjuvant setting.

Methods of the Invention

This need has now been met by the methods according to the first and second aspect of the invention. Said method of the first aspect comprises: a) providing a biological sample from the subject, b) determining the expression or methylation state of the gene and/or genomic sequence of PITX2 and/or regulatory sequences thereof within said sample; and c) determining therefrom the outcome of a treatment of said subject.

The method of the second aspect comprises: a) isolating genomic DNA from a biological sample taken of a subject; b) converting, in said genomic DNA, or a fragment thereof, cytosine unmethylated in the 5-position to uracil or to another base that is detectably dissimilar to cytosine in terms of hybridization properties; c) amplifying a region of the converted genomic DNA, or of the converted fragment thereof, using at least two primers, wherein said region comprises at least 16 contiguous nucleotides of the PITX2 gene and/or regulatory regions thereof, wherein said contiguous nucleotides comprise at least one CpG dinucleotide sequence; d) detecting the presence or absence of, or the quantity of DNA amplified in step c); determining, based on the presence or absence of, or on the quantity of said amplificate, the methylation state of the gene and/or genomic sequence of PITX2; and e) predicting from said methylation state the outcome of the neo-adjuvant treatment.

Biological Sample

The term "sample" or "biological sample" as used herein refers to biological material obtained from a subject and preferably comprises genomic DNA from all chromosomes, preferably genomic DNA covering the whole genome. The sample comprises, if a subject has cancer, cells of the cancer or free genomic DNA (including the target DNA) from cancer cells, preferably circulating genomic DNA from cancer cells. It can be derived from any suitable tissue or biological fluid such as nipple aspirate, blood, serum, plasma; cells, cell lines, blood cells, tissue, tissue biopsies and all possible combinations thereof. Preferably, said biological sample is provided in in a state selected from the group consisting of natural, frozen, lyophilized, preserved, embedded, paraffin embedded, and all possible combinations thereof. Methods for deriving samples from a subject are well known to those skilled in the art. In a preferred embodiment, the sample is a tumor biopsy or a liquid sample. The tumor biopsy is preferably a paraffin-embedded tissue sample and the liquid sample is preferably an anticoagulated blood sample.

Homeodomain Transcription Factor 2 (PITX2)

Within said biological sample, the expression or methylation state of the gene and/or genomic sequence of PITX2 and/or regulatory sequences thereof are determined. Determination of the expression may be through determination of the methylation state of one or more CpG. Alternatively, or additionally, determination of expression may be through determining the amount of mRNA encoding PITX2 or the amount of PITX2 protein. In a preferred embodiment, the said expression is determined by analysis of genomic DNA isolated from the biological sample.

Genomic DNA

The term "genomic DNA" as used herein refers to chromosomal DNA and is used to distinguish from coding DNA. As such, it includes exons, introns as well as regulatory sequences, in particular promoters, belonging to a gene. Genomic DNA may be isolated by any means standard in the art, including the use of commercially available kits. Briefly, wherein the DNA of interest is encapsulated in/by a cellular membrane the biological sample must be disrupted and lysed by enzymatic, chemical or mechanical means. In case DNA is extracted from formalin-fixed paraffin-embedded tissue deparaffinization and decrosslinking steps are required. These steps may be performed as commonly known in the art, e.g. by using a kit from commercial providers according to the supplier protocols (e.g. QiaAmp DNA FFPE tissue kit by Qiagen GmbH, Hilden, Germany). The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

In the present context, the term "genomic DNA" preferably refers to genomic sequences of or within the PITX2 gene and treated variants thereof as displayed in Table 2 and Table 3 below.

Methylation Analysis

In a preferred embodiment, determining the expression of the gene and/or genomic sequence of PITX2 and/or regulatory sequences thereof comprises determining the methylation state of the gene and/or genomic sequence of PITX2. It is particularly preferred that the methylation state of the CpG dinucleotides within the genomic sequence of said gene according to Table 2 (SEQ ID NO: 1) or in bisulfit converted derivatives thereof (SEQ ID NO: 4, SEQ ID NO: 7, SEQ ID NO: 10, SEQ ID NO: 13) are analyzed. More preferably, the methylation state of the CpG dinucleotides within the CpG rich regions of PITX2 gene with SEQ ID NO: 2 or in bisulfit converted derivatives thereof (SEQ ID NO: 5, SEQ ID NO: 8, SEQ ID NO: 11, SEQ ID NO: 14), or within the CpG rich regions of PITX2 gene with SEQ ID NO: 3 or in bisulfit converted derivatives thereof (SEQ ID NO: 6, SEQ ID NO: 9, SEQ ID NO: 12, SEQ ID NO: 15), even more preferably within the CpG rich regions of PITX2 gene with SEQ ID NO: 16 or in bisulfit converted derivatives thereof (SEQ ID NO: 19, SEQ ID NO: 22, SEQ ID NO: 25, SEQ ID NO: 28), and most preferably within the CpG rich regions of PITX2 gene with SEQ ID NO: 17 or in bisulfit converted derivatives thereof (SEQ ID NO: 20, SEQ ID NO: 23, SEQ ID NO: 26, SEQ ID NO: 29) or within the CpG rich regions of PITX2 gene with SEQ ID NO: 18 or in bisulfit converted derivatives thereof (SEQ ID NO: 21, SEQ ID NO: 24, SEQ ID NO: 27, SEQ ID NO: 30) are analysed (see Table 3).

In the present context, the genomic sequences with SEQ ID NO: 1 to 3 and 16 to 18 or the bisulfite converted sequences with SEQ ID NO: 4 to 15 and 19 to 30 corresponding thereto will also be referred to as "target DNA".

TABLE 2

Genomic sequence of the PITX2 gene and bisulfite converted variants thereof

| Gene | Accession No. | Genomic SEQ ID NO: | Pretreated methylated sequence (sense) SEQ ID NO: | Pretreated methylated sequence (antisense) SEQ ID NO: | Pretreated unmethylated sequence (sense) SEQ ID NO: | Pretreated unmethylated sequence (antisense) SEQ ID NO: |
|---|---|---|---|---|---|---|
| PITX2 | NM 002658 | 1 | 4 | 7 | 10 | 13 |

TABLE 3

Preferred CpG rich regions of PITX2 and bisulfite converted variants thereof

| Gene | Genomic SEQ ID NO: | Pretreated methylated sequence (sense) SEQ ID NO: | Pretreated methylated sequence (antisense) SEQ ID NO: | Pretreated unmethylated sequence (sense) SEQ ID NO: | Pretreated unmethylated sequence (antisense) SEQ ID NO: |
|---|---|---|---|---|---|
| PITX2 | 2 | 5 | 8 | 11 | 14 |
| PITX2 | 3 | 6 | 9 | 12 | 15 |
| PITX2 | 16 | 19 | 22 | 25 | 28 |
| PITX2 | 17 | 20 | 23 | 26 | 29 |
| PITX2 | 18 | 21 | 24 | 27 | 30 |

DNA Methylation

The term "methylation" or "DNA methylation" as used herein refers to a biochemical process involving the addition of a methyl group to the cytosine or adenine DNA nucleotides. DNA methylation at the 5 position of cytosine, especially in promoter regions, can have the effect of reducing gene expression and has been found in every vertebrate examined. In adult non-gamete cells, DNA methylation typically occurs in a CpG site.

CpG Dinucleotides

The term "CpG site" or "CpG dinucleotide", as used herein, refers to regions of DNA where a cytosine nucleotide occurs next to a guanine nucleotide in the linear sequence of bases along its length. "CpG" is shorthand for "C-phosphate-G", that is, cytosine and guanine separated by only one phosphate; phosphate links any two nucleosides together in DNA. The "CpG" notation is used to distinguish this linear sequence from the CG base-pairing of cytosine and guanine. Cytosines in CpG dinucleotides can be methylated to form 5-methylcytosine. The term "CpG site" or "CpG site of genomic DNA" is also used with respect to the site of a former (unmethylated) CpG site in DNA in which the unmethylated C of the CpG site was converted to another as described herein (e.g. by bisulfite to uracil). The application provides in Table 2 and Table 3 the genomic sequence of each relevant DNA region as well as the bisulfite converted sequences of each converted strand. Herein, bisulfite converted sequences are also referred to as "treated sequences" or "pretreated sequences". Table 3 specifically provides CpG rich regions of the PITX2 gene and treated variants thereof. CpG sites referred to are always the CpG sites of the genomic sequence, even if the converted sequence does no longer contain these CpG sites due to the conversion.

Suitable methods for quantifying CpG methylation in genomic DNA are known in the art. In the context of the present invention, methylation within the PITX2 gene and/or regulatory or promoter regions thereof may be analyzed by the any of the methods as described in WO 2007/03128 and in U.S. Pat. No. 6,265,171 to Herman, the disclosure of which is herein incorporated by reference.

DNA Conversion

Briefly, determining CpG methylation state within the PITX2 gene requires in a first step, converting, in genomic DNA, or a fragment thereof, cytosine unmethylated in the 5-position to uracil or to another base that is detectably dissimilar to cytosine in terms of hybridization properties.

The term "hybridization", when used with respect to an oligonucleotide, is to be understood as a bond of an oligonucleotide to a complementary sequence along the lines of the Watson-Crick base pairings in the sample DNA, forming a duplex structure, under moderate or stringent hybridization conditions. When it is used with respect to a single nucleotide or base, it refers to the binding according to Watson-Crick base pairings, e.g. C-G, A-T and A-U. Stringent hybridization conditions involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). Moderate conditions involve washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

The phrase "converting, in said genomic DNA, or a fragment thereof, cytosine unmethylated in the 5-position to uracil or to another base that is detectably dissimilar to cytosine in terms of hybridization properties" as used herein refers to a process of chemically treating the DNA in such a way that all or substantially all of the unmethylated cytosine bases are converted to uracil bases, or another base which is dissimilar to cytosine in terms of base pairing behaviour, i.e. that does not hybridize to guanine, while the 5-methylcytosine bases remain unchanged. The conversion of unmethylated, but not methylated, cytosine bases within the DNA sample is conducted with a converting agent. The term "converting agent" as used herein relates to a reagent capable of converting an unmethylated cytosine to uracil or to another base that is detectably dissimilar to cytosine in terms of hybridization properties. The converting agent is preferably a bisulfite such as disulfite, or hydrogen sulfite. The reaction is performed according to standard procedures (Frommer et al., 1992, Proc Natl Acad Sci USA 89:1827-31; Olek, 1996, Nucleic Acids Res 24:5064-6; EP 1394172). It is also possible to conduct the conversion enzymatically, e.g. by use of methylation specific cytidine deaminases. Most preferably, the converting agent is sodium bisulfite or bisulfite.

The disclosed invention provides treated nucleic acid sequences, derived from genomic SEQ ID NO: 1 to SEQ ID NO: 3 and SEQ ID NO: 16 to SEQ ID NO: 18, wherein the treatment is suitable to convert at least one unmethylated cytosine base of the genomic DNA sequence to uracil or another base that is detectably dissimilar to cytosine in terms of hybridization. The genomic sequences in question may comprise one, or more, consecutive or random methylated CpG positions.

DNA Amplification

In the next step, a region of the converted genomic DNA, or a region of a converted fragment thereof, is amplified, preferably in a methylation dependent manner.

The term "amplifying" or "generating an amplicon" as used herein refers to an increase in the number of copies of the target nucleic acid and its complementary sequence, or particularly a region thereof. The amplification may be performed by using any method known in the art. The amplification of nucleic acid includes methods that require multiple cycles during the amplification process or method that are performed at a single temperature. Cycling techniques are exemplified by methods requiring thermo-cycling. The methods requiring thermo-cycling include polymerase chain reaction (PCR), which is well known in the art. The PCR includes denaturing a double-stranded DNA into single stranded DNAs by thermal denaturation, annealing a primer to the single stranded DNAs; and synthesizing a complementary strand from the primer. Isothermal amplification is an amplification performed at a single temperature or where the major aspect of the amplification process is performed at a single temperature. In the PCR process, the product of the reaction is heated to separate the two strands such that another primer may bind to the template. Conversely, the isothermal techniques rely on a strand displacing polymerase in order to separate the two strands of a double strand and re-copy the template. Isothermal techniques may be classified into methods that rely on the replacement of a primer to initiate a reiterative template copying and those that rely on continued re-use or new synthesis of a single primer molecule. The methods that rely on the replacement of the primer include helicase dependant amplification (HDA), exonuclease dependent amplification, recombinase polymerase amplification (RPA), and loop mediated amplification (LAMP). The methods that rely on continued re-use or new synthesis of a single primer molecule include strand displacement amplification (SDA) or nucleic acid based amplification (NASBA and TMA).

Methylation-Specific PCR

The amplification is preferably performed by methylation-specific PCR by use of methylation-specific primer oligonucleotides, or, in an alternative embodiment, by use of primer oligonucleotides which are methylation-unspecific, but specific to bisulfite-converted DNA (i.e. hybridize only to converted DNA by covering at least one converted C). The latter method has been described in WO 2007/03128, the disclosure of which is herein incorporated by reference.

Primer Oligonucleotides

The term "primer oligonucleotide" as used herein refers to a single-stranded oligonucleotide sequence substantially complementary to a nucleic acid sequence sought to be copied (the template) and serves as a starting point for synthesis of a primer extension product. "Substantially complementary" means that a primer oligonucleotide does not need to reflect the exact sequence of the template and can comprise mismatches and/or spacers, as long as it is still capable of annealing and serving as a starting point for extension under the chosen annealing and extension conditions (e.g. of a PCR cycle).

The term "mismatch" as used herein refers to base-pair mismatch in DNA, more specifically a base-pair that is unable to form normal base-pairing interactions (i.e., other than "A" with "T" or "U", or "G" with "C").

The term "spacer" as used herein refers to a non-nucleotide spacer molecule, which increases, when joining two nucleotides, the distance between the two nucleotides to about the distance of one nucleotide (i.e. the distance the two nucleotides would be apart if they were joined by a third nucleotide). Non-limiting examples for spacers are Inosine, d-Uracil, halogenated bases, Amino-dT, C3, C12, Spacer 9, Spacer 18, and dSpacer).

Methylation-Specific Primer Oligonucleotides

In an embodiment of the method, the methylation state of preselected CpG positions within one or more of the nucleic acid sequences selected from the group comprising SEQ ID NO: 1 to SEQ ID NO: 3 and SEQ ID NO: 16 to SEQ ID NO: 18, may be detected by use of methylation-specific primer oligonucleotides. This technique (MSP) has been described in U.S. Pat. No. 6,265,171 to Herman.

The use of methylation state specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG, TpG or CpA dinucleotide. MSP primers specific for non-methylated DNA contain a "T' at the 3' position of the C position in the CpG. Preferably, therefore, the base sequence of said primers is required to comprise a sequence having a length of at least 18 nucleotides which hybridizes to a pretreated nucleic acid sequence according to SEQ ID NO: 4 to SEQ ID NO:9 or SEQ ID NO: 19 to SEQ ID NO: 24 and sequences complementary thereto, or to a pretreated nucleic acid sequence according to SEQ ID NO: 10 to SEQ ID NO: 15 or SEQ ID NO: 25 to SEQ ID NO: 30 and sequences complementary thereto, wherein the base sequence of said oligomers comprises at least one CpG, tpG or Cpa dinucleotide. In this embodiment of the method according to the invention it is particularly preferred that the MSP primers comprise between 2 and 4 CpG, tpG or Cpa dinucleotides. It is further preferred that said dinucleotides are located within the 3' half of the primer e.g. wherein a primer is 18 bases in length the specified dinucleotides are located within the first 9 bases form the 3'end of the molecule. In addition to the CpG, tpG or Cpa dinucleotides it is further preferred that said primers should further comprise several bisulfite converted bases (i.e. cytosine converted to thymine, or on the hybridizing strand, guanine converted to adenosine). In a further preferred embodiment said primers are designed so as to comprise no more than 2 cytosine or guanine bases. Methylation-specific PCR (MSP) is a methylation assay well-known in the art and was described by Herman et al. Proc. Natl. Acad. Sei. USA 93:9821-9826, 1996. In a most preferred embodiment, the step of amplifying comprises a real-time PCR as disclosed in EP 1 561 821 B1, in particular MethyLight™. In the context of the present invention, the term "MethyLight™" refers to a methylation assay comprising four oligonucleotides, i.e. two methylation un-specific primer oligonucleotides and two oligonucleotide probes that competitively hybridize to the binding site. The two methylation un-specific primers are used to amplify a segment of the treated genomic DNA containing a methylation variable oligonucleotide probe binding site.

In the context of the present disclosure, the term "variable oligonucleotide probe binding site" refers to the binding site of two differential fluorescent labelled oligonucleotide probes, detecting the fully methylated or fully unmethylated state of one or more CpG-motifs covered by the sequence of the respective probes.

Preferably, said two methylation un-specific PCR primers are oligonucleotides with SEQ-ID NO: 31 and SEQ-ID NO: 32.

Following the non-methylation specific amplification of the target region the PITX2 methylation state is determined by methylation specific detection using two different oligonucleotide probes that competitively hybridize to the binding site.

In the context of the present invention the term "methylation state" refers to the degree of methylation present in a nucleic acid of interest. This may be expressed in absolute or relative terms i.e. as a percentage or other numerical value or by comparison to another tissue and may be described as hypermethylated, hypomethylated or as having significantly similar or identical methylation state.

The two oligonucleotide probes used in the present methylation assay competitively hybridize to the binding site, one specific for the methylated version of the binding site, the other specific to the unmethlyated version of the binding site. Accordingly, one of the probes comprises a CpG at the methylation variable position (i.e. anneals to methylated bisulphite treated sites) and the other comprises a TpG at said position (i.e. anneals to unmethylated bisulphite treated sites). Each species of probe is labeled with a 5' fluorescent reporter dye and a 3' quencher dye wherein the CpG and TpG oligonucleotides are labeled with different dyes.

In a preferred embodiment, said oligonucleotide probes are oligonucleotides with SEQ-ID NO: 33 and SEQ-ID NO: 34. Said 5' fluorescent reporter dye may be any 5' fluorescent reporter dye known in the art and is particularly selected from 6-carboxyfluorescein (FAM). The 3' quencher dye may be any 3' quencher dye known in the art and is particularly selected from 5-Carboxytetramethylrhodamine (TAMRA).

In a particularly preferred embodiment, the PITX2 methylation state is determined by the art-recognized fluorescence-based real-time PCR technique described by Eads et al., Cancer Res. 59:2302-2306, 1999.

In a preferred embodiment of the invention, the amplified region of the PITX2 gene or fragment thereof is at least 16 contiguous nucleotide bases in length of a sequence selected from the group consisting of SEQ ID NO: 1 to SEQ ID NO: 3 and SEQ ID NO: 16 to SEQ ID NO: 18, wherein said sequence comprises at least one CpG dinucleotide and sequences complementary thereto, for which the amount of methylation is to be determined. The sequences of SEQ ID NO: 4 to SEQ ID NO: 15 and SEQ ID NO: 19 to SEQ ID NO: 30 provide non-naturally occurring modified versions of the nucleic acid according to SEQ ID NO: 1 to SEQ ID NO: 3 and SEQ ID NO: 16 to SEQ ID NO: 18, wherein the modification of each genomic sequence results in the synthesis of a nucleic acid having a sequence that is unique and distinct from said genomic sequence as follows. For each sense strand genomic DNA, e.g., SEQ ID NO: 1, two converted versions are disclosed. A first version wherein "C" to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" to "T," but "CpG" remains "CpG" (i.e., corresponds to case where, for all "C" residues of CpG dinucleotide sequences are methylated and are thus not converted). The 'unmethylated' converted sequences of SEQ ID NO: 1 to SEQ ID NO: 3 and SEQ ID NO: 16 to SEQ ID NO: 18 correspond to SEQ ID NO: 10 to SEQ ID NO: 15 and SEQ ID NO: 25 to SEQ ID NO: 30, wherein "C" is converted to "T" for all "C" residues, including those of "CpG" dinucleotide sequences (i.e., corresponds to case where, for the genomic sequences, all "C" residues of CpG dinucleotide sequences are unmethylated). The complementary strands are in silico built up from chemically converted, methylated and unmethylated DNA sequences (SEQ ID NO: 1 to SEQ ID NO: 3 and SEQ ID NO: 16 to SEQ ID NO: 18), representing complemented PCR products after the first amplification step (i.e. complementary sequence of fully methylated chemically converted sense strand). The 'complementary' converted sequences of SEQ ID NO: 1 to SEQ ID NO: 3 and SEQ ID NO: 16 to SEQ ID NO: 18 correspond to SEQ ID NO: 7 to SEQ ID NO: 9; SEQ ID NO: 13 to SEQ ID NO: 15; SEQ ID NO: 22 to SEQ ID NO: 24 and SEQ ID NO: 28 to SEQ ID NO: 30.

Particularly suitable methylation-specific primers for use in determining the PITX2 methylation state are given in Table 4 below.

TABLE 4

Methylation-specific primers and amplificates for use in PITX2 methylation analysis

| Gene | Forward primer SEQ ID NO: | Reverse primer SEQ ID NO: | Probe methylated SEQ ID NO: | Probe unmethylated SEQ ID NO: | Amplificate genomic SEQ ID NO: | Amplificate pretreated fully methylated sequence SEQ ID NO: | Amplificate pretreated fully un-methylated sequence SEQ ID NO: |
|---|---|---|---|---|---|---|---|
| PITX2 | 31 | 32 | 33 | 34 | 35 | 36 | 37 |

The primer and probe oligonucleotides according to SEQ ID NO: 31 to SEQ ID NO: 34 particularly anneal to nucleotide positions 10990 to 11011 (SEQ ID NO: 31), 10874 to 10887 (SEQ ID NO: 32), 10951 to 10970 (SEQ ID NO: 33) and 10944 to 10970 (SEQ ID NO: 34) of SEQ ID NO: 1, respectively. More particularly, three CpG site in the nucleotide range of from 10952 to 10967 of SEQ ID NO: 1 may be detected by use of the primers and probes referred to in Table 4.

Methylation Unspecific Primer Oligonucleotides

In an alternative embodiment, the methylation state of preselected CpG positions within one or more of the nucleic acid sequences selected from the group comprising SEQ ID NO: 1 to SEQ ID NO: 3 and SEQ ID NO: 16 to SEQ ID NO: 18 is analysed using primers which are methylation-unspecific, but specific to bisulfite-converted DNA (i.e. hybridize only to converted DNA by covering at least one converted C). In this case, methylation-specificity is achieved by using methylation-specific blocker oligonucleotides, which hybridize specifically to converted or non-converted CpG sites and thereby terminate the PCR polymerization. In this alternative embodiment, the step of amplifying comprises a real-time PCR as disclosed in WO 2007/03128, in particular HeavyMethyl™. In the context of the present invention, the term "HeavyMethyl™" refers to a methylation assay comprising methylation specific blocking probes covering CpG positions between the amplification primers.

Specifically, a "blocker oligonucleotide" or "blocking probe" may be a blocker that prevents the extension of the primer located upstream of the blocker oligonucleotide. It comprises nucleosides/nucleotides having a backbone resistant to the 5' nuclease activity of the polymerase. This may be achieved, for example, by comprising peptide nucleic acid (PNA), locked nucleic acid (LNA), Morpholino, glycol nucleic acid (GNA), threose nucleic acid (TNA), bridged nucleic acids (BNA), N3'-P5' phosphoramidate (NP) oligomers, minor groove binder-linked-oligonucleotides (MGB-linked oligonucleotides), phosphorothioate (PS) oligomers, $CrC_4$alkylphosphonate oligomers, phosphoramidates, β-phosphodiester oligonucleotides, a-phosphodiester oligonucleotides or a combination thereof. Alternatively, it may be a non-extendable oligonucleotide with a binding site on the DNA single-strand that overlaps with the binding site of a primer oligonucleotide. When the blocker is bound, the primer cannot bind and therefore the amplicon is not generated. When the blocker is not bound, the primer-binding site is accessible and the amplicon is generated. For such an overlapping blocker, it is preferable that the affinity of the blocker is higher than the affinity of the primer for the DNA. Also, a blocker oligonucleotide cannot by itself act as a primer (i.e. cannot be extended by a polymerase) due to a non-extensible 3' end.

In a preferred embodiment, a set of at least two primer oligonucleotides is used for amplifying DNA sequences of one of SEQ ID NO: 1 to SEQ ID NO: 30 and sequences complementary thereto, or segments thereof.

In a particularly preferred embodiment, said at least two primers each comprise a contiguous sequence of at least 18 nucleotides in length that is complementary to, or hybridizes under moderately stringent or stringent conditions to a sequence selected from the group consisting of SEQ ID NO: 1 to SEQ ID NO: 30 and sequences complementary thereto, or segments thereof.

Particular methylation un-specific primers for use in determining the PITX2 methylation state are listed in Table 5.

The methylation state of the target DNA may be determined by means of one or more methods taken from the group consisting oligonucleotide hybridization analysis, Ms-SnuPE, sequencing, Real Time detection probes and oligonucleotide array analysis. These methods may be performed as commonly know in the art and/or as disclosed in WO 2007/03128.

In a particularly preferred embodiment, PITX2 methylation state is determined by quantitative real-time PCR (QM-PCR) as described by Harbeck et al. 2008; J Clin Oncol; 26:5036-5042 or as in patent EP1561821 B1.

In a preferred embodiment, the methylation state is determined using oligonucleotides detecting the cytosine methylation state within genomic or pre-treated DNA, according to SEQ ID NO: 1 to SEQ ID NO: 30. It is particularly preferred that said oligonucleotides comprise a nucleic acid sequence having a length of at least nine nucleotides which hybridizes, under moderately stringent or stringent conditions (as defined herein above), to a treated nucleic acid sequence according to SEQ ID NO: 4 to SEQ ID NO: 15 and SEQ ID NO: 19 to SEQ ID NO: 30 and/or sequences complementary thereto, or to a genomic sequence according to SEQ ID NO: 1 to SEQ ID NO: 3 or SEQ ID NO: 16 to SEQ ID NO: 18 and/or sequences complementary thereto. Most preferably, detection oligonucleotides for determining the methylation state of PITX2 are selected from SEQ ID NO: 52 to SEQ ID NO: 71.

Predictive Value of PITX2 Hypomethylation

From the methylation state determined by any of the herein described or referred to methods, the outcome of neo-adjuvant treatment of an TNBC patient may be predicted. Specifically, it was found that PITX2 hypomethylation is indicative for a poor clinical outcome of anthracycline-based neo-adjuvant chemotherapy.

The term "poor clinical outcome" as used herein means the absence of pathological complete remission (pCR), i.e. the presence of residual invasive cancer after completion of neo-adjuvant systemic therapy. While TNBC patients with pCR have a good prognosis and do not need further systemic treatment, patients without pCR might benefit from further adjuvant systemic therapy.

TABLE 5

Methylation un-specific primers and amplificates for use in PITX2 methylation analysis

| Gene | Forward primer SEQ ID NO: | Reverse primer SEQ ID NO: | Amplificate genomic SEQ ID NO: | Amplificate pretreated methylated sequence (sense) SEQ ID NO: | Amplificate pretreated methylated sequence (antisense) SEQ ID NO: | Amplificate pretreated un-methylated sequence (sense) SEQ ID NO: | Amplificate pretreated un-methylated sequence (antisense) SEQ ID NO: |
|---|---|---|---|---|---|---|---|
| PITX2 | 38 | 40 | 42 | 44 | 46 | 48 | 50 |
| PITX2 | 39 | 41 | 43 | 45 | 47 | 49 | 51 |

The resulting amplification product is isolated and used as a template for determining the methylation state of at least one CpG dinucleotide.

Accordingly, in a next step, the methylation state of the target DNA is determined, based on the presence or absence of, or on the quantity of said amplificate.

In the context of the present invention the term "methylation state" refers to the degree of methylation present in a nucleic acid of interest. This may be expressed in absolute or relative terms i.e. as a percentage or other numerical value or by comparison to another tissue and may be described as hypermethylated, hypomethylated or as having significantly similar or identical methylation state.

Preferably, the term "poor clinical outcome" as used herein refers to pCR 0-1 according to Sinn et al. (see Table 1).

The term "hypomethylation" as used herein refers to an aberrant methylation pattern or state (i.e. the presence or absence of methylation of one or more nucleotides), wherein one or more nucleotides, preferably C(s) of a CpG site(s), are un-methylated compared to a control.

In an embodiment, said control may be the same genomic DNA from a non-cancer cell of the patient or a subject not suffering or having suffered from the cancer the patient is treated for, preferably any cancer (healthy control). In particular, it may refer to a decreased presence of 5-mCyt at one or a plurality of CpG dinucleotides within a DNA sequence comprised in a biological sample, relative to the amount of 5-mCyt found at corresponding CpG dinucleotides within a healthy control DNA sample.

In an alternative embodiment, the term "control" as used herein may refer to a reference sample comprising control DNA with known DNA concentration and known target methylation state. In this alternative embodiment, the control DNA is preferably, but not necessarily, human DNA that is artificially methylated, preferably substantially fully methylated. Preferably, said artificial methylation is achieved by using DNA-Methyltransferases. The DNA itself can be, for example, cell line DNA, plasmid DNA, artificial DNA, or combinations/mixtures thereof. Substantially fully methylated genomic DNA preferably is DNA, particularly genomic DNA, which has all or substantially all CpG sites methylated. "Substantially all" in this respect means at least 95%, 96%, 97%, 98%, 99%, 99.5% or 99.9%. It is preferred that the methylation of all or substantially all CpG sites is achieved by treating the DNA with a CpG methyltransferase in a manner that provides for the methylation of all or substantially all CpG sites.

In a preferred embodiment, the term "hypomethylation" as used herein refers to a degree of methylation of the target DNA of up to 95%, up to 90%, up to 80%, up to 70%, up to 60%, up to 50%, up to 40%, up to 30%, up to 20%, or up to 10% lower than a degree of methylation of a control as defined herein.

In a further preferred embodiment, the term "hypomethylation" as used herein refers to a percent methylation ratio (PMR) of the target DNA of less than 5% PMR, less than 4% PMR, or less than 3% PMR, and, preferably, of less than 2% PMR, or less than 1% PMR. Said percent methylation ratio (PMR) may be determined by data transformation of CT values obtained from quantitative methylation-specific PCR and a modified $2exp^{CT}$ method for a duplex probe system, with internal calibration and standardization according to the following formula:

$$PMR(sample\ well):100/(1+2^{exp}(CT_{meth.}-CT_{unmeth.})).$$

$$MV\ PMR(sample\ duplicate):(PMR(sample\ well\ 1)+PMR(sample\ well\ 2))/2$$

Error (absolute): STDEV MV PMR (sample duplicate).

meth.=methylated signal unmeth.=unmethylated signal

PMR=Percent Methylation Ratio

MV PMR (sample duplicate): Mean value of PMR values calculated for each separate well in the technical assay duplicate of one sample.

CT=Cycle Threshold. PCR cycle number, at which the reporter dye fluorescent signal reaches an assay specific threshold. For further analysis the mean value and STDEV of technical replicates (n=2) was established.

STDEV=Standard deviation of the Mean value PMR for the technical replicates.

Included control references plasmid mixtures (2500 copies input per well: 1:1 mixture in case of REF50) containing the bisulfite-converted fully methylated and fully unmethylated sequence to be amplified by the assay can be used for absolute quantification of methylated and unmethylated copies of the PITX2 gene promoter in a sample according to the following formula:

$$Copy\ number\ methylated(sample):1250/(2^{exp}(CT_{meth\ sample}-CT_{meth\ REF50})).$$

$$Copy\ number\ unmethylated(sample):1250/(2^{exp}(CT_{unmeth\ sample}-CT_{unmeth\ REF50})).$$

$CT_{meth\ REF50}$: CT value of methylated signal of reference 50 sample (1250 methylated and 1250 unmethylated copies input per assay well).

$CT_{unmeth\ REF50}$: CT value of unmethylated signal of reference 50 sample (1250 methylated and 1250 unmethylated copies input per assay well).

The term "PITX2 hypomethylation" as used herein refers to hypomethylation of the gene and/or genomic sequence of homeodomain transcription factor 2 (PITX2) and/or regulatory sequences thereof and, preferably, to hypomethylation of one or more CpG sites within said gene and/or genomic sequence and/or regulatory regions, preferably within the genomic region with SEQ ID NO: 1, more preferably within the genomic region with SEQ ID NO: 2 and SEQ ID NO: 3 and most preferably within the genomic region with SEQ ID NO: 2.

Selection of Therapy

Depending on the methylation state determined by any of the herein described or referred to methods, a suitable treatment regimen for a patient suffering from triple-negative breast cancer (TNBC) may be determined. While anthracycline-based neoadjuvant chemotherapy is recommended in the absence PITX2 hypomethylation, an alternative, non-anthracycline-based therapy should be selected for TNBC patients showing said hypomethylation.

In a preferred embodiment, anthracycline-based neoadjuvant chemotherapy is selected for patients exhibiting a percent methylation ratio (PMR) value of >1% PMR and, preferably, for patients exhibiting a percent methylation ratio (PMR) value of >2% PMR.

The invention is described by way of the following examples which is to be construed as merely illustrative and not limitative of the scope of the invention.

Example 1

A retrospective analysis of 120 tumor specimens from triple-negative breast cancer patients treated in the neoadjuvant setting with anthracycline-based therapy was conducted and the optimal cut-off value of the methylation state of PITX2 was determined to predict pCR in TNBC patients.

Example 2

In addition, a prospective clinical trial was conducted to support the retrospective analysis results. This study has prospectively determined diagnostic efficacy of the "PITX2-Test" to predict pCR for anthracycline-based combination therapy. The prospective study was outlined as follows:

Title

Prospective trial to predict the efficacy of platinum-based neo-adjuvant chemotherapy by BRCAness and PITX2 in triple-negative breast cancer patients ($P^4$-trial))

Study Design

Except for some biopsy-tissue obtained during routinely performed diagnostic biopsy and three blood samples taken, TNBC patients were treated as per standard of care. Standard of care for these patients consists of 24 weeks NAC (4 cycles of EC, followed by 12 weeks of carboplatin), followed by primary surgery. Afterwards, patients with no pCR received further adjuvant treatment with 12×paclitaxel weekly while patients with pCR were submitted to active surveillance. Primary surgery was considered end of the active study part, while follow-up was conducted for 3 years to determine disease-free survival (DFS) and overall survival (OS).

Tissue and Blood Sampling

Tissue: Pre-treatment core-biopsies were collected, formalin-fixed and paraffin-embedded (FFPE). FFPE tumor tissue samples were provided for evaluation by the PITX2- and MLPA tests. Detailed instructions were supplied to all sites to allow for consistent sampling and processing of the tissues.

Blood: Anticoagulated EDTA-blood samples were taken at three time points to analyze free circulating DNA for PITX2 methylation state.

Diagnostic PITX2-Test

The methylation state of the promoter region of the PITX2 gene was determined as described by Harbeck et al. 2008; J Clin Oncol; 26:5036-5042. For this, FFPE tissue was sampled and sent to a central laboratory to assess the DNA-methylation state. The central laboratory performed DNA extraction, bisulfite-conversion and quantitative methylation-specific real-time PCR. PITX2 methylation scores ("PITX2-Test") were calculated and categorized as PITX2-high or PITX2-low according to a pre-defined cut-off.

pCR Definition and Assessment pCR was defined as absence of residual invasive cancer by histological evaluation (hematoxylin-eosin staining) of the complete resected breast specimen and all sampled regional lymph nodes, following completion of neo-adjuvant systemic therapy (i.e. ypT0/Tis ypN0 in the current AJCC staging system). Histological sections of FFPE tumor blocks were evaluated for pathological response by local pathologists and a central pathologist.

Objectives

Primary Objective

Employ PITX2-Test as biomarker test for prediction of pCR in TNBC patients following NAC EC/carboplatin therapy (pCR rate of PITX2-low is ≤20% compared to PITX2-high is ≥50%)

Secondary Objectives

Determine BRCAness in FFPE tumor specimens as a predictive marker for pCR in TNBC patients following EC/carboplatin therapy (pCR rate of BRCAness-positive patients is ≥20% higher compared to BRCAness-negative patients)

Determine diagnostic efficacy (sensitivity, specificity, accuracy, PPV and NPV) of PITX2-Test score determined in FFPE tumor specimens to predict pCR in patients with TNBC following NAC Determine PITX2-Test score in FFPE tumor specimens to predict patient outcome (DFS/OS)

Determine correlation of clinico-pathological factors (stage, nuclear grade, nodal state, pathological remission grade according to Sinn, age, therapy schedule) with PITX2-Test score obtained by the PITX2-Test Determine correlation of clinico-pathological factors (stage, nuclear grade, nodal state, pathological remission grade according to Sinn, age, therapy schedule) with BRCAness as the predictive test Exploratory Objectives Determine correlation of PITX2 quantified in FFPE tumor specimens with PITX2 quantified from circulating DNA in blood.

Patient Population

Major Inclusion Criteria

1. Female
2. ≥18 years old at time of written informed consent
3. Written informed consent to provide biomarker samples, clinico-pathological data and to comply with 60 months follow-up
4. Patients with histologically confirmed, non-metastatic TNBC (HER2-negative by FISH or IHC staining 0 or 1+, 2+(however, only if FISH is negative), ER- and PR-negative per local immunohistochemistry assessment, <10% reactive cells)
5. Indication for primary, systemic, neo-adjuvant chemotherapy Statistical Methodology Sample Size Calculation The primary study objective was to determine the diagnostic efficacy by comparing the pCR rate in PITX2-low patients of <20% to the pCR rate in PITX2-high patients of >50%. It was further assumed that the prevalence of PITX2-low patients will be approximately 33%. Based on these assumptions using a power of 90% and a significance level of 5% (two-sided), the total sample size was determined to be about 200 patients.

Statistical Analyses:

Primary objectives: The primary study objective was to determine the diagnostic efficacy by comparing the pCR rate in PITX2-low patients to the pCR rate in PITX2-high patients. This comparison will be performed with the Chi-square test. In addition, logistic regression analysis was applied in order to identify variables which are also associated with the pCR-rate. Computations are performed using the PASS11 software.

Secondary objectives: For determination of BRCAness as a predictive marker for pCR in TNBC patients following EC/carboplatin therapy (pCR rate of BRCAness-positive patients is ≥20% higher compared to BRCAness-negative patients), a sample size of about 200 patients is required using a power of 90% and a significance level of 5% (two-sided). The predictive potential of the PITX2-Test score was tested by Kaplan Meier analyses displaying OS and DFS for PTIX2-high and PTIX2-low patients. Clinico-pathological factors (stage, nuclear grade, nodal state, pathological remission grade according to Sinn, age, therapy schedule) was included as covariates to test whether PITX2 DNA-methylation adds predictive and/or prognostic statistically independent information. For this, multivariable Cox proportional models were applied to calculate hazard ratios and their 95% confidence intervals.

Example 3

An assay was established to assess the DNA-methylation status of the PITX2 promoter gene extracted from formalin-fixed and paraffin-embedded (FFPE) breast tumor tissue (herein referred to as "PITX2-Test").

The PITX2-Test predicts response to therapy in triple negative breast cancer patients (TNBC) treated with systemic cancer therapy in the (neo-)adjuvant setting. In short, it comprises the extraction of DNA from formalin fixed, paraffin embedded core biopsy sections (5 μm with an overall surface area of 30-600 $mm^2$, 1-2 sections, QIAamp DSP$^{CE}$ DNA FFPE Kit, Qiagen, Hilden), concentration determination by OD measurement (QiaXpert, Qiagen Hilden), bisulfite conversion (Epitect Fast Bisulfite Kit, Qiagen, Hilden, optional with semi-automated clean up step on the QIAcube, Qiagen, Hilden) and semi-quantitative analysis of the DNA-Methylation status in the promoter region of the PITX2 gene by quantitative real-time PCR with dual labelled Taqman probes specific for the methylated and unmethylated status of 3 CpGs in the PITX2 promoter gene on the Rotorgene Q 5-plex HRM (Qiagen, Hilden) platform using the Rotorgene Q software for data analysis. An overview of the workflow of the PITX2-Test is given in FIG. 1. Specifically, this test was performed as follows:

DNA Isolation from Formalin-Fixed Paraffin-Embedded (FFPE) Breast Cancer Tissue 1-2×5 μm sections with an overall surface area of 30-600 mm2 were cut from FFPE-tumor tissue blocks according to manufacturer instructions (QIAamp DSP$^{CE}$ DNA FFPE Kit). Optionally, a macro-dissection of the paraffin-embedded tumor samples has been performed for enrichment of tumor cell content in the extraction sample. FFPE-material was transferred to a nuclease-free 1.5 ml reaction tube and deparaffinization using xylene and ethanol was performed. Subsequently, a proteinase K digestion step was performed overnight, formaline-crosslinks were de-modified by a decrosslinking step at 90° C. for 1 hour and DNA was purified according to manufacturer's instructions.

OD Determination of Extracted DNA

DNA concentration was determined and DNA quality was controlled by spectrophotometric analysis of OD 260/280 and OD 230/260 ratios using a QIAxpert UV/VIS spectrophotometer.

Bisulfite Conversion

For quantitative methylation specific analysis bisulfite conversion of extracted DNA was performed using the Epitect Fast Bisulfite Kit according to manufacturer's instructions. Specifically, 120-1000 ng (400 ng recommended input amount) DNA solution was added to a 200 μl PCR-reaction tube (e.g. Eppendorf PCR-Tube) and adjusted to a final volume of 40 μl with nuclease-free water.

85 μl bisulfite solution immediately followed by 15 μl DNA-Protect-Buffer (green color) were added, the cap was immediately closed and subsequently vortexed until a homogeneously blue coloured reaction mix was obtained. Bisulfite conversion of the DNA was mediated by the following thermal program in a standard Thermocycler (e.g. Eppendorf PCR Cycler):

5 min, 95° C. (1. Denaturing step)
10 min, 60° C. (Incubation)
5 min, 95° C. (2. Denaturing step)
10 min, 60° C. (Incubation)
infinite, 20° C. (storage)

Sample clean up followed the manual instructions or was performed semi-automated on the QIAcube platform.

Quantitative Methylation-Specific PCR (qMS-PCR, Methylight)

For the PITX2 marker a Methylight™ reaction system on the basis of fluorescent labelled hydrolysis probes was established (for details it is referred to European Patent EP 1 561821). The Methylight™ system contains two differently fluorescent labelled probes (FAM- and HEX fluorescent dyes plus Quencher e.g. with TAMRA or BHQ1), specific for methylated (FAM-label) and unmethylated (HEX-label) status of clinical response predictive CpG-sites in the PITX2 gene. As reference control 2500 copies of plasmids containing the bisulfite-converted fully methylated and fully unmethylated sequence to be amplified by the assay were included as positive controls (Reference 50 with a ratio meth:unmeth 1:1 and Reference 10 with a ration meth:unmeth 1:9) as well as genomic DNA as negative control and no template controls were used. Assessment of each sample was performed in technical duplicates or single reactions in a reaction volume of 20 μl, as followed: 1× Reaction mix: 10 μl Quantinova Probe PCR mastermix (2×, Qiagen, Hilden); 2 μl 10× Primer and probe mastermix containing methylated and unmethylated probe (2 μM) and both primers (6 μM); 5 μl bisDNA (up to 30-250 ng); 3 μl $H_2O$ ad 20 μl end volume. Final reaction concentrations of primers and probes were 600 nM and 200 nM. 15 μl of the mastermix (containing primers and probes, qPCR Mastermix and water) were pipetted in 4-cap-strips for analysis on the Rotorgene qPCR platform (Qiagen, Hilden) and 5 μl of bisulfite-converted DNA or control samples were added, the strips sealed and qPCR performed according to the following protocol:

A standard qPCR protocol template (qPCR PITX2 template) with 2 Reporter-Dyes (green channel (FAM) and yellow channel (HEX)) was used with the Rotor Gene Q Software 2.3.1. No internal reference dye was used. Autogain compensation on sample Pos 1 was performed before begin of 1$^{st}$ fluorescence signal acquisition in qPCR cycle 1 to optimize gain setting for both reporter dyes. Detection of the respective methylation status was performed in channel green- (methylated Status; 516 nm) and channel yellow-filter modus (unmethylated Status; 555 nm). Thermal PCR program contained a polymerase activation step for 2 min at 95° C., followed by 40 cycles with 5 sec, 95° C. (denaturing step) and 5 sec, 60° C. (annealing and elongation step). Fluorescence signal readout follows at each end of the cycle.

Data Analysis

Cycle threshold values (CT) were determined automatically for each marker separately by the Rotor Gene Q Software2.3.1. (dynamic well compensation, adaptive baseline correction for cycles 2-10, Threshold-setting for channel green: 0.058 and for channel yellow: 0.015) by the course of the fluorescent signal readout during the PCR cycle program and including adaptive baseline correction. Data transformation of CT values in percent methylation ratio (PMR) values is facilitated by a modified 2exp$^{\Delta CT}$ method for a duplex probe system, with internal calibration and standardization according to the following formula:

$$PMR(sample\ well):100/(1+2^{exp}(CT_{meth.}-CT_{unmeth.})).$$

$$MV\ PMR(sample\ duplicate):(PMR(sample\ well\ 1)+PMR(sample\ well\ 2))/2$$

Error (absolute): STDEV MV PMR (sample duplicate).
meth.=methylated signal
unmeth.=unmethylated signal
PMR=Percent Methylation Ratio
MV PMR (sample duplicate): Mean value of PMR values calculated for each separate well in the technical assay duplicate of one sample.
CT=Cycle Threshold. PCR cycle number, at which the reporter dye fluorescent signal reaches an assay specific threshold. For further analysis the mean value and STDEV of technical replicates (n=2) was established.
STDEV=Standard deviation of the Mean value PMR for the technical replicates.

Assay performance quality control: The CT value of at least one probe signal of the duplex system had to be <31.5.

Example 4

In addition, PMR value variations (heterogeneity) between consecutive tumour tissue sections were determined and reproducibility of PMR values were assessed in 12 independent qPCR runs.

Therefore, five tissue sections of 5 μm thickness each were obtained from an FFPE-tumor block of a breast cancer patient (TEC3). DNA was extracted from these tissue sections, bisulfite-converted and PMR (%) determined in 12 independent qPCR runs performed in duplicates according to the assay described in Example 3 above (see FIG. 1). An overview of this workflow is provided in FIG. 2.

Results

The mean values of the 24 PMR analyses for each of the 5 tissue sections are shown in FIG. 4.

The mean values and standard deviations of the 12 qPCR runs (design identical to the graph above) as well as the maximum and minimum values (REF50P and REF10P are references in the assay) are given in Table 6 below:

TABLE 6

| Sample | MV all | STDEV all | CV all | Maximum | Minimum |
|---|---|---|---|---|---|
| REF50P | 62.42 | 2.91 | 4.66% | 67.13 | 57.57 |
| REF10P | 9.61 | 1.27 | 13.26% | 11.89 | 7.57 |
| TEC3.1 | 77.86 | 3.54 | 4.55% | 83.98 | 69.97 |
| TEC3.2 | 79.37 | 3.21 | 4.04% | 86.98 | 74.54 |
| TEC3.3 | 76.20 | 4.22 | 5.53% | 83.12 | 69.82 |
| TEC3.4 | 75.25 | 4.65 | 6.18% | 84.35 | 64.95 |
| TEC3.5 | 74.51 | 5.06 | 6.79% | 84.16 | 62.71 |
| MV TEC3.1-5 | 76.64 | 1.98 | 2.58% | | |

The experiment was repeated with 7 other breast cancer FFPE tumor blocks. Regarding the tumor tissue heterogeneity of the gene promoter PITX2 DNA-methylation status, comparable results were obtained as shown above.

Conclusion

Tissue heterogeneity of the gene promoter PITX2 DNA-methylation status (PMR %) is very low as assessed in 5 consecutive sections. Reproducibility is very solid with a coefficient of variation (CV) of 2.58%.

Example 5

In addition, the gene promoter DNA-methylation status of PITX2 was assessed in full-face breast cancer FFPE-tissue sections with either low or high tumor cell content and compared to macro-dissected tissue enriched for tumor cell content from the same FFPE tumor blocks.

Therefore, macrodissections were performed first by inspection of a corresponding hematoxyline and eosine stained section for tumor area with high tumor content by an experienced pathologist, marking of the corresponding tumor area on an unstained and unprocessed FFPE section by optical overlay with a permanent marker, scratching of associated low tumor containing tissue areas with a scalpel blade and transfer of tumor enriched areas as well as low tumor containing areas in separate Eppendorf tubes (corresponding to samples TECXXXT and TECXXXN) and processed according to the same workflow as in Example 3. Full face sections were prepared from whole sections (TECXXXff) by the same workflow as in Example 3 (see FIG. 3). DNA was extracted from these tissue sections, bisulfite-converted and PMR (%) determined according to the assay described in Example 3 above (see FIG. 1).

Results

The mean values of the PMR analyses for macro-dissected tissue areas with high (T) or low (N) tumor cell content as compared to full-face FFPE tumor tissue sections (ff) are shown in FIG. 5.

Conclusion

For macro-dissected breast cancer with high tumor cell content (T) and full-face sections (ff) of the same tumor block similar results were obtained for the PITX2 DNA-methylation status. Macrodissected FFPE tumor sections containing low tumor cell content (N) displayed lower PMR values compared to non-dissected full-face specimens.

Example 6

Further, the PITX2 DNA-methylation status was determined in 21 FFPE core biopsies taken from patients afflicted with triple-negative breast cancer (TNBC) treated with neoadjuvant anthracycline-based chemotherapy and correlated to pathological complete remission data (pCR).

Patient Selection

Only TNBC patients were included in the study, who were estrogen-receptor (ER) and progesterone-receptor (PR) negative with <1% ER/PR-positive tumor cells and with negative HER2 status (immunoreactive score 0 or 1 if FISH HER2 amplification test was negative).

PITX2-Methylation Assay and pCR Correlation DNA extraction from FFPE core biopsy sections, bisulfite conversion and semi-quantitative analysis of the DNA-methylation status in the promoter region of the PITX2 gene was performed in accordance with the PITX2-methylation assay described in Example 3 above (see FIG. 1). The PITX2 DNA methylation status (PMR %) in TNBC FFPE tumor tissue sections was correlated with pathological complete remission (pCR) according to Sinn et al. (see Table 1).

Experimental Outline

Two independent Experiments 1 and 2 were performed and the results correlated with each other.

Experiment 1:

Two independent experimental runs were performed and mean values for both experiments were taken. TNBC patients included pCR 2-4 according to Sinn et al. The raw data and correlation results of the two independent experimental runs of Experiment 1 are given in in Table 7 and FIG. 6.

TABLE 7

| Raw data of Experiment 1 | | | |
|---|---|---|---|
| pCR according to Sinn | Sample 1st run | MV both runs | CV both runs |
| 1 | Tneo15 | 0.01 | 0.00 |
| 1 | Tneo31 | 0.13 | 0.04 |
| 1 | Tneo14 | 0.13 | 0.04 |
| 0-1 | Tneo48 | 0.17 | 0.09 |
| 1 | Tneo42 | 0.20 | 0.03 |
| 1 | Tneo10 | 0.23 | 0.21 |
| 1 | Tneo43 | 1.58 | 1.79 |
| 1 | Tneo49 | 1.91 | 1.35 |
| 4 | Tneo04 | 0.02 | 0.01 |
| 4 | Tneo32 | 0.03 | 0.01 |
| 4 | Tneo18 | 0.04 | 0.02 |
| 4 | Tneo12 | 0.04 | 0.01 |
| 4 | Tneo47 | 0.04 | 0.01 |
| 4 | Tneo03 | 0.06 | 0.02 |
| 2 | Tneo28 | 0.13 | 0.14 |
| 4 | Tneo11 | 0.30 | 0.23 |
| 4 | Tneo40 | 2.67 | 1.73 |
| 3 | Tneo19 | 4.10 | 0.54 |
| 4 | Tneo22 | 6.04 | 0.78 |
| 2 | Tneo34 | 25.37 | 5.08 |

Results

PMR (%) mean values of TNBC FFPE tumor tissues samples for patients with no response (Sinn 0-1) were 0.54%, patients with pCR (Sinn 2-4) had a mean value of 3.24%, i.e. a 6-fold increase of PMR (%).

Applying a cut-off value of 2% PMR leaves 8 out of 8 patient tumor samples with no identification of therapy response (Sinn 0-1).

Applying the same cut-off value of 2% PMR, 4 out of 12 patient tumor samples with pCR (Sinn 2-4) had PMRs above 2%.

If PITX2 is methylated >2% PMR, 4 out of 4 PITX2-methylated samples were pCR (Sinn 2-4) corresponding to a positive predictive value* of 100%.

If the PITX2-DNA is methylated <2% PMR, 8 out of 16 tumor samples were defined no-responders, corresponding to a negative-predictive*value of 50%.

Positive predictive value is referring to the number of correctly predicted responders divided by the total number of patients with a positive biomarker result, whereas negative predictive value is referring to the number of correctly predicted non-responders divided by the total number of patients with a negative biomarker result.

Correlation of Experimental Results

Further, the results of the two independent qPCR runs (using independent bisulfite conversion batches) from Experiment 1 were correlated with each other as demonstrated in FIG. 7. A high statistical correlation for the two independent qPCR runs was obtained with a correlation coefficient of R=0.983, proving that sufficient DNA is extracted from breast cancer FFPE core biopsies to obtain reproducible PITX2 PMR values.

Experiment 2:

A single experimental run was performed, wherein TNBC patients showing 3 and 4 according to Sinn et al. were included in the analysis. The raw data from Experiment 2 is given in Table 8 and the correlation results of PITX2 DNA-methylation status and pathological complete remission (pCR) are given in Table 9 below:

TABLE 8

Raw data of Experiment 2

| pCR according to Sinn | Sample 1st run | PMR duplicate | STDEV duplicate |
|---|---|---|---|
| 1 | Tneo15 | 0.01 | 0.00 |
| 1 | Tneo23 | 0.02 | 0.00 |
| 1 | Tneo10 | 0.08 | 0.01 |
| 1 | Tneo31 | 0.16 | 0.01 |
| 1 | Tneo14 | 0.16 | 0.04 |
| 1 | Tneo42 | 0.22 | 0.01 |
| 0-1 | Tneo48 | 0.23 | 0.24 |
| 1 | Tneo43 | 0.31 | 0.29 |
| 1 | Tneo49 | 0.96 | 0.96 |
| 1 | Tneo24 | 12.95 | 0.88 |
| 4 | Tneo32 | 0.03 | 0.00 |
| 4 | Tneo04 | 0.03 | 0.00 |

TABLE 8-continued

Raw data of Experiment 2

| pCR according to Sinn | Sample 1st run | PMR duplicate | STDEV duplicate |
|---|---|---|---|
| 4 | Tneo12 | 0.03 | 0.00 |
| 4 | Tneo47 | 0.05 | 0.00 |
| 4 | Tneo18 | 0.05 | 0.01 |
| 4 | Tneo03 | 0.08 | 0.01 |
| 4 | Tneo11 | 0.46 | 0.18 |
| 4 | Tneo40 | 1.45 | 0.01 |
| 4 | Tneo25 | 2.15 | 0.50 |
| 3 | Tneo19 | 4.48 | 1.87 |
| 4 | Tneo22 | 6.59 | 1.11 |

TABLE 9

Correlation results of Experiment 2

| | pCR 0-1 | pCR 3-4 |
|---|---|---|
| Sample number | 10 | 11 |
| <PMR 1% | 9 | 7 |
| ≥PMR 1% | 1 | 4 |

Results

Applying a cut-off value of 1% PMR, 9 out of 16 patient tumor samples are with no response (Sinn 0-1), with PMRs <1%.

Applying the same cut-off value of 1% PMR, 4 out of 5 patient tumor samples with pCR (Sinn 3-4) showed PMRs >1%.

If PITX2-DNA is methylated >1% PMR, 4 out of 5 PITX2 DNA-methylated samples were pCR Sinn 3-4, corresponding to a positive predictive value* of 80%.

If PITX2-DNA is methylated <1% PMR, 9 out of 16 tumor samples were no-responders, corresponding to a negative predictive* value of 56%.

Positive predictive value is referring to the number of correctly predicted responders divided by the total number of patients with a positive biomarker result, whereas negative predictive value is referring to the number of correctly predicted non-responders divided by the total number of patients with a negative biomarker result.

CONCLUSIONS

In the above experiments a cut-off value of 2% PMR was determined for patients whose tumor had responded to neoadjuvant anthracycline-based chemotherapy according to Sinn 2 to 4 (Experiment 1), and a cut-off value of 1% PMR was determined for responses according to Sinn 3 and 4 (Experiment 2).

The invention claimed is:

1. A method of treating a human subject afflicted with triple-negative breast cancer (TNBC) comprising the steps:

a) providing a breast cancer tissue sample from the subject;

b) determining the methylation state of CpG dinucleotides within a genomic sequence of the homeodomain transcription factor 2 (PITX2) gene, wherein said CpG dinucleotides are the CpG dinucleotides that are in the nucleotide range of 10952-10967 of SEQ ID NO: 1, within said breast cancer tissue sample;

c) selecting a treatment regimen for the subject selected from the group consisting of:

(i) in the absence of PITX2 hypomethylation of said CpG dinucleotides treating the subject with an anthracycline-based neoadjuvant TNBC chemotherapy treatment; and (ii) in the presence of PITX2 hypomethylation of said CpG dinucleotides treating the subject with a non-anthracycline-based TNBC therapy treatment; and d) treating the human subject with the selected treatment regimen of step c).

2. The method according to claim 1, wherein in step b) said methylation state is determined by analysis of genomic DNA isolated from the breast cancer tissue sample.

3. The method according to claim 2, wherein determining the methylation state comprises converting, in said genomic DNA, or a fragment thereof, cytosine unmethylated in the 5-position to uracil.

4. The method according to claim 3, comprising contacting the genomic DNA isolated from the breast cancer tissue sample with at least one reagent, or a series of reagents that distinguishes between methylated and non-methylated CpG dinucleotides.

5. The method according to claim 1, wherein the hypomethylation is a degree of methylation of the genomic sequence of up to 95%, up to 90%, up to 80%, up to 70%, up to 60%, up to 50%, up to 40%, up to 30%, up to 20%, or up to 10% lower than a degree of methylation of a control.

6. The method according to claim 1, wherein the hypomethylation is a percent methylation ratio (PMR) of the genomic sequence of less than 5% PMR, less than 4% PMR, less than 3% PMR, less than 2% PMR, or less than 1% PMR.

7. The method according to claim 1, wherein the absence of PITX2 hypomethylation comprises the subject exhibiting a percent methylation ratio (PMR) value of >1% PMR, or a percent methylation ratio (PMR) value of >2% PMR.

8. A method for treating a human subject afflicted with triple-negative breast cancer (TNBC) comprising:

a) isolating genomic DNA comprising the PITX2 gene from a breast cancer tissue sample of the subject;

b) converting in the PITX2 gene of said genomic DNA, or a fragment thereof, cytosine unmethylated in the 5-position to uracil;

c) amplifying in said converted genomic DNA a fragment of the PITX2 gene comprising the region corresponding to SEQ ID NO: 17 d) determining, in the amplified fragment, the methylation state of CpG dinucleotides the PITX2 gene, wherein said CpG dinucleotides are the CpG dinucleotides that are in the nucleotide range of 10952-10967 of SEQ ID NO: 1;

e) selecting a treatment regimen for the subject selected from the group consisting of:

(i) in the absence of PITX2 hypomethylation of said CpG dinucleotides treating the subject with an anthracycline-based neoadjuvant TNBC chemotherapy treatment; and (ii) in the presence of PITX2 hypomethylation of said CpG dinucleotides treating the subject with a non-anthracycline-based TNBC therapy treatment; and d) treating the human subject with the selected treatment regimen of step c).

9. The method according to claim 8, wherein the PITX2 hypomethylation is a degree of methylation of up to 95%, up to 90%, up to 80%, up to 70%, up to 60%, up to 50%, up to 40%, up to 30%, up to 20%, or up to 10% lower than a degree of methylation of a control.

10. The method according to claim 8, wherein the PITX2 hypomethylation is a percent methylation ratio (PMR) of less than 5% PMR, less than 4% PMR, less than 3% PMR, less than 2% PMR, or less than 1% PMR.

11. The method according to claim 8, wherein the absence of PITX2 hypomethylation comprises the subject exhibiting a percent methylation ratio (PMR) value of >1% PMR, or a percent methylation ratio (PMR) value of >2% PMR.

12. The method according to claim 1, wherein the breast cancer tissue sample is provided in a state selected from the group consisting of natural, frozen, lyophilized, preserved, embedded, paraffin embedded, and all possible combinations thereof.

* * * * *

SEQUENCE LISTING

```
<160> NUMBER OF SEQ ID NOS: 71

<210> SEQ ID NO 1
<211> LENGTH: 32001
<212> TYPE: DNA
<213> ORGANISM: Homo sapiens

<400> SEQUENCE: 1

catggactgc gtgatcacta aacttggcac ttcagggggc atatcttttt tgagtaactc     60
```

-continued

```
tcataaacat gcctgcctgc aggacatcca gattttctgg tttggtagta aagcaacata    120
agaataatct tgaacctgat gttcatcctt gccttctttc taattccagg agccctctga    180
ggtctggact aactcactga ttaggaaata gtatttggaa aggctaaaca aaatactatt    240
tccagggaaa tagtatttgg aaaggctaaa caaaatatac tttcttagtt ttctcaaacc    300
tctcagaaga tatatttttt aaaaaataaa ctaagctagc aacatttaaa ctaaatcttt    360
gccttgctta caatacaaaa gatgataaaa aaattgttgg gaaggtgaga aattaacttc    420
acctataatt agaagtaaag ttttcattta aaaatgtaat accacttaaa ttcaatttgg    480
gaaacaaaaa ggactcaaaa aacagtctgc taaagccaat ttgcaaacaa gtgcgctctc    540
tttttcttta agttgtatct caggttcaga gcacatgtgc aggtttgtta tgtaggtaaa    600
cctgtcacag ggatttgttg tacagattat tttgtcaccc aggtactaag cctcgtaccc    660
aatagttatt ttttctgatc ctctcccctc tcccatccgc caccttccaa taggccccag    720
tgtctgttgt tcctctcttt gtatctatga gttctcctca tttagctccc acttataagt    780
gagaacatgc gttatttggt ttctggtcc tgatttagtt tgctaaggat aatggcctcc     840
agctccatcc atatttctgc aaaaggcatg atctcattct ttttttaact attccactct    900
ctctattact ctttcttctt cccccaatcc tgaaccctac catgtcagtt taaccactcc    960
ttttctttcc tttttctttg ctcatttgca catagttaaa agatgccatg aatttttctt   1020
tttaattcag catatgccca ttaaagatct aaaaatatta tttacatcat ccagaactca   1080
gcttaagaaa ttaccaaaaa ataaagctac cagaaagtaa ctgaatcatc ttgttgagcc   1140
acaatcctag acctcgactc tgctttttcc tcattttagg caggtcattc cttttccttt   1200
cttaaattgt tttctctgta ttcaataaca cattcttgtg gattcagaaa gggtggagta   1260
tgaggaaaag gaatatgata tatgtaccct agaggaaaac aataaataaa tatttcagga   1320
tggaaaacat tatttttatt tttattgagt tttctagagt ctatttgatt tgtgtaaatc   1380
agaaaccagt agaatgacat taatgaatta atgaaaagca gaatgagtta tcagttgtaa   1440
caaaaagaat aaagaatttc aagaacacag ctttaatcat gcatggctgc ggggagagaa   1500
aaataacaaa atgctctcag tgaatacatc tctgagagaa gaaaggaaat acttaaggag   1560
aggataaaaa gagcaaatat caaaaatagg agtaagaacc ctattgcttt ttttagttga   1620
caaataaaaa ttgtatatat ttactgtgga caacatgata ttttgaggat tacgatcact   1680
tttgattcat aaattacatt caagaaaaag aaattctcaa aaagtttggg aacatatgaa   1740
gttgaaagaa cattaatact cagataagga cagtacatga caaattattc ttgctccaac   1800
attttctctc aggaaattta aacatctttc agtgaagcac cagtttcttg aaatcaagca   1860
tgagaaaaaa aactaaattc acctgtggaa aaaaagacac agctaaacaa aaaagcggtt   1920
gttataacct caagagtggc atgaacaaaa tgatcaacat tctcccaagt gacagcacaa   1980
atatcaaaag tcctaataag tggaagtggt cctgtcatga caaaaggtgt ggtatttgta   2040
caatttccag ataagaacaa agtcatgacg ctaagacagt agcagcactg tttgttacac   2100
gtgatatttg aaaaatatga caaccatctc aatctgctca agtagcactc atggtgaggg   2160
tgaaatttta tcaacattgg ttaacttatg gtgttttaaa aaactagcaa ggagataaat   2220
tgatggatta aaagataaac tactcacagg cagacaaaca gaaggacaga tagagttaca   2280
atcaaacatg tactttactc aggcagaaag ataataacca gcccccaaga agtgatgtgt   2340
ctgctagaaa agccctgaac atagaatttc ctgactttgt ttttaattta gttctttcag   2400
gcatcacgct gcataaccag gtgtaactct ctaaaagtct ctatgacaga attttccatc   2460
```

```
tgttaaatta ggctaataat attttcatct ttttttaggg taaagatgtg aaatatttgg   2520
agaactctgg aaaacatgcc ccctactaat tagagctttt tgatgtgaca tcattttctt   2580
cagtacttgg agtttagtca atagatatac agtgtagctg tgaaattatg aagcatgaga   2640
atgcattacc aagggaccgt aggaggctct ttactgaaaa gtgtagctgg ctatatttct   2700
ggaagtaatt taaacatagg ctgagggaga ggagtaccct ctagatcctt tccagacctt   2760
actttctatg aattctaatt tctctttccc atttagaaaa aacaatgaga tccacagcgt   2820
agagatagaa aataaggctc tgtgtgccct caaaccttac tttcaaaaat accacagcat   2880
tctggacgag atagtcttga attcttgcaa cagcacaggt atgagagttt ttaccagaaa   2940
acaggagact ggattgattc tttcattctc ctcctatgct tcctaaaact gaaaagccat   3000
atatacaaat tatatttatc tatccctcct ggaaaaggcc aaaatgaatc caattttgga   3060
tcattttcaa taatgggaca aacctgaatt gagaataacc tttagaatca gtcctgtctt   3120
tttgtgataa aatggacttg tagaaagcta cctggtgttc tcccctagct aacattctac   3180
cacaaacaac gggtatgtaa tccagtattg ctccccacag gctatgtcct tggaatcact   3240
atctttgcac tccatttgtc tgctgacatc cttccaccca agatgtcttc ttcagcacaa   3300
gaagtcattt ctcttaaaat ttcaaatgac tttactacaa taatagagtt gctaactaga   3360
cctaggcaag taatgataat aaaaatctga tttctactta gagtgtagca tggtttaaca   3420
caacaaccag agtcctaaca ggtttttcta gatttcactc ctactcaact tgcatgttct   3480
tgcaatatag atgttcttat tactcggtcc ttacttccat ctctctttgc ttctggaata   3540
aaactactta aacccaattc agagatttta ttctcccttg gaattactgg gaaacagttc   3600
tagtaaacca tattcctgag atcctatatt aggcttagtc caaactgacc atctaagcat   3660
taattttcct gtggctcagg aatatccctg agcttacctt tctcttccta aactgcccag   3720
gacaaatacc ggagtttggc ttttctgctt tctcatccaa tcatttctcg tttcctcctc   3780
tttagcattt aaaacatttc tgactttctc catccctcaa gaaatatatt tgctttcctg   3840
tctctgcatt attcttttgt ttatgaaata ttccataggt aagttctata tttccttccc   3900
ccagaggccc ctggtcttct ggttccagtt gccattggtt cagtgtacta gttaacattt   3960
tggactttgg agttacacaa acctagattc aaattcccac tatgccactt actgcctacg   4020
tgacctgaag caatatccta tccactgtgg cctccagcag ttataagctt gtgctctaac   4080
cagctgggtg accttgggcc agtgacacaa tcatggcaaa cctcactgtc ttcatttgta   4140
aaatgacagt acctaccttg tagtgttggc ataaggaata agtgtgattg tcaatacaaa   4200
agtgtttagt acaatagcta aattaactaa gcactctgta aatattagtt tttaccatta   4260
ttactaattc aaatgactag atgcattttg tgtataccag gtttcctgag ttcactttgt   4320
tctcaacaaa tactattatt cctagcatgt ggcctatatc acacttcatt agccagagga   4380
catgtgaagc ttagagtgga aagctagggc agcaggaagc attgccacac tttacacagt   4440
caaagccatt taaacatgtc tgaatttgag ctctgctgag tccttacttg cccccatctc   4500
tcctgtgtgc tccagcttac taataaagca ggtttaatat aaatacacta aaagcctaaa   4560
cattgagatc atgataatga atatgagggc tatgactata aaatatcatt gaaccagaga   4620
cctgctacga aaccacatgg tgaagaccac aagggaggaa tctgcataca caccgagtgc   4680
cttgggatcc caaagtggga agagtcagtg ccccaattaa agagaaactc ggggtaggga   4740
atcaaccaca acatcagtca ccttactgaa cccaggcttg tttcagctga cgtagctgcc   4800
```

-continued

```
aatttccaat gtcccctccc tccctaattg ctctcaatct attcctccag aaactgaaag   4860
cccatcaaag aggatatctt cccagagagt tgttccagtt actacaagct cttgctagaa   4920
attccaagaa agtttacaag gtacctttat aaggtggcat tgagtaagtc agaagcattc   4980
caagtaccaa ttatcatgca aataagggct ttacttttag attttgttgt ttgtggtggt   5040
ggtgatgctg gtgttctctc tggaatccag cccaatctcc aaaaaagtaa aaggagtaca   5100
aatagtaata caaattatta ttacttacac caattaaaat agaagttttg aatgagcaag   5160
gagctagagg aggtaaaaac tgggaacttc gtatattaaa aggtttttat aatttgaaaa   5220
ctaagattat gctggccaaa taggctgttt taaaatcagc atagtaatca aatttgcttg   5280
taatgaatgt agacccaaac agtgatgtca gacctgataa ggacttgcaa accctaaaag   5340
agtgcaaaaa gaccatagaa gaacaatatt atattcctgc acttacagaa atggtcagct   5400
caagagatgt atccagttca gggtggctgt aagcttcatt ttctgaactt gctaccagaa   5460
gttaaaagaa attctgtata actgcttttg atggaaacac aaattggttg atgtaaatga   5520
aatacataaa gcagttggtg tcttattcat tcccacaatt ataaatgaaa ttaaatgatc   5580
aaaaattata gactttgggg atcttctttt cactgaggag cccatggaat ttgtcttctc   5640
tagtaccaat aactgtgttg acctattttt tcctgtctaa ctctgtatat attaaaacta   5700
ggtggttacg aacaaaaccc agaaatacaa tttacattct aataaaatga ctttaaaatt   5760
attccacttt ttactgtggc tttacctgtt gtcccacaat gcaggtttct ctgggcctct   5820
gcttagaatg actctgtcaa tgtagatgac agccagagtt gaatggggaa tccagaaact   5880
ggggattcgg gctcttgatg caatctatat gccaatctac ttcattagtt cttcttttat   5940
ttacagtttg gtaaagaata tgggtggagc tgttctgggc tcacttgcac acatgtccaa   6000
actgctttga aaaaggaagg gcaagaaaga gtggtatcca agttggaatc aggcaggcat   6060
ttcagatcaa gagacgaact ggaaagggaa catctgttag ataccctggg tttgaaggca   6120
gtctgtgtaa gttttcatat ctctgagtgt gtgcacacag tggagagggt ggagcctgcc   6180
atcctcaaat ctgaaaagat tgagagattt cagagggccc agatgtgcca aaggtcagag   6240
ggatcaatat acaggcccta ccacggaaag gcggggaaaa ggttcgaata gaaaactgct   6300
gcagaaggga agccactgag aggtaaggga gtttctgaat aattaaaaag ttaagaataa   6360
gcaaaaggaa ggaggtcggg tgggggataa aaaaaagcag ttgatgtggt aattaagaat   6420
ttggtgggag cctgggcagg tcacctcctt tctcagatca gagccccatc agaaattctt   6480
tcaagtgtcc ttctgcgtcg ccaaagatga caacagcaaa tcaataagtg cttgaaatga   6540
aaggggatgt tgactagccc ccaggctaca gatttcccgc cgccagcctt ttctgaactc   6600
ctatagcgtg cctttgcacc gcctctctta agaagagcta ccttttattc ctattctcag   6660
gacgaaggta agtgctcagt tagcatatct attaaatgtc agctttggtt ccagctctcc   6720
gtttgcgcgg aaagctcact gccatagcgc gcccagcctg ccggaggggc agacagaaaa   6780
agcaagcttg gcctggcgac ttgcggggcc acgcacctcc agggctggcc cggagtcttc   6840
cagagtttaa cgctcctggg ttagaactgt aaggtcccgg tccgagcaaa gggcctgagc   6900
caccgtagcc gtgggagcgt tccttccact tgaatgcact cactcacaaa caagcacaaa   6960
atctttttaa cagcagagga gaaagacccc tgctccaaaa ttaaagctgg gaatcaccgg   7020
aaactccgtt ttgagtgcga gatattggtc tgttaccttt ctaatcttca tatccctcct   7080
gtaatatgtc ttgatttaac aatctttcca gcgcccagca ttgcccggac gttttaattg   7140
ggtaattcat tagtgagtca atacaggcat ttatatattc ttttagctca agtggttaag   7200
```

```
tactaatttc gaaatgatta taaaacaccg gaatcggcaa cgcatagtaa ttttaattta   7260
tatgcaaatc aattggttca tcttaaatgc cttttttaaa aaaacaatta ttgtattgta   7320
gcatcggagg catggatcaa acctctagaa tagacaattc ggaaacaaga cctggactag   7380
gaagacaatt tagaacagcc aacaaatcaa taatgtttga ggcagttaaa catcgctagc   7440
cattggtatt tacatactcg cttgttgtca gataaggagc tggggaaatt gcttgccagg   7500
gttgagatca taatccagag tgaagaaagt aaatggtagc acacagcccg tcacagcggg   7560
ctctgaaata atactgtacc tttcccaaat cctgactctt gggtgacagg gagttggcgg   7620
aggtcacccc acatttgtcc acggttttgc cccaatttga tcacgaaatt gttgttctcc   7680
ctgagctttc caatttgatt accattctaa cggttctgtc acttgtctca acatattggg   7740
gggaggagtg taattgagat tctcattaaa aattatctga acccacttag ccagcactgt   7800
ttcatctaag cttagtttta tgggctgtat ttaattccct gtgcccccca cacattaaaa   7860
tcagatcatc aaaatgtcgg taggaaaggg tgaaggaaat ggtccaatgc tccagtttac   7920
tggaagacta ttatctttag acatagttca aaattttgag gaaataaaaa ggatatacgc   7980
tttgggggga aaatgtttta atattctaga atgggggtat tactcccccc attccagaga   8040
atccgcactg gagttgttta tgtaaaaatg taacatcctt gaaattcaca gatacgtaag   8100
gttagtgtct ccccttcccc aggctcccag tccaggcgat ctagccctaa aggagctagt   8160
acctttgatg ctacaatctt gtttacatct gcagggcaga gaattgcttg ctttgcttgg   8220
acgctccctc caccccttc taatttgaag taatcggaat ctaaatacag tcgccaaggc   8280
ccgctcttcc tttactgctt tgacaaggga aaaacctgaa atccacgtct taaatcagct   8340
cggtggtttg tagcccccca gcaccctgct tctacgattg catgcctaat gtattccctg   8400
gtgattctgg gcattaatta gttgtttaat aggagtatga ctaaaaatgt aaaagaagga   8460
ttaggagcgt gaaacgtatg tccagctcct tccacacact cgaggaggga atgagaatca   8520
ttctgtatct tctatttctc caggagccat ttgcatttcc caccagctgc tcacttcagc   8580
tgcactggcg ctgggcaagg cgaggaccca aaagctcagc gcagtgtctg cggcggccgg   8640
gactggggtt aaccagcctc tggcgggcga gactccagac agaagggggg cgagaggaac   8700
gtgagcttcc cgagcccctt cctctcagcc ctggtttgca aacctctgaa acctgaaagg   8760
ggagggagtt gcacgcgcgt atctttgcgt cttttcagcg caactccctt ccctctccct   8820
gtgtctctcc gcggatctct gaatctttct gtctttggtt ttctcattct cttccaactt   8880
ttccatgaga ttgcctatcc tcgccaccag ctgaaggcaa ggccgttctg ctacgagcgc   8940
ctcttaatct ctacaaaatg aaaagaaaaa aagggaggat tattagccca ttactcagag   9000
gaatggggag gctgcaaaaa tcgtcgatgg gcagaggtga agatgtcttt ctcggactgc   9060
actttccggt gtcctgtaac tagagttcag ttgtgggact tgttgaagaa atttgatttt   9120
cttgcctcgg cgagatttca aaaaccagaa atagaaattc tcagagtcag agaggaaata   9180
caattaaaca gcacgtgggc attttccccc tcatttctct ccccttaaat aacactgctt   9240
tgagtttcca ctgggtaaag agagaaagtt tgagttttca cggatgttac gtggaggtta   9300
gaaatggctt aaaatgtaga tctctaatca gttttcttcg tggctgaaga ggctaaccct   9360
ttccataaaa tgagtccatc tgtcgactgt tagctatttc aaagtgaagg gatttagcac   9420
tcaaaacaaa ttgagcaagt ttgtttgcct gtttttactg ctaactcaaa tgaattcaaa   9480
acacggagta attcaagaaa acacataaca tgttccagac agcccccaaa agtagggaaa   9540
```

-continued

```
gcccagcacc tatatagtga ctagggttag ttttaagcgc caagcttttt taaacgtatc   9600
tattttatgc acattctccc gagtcactat atatttctaa aattgcgagt attggtatat   9660
tgatttagga agagcaatac aacttttaga gggaacttta ttctcaatta gggaccaaag   9720
agatgtcttt ttaatagcgg gcctgagttt tgctctcaag caggaattaa tattggtggg   9780
aaaatccgaa tccaggagca atggctgtgt tccggcactt tccaaaaaca tacattaaca   9840
ggatgccctt gagattgaaa aaacattgtc ccatatgcct ggcagaagcc ttcacacctg   9900
gtcctccagg cgaattatat ttatagtcct tccactcaga ggcaggacag agccaaaata   9960
ttctgctcac taccaaaata cacatctttg ctcaagtcaa gaaatcagaa aatcagggtt  10020
cagaagtaag gcacactttt cgagtgagaa tatgccctgt aatttcacat actctttgct  10080
ttgcaggagc aaatgtggac ttgagggaaa ctctctcccc cacccccact tctatcccgt  10140
gcaatttaat accatcctcg ccaggaacct taacctcgtc attttaaaaa atgagatatc  10200
cgtgacccag ggtgaacttg ttgaatgtag gtacagcaga ggaaattcta gactctatga  10260
gcgtctgagc cttgtccagt gcaaaccctt cgtgaacact gggtcagtgc gtggccgtgc  10320
ccacctgtgc gccgacactc tcagcatgcc tggtccaccc gccttgacct cgggcgcggt  10380
gtcccagcta agctgggccc agcgtcccgg ccttccccag ctgacaagcc tagctcgttc  10440
gctcccggct gtggccctcc caccctctcc cactagctca ctccattctt ctagatttct  10500
cttcactcat cctctcccat ccccaccgcg cccacctcca ctcccgccct ctaccggtct  10560
ctcactttcc tccctccgca gtccctcttt gctgtgacct ctttcctcaa ctctgcaggc  10620
ctgaaagaag gtcacacacg cacgctcaca cccacactcc acacgcctcg tcccaaacaa  10680
ccccatgaac attgtccttt gttccgtctc ttgggccact ttccctgtcg cttcctccca  10740
gcccgtcctg atttgctccc caaaagtacg tttctgtctc cccgctgccc tggcgctccc  10800
cctttgattt attagggctg ccgggttggc gcagattgct ttttcttctc ttccatccca  10860
tcctcccttc tggtcctcct ttccacagtg ggagtccgtg ctcctgctcc tcggttggct  10920
cctaagtgcc ccgccaggtc ccctctcctt tcgctctccc ggctccggct cccgactctt  10980
cggcccgctg gcatctgctt ccctcccctg cctcgtttct cgtcgcccct gctcgctccc  11040
cccggcgctc gcccgggcgc tgtgctcgct cctggatcgc cagccgcgca gccgggctcg  11100
gccggccgcc cgcgcgccac tgtgcagtgg agtttggtgg aatctctgct gacgtcacgt  11160
cactccccac acggagtagg agcagaggga agagagaggg atgagaggga gggagaggag  11220
agagagtgcg agaccgagcg agaaagctgg agaggagcag aaagaaactg ccagtggcgg  11280
ctagatttcg gaggccccag tgcacccgtg gactccttcg gaacttggca ccctcaggag  11340
ccctgcagtc ctctcaggcc cggctttcgg gcgcttgccg tgcagccgga ggctcggctc  11400
gctggaaatc gccccgggaa gcagtgggac gcggagacag cagctctctc ccggtagccg  11460
gtaagtggag gccatctatc ccgcagggat gtgagataat gcgagtctgg aaatttgttc  11520
cacttcggag aatcttcacc gtaggtgatt tgtggctttt ggggctaagt ttcgcccaag  11580
gtaacgcagt cggcaaacag accttgcaaa gccctgttcc tttcgtcccc cgccacagac  11640
actaacaatc tacagggtgc tgaagtcgag agggaagcca gaccgtggct ggcatttaaa  11700
acgaggtatc ttcccttaaa tctcggtgcc aacactgcag gaacaaatcc tcgggccaag  11760
gattagcatt ctcaagataa agggctgggt acaaagtttc agctactgga agattagccc  11820
ccttcccatt gttatccatt gggaaaaaaa agaaaagaaa aagattccat cttaactggc  11880
agttagtgac ctctcaggcc caagcgaatt acctgggagc caggcctgga tgccaagctc  11940
```

-continued

```
tcaccatttc tttggattgt aactccttta aattgatcac cagtcaactc caatctggca  12000
cttcaggaga tacactttaa atggatgcag agaattattt tccagctgga gattaagaaa  12060
aaaattttcg attctaaacc tccgaaatat gttcctcttt tccagtttaa ccactttact  12120
ttcttaagca atttagaaat caaactatca taaggtggtg tgattttttt ttactctttt  12180
gtgtgagtat tgtcttacta aactaaacgg aaaaaacttt taccattata aatgtaaata  12240
tcagaattca tacattctaa aatattttta tgaaaaatta atctgattta aagaaatttc  12300
cttgcatttg ttttagtcta tcaatcaaaa ctaaagatgc ttttatcaca caaaatatca  12360
ttttggcaga aatccatcta aaattcaaat accaataata tcaagaaaac aaagcacata  12420
agcaaaataa attgaagatt tttgttgatg taacatgagc atacaacatt tcaataacca  12480
aactttccct aaaaaattaa atagccactt catttgtgga atgttttact ttaactcagc  12540
aaaattacac ttaaattatt taggtgcttt gttccttaag ttaagcgtgt ttgtcttcaa  12600
atgttcctaa agcacttata ttaattggtt gtaaagaacg catacacatg gtaaaataca  12660
gaactgaact gagcagtatt ttaatttcct taaataatta cttactacaa attaatttac  12720
tggctaattt cacaatttag ttcatttaaa acacatgttc ctgtgctgtt tatttttaaa  12780
ctttccatta aagattttgt tatggggtaa caaagtgtat gaaaaggggg gaaatgtgaa  12840
aggatctggg attattcgaa ctgtattttt cctgcacttt cagtcttgcg gtagtcatca  12900
gaaattattt tttagcaaat tgttttattt cttagggctt gcctgcctgc tttgccatgg  12960
ttcctcgtcc tccgttagcc gtgtagtgct ttttgtgtgc tcacaatata aaacccaagt  13020
tggccaaaac aagagtcctt ggcatataca ttccaactag aacatgaact ttgggggtga  13080
gaactacctc ccatcaggaa aagtctccca tctcaatttg tgagattagc cattgaagcc  13140
agttccgaag tctggcagcc aaatttctca cagaagactt gtcttgatag ggcaagttta  13200
aggatcagca ggcgggaatt ggaggtctct ttttaaaaaa ttatcttccc cagttattta  13260
gactcagttc ttctagtagg cctggtcatt aaatgaagca taaaaatgca agtctcaagg  13320
ctcattttga ctgcaaaata aatctccaag tcacaaggac atgtaggagt gagctaagga  13380
acacgccttg accttctttt cagtccttag agtggagctc tatgagttct tgaagatttg  13440
ttttgtattg ctttgtttgg tcttcagcac tgaagcacgg ggaagtgggg ggaagaatgt  13500
gtaataattg actgacttta caccaagcaa cgcaatcttt ttcttttgta tatttcattc  13560
tttaaaaaaa ataaataaat aaaaactatt tgcagttacc atctgcagtg ctccggctac  13620
cagctaataa tgcagccagt tcagacatat aaaaaaaaaa gattatcgaa atgatgatga  13680
catgcaaatt tcctccgaaa ttatcataag taaacatttg aagtctggac taataaaatc  13740
ccatctgtgt tacttcatat cgagttagta gaaagctgtg ataatgaatt ttgtaatatc  13800
tcacgaacag acatctcaat cagggactaa tcctgtgatt ttactgcaga atcactaaat  13860
ctggagccgc caaactgcta cttctgggcc cacgggccca caaggatcga atcggcagag  13920
tccccgcccg cgttctcgct agcgggtggg ggaaccgcct ggccgtcccc accctggatc  13980
cccacgccac agcgccgggc agcccctcct gtaggcagcg accttggcca gaggctcccc  14040
agggcccagc tcccttcagg agaggccgag acgcagggaa acggtactca ggccagaggc  14100
aggcccgcag ctccctgccc cgcctctgtg cctccgccaa cccgacaacg cttgctccca  14160
ccccgatccc cgcacccgcg cgaagtgggc cctccggtcg tcggcgtacc ctggttagcg  14220
tggagagagg caggcgctga gatcgaaggg gcctagggag ccctggacct tcttttcttg  14280
```

-continued tctttaaagc aaccgcggct cttctaccca cccggtggag cccctcgaga cccacctctc 14340
ccggcttgcc tgtggcagag aagggggagc gcgttaaatg cttggctcgc tgcgttgtgg 14400
ttgaaaacgt gaaaaagatt tggctcgccc gggagagaaa gggggagaac tgggtagcag 14460
ttataccaga gctatttctc cgtccttggc gggcagtaaa ccctccaaga acgtttgccc 14520
tgctctcctc agtctcgctc agtccaccca gtgtctctcc tctgcgatct taaatcatac 14580
tttagggtaa ttatttgtag taagtaaata aatggccggg ttagtatctc taggagaaag 14640
tgtggctaaa tatggaaaag tggctcctga tggatgagag gcccgaactc agctcgctcc 14700
tgaaacaccc taggccaaga gcccgttcgt ttcagaatta cagaaaaccg agggaaactg 14760
ctgtctagga caggggcacg ttggcgctga tgttctacaa atgtttaccg agctccaact 14820
aatggacaag cactgaaggg tggtctttgc atacagcttc ccaaagagaa aagtcctctc 14880
cacccaccca ctcccgctgc cattgcgttc agatgagttc ttaaccccgg caccgagatt 14940
cttgaaagta ggtccacagc ctccccagca cactgtggct ttatagtcct ctaacctctg 15000
ggcacttttg cggcaactct ggagggagat cccctcttga taaataaatg tcctgggccc 15060
gaggctaggc tggagatgct gctgcacagc cagaggctgt caggtcggaa aaacacgcct 15120
gaagcctagc acacagtagg cgcctaacag ctagtgtaac gtagtctcat ctgagccctg 15180
ctcactcgac ggccgccgct tcttacagcc ttccttctct tctgttttgc agataacggg 15240
gaatggagac caactgccgc aaactggtgt cggcgtgtgt gcaattaggt aagaaccccc 15300
ttctcctgcc cgggtcatcg gacgggaggc cgcgccacgt gagggcggca agagggcact 15360
ggccctgcgg cgaggcccca gcgaggggcg cttccccgag gggccagcct gggcaggaag 15420
gaaatcagaa ccaaatcgcc agtggcctct ccctgtggcg gggcggtgga ctaggaagca 15480
gcggcgcgct gtgtaccgaa gccccccagc ctactcctcc cggctggaac cgccggcaac 15540
cggggaggcg cagaaagagt acgccatcct gccccgggtt gccagagggt ccgggggacg 15600
gggatgccgt cagctctttc ctctaactgg gtctttgctc tttgtccctc tttctcctcc 15660
ggcctgcctc gcccctcccc ctcctcccgt ccccggctcc tttcggccgc ggtccgggac 15720
gcctctctcc gcacgtgggg cgggcgcgcg cgtggcccag gcgtgcagcc ggcggccgtt 15780
gaatgtctct tctccaaaga ctccgaaatc aaaaaggtcg agttcacgga ctctcctgag 15840
agccgaaaag aggcagccag cagcaagttc ttcccgcggc agcatcctgg cgccaatggt 15900
aaggccggga gggaagcgca ggccgcgcgc tgggcacccg cctccgggac tctgggcctc 15960
gggcgaagcg caagaaggcg aggccgccag acctgacgcg cctgctgctt gaacttagac 16020
actccgcctc tgggtgggac gggaagcagc cgtcccaggg acgttaattc ctttccccaa 16080
attatactgc actcctgaga cccaacacct ctctctccct ctcgctcgct ccctgtggtc 16140
tgatcccctg cgcacgctcc agcaaacctc ggcgtctagg ctggcgtgga aaagtggtcc 16200
aacagcgacc tctgtcgctc gttatatccc gctgcgcgca gcaccaccag ggcccactca 16260
gtcactcagg ctctcagcca cgccccaccc agacttgtgg gtgcgcggtt catcgcggga 16320
ggcaagcaag ggaaacttga gttggcgaag gtttgctttg gctggttggg ggaggggcgg 16380
ggggccgaca acatccctga agagctggag ggcagccact gtgcttagca gcccagggta 16440
gaatggaggt ttgcccctgt cgacgcgaac ctgcctgaag tactggttgc caggccttgg 16500
gttttggcga tgtcgttgct tgattggctg gtttcactct ggaggaatcg agggacattg 16560
ccagaggagg tctacaggct tatgtaaaaa gttaaaaagt ctccaaccta cgccacaggc 16620
ctttcctgaa ttgaaacttg ttctatgggg cggagggggg ggtgtaaggg atggaggagg 16680

-continued

```
gaagatgcct ttcttttcaa atacatggaa aaaaacccct caaatttact gttcctctat  16740
tttcctggct ccgtagtaaa taagtgccta gccttaggag gctattgacc tttgataatg  16800
tgagcagata aagccccccc ccccccacag ccctcggccc ctaacccccct ctttccggat  16860
taaagtgtaa gaatacaaat gtaatatggg atggaggggg gcgatttggg accccggtca  16920
aaaaaacaaa ccgtattact aagaagaaaa caaaggtctt gcattggagt ttccccgtga  16980
atctgagaga aaatgatcat ttgttgaaat gaagcgtcta aagcgatcca gtgcttcacg  17040
cccggacact gcactacacc gccagtcgcc ctgctgggcc agttaaacgc tcacttgtcc  17100
gggattaacc ccatggggtt aaatgggggc aatgcagaga taacgtcgcg tgatttctgt  17160
catttagatt gtgttaaatt cttcttctgt ttgataatcg gtagtaaaaa taaattatta  17220
gaccgtagta tgtttgggat atggttaaaa atcaagagca gcgatgactt ctggggagaa  17280
tgctttgcgc gggctcagcc ctggctccgg ccagactaga ggagctcccc aatctcgctt  17340
cgcgcggggc gggctcgcag tcgccaagcc gaggctgaca tttcttattg tgctgggagc  17400
cagagagacg caaaatgtct ccttccccca gtccctaccc caggtttcct agacatgggg  17460
aatgcattct gaggacaggt ggagaagcct acggtaggat ggggtcctcg taggtgagca  17520
ggaaacggct aagagcagag gagttctgct tgcgccagtc acaagccgcg caggcgcccc  17580
tggtcgttcg cttttgataa ctagcacata aagaactaga aataatgaat gattgctttc  17640
ttaaccatta ctttcaggcc cgcattgttt tagtgcacgt gaaaggctct tcccctacac  17700
tcaatatgtc tttttctact ttttgaccga aaagaaaaat tgctgcctaa acacgtttaa  17760
tgccattaat taagaaaagg catgtaatgg gaagaaatgc tgaaaatctt gatttaattg  17820
gcttttaagg aactagtaga cgacaaaaaa aaatcacacg agtgggcaaa gctatagcac  17880
tgctgaagga tagagcacct atccttccct gattttaagt taacttatgg aatatccaaa  17940
gtcctggcca cagcctgctt gtaaaacaaa aggatttatt tcttgtgttt ttttaaagtt  18000
tttctttgct tttaaagaga aaaaaagttc acaatgacat atgacttctt caaaaggccg  18060
tgatagtcta ttacgctacc ctctccgcct ctgcccccaa cgccgcccaa aaataccatg  18120
tcctcgttaa agactaaacg ttctgtatag gcagagtcca cctctaagca gtccaggctc  18180
tgccttcctt ccctagtgag tcccattctc cttggtatcc attgggcgga tgcccagcct  18240
ggatagaacc ccgaaacggg ggtagcacga gagcgactgg agacccctaa aagccagagg  18300
tttgagagag ggtggacgca gctagcagaa gatggtgtag aagccagctg agaacgaccc  18360
cctagagcaa agagaccttt ctttggcttt tcttgctttg gggtcctgga aaggaactca  18420
taaaatggtc ttcaccctca ggaggaggac ggactgaccc tcctctgtca ctggcttaaa  18480
aagtttcagg gcggcggctc tgggttccgt gctgaaatcg gactgcactg cagccccttt  18540
ggacctgacg cctggctttg cgtcccgaca aggggcgggt acttcccccg gcctccccca  18600
ggaacgcatt aattgttaaa tagctttggc ccagtggatg ggctgaaagt gttcgaccca  18660
agtcgctggt gtgcacagac ttcctccctc tgggaggtgg gctccatggc ccgttgtggc  18720
acccccagcc gcgacacaca ccttcacacg cggcagcagc tcggtcccaa ccttcttcga  18780
aggacctggg ttaaccctgg cggccttggc ggccgcagac ccctctccgc cgccccgccc  18840
ccgcgcctct cattcaatca gcgaatgttt gcggagcata tactacgtgg actcctaatg  18900
taccccctga aagcaaataa tacagttttc ctcgccgtca tgaagggatt ttaatcctaa  18960
catggacacc agcgagatca gcccagaccg tctctagcaa aacgcaaaat ggtggtgcgt  19020
```

-continued ggggtggtga ccaaggtcct gagccttgtc agaaagaagg ggatgtgtag agaaaggtgg 19080
agaactctag ctgtggctag cgcggaaggg acaggtgctt gccgaagggg gcatgaggct 19140
tgaggaaaaa gcaacgaaat aggggtaagg agagttttcc attttctttc ctccgcccga 19200
cctccgccat cccattctcc cctcccctcc cccacccccc gcgccaatca aatctgcagc 19260
tcacttgaaa ggtgccccgc cgcgttgtgg tttttcaccc ccaggggaaa ttgtaccagt 19320
tgtccgaaag tagtcagtcc ctgcggatcc ctgcccgcaa aagtggtctt cacaggtcgc 19380
gttcctcgct gctgactcgg tacacaaagt ttcttaaggc tggttcggct gttattcctc 19440
accgcccgct gctaatatat gcagcagttg ttagagcggc tcgggggaaa aggaaatgta 19500
taacgaaagc ttattcgtga gcaggaatat actaatggaa caatctgatg tcttcttaat 19560
cctatgtaaa aagctttgtc gtcttcctaa tattgactga atgggtaatt aatggctctt 19620
catctaggcg aataccctgt aatccaagat aggcaaaaga caacaagccc aaggtagaag 19680
acaaaaggcc caactgcagc ggcgtttgcc cgcctcctac cccccagggt ctctgactag 19740
gaaagttttc tctcagagga gaaaaaggca ggagtgggag aatatatacc tatcatttcg 19800
gggctagact tcaccgcagc acctgaccac ccagctcagt tttctgttac tctgtctttc 19860
cacctccagt ccttctccct gcattttttt ttcttcttaa ctcctctagg atgacctcct 19920
accaccaccg ccattatggt cctaataacc tttcccccta aaccccacat ctttcacttc 19980
agcaaccaat gaggctgttt tctgatccag gaggagattc ttttctttta gaacccaatg 20040
cgtagagtct ttgagaacta aagtagttgg taggggagga agaaattaat agaaagggag 20100
agagcataca gaattgtgtg tgtatgttaa agagcgacca ggaatgacag agtcaacttc 20160
tttgtgagga tctgacggga agagtgtcca agactctacc agcatgtttt taacaggctg 20220
acattttaat ttaaaccttt agaagtaata tattacttgg gttactacaa tgaggtgggt 20280
tccttttttt ttgtcagctg acagctttta aaatattatt tcgctaggga aataaaagct 20340
tcatctcaga ttataggtgg gtatttttgg atttaggtga tttatggtca ccatgacaac 20400
taatgctgaa tgttagctac cagcatgtct gggagagaga aaacagaaag aagggagagc 20460
aaaagaaata gaaaagggag atggacataa gctggagagg gaagaaaaga gaaaaagagg 20520
aagacagatg agtgtttaat ccaactgttg tttaaaaaag tggcgggggg gtgggacttc 20580
atttagcccc ttgccacttc cttctttcct gacctggata tctatgctca atttcatatt 20640
ccacccttcc ttccccttct ccaaacacat gtgctatacc attctcctta ttttacttag 20700
ttcggcaagt agttgctttc tggagactca gtgacaccta ggaaaactgt ggcagtaaca 20760
tgcaaatgtg aggaagcatt aacagcatgt tcgttgagtg attttagcaa atgccccctc 20820
ctctaatctc tttctcttct cttccccagg ccactgtgag gtggtaactc ccactgccat 20880
ctgaacactg ttcccccagg tagttacccc aaatctcaaa tggttgagca gctagagctg 20940
tgggttggaa aaatgggtac catttgcagg gacccagaga gggtggctgt tgctcaatat 21000
atctacagac ttccaattca gaaaataatc ttcccctttt gacaagccag agctttttaa 21060
attccattta ggaaatgggg aaaaggacag ctacagtgaa gcttttaatt tctgggttat 21120
ttggttccat agctatgagg ggtggtgggt agtggactgt tttcagcttg gtttgtatgc 21180
agagaaaagc cagatattgg agggggtggg gcacttctcg ggcaggatgc aaggtctcca 21240
tctgacctct gcgccttacc aggagctcac acactcacgc ccatcacgtg gctccaagct 21300
gagtccaggc gggcctcgtc cttgagctag cttgggcagg gcaggactcc cacccgtcta 21360
aggcctaaca gctcagggag atgtctaatt aagccatctt ctgggtgaac tctgaagaca 21420
gactctttcc aaaagtcaga gatcacttgg ttgagtccca ggccagattg atacggagag 21480
tttggcggca cagcccaacc gctcactgcc atggccagag ggactttgca caactaacac 21540
tgaagagtgt gaaattaaat aagactttaa gactggtaat cggtggcaaa taccagcaca 21600
aaacacggct gaccccatgt cacacatttc cctcctctag ggtctttctt tgaaagaata 21660
agcaagaaac cccaatcgag acaacccctg atgtctccca gactcaaaac ctcacgccgg 21720
cactgggctt tccttctttg ccccacgtga gccatgcagc acctctagtt tccctaccag 21780
gatcccacca atgttctccg tattggaaat ttctgtgtta gaggctgaac tcatagtaat 21840
ttctaaaacc aattaagaag aacttagcca gaggtcacag taatgctgga atcacaaaat 21900
gcataagatt tattttcttc tggccccttt ctcatccatg ctgcctatgc ctgtgcaccc 21960
acaagtctta tgtacattaa atctccaaaa tcaaccacca ccatgccaca gagttttcac 22020
tggacagtgt ttcttagttc ccaccacata cctccttttc cccatgcaga cttatcatgt 22080
tggtgtcctg ccacacaggg ggcctgagaa gaatgtcacc caatcgccgc tgctgtgagt 22140
gtgtaaagtg attaggagat taggagaatg ttgaaactcc tgctggaaaa atgcaaagaa 22200
aatcctcact ttgagtcagt tgtttacaga gccagtgtgt gtgtgcgtgt gtgtgtctgt 22260
aatataaaat ggatgtgaat atatatatac aaatagatat ggttttgctt ttactttaat 22320
ctgaattatc tagataattg tctttattca ccacttgact tcaatgggtc cacacaaatt 22380
aggacacctt atctttttag gcatctaggc tgctgctgat ccccagtgct tccaacatct 22440
cgcacacgtt ggcactatga ggagcagtca cgtgcccttg ggtttttcaa ccactttgga 22500
ggctgattga ggtccttcat acatgtatat ttgtcgtgat gaaagttcca tcggtagagt 22560
ggagccacca gagcttttat caaaattctg tgggtttatg agagatgggt ttagaaatct 22620
atatggctct gtggggcttc tcggctttct aaaataaggc attaacaccc aagcttccaa 22680
aaatatttgc agctctgggg tttgaatctt gaaaaacaag gagtgagggg ctgtgtatac 22740
taactacagt ggagattttt ttcattcttt aatgtgatgg agtcccttca tgaaatgaag 22800
ctttaagggg catggtattg tggggaccac agctattctg aggtttaaaa gaagaaactg 22860
gaatatgatt agtaaacaca ttcagcagaa aagagctgga ttcttattga cttagttata 22920
ggtcatcggc tggcagtgca atgggaggaa atatttactt tacacatata ctttatgatc 22980
ttgggggaat tagaggaaat tcaataagaa aacggctaga aacatttaaa acccttattt 23040
aaaagactta agcaaattag agtcttatca gattaaaaac cactacaaat gtaagagcat 23100
tgtcttcagt gaaacgctgt ggggtctgag aaggagattc tccgccaaat ctccgggata 23160
aaatgcgtca tttaagcacc agataatgag cagaatgtaa attaatttaa ccttctttac 23220
caacaggctg ctagtgtaat gtgtataatt tagtgataag attgcaggac ctaatatagc 23280
tggatgtatg agcctcagct aatgcagacc tgtcacatga ggatgtgttt tactctgagc 23340
aggtgtctgt atgtgtggaa tggggtaaag tggaataaaa ggttaaaagc agaaatgctg 23400
atttaaagct tactatgaag aaattcctcc cttgcagcta aattattctt aaagtgggat 23460
gatactggtg aagaaagact gaaaaacaat tctcatgtgc gtctttggac tgcaagttta 23520
aaatggggag gagttgcaga tagggtttgg gggtggtcag ggcaaaggag agacacataa 23580
gttgcaaata tatttgtagt ctgcttcatc cactttgttc cacatcgaat aagtttccca 23640
atcttgtgaa caaggacaag gagggagtgt tttaaagata cttcatgctg gcattgcaaa 23700
tcattgactg taatgtcaaa caaatacaca ttcagagatg ataacactaa ctccatagta 23760

-continued aaacaatcgc ccatgcagaa acccagagga gattagtttg tcctctccag ctgacctatg 23820
ctgggggaca aaaggacttt caaaaattat tttgaatatg tttggatttc tttctttaat 23880
ttctttggaa attaaatttg cttggaaaca gtgctataaa gagttgatgt ctccaaaggt 23940
gatttttttt gttttatata aataaggttt tgcttttgct agttgagcgc agttctaggc 24000
ttttcgccct tagctcacac acaccccttc tgcctgcttg gactttaatg gctcaagaca 24060
gccttgagct cactgggaaa agaaaatgac tgttaaaaat tatccttgaa attggttatt 24120
tggcaacatt cttaattgta tggaaattca ttaaggcata tttcatatat aattagctca 24180
aggttgttga ttctacaggc tttatggatt taaatctgat tgataataaa gtaaacaaga 24240
gagtcgaatt taaagcgtgg ctctctcggg ttaggacgag cttaatacag tgtacaagga 24300
atttgaaaga tctaggatat gtgtcttaat caacgttaag tagaatggat aagctttcag 24360
cattttgaaa acgctgggtt agggtttctc ttctattgtg tgttttctgt ctggggacta 24420
ataagcatca cagagaacgt gatctgaggc gactttttat tcttgtataa atccagagtg 24480
aaccaccaaa cagttgttcg tttaaagtca aggtaatttt cttttgacgg gtccatttgc 24540
ttctcgattt ctaatttatt agcctgcctt ttcagggctc tgtcttcttt gcaattaaag 24600
cttcttcaga ttagcgcagc attcacttga caggctgttt ggaaaattta agatcggaga 24660
ggtgatttgt tgctgttttt caaattttct agttttaagt aacgtgtctc ctttttatat 24720
ggggtggggg attggaaatg gatgtagtga gacacaaaga gtgggtgtct tgttgatcct 24780
tgtacctttc tcttcttgac cattccactc tcttctccca agccttcgac tcctagcctc 24840
atctcttcac ctttgggttc gtactaaaag ccggatcgcc ttgggctggg caggagctga 24900
attcccggga gcttgcctgt gtagacccag tgcgcacggc gaggcagtag cccggccccg 24960
cactgctgat aggtgcaggc aggacagtcc ctccaccgcg gctcggggcg tcctgattgg 25020
tgcggagcca cgtcagtcgc acccggagaa gggtctggga ggaggcggag gcggagaggg 25080
ctggggaggg ccgcggcgga gtgacgtctc ggcaccagga agcccgcctc tggttttaag 25140
atgttaggcc aacagggaag cgcggagccg cagatctggt ccgtcgctcg cctgggtgcc 25200
tggagctgag ctgcggcaag gcccggctcc tgttcgaccg cccgaggggt gtgcgtgtgc 25260
gcgttgcgga gggtgcgctc agagggccgc gtcgtggctg cagcggctgc tgccgccgca 25320
ggggatctaa tatcacctac ctgtccctgt cactcttgac acttctctgt cagggctgcc 25380
gcgtgggggg ggggcgggca gagcgcggtc ggcgttagct ttccttattg gaggggttct 25440
tgggggaggg agggagagaa gaagggggtc tttgcccact cttgtttcgc tttggagctt 25500
ggaagcctgc tccctaaaga cgctctgagt ggtgcccttc tgcccacatc ccatgtcttc 25560
gtttgcccgc tgactttccg tctccggact ttttcgcttg agccttccgg aggagacggg 25620
ggcagcttgg cttgagaact cggcgggggt tgcgtcccct ggctctcccc gcagcgggga 25680
aactccgcgc ctagagcgcg acccggagcg ggcagcggcg gctacggggg ctcggcgggg 25740
cagtagccaa ggactagtag agcgtcgcgc tccctcgtcc atgaactgca tgaaaggccc 25800
gcttcacttg gagcaccgag cagcggggac caagctgtcg gccgtctcct catcttcctg 25860
tcaccatccc cagccgttag ccatggcttc ggttctggct cccggtcagc cccggtcgct 25920
ggactcctcc aagcacaggc tggaggtgca caccatctcc gacacctcca gcccggaggc 25980
cgcaggtaag gcgccgcgcc gccctgcaga cattcccgct cagctgctct gcgccacccg 26040
ctccctctcg ccccaaggaa gtcagcccct ccggggggag gcgtggtggg agtggtcgtt 26100
cgcctggctc cccgcagaac ttccgggagc cggaattttg actaccccgc atccctttag 26160
ttctccctcg accggcccgg ctcctggggc gctaagggcg cgagcaattc tgccgccctc 26220
tctattcgta ccctggcctc ccttctgttt cctgggtcac aaaaatccca gcatcttgat 26280
tcgaggacct tcagaggccg ccgacctctg tccctgtttt cctctcggct ttcagctccc 26340
gaggagctcc actcgttagg aaattgcctg aaaccactca gaaatgccct tcgcgaagag 26400
gcattttttt tttttttttg ggaaagggcc ggcgaacttc ggtgcccaac cgaatcccca 26460
catcttttcc tagccttccc aaaccgcatg gaaatctgag ctttctgcga gggggagggg 26520
ggtctgtaaa ccacgcgcgt gtgcgcgtcc caggagattt ggtgtgtctg cgcagaggtg 26580
tataaatata cttgaaagca caggctataa aagtgaatgt gccgctgcag tgagataaac 26640
atgtaaataa aacgtgcggc gctgggggag gggaggaaat ggggcgcgga cacccacact 26700
tgcgcctgca caccccacag gcgcagcgct cctcgcggcc cggagccgcc gcgcgcaccc 26760
tcctccggcg ccaggcagcc cagctcttcc acggcttctg ccgccggtcc agttggcgtc 26820
cgcgttgcag gtgggcatgc tgacgggaaa gtgtgtgtgt ttcgttttca gagaaagata 26880
aaagccagca ggggaagaat gaggacgtgg gcgccgagga cccgtctaag aagaagcggc 26940
aaaggcggca gcggactcac tttaccagcc agcagctcca ggagctggag gccactttcc 27000
agaggaaccg ctacccggac atgtccacac gcgaagaaat cgctgtgtgg accaacctta 27060
cggaagcccg agtccgggta ggagccagca cggagtctgg gagggatggg gggaggatgt 27120
tgtggaggta caggccaagt agaccaggag agaatgtgga aggcagcgcc gcctgggagg 27180
gcgccggtgg ggcgcagctt tgcaaaggca gaaggcctcg cggcggcctg gttgcgagat 27240
tacagttccc tctccgaggc cgacaggact gccgccctgg ctcaggctcc cagagcggca 27300
ccggctcact gccccgccat cccgcgatct cacgagctgg gctgcatggg caatcccctg 27360
cacaggacat tgtgttcctg gcttgcagtt gccagagcag agctaataaa atccctacca 27420
ggccaagagc cgcgaacagg ctccaacctg tgagccttta acaaggaaaa cccgccagag 27480
acacggaaga gttggccctc cctgggaaac ctttgtcccg gccctggccc agctttttcc 27540
ctcctgggct cgcgcttctt acaccttctt tacggttgtt tcggccattc aggtctctcc 27600
cacacaccct atttcctagt tttgtgatct ccgggagcaa agttttaata cacaactact 27660
agtcctctta gaaggagaaa gaaaaaaaga agaaagactt ttctgcttgg tttatttatc 27720
ttctctcagg agttgaactc tggaaattga aactcacacc ccctcttcta aattataatc 27780
atagttttgt aaaaagggct taccttaact ttgtagcaaa tctgtacttt atggattggc 27840
aaaaatgagc tcaaataaat aacccaatag caacgtcctg gtttatgctg gtcggtggaa 27900
gattccaaat ttgttaggat tctggaagca gaaaacagaa tcaagcaaat caagcggcat 27960
ccagaggctt tgctgttaaa aaaaaaaaat taagtgctct gggtagaaaa aataaagccc 28020
ccggttagag cagagcaaac aaaaagaaga aaacaacgat aaaaagaata aagaccaaaa 28080
tgctctccca aatcagaggg aatgaagaca ctctctgggt ggcatttgtg caaggcatga 28140
ggctatgctg gtggataaaa ggccgggaag aagttgaaaa tggttttagt ttaactgtcc 28200
agagccagag ctgggtcctg ggcggcgtgg ttttgagcaa ggtcagtctt tcattagctc 28260
tcttgcacat caagggaacg ggcctctcac gtactcttct cgcctgagca aagtttagat 28320
ggcctagggt agaaatggca agtaattaaa gacagagtct atgggttttc tgggatcctt 28380
cgaaaacgcc ctcccacccc gcccgctatt ccgcagctcc accctagtgc tttgtagccg 28440
cggcgctggg ctctccttgc agctgcctct ccttccaggg cggctgcttg tcgagccaag 28500

-continued tgggagtgag gcgtgctttt tatagcagtc gggtgcaaag aggaaggggg ataaaaagga 28560
aatcaagaat gaaaggaaaa agagaaaaag cggattacac ggctgggccc ggcggagatg 28620
tgtaatgtga aacatcactg gtgtcagctc ggatatctca ggccaggcct ctctccaata 28680
cacaaaagcc gccgtctggg gcgacaggga ggcccgatgt ggattgggat cggggttgcg 28740
gctgggccac cggacacggg tggaagccgg ccggcctggg tggccgcctg caaagccaaa 28800
cgacccggct gggcctggcg cgcggacagg cctgtggtgg gcttagggta aagaagaggc 28860
agagcgaaag aaggggggaat ctccaaaact accctttccg ggttcccgga gtttaatatg 28920
ccaagctcct ggagttaacg agctgacgaa gaggtggtct tttgctcttt atttggttgt 28980
tttgctaggc gagaaagagt gttggcggcc tagtccctgt taagggagca cgtaccaggg 29040
ggtgggggac gacagtggag gtcagggaag gaagggagga attgcgtggg agaaagagcg 29100
atcctctagt gcccttccag ccccttctcc tcatccgtgg gtctgtggct ttggaatgga 29160
agcaagtttg caaggtgccc cgggaagggt tggaaaagcc tgctgccccg cgtttgtttt 29220
acattaagtg tttttggacc tggagaaacg cctggctgag tgatcaaacc gtccgcaggt 29280
ctccatgcgt tcggctgagg tttgtggcgt agctccgagt cccagctcgc aggccagagc 29340
agaccaggtc tcctgcgctt ggtggagacc cgggccagta actgaaagct ggccctggta 29400
tcttggtgtg cagggcggtg cagtgaagcg aggccagggt gtgtgagtgc gctagcgtgt 29460
gtgtcggggg aaggcggggg ttggcctccg atggaagttt tagtaatctg cactgtggca 29520
tctgtttgct cccttgcccc aaccgccccc aggtttggtt caagaatcgt cgggccaaat 29580
ggagaaagag ggagcgcaac cagcaggccg agctatgcaa gaatggcttc gggccgcagt 29640
tcaatgggct catgcagccc tacgacgaca tgtacccagg ctattcctac aacaactggg 29700
ccgccaaggg ccttacatcc gcctccctat ccaccaagag cttcccccttc ttcaactcta 29760
tgaacgtcaa ccccctgtca tcacagagca tgttttcccc acccaactct atctcgtcca 29820
tgagcatgtc gtccagcatg gtgccctcag cagtgacagg cgtcccgggc tccagtctca 29880
acagcctgaa taacttgaac aacctgagta gcccgtcgct gaattccgcg gtgccgacgc 29940
ctgcctgtcc ttacgcgccg ccgactcctc cgtatgttta tagggacacg tgtaactcga 30000
gcctggccag cctgagactg aaagcaaagc agcactccag cttcggctac gccagcgtgc 30060
agaacccggc ctccaacctg agtgcttgcc agtatgcagt ggaccggccc gtgtgagccg 30120
cacccacagc gccgggatcc taggaccttg ccggatgggg caactccgcc cttgaaagac 30180
tgggaattat gctagaaggt cgtgggcact aaagaaaggg agagaaagag aagctatata 30240
gagaaaagga aaccactgaa tcaaagagag agctcctttg atttcaaagg gatgtcctca 30300
gtgtctgaca tctttcacta caagtatttc taacagttgc aaggacacat acacaaacaa 30360
atgtttgact ggatatgaca ttttaacatt actataagct tgttattttt taagtttagc 30420
attgttaaca tttaaatgac tgaaaggatg tatatatatc gaaatgtcaa attaatttta 30480
taaaagcagt tgttagtaat atcacaacag tgtttttaaa ggttaggctt taaaataaag 30540
catgttatac agaagcgatt aggatttttc gcttgcgagc aagggagtgt atatactaaa 30600
tgccacactg tatgtttcta acatattatt attattataa aaaatgtgtg aatatcagtt 30660
ttagaatagt ttctctggtg gatgcaatga tgtttctgaa actgctatgt acaacctacc 30720
ctgtgtataa catttcgtac aatattattg ttttactttt cagcaaatat gaaacaaatg 30780
tgttttattt catgggagta aaatatactg catacaaatt ggtctggatt ctttctcccc 30840
tcctctgtca ctaacttggc caggacatct cagtcactgc ttcctaaaca aaccagttcc 30900

```
ctctgcctgc ctagttaaac atacaaggca gcagtcctta tttaaatttg gtagaaataa  30960

atgatagcca ttcatcagaa actaaaaaga aaaaaaaagg cattcccggg ggggaaaagg  31020

gctacaaaat ctaattttgt ctctccaatt tttctttggc ttaaacctag aggattccat  31080

tatggctagc aaataatatg aaaaagaaaa aagaagaaag aaatttagca agtccatcag  31140

cttaaaatga ctctcaagtt tactccttta cggggaaacc tacacctcta gcaaattgtt  31200

ctggagaaat atttgtgcat gtatacatgt atagtttata tgcatttctc tcaggaggaa  31260

tacatctata ataaatttac agggaaacat ctccagttca aaatatttag gcttccacgt  31320

ttatcttcag gcttaagtag agagatcctt catgttatat tgcattacta tttccaaatc  31380

ctttggagac attaaaagaa acaaagatga tttctaataa ctacagccct tcagtttctc  31440

aaagaactca ggggttgaga ggttagagtg gagtttcctg agtcttgtcg agcaatatgt  31500

agttgaggca aaggtcatgc tcccggtgtt ttgttttaaa taatattgac ccattaattc  31560

taaacctgct tgttcctgaa attatacagg attatagttt gcaaactgca ggacaatgaa  31620

gcaaatcaag atgaattaca gccctggccc tccctgccat cctctgacat ctaaacaggg  31680

aatgagttcg gtgtgagtgt ttaaatgaac tttaagcacc cgatccttct ttatccgcga  31740

ttttcagctt taaaaaaatg tgaaatttga tttcataaca aatagaaaca aataccactt  31800

agtcccagag aattcatcct catggcgcta ggagggtcgt tgtggaggtg gggggaggga  31860

tgtgctgaga tcttttgtta tgcttgtcaa ccccccgcac aaccaaagtg ggcgagaaca  31920

aacaccacgc tggggaactt agagcaaaaa gtaaccgccg attttctgga gccgacaata  31980

tcattgtttt ttcgccttag t                                            32001
```

<210> SEQ ID NO 2
<211> LENGTH: 12001
<212> TYPE: DNA
<213> ORGANISM: Homo sapiens

<400> SEQUENCE: 2

```
catggactgc gtgatcacta aacttggcac ttcagggggc atatcttttt tgagtaactc     60

tcataaacat gcctgcctgc aggacatcca gattttctgg tttggtagta aagcaacata    120

agaataatct tgaacctgat gttcatcctt gccttctttc taattccagg agccctctga    180

ggtctggact aactcactga ttaggaaata gtatttggaa aggctaaaca aaatactatt    240

tccagggaaa tagtatttgg aaaggctaaa caaaatatac tttcttagtt ttctcaaacc    300

tctcagaaga tatatttttt aaaaaataaa ctaagctagc aacatttaaa ctaaatcttt    360

gccttgctta caatacaaaa gatgataaaa aaattgttgg gaaggtgaga aattaacttc    420

acctataatt agaagtaaag ttttcattta aaaatgtaat accacttaaa ttcaatttgg    480

gaaacaaaaa ggactcaaaa aacagtctgc taaagccaat ttgcaaacaa gtgcgctctc    540

tttttcttta agttgtatct caggttcaga gcacatgtgc aggtttgtta tgtaggtaaa    600

cctgtcacag ggatttgttg tacagattat tttgtcaccc aggtactaag cctcgtaccc    660

aatagttatt ttttctgatc ctctcccctc tcccatccgc caccttccaa taggccccag    720

tgtctgttgt tcctctcttt gtatctatga gttctcctca tttagctccc acttataagt    780

gagaacatgc gttatttggt ttctggtcc tgatttagtt tgctaaggat aatggcctcc    840

agctccatcc atatttctgc aaaaggcatg atctcattct ttttttaact attccactct    900

ctctattact ctttcttctt cccccaatcc tgaaccctac catgtcagtt taaccactcc    960
```

-continued

```
ttttctttcc tttttctttg ctcatttgca catagttaaa agatgccatg aatttttctt   1020
tttaattcag catatgccca ttaaagatct aaaaatatta tttacatcat ccagaactca   1080
gcttaagaaa ttaccaaaaa ataaagctac cagaaagtaa ctgaatcatc ttgttgagcc   1140
acaatcctag acctcgactc tgctttttcc tcattttagg caggtcattc cttttccttt   1200
cttaaattgt tttctctgta ttcaataaca cattcttgtg gattcagaaa gggtggagta   1260
tgaggaaaag gaatatgata tatgtaccct agaggaaaac aataaataaa tatttcagga   1320
tggaaaacat tatttttatt tttattgagt tttctagagt ctatttgatt tgtgtaaatc   1380
agaaaccagt agaatgacat taatgaatta atgaaaagca gaatgagtta tcagttgtaa   1440
caaaaagaat aaagaatttc aagaacacag ctttaatcat gcatggctgc ggggagagaa   1500
aaataacaaa atgctctcag tgaatacatc tctgagagaa gaaaggaaat acttaaggag   1560
aggataaaaa gagcaaatat caaaaatagg agtaagaacc ctattgcttt ttttagttga   1620
caaataaaaa ttgtatatat ttactgtgga caacatgata ttttgaggat tacgatcact   1680
tttgattcat aaattacatt caagaaaaag aaattctcaa aaagtttggg aacatatgaa   1740
gttgaaagaa cattaatact cagataagga cagtacatga caaattattc ttgctccaac   1800
attttctctc aggaaattta aacatctttc agtgaagcac cagtttcttg aaatcaagca   1860
tgagaaaaaa aactaaattc acctgtggaa aaaaagacac agctaaacaa aaaagcggtt   1920
gttataacct caagagtggc atgaacaaaa tgatcaacat tctcccaagt gacagcacaa   1980
atatcaaaag tcctaataag tggaagtggt cctgtcatga caaaaggtgt ggtatttgta   2040
caatttccag ataagaacaa agtcatgacg ctaagacagt agcagcactg tttgttacac   2100
gtgatatttg aaaaatatga caaccatctc aatctgctca agtagcactc atggtgaggg   2160
tgaaatttta tcaacattgg ttaacttatg gtgttttaaa aaactagcaa ggagataaat   2220
tgatggatta aaagataaac tactcacagg cagacaaaca gaaggacaga tagagttaca   2280
atcaaacatg tactttactc aggcagaaag ataataacca gcccccaaga agtgatgtgt   2340
ctgctagaaa agccctgaac atagaatttc ctgactttgt ttttaattta gttctttcag   2400
gcatcacgct gcataaccag gtgtaactct ctaaaagtct ctatgacaga attttccatc   2460
tgttaaatta ggctaataat attttcatct ttttttaggg taaagatgtg aaatatttgg   2520
agaactctgg aaaacatgcc ccctactaat tagagctttt tgatgtgaca tcattttctt   2580
cagtacttgg agtttagtca atagatatac agtgtagctg tgaaattatg aagcatgaga   2640
atgcattacc aagggaccgt aggaggctct ttactgaaaa gtgtagctgg ctatatttct   2700
ggaagtaatt taaacatagg ctgagggaga ggagtaccct ctagatcctt tccagacctt   2760
actttctatg aattctaatt tctctttccc atttagaaaa aacaatgaga tccacagcgt   2820
agagatagaa aataaggctc tgtgtgccct caaaccttac tttcaaaaat accacagcat   2880
tctggacgag atagtcttga attcttgcaa cagcacaggt atgagagttt ttaccagaaa   2940
acaggagact ggattgattc tttcattctc ctcctatgct tcctaaaact gaaaagccat   3000
atatacaaat tatatttatc tatccctcct ggaaaaggcc aaaatgaatc caattttgga   3060
tcattttcaa taatgggaca aacctgaatt gagaataacc tttagaatca gtcctgtctt   3120
tttgtgataa aatggacttg tagaaagcta cctggtgttc tcccctagct aacattctac   3180
cacaaacaac gggtatgtaa tccagtattg ctccccacag gctatgtcct tggaatcact   3240
atctttgcac tccatttgtc tgctgacatc cttccaccca agatgtcttc ttcagcacaa   3300
gaagtcattt ctcttaaaat ttcaaatgac tttactacaa taatagagtt gctaactaga   3360
```

cctaggcaag taatgataat aaaaatctga tttctactta gagtgtagca tggtttaaca 3420
caacaaccag agtcctaaca ggtttttcta gatttcactc ctactcaact tgcatgttct 3480
tgcaatatag atgttcttat tactcggtcc ttacttccat ctctctttgc ttctggaata 3540
aaactactta aacccaattc agagatttta ttctcccttg gaattactgg gaaacagttc 3600
tagtaaacca tattcctgag atcctatatt aggcttagtc caaactgacc atctaagcat 3660
taattttcct gtggctcagg aatatccctg agcttacctt tctcttccta aactgcccag 3720
gacaaatacc ggagtttggc ttttctgctt tctcatccaa tcatttctcg tttcctcctc 3780
tttagcattt aaaacatttc tgactttctc catccctcaa gaaatatatt tgctttcctg 3840
tctctgcatt attcttttgt ttatgaaata ttccataggt aagttctata tttccttccc 3900
ccagaggccc ctggtcttct ggttccagtt gccattggtt cagtgtacta gttaacattt 3960
tggactttgg agttacacaa acctagattc aaattcccac tatgccactt actgcctacg 4020
tgacctgaag caatatccta tccactgtgg cctccagcag ttataagctt gtgctctaac 4080
cagctgggtg accttgggcc agtgacacaa tcatggcaaa cctcactgtc ttcatttgta 4140
aaatgacagt acctaccttg tagtgttggc ataaggaata agtgtgattg tcaatacaaa 4200
agtgtttagt acaatagcta aattaactaa gcactctgta aatattagtt tttaccatta 4260
ttactaattc aaatgactag atgcattttg tgtataccag gtttcctgag ttcactttgt 4320
tctcaacaaa tactattatt cctagcatgt ggcctatatc acacttcatt agccagagga 4380
catgtgaagc ttagagtgga aagctagggc agcaggaagc attgccacac tttacacagt 4440
caaagccatt taaacatgtc tgaatttgag ctctgctgag tccttacttg cccccatctc 4500
tcctgtgtgc tccagcttac taataaagca ggtttaatat aaatacacta aaagcctaaa 4560
cattgagatc atgataatga atatgagggc tatgactata aaatatcatt gaaccagaga 4620
cctgctacga aaccacatgg tgaagaccac aagggaggaa tctgcataca caccgagtgc 4680
cttgggatcc caaagtggga agagtcagtg ccccaattaa agagaaactc ggggtaggga 4740
atcaaccaca acatcagtca ccttactgaa cccaggcttg tttcagctga cgtagctgcc 4800
aatttccaat gtcccctccc tccctaattg ctctcaatct attcctccag aaactgaaag 4860
cccatcaaag aggatatctt cccagagagt tgttccagtt actacaagct cttgctagaa 4920
attccaagaa agtttacaag gtacctttat aaggtggcat tgagtaagtc agaagcattc 4980
caagtaccaa ttatcatgca aataagggct ttacttttag attttgttgt ttgtggtggt 5040
ggtgatgctg gtgttctctc tggaatccag cccaatctcc aaaaaagtaa aaggagtaca 5100
aatagtaata caaattatta ttacttacac caattaaaat agaagttttg aatgagcaag 5160
gagctagagg aggtaaaaac tgggaacttc gtatattaaa aggtttttat aatttgaaaa 5220
ctaagattat gctggccaaa taggctgttt taaaatcagc atagtaatca aatttgcttg 5280
taatgaatgt agacccaaac agtgatgtca gacctgataa ggacttgcaa accctaaaag 5340
agtgcaaaaa gaccatagaa gaacaatatt atattcctgc acttacagaa atggtcagct 5400
caagagatgt atccagttca gggtggctgt aagcttcatt ttctgaactt gctaccagaa 5460
gttaaaagaa attctgtata actgcttttg atggaaacac aaattggttg atgtaaatga 5520
aatacataaa gcagttggtg tcttattcat tcccacaatt ataaatgaaa ttaaatgatc 5580
aaaaattata gactttgggg atcttctttt cactgaggag cccatggaat ttgtcttctc 5640
tagtaccaat aactgtgttg acctattttt tcctgtctaa ctctgtatat attaaaacta 5700

```
ggtggttacg aacaaaaccc agaaatacaa tttacattct aataaaatga ctttaaaatt   5760
attccacttt ttactgtggc tttacctgtt gtcccacaat gcaggtttct ctgggcctct   5820
gcttagaatg actctgtcaa tgtagatgac agccagagtt gaatggggaa tccagaaact   5880
ggggattcgg gctcttgatg caatctatat gccaatctac ttcattagtt cttcttttat   5940
ttacagtttg gtaaagaata tgggtggagc tgttctgggc tcacttgcac acatgtccaa   6000
actgctttga aaaaggaagg gcaagaaaga gtggtatcca agttggaatc aggcaggcat   6060
ttcagatcaa gagacgaact ggaaagggaa catctgttag ataccctggg tttgaaggca   6120
gtctgtgtaa gttttcatat ctctgagtgt gtgcacacag tggagagggt ggagcctgcc   6180
atcctcaaat ctgaaaagat tgagagattt cagagggccc agatgtgcca aaggtcagag   6240
ggatcaatat acaggcccta ccacggaaag gcggggaaaa ggttcgaata gaaaactgct   6300
gcagaaggga agccactgag aggtaaggga gtttctgaat aattaaaaag ttaagaataa   6360
gcaaaaggaa ggaggtcggg tgggggataa aaaaaagcag ttgatgtggt aattaagaat   6420
ttggtgggag cctgggcagg tcacctcctt tctcagatca gagccccatc agaaattctt   6480
tcaagtgtcc ttctgcgtcg ccaaagatga caacagcaaa tcaataagtg cttgaaatga   6540
aaggggatgt tgactagccc ccaggctaca gatttcccgc cgccagcctt ttctgaactc   6600
ctatagcgtg cctttgcacc gcctctctta agaagagcta ccttttattc ctattctcag   6660
gacgaaggta agtgctcagt tagcatatct attaaatgtc agctttggtt ccagctctcc   6720
gtttgcgcgg aaagctcact gccatagcgc gcccagcctg ccggaggggc agacagaaaa   6780
agcaagcttg gcctggcgac ttgcggggcc acgcacctcc agggctggcc cggagtcttc   6840
cagagtttaa cgctcctggg ttagaactgt aaggtcccgg tccgagcaaa gggcctgagc   6900
caccgtagcc gtgggagcgt tccttccact tgaatgcact cactcacaaa caagcacaaa   6960
atctttttaa cagcagagga gaaagacccc tgctccaaaa ttaaagctgg gaatcaccgg   7020
aaactccgtt ttgagtgcga gatattggtc tgttaccttt ctaatcttca tatccctcct   7080
gtaatatgtc ttgatttaac aatctttcca gcgcccagca ttgcccggac gttttaattg   7140
ggtaattcat tagtgagtca atacaggcat ttatatattc ttttagctca agtggttaag   7200
tactaatttc gaaatgatta taaaacaccg gaatcggcaa cgcatagtaa ttttaattta   7260
tatgcaaatc aattggttca tcttaaatgc ctttttttaaa aaaacaatta ttgtattgta   7320
gcatcggagg catggatcaa acctctagaa tagacaattc ggaaacaaga cctggactag   7380
gaagacaatt tagaacagcc aacaaatcaa taatgtttga ggcagttaaa catcgctagc   7440
cattggtatt tacatactcg cttgttgtca gataaggagc tggggaaatt gcttgccagg   7500
gttgagatca taatccagag tgaagaaagt aaatggtagc acacagcccg tcacagcggg   7560
ctctgaaata atactgtacc tttcccaaat cctgactctt gggtgacagg gagttggcgg   7620
aggtcacccc acatttgtcc acggttttgc cccaatttga tcacgaaatt gttgttctcc   7680
ctgagctttc caatttgatt accattctaa cggttctgtc acttgtctca acatattggg   7740
gggaggagtg taattgagat tctcattaaa aattatctga acccacttag ccagcactgt   7800
ttcatctaag cttagtttta tgggctgtat ttaattccct gtgcccccca cacattaaaa   7860
tcagatcatc aaaatgtcgg taggaaaggg tgaaggaaat ggtccaatgc tccagtttac   7920
tggaagacta ttatctttag acatagttca aaattttgag gaaataaaaa ggatatacgc   7980
tttgggggga aaatgtttta atattctaga atgggggtat tactcccccc attccagaga   8040
atccgcactg gagttgttta tgtaaaaatg taacatcctt gaaattcaca gatacgtaag   8100
```

-continued

```
gttagtgtct ccccttcccc aggctcccag tccaggcgat ctagccctaa aggagctagt   8160
acctttgatg ctacaatctt gtttacatct gcagggcaga gaattgcttg ctttgcttgg   8220
acgctccctc cacccccttc taatttgaag taatcggaat ctaaatacag tcgccaaggc   8280
ccgctcttcc tttactgctt tgacaaggga aaaacctgaa atccacgtct taaatcagct   8340
cggtggtttg tagcccccca gcaccctgct tctacgattg catgcctaat gtattccctg   8400
gtgattctgg gcattaatta gttgtttaat aggagtatga ctaaaaatgt aaaagaagga   8460
ttaggagcgt gaaacgtatg tccagctcct tccacacact cgaggaggga atgagaatca   8520
ttctgtatct tctatttctc caggagccat ttgcatttcc caccagctgc tcacttcagc   8580
tgcactggcg ctgggcaagg cgaggaccca aaagctcagc gcagtgtctg cggcggccgg   8640
gactggggtt aaccagcctc tggcgggcga gactccagac agaagggggg cgagaggaac   8700
gtgagcttcc cgagcccctt cctctcagcc ctggtttgca aacctctgaa acctgaaagg   8760
ggagggagtt gcacgcgcgt atctttgcgt cttttcagcg caactccctt ccctctccct   8820
gtgtctctcc gcggatctct gaatctttct gtctttggtt ttctcattct cttccaactt   8880
ttccatgaga ttgcctatcc tcgccaccag ctgaaggcaa ggccgttctg ctacgagcgc   8940
ctcttaatct ctacaaaatg aaaagaaaaa aagggaggat tattagccca ttactcagag   9000
gaatggggag gctgcaaaaa tcgtcgatgg gcagaggtga agatgtcttt ctcggactgc   9060
actttccggt gtcctgtaac tagagttcag ttgtgggact tgttgaagaa atttgatttt   9120
cttgcctcgg cgagatttca aaaaccagaa atagaaattc tcagagtcag agaggaaata   9180
caattaaaca gcacgtgggc attttccccc tcatttctct ccccttaaat aacactgctt   9240
tgagtttcca ctgggtaaag agagaaagtt tgagttttca cggatgttac gtggaggtta   9300
gaaatggctt aaaatgtaga tctctaatca gttttcttcg tggctgaaga ggctaaccct   9360
ttccataaaa tgagtccatc tgtcgactgt tagctatttc aaagtgaagg gatttagcac   9420
tcaaaacaaa ttgagcaagt ttgtttgcct gtttttactg ctaactcaaa tgaattcaaa   9480
acacggagta attcaagaaa acacataaca tgttccagac agcccccaaa agtagggaaa   9540
gcccagcacc tatatagtga ctagggttag ttttaagcgc caagcttttt taaacgtatc   9600
tattttatgc acattctccc gagtcactat atatttctaa aattgcgagt attggtatat   9660
tgatttagga agagcaatac aacttttaga gggaacttta ttctcaatta gggaccaaag   9720
agatgtcttt ttaatagcgg gcctgagttt tgctctcaag caggaattaa tattggtggg   9780
aaaatccgaa tccaggagca atggctgtgt tccggcactt tccaaaaaca tacattaaca   9840
ggatgccctt gagattgaaa aaacattgtc ccatatgcct ggcagaagcc ttcacacctg   9900
gtcctccagg cgaattatat ttatagtcct tccactcaga ggcaggacag agccaaaata   9960
ttctgctcac taccaaaata cacatctttg ctcaagtcaa gaaatcagaa aatcagggtt  10020
cagaagtaag gcacactttt cgagtgagaa tatgccctgt aatttcacat actctttgct  10080
ttgcaggagc aaatgtggac ttgagggaaa ctctctcccc cacccccact tctatcccgt  10140
gcaatttaat accatcctcg ccaggaacct taacctcgtc attttaaaaa atgagatatc  10200
cgtgacccag ggtgaacttg ttgaatgtag gtacagcaga ggaaattcta gactctatga  10260
gcgtctgagc cttgtccagt gcaaaccctt cgtgaacact gggtcagtgc gtggccgtgc  10320
ccacctgtgc gccgacactc tcagcatgcc tggtccaccc gccttgacct cgggcgcggt  10380
gtcccagcta agctgggccc agcgtcccgg ccttccccag ctgacaagcc tagctcgttc  10440
```

-continued

```
gctcccggct gtggccctcc caccctctcc cactagctca ctccattctt ctagatttct  10500
cttcactcat cctctcccat ccccaccgcg cccacctcca ctcccgccct ctaccggtct  10560
ctcactttcc tccctccgca gtccctcttt gctgtgacct ctttcctcaa ctctgcaggc  10620
ctgaaagaag gtcacacacg cacgctcaca cccacactcc acacgcctcg tcccaaacaa  10680
ccccatgaac attgtccttt gttccgtctc ttgggccact ttccctgtcg cttcctccca  10740
gcccgtcctg atttgctccc caaaagtacg tttctgtctc cccgctgccc tggcgctccc  10800
cctttgattt attagggctg ccgggttggc gcagattgct ttttcttctc ttccatccca  10860
tcctcccttc tggtcctcct ttccacagtg ggagtccgtg ctcctgctcc tcggttggct  10920
cctaagtgcc ccgccaggtc ccctctcctt tcgctctccc ggctccggct cccgactctt  10980
cggcccgctg gcatctgctt ccctcccctg cctcgtttct cgtcgcccct gctcgctccc  11040
cccggcgctc gcccgggcgc tgtgctcgct cctggatcgc cagccgcgca gccgggctcg  11100
gccggccgcc cgcgcgccac tgtgcagtgg agtttggtgg aatctctgct gacgtcacgt  11160
cactccccac acggagtagg agcagaggga agagagaggg atgagaggga gggagaggag  11220
agagagtgcg agaccgagcg agaaagctgg agaggagcag aaagaaactg ccagtggcgg  11280
ctagatttcg gaggccccag tgcacccgtg gactccttcg gaacttggca ccctcaggag  11340
ccctgcagtc ctctcaggcc cggctttcgg gcgcttgccg tgcagccgga ggctcggctc  11400
gctggaaatc gccccgggaa gcagtgggac gcggagacag cagctctctc ccggtagccg  11460
gtaagtggag gccatctatc ccgcagggat gtgagataat gcgagtctgg aaatttgttc  11520
cacttcggag aatcttcacc gtaggtgatt tgtggctttt ggggctaagt ttcgcccaag  11580
gtaacgcagt cggcaaacag accttgcaaa gccctgttcc tttcgtcccc cgccacagac  11640
actaacaatc tacagggtgc tgaagtcgag agggaagcca gaccgtggct ggcatttaaa  11700
acgaggtatc ttcccttaaa tctcggtgcc aacactgcag gaacaaatcc tcgggccaag  11760
gattagcatt ctcaagataa agggctgggt acaaagtttc agctactgga agattagccc  11820
ccttcccatt gttatccatt gggaaaaaaa agaaaagaaa aagattccat cttaactggc  11880
agttagtgac ctctcaggcc caagcgaatt acctgggagc caggcctgga tgccaagctc  11940
tcaccatttc tttggattgt aactccttta aattgatcac cagtcaactc caatctggca  12000
c                                                                  12001
```

```
<210> SEQ ID NO 3
<211> LENGTH: 4001
<212> TYPE: DNA
<213> ORGANISM: Homo sapiens

<400> SEQUENCE: 3
```

```
ttttcgccct tagctcacac acaccccttc tgcctgcttg gactttaatg gctcaagaca     60
gccttgagct cactgggaaa agaaaatgac tgttaaaaat tatccttgaa attggttatt    120
tggcaacatt cttaattgta tggaaattca ttaaggcata tttcatatat aattagctca    180
aggttgttga ttctacaggc tttatggatt taaatctgat tgataataaa gtaaacaaga    240
gagtcgaatt taaagcgtgg ctctctcggg ttaggacgag cttaatacag tgtacaagga    300
atttgaaaga tctaggatat gtgtcttaat caacgttaag tagaatggat aagctttcag    360
cattttgaaa acgctgggtt agggtttctc ttctattgtg tgttttctgt ctggggacta    420
ataagcatca cagagaacgt gatctgaggc gactttttat tcttgtataa atccagagtg    480
aaccaccaaa cagttgttcg tttaaagtca aggtaatttt cttttgacgg gtccatttgc    540
```

-continued

```
ttctcgattt ctaatttatt agcctgcctt ttcagggctc tgtcttcttt gcaattaaag    600
cttcttcaga ttagcgcagc attcacttga caggctgttt ggaaaattta agatcggaga    660
ggtgatttgt tgctgttttt caaattttct agttttaagt aacgtgtctc ctttttatat    720
ggggtggggg attggaaatg gatgtagtga gacacaaaga gtgggtgtct tgttgatcct    780
tgtacctttc tcttcttgac cattccactc tcttctccca agccttcgac tcctagcctc    840
atctcttcac ctttgggttc gtactaaaag ccggatcgcc ttgggctggg caggagctga    900
attcccggga gcttgcctgt gtagacccag tgcgcacggc gaggcagtag cccggccccg    960
cactgctgat aggtgcaggc aggacagtcc ctccaccgcg gctcggggcg tcctgattgg   1020
tgcggagcca cgtcagtcgc acccggagaa gggtctggga ggaggcggag gcggagaggg   1080
ctggggaggg ccgcggcgga gtgacgtctc ggcaccagga agcccgcctc tggttttaag   1140
atgttaggcc aacagggaag cgcggagccg cagatctggt ccgtcgctcg cctgggtgcc   1200
tggagctgag ctgcggcaag gcccggctcc tgttcgaccg cccgaggggt gtgcgtgtgc   1260
gcgttgcgga gggtgcgctc agagggccgc gtcgtggctg cagcggctgc tgccgccgca   1320
ggggatctaa tatcacctac ctgtccctgt cactcttgac acttctctgt cagggctgcc   1380
gcgtgggggg ggggcgggca gagcgcggtc ggcgttagct ttccttattg gaggggttct   1440
tgggggaggg agggagagaa gaagggggtc tttgcccact cttgtttcgc tttggagctt   1500
ggaagcctgc tccctaaaga cgctctgagt ggtgcccttc tgcccacatc ccatgtcttc   1560
gtttgcccgc tgactttccg tctccggact ttttcgcttg agccttccgg aggagacggg   1620
ggcagcttgg cttgagaact cggcgggggt tgcgtcccct ggctctcccc gcagcgggga   1680
aactccgcgc ctagagcgcg acccggagcg ggcagcggcg gctacggggg ctcggcgggg   1740
cagtagccaa ggactagtag agcgtcgcgc tccctcgtcc atgaactgca tgaaaggccc   1800
gcttcacttg gagcaccgag cagcggggac caagctgtcg gccgtctcct catcttcctg   1860
tcaccatccc cagccgttag ccatggcttc ggttctggct cccggtcagc cccggtcgct   1920
ggactcctcc aagcacaggc tggaggtgca caccatctcc gacacctcca gcccggaggc   1980
cgcaggtaag gcgccgcgcc gccctgcaga cattcccgct cagctgctct gcgccacccg   2040
ctccctctcg ccccaaggaa gtcagcccct ccggggggag gcgtggtggg agtggtcgtt   2100
cgcctggctc cccgcagaac ttccgggagc cggaattttg actaccccgc atccctttag   2160
ttctccctcg accggcccgg ctcctggggc gctaagggcg cgagcaattc tgccgccctc   2220
tctattcgta ccctggcctc ccttctgttt cctgggtcac aaaaatccca gcatcttgat   2280
tcgaggacct tcagaggccg ccgacctctg tccctgtttt cctctcggct ttcagctccc   2340
gaggagctcc actcgttagg aaattgcctg aaaccactca gaaatgccct tcgcgaagag   2400
gcattttttt tttttttttg ggaaagggcc ggcgaacttc ggtgcccaac cgaatcccca   2460
catcttttcc tagccttccc aaaccgcatg gaaatctgag ctttctgcga gggggagggg   2520
ggtctgtaaa ccacgcgcgt gtgcgcgtcc caggagattt ggtgtgtctg cgcagaggtg   2580
tataaatata cttgaaagca caggctataa aagtgaatgt gccgctgcag tgagataaac   2640
atgtaaataa aacgtgcggc gctgggggag gggaggaaat ggggcgcgga cacccacact   2700
tgcgcctgca caccccacag gcgcagcgct cctcgcggcc cggagccgcc gcgcgcaccc   2760
tcctccggcg ccaggcagcc cagctcttcc acggcttctg ccgccggtcc agttggcgtc   2820
cgcgttgcag gtgggcatgc tgacgggaaa gtgtgtgtgt ttcgttttca gagaaagata   2880
```

-continued

```
aaagccagca ggggaagaat gaggacgtgg gcgccgagga cccgtctaag aagaagcggc   2940
aaaggcggca gcggactcac tttaccagcc agcagctcca ggagctggag gccactttcc   3000
agaggaaccg ctacccggac atgtccacac gcgaagaaat cgctgtgtgg accaacctta   3060
cggaagcccg agtccgggta ggagccagca cggagtctgg gagggatggg gggaggatgt   3120
tgtggaggta caggccaagt agaccaggag agaatgtgga aggcagcgcc gcctgggagg   3180
gcgccggtgg ggcgcagctt tgcaaaggca gaaggcctcg cggcggcctg gttgcgagat   3240
tacagttccc tctccgaggc cgacaggact gccgccctgg ctcaggctcc cagagcggca   3300
ccggctcact gccccgccat cccgcgatct cacgagctgg gctgcatggg caatcccctg   3360
cacaggacat tgtgttcctg gcttgcagtt gccagagcag agctaataaa atccctacca   3420
ggccaagagc cgcgaacagg ctccaacctg tgagccttta acaaggaaaa cccgccagag   3480
acacggaaga gttggccctc cctgggaaac ctttgtcccg gccctggccc agctttttcc   3540
ctcctgggct cgcgcttctt acaccttctt tacggttgtt tcggccattc aggtctctcc   3600
cacacaccct atttcctagt tttgtgatct ccgggagcaa agttttaata cacaactact   3660
agtcctctta gaaggagaaa gaaaaaaaga agaaagactt ttctgcttgg tttatttatc   3720
ttctctcagg agttgaactc tggaaattga aactcacacc ccctcttcta aattataatc   3780
atagttttgt aaaaagggct taccttaact ttgtagcaaa tctgtacttt atggattggc   3840
aaaaatgagc tcaaataaat aacccaatag caacgtcctg gtttatgctg gtcggtggaa   3900
gattccaaat ttgttaggat tctggaagca gaaaacagaa tcaagcaaat caagcggcat   3960
ccagaggctt tgctgttaaa aaaaaaaaat taagtgctct g                       4001
```

<210> SEQ ID NO 4
<211> LENGTH: 32001
<212> TYPE: DNA
<213> ORGANISM: Homo sapiens

<400> SEQUENCE: 4

```
tatggattgc gtgattatta aatttggtat tttagggggt atattttttt tgagtaattt     60
ttataaatat gtttgtttgt aggatattta gattttttgg tttggtagta aagtaatata    120
agaataattt tgaatttgat gtttattttt gttttttttt taattttagg agtttttttga    180
ggtttggatt aatttattga ttaggaaata gtatttggaa aggttaaata aaatattatt    240
tttagggaaa tagtatttgg aaaggttaaa taaaatatat ttttttagtt tttttaaatt    300
ttttagaaga tatatttttt aaaaaaataaa ttaagttagt aatatttaaa ttaaattttt    360
gttttgttta taatataaaa gatgataaaa aaattgttgg gaaggtgaga aattaatttt    420
atttataatt agaagtaaag tttttattta aaaatgtaat attatttaaa tttaatttgg    480
gaaataaaaa ggatttaaaa aatagtttgt taaagttaat ttgtaaataa gtgcgttttt    540
ttttttttta agttgtattt taggtttaga gtatatgtgt aggtttgtta tgtaggtaaa    600
tttgttatag ggatttgttg tatagattat tttgttattt aggtattaag tttcgtattt    660
aatagttatt ttttttgatt tttttttttt ttttattcgt tattttttaa taggttttag    720
tgtttgttgt tttttttttt gtatttatga gtttttttta tttagttttt atttataagt    780
gagaatatgc gttatttggt tttttggttt tgatttagtt tgttaaggat aatggttttt    840
agttttattt atatttttgt aaaaggtatg attttatttt ttttttaatt attttatttt    900
ttttattatt tttttttttt tttttaattt tgaattttat tatgttagtt taattatttt    960
tttttttttt tttttttttg tttatttgta tatagttaaa agatgttatg aatttttttt   1020
```

```
tttaatttag tatatgttta ttaaagattt aaaaatatta tttatattat ttagaattta   1080
gtttaagaaa ttattaaaaa ataaagttat tagaaagtaa ttgaattatt ttgttgagtt   1140
ataattttag atttcgattt tgtttttttt ttattttagg taggttattt tttttttttt   1200
tttaaattgt tttttttgta tttaataata tatttttgtg gatttagaaa gggtggagta   1260
tgaggaaaag gaatatgata tatgtatttt agaggaaaat aataaataaa tattttagga   1320
tggaaaatat tatttttatt tttattgagt tttttagagt ttatttgatt tgtgtaaatt   1380
agaaattagt agaatgatat taatgaatta atgaaaagta gaatgagtta ttagttgtaa   1440
taaaaagaat aaagaatttt aagaatatag ttttaattat gtatggttgc ggggagagaa   1500
aaataataaa atgtttttag tgaatatatt tttgagagaa gaaaggaaat atttaaggag   1560
aggataaaaa gagtaaatat taaaaatagg agtaagaatt ttattgtttt ttttagttga   1620
taaataaaaa ttgtatatat ttattgtgga taatatgata ttttgaggat tacgattatt   1680
tttgatttat aaattatatt taagaaaaag aaatttttaa aaagtttggg aatatatgaa   1740
gttgaaagaa tattaatatt tagataagga tagtatatga taaattattt ttgttttaat   1800
attttttttt aggaaattta aatatttttt agtgaagtat tagtttttttg aaattaagta   1860
tgagaaaaaa aattaaattt atttgtggaa aaaaagatat agttaaataa aaaagcggtt   1920
gttataattt taagagtggt atgaataaaa tgattaatat ttttttaagt gatagtataa   1980
atattaaaag ttttaataag tggaagtggt tttgttatga taaaaggtgt ggtatttgta   2040
taatttttag ataagaataa agttatgacg ttaagatagt agtagtattg tttgttatac   2100
gtgatatttg aaaaatatga taattatttt aatttgttta agtagtattt atggtgaggg   2160
tgaaatttta ttaatattgg ttaatttatg gtgttttaaa aaattagtaa ggagataaat   2220
tgatggatta aaagataaat tatttatagg tagataaata gaaggataga tagagttata   2280
attaaatatg tattttattt aggtagaaag ataataatta gtttttaaga agtgatgtgt   2340
ttgttagaaa agttttgaat atagaatttt ttgattttgt ttttaattta gtttttttag   2400
gtattacgtt gtataattag gtgtaatttt ttaaaagttt ttatgataga atttttttatt   2460
tgttaaatta ggttaataat atttttattt ttttttaggg taaagatgtg aaatatttgg   2520
agaattttgg aaaatatgtt ttttattaat tagagttttt tgatgtgata ttattttttt   2580
tagtatttgg agtttagtta atagatatat agtgtagttg tgaaattatg aagtatgaga   2640
atgtattatt aagggatcgt aggaggtttt ttattgaaaa gtgtagttgg ttatattttt   2700
ggaagtaatt taaatatagg ttgagggaga ggagtatttt ttagattttt tttagatttt   2760
attttttatg aattttaatt tttttttttt atttagaaaa aataatgaga tttatagcgt   2820
agagatagaa aataaggttt tgtgtgtttt taaattttat ttttaaaaat attatagtat   2880
tttggacgag atagttttga atttttgtaa tagtataggt atgagagttt ttattagaaa   2940
ataggagatt ggattgattt ttttattttt tttttatgtt ttttaaaatt gaaaagttat   3000
atatataaat tatatttatt tatttttttt ggaaaaggtt aaaatgaatt taattttgga   3060
ttatttttaa taatgggata aatttgaatt gagaataatt tttagaatta gttttgtttt   3120
tttgtgataa aatggatttg tagaaagtta tttggtgttt ttttttagtt aatattttat   3180
tataaataac gggtatgtaa tttagtattg ttttttatag gttatgtttt tggaattatt   3240
atttttgtat tttatttgtt tgttgatatt tttttattta agatgttttt tttagtataa   3300
gaagttattt tttttaaaat tttaaatgat tttattataa taatagagtt gttaattaga   3360
```

-continued

```
tttaggtaag taatgataat aaaaatttga tttttattta gagtgtagta tggtttaata   3420

taataattag agttttaata ggttttttta gattttattt ttatttaatt tgtatgtttt   3480

tgtaatatag atgtttttat tattcggttt ttatttttat ttttttttgt ttttggaata   3540

aaattattta aatttaattt agagatttta ttttttttttg gaattattgg gaaatagttt  3600

tagtaaatta tatttttgag attttatatt aggtttagtt taaattgatt atttaagtat   3660

taattttttt gtggtttagg aatatttttg agtttatttt ttttttttta aattgtttag   3720

gataaatatc ggagtttggt tttttttgttt ttttatttaa ttatttttcg tttttttttt  3780

tttagtattt aaaatatttt tgattttttt tattttttaa gaaatatatt tgtttttttg   3840

tttttgtatt atttttttgt ttatgaaata ttttataggt aagttttata tttttttttt   3900

ttagaggttt ttggtttttt ggttttagtt gttattggtt tagtgtatta gttaatattt   3960

tggattttgg agttatataa atttagattt aaatttttat tatgttattt attgtttacg   4020

tgatttgaag taatatttta tttattgtgg tttttagtag ttataagttt gtgttttaat   4080

tagttgggtg attttgggtt agtgatataa ttatggtaaa ttttattgtt tttatttgta   4140

aaatgatagt atttattttg tagtgttggt ataaggaata agtgtgattg ttaatataaa   4200

agtgtttagt ataatagtta aattaattaa gtattttgta aatattagtt tttattatta   4260

ttattaattt aaatgattag atgtattttg tgtatattag gtttttttgag tttattttgt  4320

ttttaataaa tattattatt tttagtatgt ggtttatatt atattttatt agttagagga   4380

tatgtgaagt ttagagtgga aagttagggt agtaggaagt attgttatat tttatatagt   4440

taaagttatt taaatatgtt tgaatttgag ttttgttgag tttttatttg tttttatttt   4500

ttttgtgtgt tttagtttat taataaagta ggtttaatat aaatatatta aaagtttaaa   4560

tattgagatt atgataatga atatgagggt tatgattata aaatattatt gaattagaga   4620

tttgttacga aattatatgg tgaagattat aagggaggaa tttgtatata tatcgagtgt   4680

tttgggattt taaagtggga agagttagtg ttttaattaa agagaaattc ggggtaggga   4740

attaattata atattagtta ttttattgaa tttaggtttg ttttagttga cgtagttgtt   4800

aatttttaat gttttttttt tttttaattg tttttaattt atttttttag aaattgaaag   4860

tttattaaag aggatatttt tttagagagt tgttttagtt attataagtt tttgttagaa   4920

attttaagaa agtttataag gtatttttat aaggtggtat tgagtaagtt agaagtattt   4980

taagtattaa ttattatgta aataagggtt ttatttttag attttgttgt ttgtggtggt   5040

ggtgatgttg gtgttttttt tggaatttag tttaattttt aaaaaagtaa aaggagtata   5100

aatagtaata taaattatta ttatttatat taattaaaat agaagttttg aatgagtaag   5160

gagttagagg aggtaaaaat tggaatttc gtatattaaa aggtttttat aatttgaaaa    5220

ttaagattat gttggttaaa taggttgttt taaaattagt atagtaatta aatttgtttg   5280

taatgaatgt agatttaaat agtgatgtta gatttgataa ggatttgtaa attttaaaag   5340

agtgtaaaaa gattatagaa gaataatatt atatttttgt atttatagaa atggttagtt   5400

taagagatgt atttagttta gggtggttgt aagttttatt ttttgaattt gttattagaa   5460

gttaaaagaa attttgtata attgtttttg atggaaatat aaattggttg atgtaaatga   5520

aatatataaa gtagttggtg ttttatttat ttttataatt ataaatgaaa ttaaatgatt   5580

aaaaattata gattttgggg attttttttt tattgaggag tttatggaat ttgttttttt   5640

tagtattaat aattgtgttg atttattttt ttttgtttaa ttttgtatat attaaaatta   5700

ggtggttacg aataaaattt agaaatataa tttatatttt aataaaatga ttttaaaatt   5760
```

```
attttatttt ttattgtggt tttatttgtt gttttataat gtaggttttt ttgggttttt   5820
gtttagaatg attttgttaa tgtagatgat agttagagtt gaatggggaa tttagaaatt   5880
ggggattcgg gtttttgatg taatttatat gttaatttat tttattagtt ttttttttat   5940
ttatagtttg gtaaagaata tgggtggagt tgttttgggt ttatttgtat atatgtttaa   6000
attgttttga aaaaggaagg gtaagaaaga gtggtattta agttggaatt aggtaggtat   6060
tttagattaa gagacgaatt ggaaagggaa tatttgttag atattttggg tttgaaggta   6120
gtttgtgtaa gtttttatat ttttgagtgt gtgtatatag tggagagggt ggagtttgtt   6180
atttttaaat ttgaaaagat tgagagattt tagagggttt agatgtgtta aaggttagag   6240
ggattaatat ataggtttta ttacggaaag gcggggaaaa ggttcgaata gaaaattgtt   6300
gtagaaggga agttattgag aggtaaggga gtttttgaat aattaaaaag ttaagaataa   6360
gtaaaaggaa ggaggtcggg tgggggataa aaaaaagtag ttgatgtggt aattaagaat   6420
ttggtgggag tttgggtagg ttattttttt ttttagatta gagttttatt agaaattttt   6480
ttaagtgttt ttttgcgtcg ttaaagatga taatagtaaa ttaataagtg tttgaaatga   6540
aaggggatgt tgattagttt ttaggttata gatttttcgt cgttagtttt ttttgaattt   6600
ttatagcgtg tttttgtatc gtttttttta agaagagtta ttttttattt ttatttttag   6660
gacgaaggta agtgtttagt tagtatattt attaaatgtt agttttggtt ttagtttttc   6720
gtttgcgcgg aaagtttatt gttatagcgc gtttagtttg tcggaggggt agatagaaaa   6780
agtaagtttg gtttggcgat ttgcggggtt acgtattttt agggttggtt cggagttttt   6840
tagagtttaa cgtttttggg ttagaattgt aaggtttcgg ttcgagtaaa gggtttgagt   6900
tatcgtagtc gtgggagcgt tttttttatt tgaatgtatt tatttataaa taagtataaa   6960
atttttttaa tagtagagga gaaagatttt tgttttaaaa ttaaagttgg gaattatcgg   7020
aaatttcgtt ttgagtgcga gatattggtt tgttattttt ttaattttta tatttttttt   7080
gtaatatgtt ttgatttaat aatttttttta gcgtttagta ttgttcggac gttttaattg   7140
ggtaatttat tagtgagtta atataggtat ttatatattt ttttagttta agtggttaag   7200
tattaatttc gaaatgatta taaaatatcg gaatcggtaa cgtatagtaa ttttaattta   7260
tatgtaaatt aattggttta ttttaaatgt ttttttttaaa aaaataatta ttgtattgta   7320
gtatcggagg tatggattaa atttttagaa tagataattc ggaaataaga tttggattag   7380
gaagataatt tagaatagtt aataaattaa taatgtttga ggtagttaaa tatcgttagt   7440
tattggtatt tatatattcg tttgttgtta gataaggagt tggggaaatt gtttgttagg   7500
gttgagatta taatttagag tgaagaaagt aaatggtagt atatagttcg ttatagcggg   7560
ttttgaaata atattgtatt ttttttaaat tttgattttt gggtgatagg gagttggcgg   7620
aggttatttt atatttgttt acggttttgt tttaatttga ttacgaaatt gttgtttttt   7680
ttgagttttt taatttgatt attattttaa cggttttgtt atttgtttta atatattggg   7740
gggaggagtg taattgagat ttttattaaa aattatttga atttatttag ttagtattgt   7800
tttatttaag tttagtttta tgggttgtat ttaatttttt gtgtttttta tatattaaaa   7860
ttagattatt aaaatgtcgg taggaaaggg tgaaggaaat ggtttaatgt tttagtttat   7920
tggaagatta ttatttttag atatagttta aaattttgag gaaataaaaa ggatatacgt   7980
tttgggggga aaatgtttta atattttaga atgggggtat tatttttttt attttagaga   8040
attcgtattg gagttgttta tgtaaaaatg taatattttt gaaatttata gatacgtaag   8100
```

```
gttagtgttt tttttttttt aggtttttag tttaggcgat ttagttttaa aggagttagt   8160
atttttgatg ttataatttt gtttatattt gtagggtaga gaattgtttg ttttgtttgg   8220
acgttttttt tatttttttt taatttgaag taatcggaat ttaaatatag tcgttaaggt   8280
tcgttttttt tttattgttt tgataaggga aaaatttgaa atttacgttt taaattagtt   8340
cggtggtttg tagtttttta gtattttgtt tttacgattg tatgtttaat gtattttttg   8400
gtgattttgg gtattaatta gttgtttaat aggagtatga ttaaaaatgt aaaagaagga   8460
ttaggagcgt gaaacgtatg tttagttttt tttatatatt cgaggaggga atgagaatta   8520
ttttgtattt tttatttttt taggagttat ttgtattttt tattagttgt ttattttagt   8580
tgtattggcg ttgggtaagg cgaggattta aaagtttagc gtagtgtttg cggcggtcgg   8640
gattggggtt aattagtttt tggcgggcga gattttagat agaagggggg cgagaggaac   8700
gtgagttttt cgagtttttt ttttttagtt ttggtttgta aatttttgaa atttgaaagg   8760
ggagggagtt gtacgcgcgt atttttgcgt tttttttagcg taattttttt tttttttttt   8820
gtgttttttc gcggattttt gaattttttt gtttttggtt tttttatttt tttttaattt   8880
ttttatgaga ttgtttattt tcgttattag ttgaaggtaa ggtcgttttg ttacgagcgt   8940
tttttaattt ttataaaatg aaaagaaaaa aagggaggat tattagttta ttatttagag   9000
gaatggggag gttgtaaaaa tcgtcgatgg gtagaggtga agatgttttt ttcggattgt   9060
atttttcggt gttttgtaat tagagtttag ttgtgggatt tgttgaagaa atttgatttt   9120
tttgtttcgg cgagatttta aaaattagaa atagaaattt ttagagttag agaggaaata   9180
taattaaata gtacgtgggt attttttttt ttattttttt ttttttaaat aatattgttt   9240
tgagttttta ttgggtaaag agagaaagtt tgagttttta cggatgttac gtggaggtta   9300
gaaatggttt aaaatgtaga tttttaatta gtttttttcg tggttgaaga ggttaatttt   9360
ttttataaaa tgagtttatt tgtcgattgt tagttatttt aaagtgaagg gatttagtat   9420
ttaaaataaa ttgagtaagt ttgtttgttt gtttttattg ttaatttaaa tgaatttaaa   9480
atacggagta atttaagaaa atatataata tgttttagat agtttttaaa agtagggaaa   9540
gtttagtatt tatatagtga ttagggttag ttttaagcgt taagtttttt taaacgtatt   9600
tattttatgt atatttttttc gagttattat atatttttaa aattgcgagt attggtatat   9660
tgatttagga agagtaatat aatttttaga gggaatttta tttttaatta gggattaaag   9720
agatgttttt ttaatagcgg gtttgagttt tgtttttaag taggaattaa tattggtggg   9780
aaaattcgaa tttaggagta atggttgtgt ttcggtattt tttaaaaata tatattaata   9840
ggatgttttt gagattgaaa aaatattgtt ttatatgttt ggtagaagtt tttatatttg   9900
gtttttttagg cgaattatat ttatagtttt tttatttaga ggtaggatag agttaaaata   9960
ttttgtttat tattaaaata tatatttttg tttaagttaa gaaattagaa aattagggtt  10020
tagaagtaag gtatattttt cgagtgagaa tatgttttgt aattttatat atttttttgtt  10080
ttgtaggagt aaatgtggat ttgagggaaa tttttttttt tatttttatt tttatttcgt  10140
gtaatttaat attattttcg ttaggaattt taatttcgtt attttaaaaa atgagatatt  10200
cgtgatttag ggtgaatttg ttgaatgtag gtatagtaga ggaaatttta gattttatga  10260
gcgtttgagt tttgtttagt gtaaattttt cgtgaatatt gggttagtgc gtggtcgtgt  10320
ttatttgtgc gtcgatattt ttagtatgtt tggtttattc gttttgattt cgggcgcggt  10380
gttttagtta agttgggttt agcgtttcgg tttttttttag ttgataagtt tagttcgttc  10440
gttttcggtt gtggtttttt tatttttttt tattagttta ttttattttt ttagattttt  10500
```

```
ttttatttat ttttttttat ttttatcgcg tttattttta ttttcgtttt ttatcggttt  10560
tttatttttt tttttcgta gttttttttt gttgtgattt ttttttttaa ttttgtaggt  10620
ttgaaagaag gttatatacg tacgtttata tttatatttt atacgtttcg ttttaaataa  10680
ttttatgaat attgtttttt gtttcgtttt ttgggttatt ttttttgtcg ttttttttta  10740
gttcgttttg atttgttttt taaaagtacg tttttgtttt ttcgttgttt tggcgttttt  10800
tttttgattt attagggttg tcgggttggc gtagattgtt tttttttttt ttttatttta  10860
tttttttttt tggttttttt ttttatagtg ggagttcgtg tttttgtttt tcggttggtt  10920
tttaagtgtt tcgttaggtt tttttttttt tcgtttttc ggtttcggtt ttcgattttt  10980
cggttcgttg gtatttgttt tttttttttg tttcgttttt cgtcgttttt gttcgttttt  11040
ttcggcgttc gttcgggcgt tgtgttcgtt tttggatcgt tagtcgcgta gtcgggttcg  11100
gtcggtcgtt cgcgcgttat tgtgtagtgg agtttggtgg aatttttgtt gacgttacgt  11160
tattttttat acggagtagg agtagaggga agagagaggg atgagaggga gggagaggag  11220
agagagtgcg agatcgagcg agaaagttgg agaggagtag aaagaaattg ttagtggcgg  11280
ttagatttcg gaggttttag tgtattcgtg gatttttttcg gaatttggta tttttaggag  11340
ttttgtagtt tttttaggtt cggttttcgg gcgtttgtcg tgtagtcgga ggttcggttc  11400
gttggaaatc gtttcgggaa gtagtgggac gcggagatag tagttttttt tcggtagtcg  11460
gtaagtggag gttatttatt tcgtagggat gtgagataat gcgagtttgg aaatttgttt  11520
tatttcggag aatttttatc gtaggtgatt tgtggttttt ggggttaagt ttcgtttaag  11580
gtaacgtagt cggtaaatag atttgtaaa gttttgtttt tttcgttttt cgttatagat  11640
attaataatt tatagggtgt tgaagtcgag agggaagtta gatcgtggtt ggtatttaaa  11700
acgaggtatt tttttttaaa tttcggtgtt aatattgtag gaataaattt tcgggttaag  11760
gattagtatt tttaagataa agggttgggt ataaagtttt agttattgga agattagttt  11820
tttttttatt gttatttatt gggaaaaaaa agaaaagaaa aagattttat tttaattggt  11880
agttagtgat tttttaggtt taagcgaatt atttgggagt taggtttgga tgttaagttt  11940
ttattatttt tttggattgt aattttttta aattgattat tagttaattt taatttggta  12000
ttttaggaga tatattttaa atggatgtag agaattattt tttagttgga gattaagaaa  12060
aaaatttcg attttaaatt ttcgaaatat gttttttttt tttagtttaa ttattttatt  12120
tttttaagta atttagaaat taaattatta taaggtggtg tgattttttt ttattttttt  12180
gtgtgagtat tgttttatta aattaaacgg aaaaaaattt tattattata aatgtaaata  12240
ttagaattta tatattttaa aatattttta tgaaaaatta atttgattta aagaaatttt  12300
tttgtatttg ttttagttta ttaattaaaa ttaaagatgt ttttattata taaaatatta  12360
ttttggtaga aatttattta aaatttaaat attaataata ttaagaaaat aaagtatata  12420
agtaaaataa attgaagatt tttgttgatg taatatgagt atataatatt ttaataatta  12480
aattttttttt aaaaaattaa atagttattt tatttgtgga atgttttatt ttaatttagt  12540
aaaattatat ttaaattatt taggtgtttt gtttttttaag ttaagcgtgt ttgtttttaa  12600
atgtttttaa agtatttata ttaattggtt gtaaagaacg tatatatatg gtaaaatata  12660
gaattgaatt gagtagtatt ttaatttttt taaataatta tttattataa attaatttat  12720
tggttaattt tataatttag tttatttaaa atatatgttt ttgtgttgtt tatttttaaa  12780
ttttttatta aagattttgt tatggggtaa taaagtgtat gaaaaggggg gaaatgtgaa  12840
```

-continued

```
aggatttggg attattcgaa ttgtattttt tttgtatttt tagttttgcg gtagttatta  12900
gaaattattt tttagtaaat tgttttattt tttagggttt gtttgtttgt tttgttatgg  12960
tttttcgttt ttcgttagtc gtgtagtgtt ttttgtgtgt ttataatata aaatttaagt  13020
tggttaaaat aagagttttt ggtatatata ttttaattag aatatgaatt ttgggggtga  13080
gaattatttt ttattaggaa aagtttttta ttttaatttg tgagattagt tattgaagtt  13140
agtttcgaag tttggtagtt aaatttttta tagaagattt gttttgatag ggtaagttta  13200
aggattagta ggcgggaatt ggaggttttt ttttaaaaaa ttattttttt tagttattta  13260
gatttagttt ttttagtagg tttggttatt aaatgaagta taaaaatgta agttttaagg  13320
tttattttga ttgtaaaata aatttttaag ttataaggat atgtaggagt gagttaagga  13380
atacgttttg attttttttt tagtttttag agtggagttt tatgagtttt tgaagatttg  13440
ttttgtattg ttttgtttgg tttttagtat tgaagtacgg ggaagtgggg ggaagaatgt  13500
gtaataattg attgatttta tattaagtaa cgtaattttt tttttttgta tattttattt  13560
tttaaaaaaa ataaataaat aaaaattatt tgtagttatt atttgtagtg tttcggttat  13620
tagttaataa tgtagttagt ttagatatat aaaaaaaaaa gattatcgaa atgatgatga  13680
tatgtaaatt tttttcgaaa ttattataag taaatatttg aagtttggat taataaaatt  13740
ttatttgtgt tattttatat cgagttagta gaaagttgtg ataatgaatt ttgtaatatt  13800
ttacgaatag atattttaat tagggattaa ttttgtgatt ttattgtaga attattaaat  13860
ttggagtcgt taaattgtta tttttgggtt tacgggttta taaggatcga atcggtagag  13920
ttttcgttcg cgttttcgtt agcgggtggg ggaatcgttt ggtcgttttt attttggatt  13980
tttacgttat agcgtcgggt agtttttttt gtaggtagcg attttggtta gaggtttttt  14040
agggtttagt tttttttagg agaggtcgag acgtagggaa acggtattta ggttagaggt  14100
aggttcgtag tttttttgttt cgtttttgtg ttttcgttaa ttcgataacg tttgttttta  14160
tttcgatttt cgtattcgcg cgaagtgggt ttttcggtcg tcggcgtatt ttggttagcg  14220
tggagagagg taggcgttga gatcgaaggg gtttagggag ttttggattt tttttttttg  14280
tttttaaagt aatcgcggtt tttttattta ttcggtggag tttttcgaga tttatttttt  14340
tcggtttgtt tgtggtagag aagggggagc gcgttaaatg tttggttcgt tgcgttgtgg  14400
ttgaaaacgt gaaaaagatt tggttcgttc gggagagaaa gggggagaat tgggtagtag  14460
ttatattaga gttatttttt cgtttttggc gggtagtaaa ttttttaaga acgtttgttt  14520
tgtttttttt agtttcgttt agtttattta gtgttttttt tttgcgattt taaattatat  14580
tttagggtaa ttatttgtag taagtaaata aatggtcggg ttagtatttt taggagaaag  14640
tgtggttaaa tatggaaaag tggtttttga tggatgagag gttcgaattt agttcgtttt  14700
tgaaatattt taggttaaga gttcgttcgt tttagaatta tagaaaatcg agggaaattg  14760
ttgtttagga taggggtacg ttggcgttga tgttttataa atgtttatcg agttttaatt  14820
aatggataag tattgaaggg tggtttttgt atatagtttt ttaaagagaa aagttttttt  14880
tatttattta ttttcgttgt tattgcgttt agatgagttt ttaatttcgg tatcgagatt  14940
tttgaaagta ggtttatagt ttttttagta tattgtggtt ttatagtttt ttaatttttg  15000
ggtatttttg cggtaatttt ggagggagat ttttttttga taaataaatg ttttgggttc  15060
gaggttaggt tggagatgtt gttgtatagt tagaggttgt taggtcggaa aaatacgttt  15120
gaagtttagt atatagtagg cgtttaatag ttagtgtaac gtagttttat ttgagttttg  15180
tttattcgac ggtcgtcgtt ttttatagtt tttttttttt tttgttttgt agataacggg  15240
```

gaatggagat taattgtcgt aaattggtgt cggcgtgtgt gtaattaggt aagaattttt 15300
tttttttgtt cgggttatcg gacgggaggt cgcgttacgt gagggcggta agagggtatt 15360
ggttttgcgg cgaggtttta gcgaggggcg ttttttcgag gggttagttt gggtaggaag 15420
gaaattagaa ttaaatcgtt agtggttttt ttttgtggcg gggcggtgga ttaggaagta 15480
gcggcgcgtt gtgtatcgaa gtttttagt ttattttttt cggttggaat cgtcggtaat 15540
cggggaggcg tagaaagagt acgttatttt gtttcgggtt gttagagggt tcgggggacg 15600
gggatgtcgt tagttttttt ttttaattgg gtttttgttt tttgtttttt ttttttttc 15660
ggtttgtttc gttttttttt ttttttcgt tttcggtttt tttcggtcgc ggttcgggac 15720
gttttttttc gtacgtgggg cgggcgcgcg cgtggtttag gcgtgtagtc ggcggtcgtt 15780
gaatgttttt tttttaaaga tttcgaaatt aaaaaggtcg agtttacgga ttttttttgag 15840
agtcgaaaag aggtagttag tagtaagttt ttttcgcggt agtattttgg cgttaatggt 15900
aaggtcggga gggaagcgta ggtcgcgcgt tgggtattcg ttttcgggat tttgggtttc 15960
gggcgaagcg taagaaggcg aggtcgttag atttgacgcg tttgttgttt gaatttagat 16020
atttcgtttt tgggtgggac gggaagtagt cgttttaggg acgttaattt tttttttaa 16080
attatattgt atttttgaga tttaatattt tttttttttt ttcgttcgtt ttttgtggtt 16140
tgattttttg cgtacgtttt agtaaatttc ggcgtttagg ttggcgtgga aaagtggttt 16200
aatagcgatt tttgtcgttc gttatatttc gttgcgcgta gtattattag ggtttattta 16260
gttatttagg tttttagtta cgttttattt agatttgtgg gtgcgcggtt tatcgcggga 16320
ggtaagtaag ggaaatttga gttggcgaag gtttgttttg gttggttggg ggaggggcgg 16380
ggggtcgata atatttttga agagttggag ggtagttatt gtgtttagta gtttagggta 16440
gaatggaggt ttgtttttgt cgacgcgaat ttgtttgaag tattggttgt taggttttgg 16500
gttttggcga tgtcgttgtt tgattggttg gttttatttt ggaggaatcg agggatattg 16560
ttagaggagg tttataggtt tatgtaaaaa gttaaaaagt ttttaattta cgttataggt 16620
tttttttgaa ttgaaatttg ttttatgggg cggagggggg ggtgtaaggg atggaggagg 16680
gaagatgttt tttttttttaa atatatggaa aaaaattttt taaatttatt gttttttat 16740
ttttttggtt tcgtagtaaa taagtgttta gttttaggag gttattgatt tttgataatg 16800
tgagtagata aagttttttt tttttatag ttttcggttt ttaattttttt tttttcggat 16860
taaagtgtaa gaatataaat gtaatatggg atggaggggg gcgatttggg atttcggtta 16920
aaaaaataaa tcgtattatt aagaagaaaa taaaggtttt gtattggagt tttttcgtga 16980
atttgagaga aaatgattat ttgttgaaat gaagcgttta aagcgattta gtgttttacg 17040
ttcggatatt gtattatatc gttagtcgtt ttgttgggtt agttaaacgt ttatttgttc 17100
gggattaatt ttatggggtt aaatgggggt aatgtagaga taacgtcgcg tgatttttgt 17160
tatttagatt gtgttaaatt ttttttttgt ttgataatcg gtagtaaaaa taaattatta 17220
gatcgtagta tgtttgggat atggttaaaa attaagagta gcgatgattt ttggggagaa 17280
tgttttgcgc gggtttagtt ttggtttcgg ttagattaga ggagtttttt aatttcgttt 17340
cgcgcggggc gggttcgtag tcgttaagtc gaggttgata ttttttattg tgttgggagt 17400
tagagagacg taaaatgttt tttttttta gtttttattt taggtttttt agatatgggg 17460
aatgtatttt gaggataggt ggagaagttt acggtaggat ggggttttcg taggtgagta 17520
ggaaacggtt aagagtagag gagttttgtt tgcgttagtt ataagtcgcg taggcgtttt 17580

-continued tggtcgttcg tttttgataa ttagtatata aagaattaga aataatgaat gattgttttt 17640
ttaattatta tttttaggtt cgtattgttt tagtgtacgt gaaaggtttt ttttttatat 17700
ttaatatgtt ttttttttatt ttttgatcga aaagaaaaat tgttgtttaa atacgtttaa 17760
tgttattaat taagaaaagg tatgtaatgg gaagaaatgt tgaaaatttt gatttaattg 17820
gtttttaagg aattagtaga cgataaaaaa aaattatacg agtgggtaaa gttatagtat 17880
tgttgaagga tagagtattt attttttttt gattttaagt taatttatgg aatatttaaa 17940
gttttggtta tagtttgttt gtaaaataaa aggatttatt ttttgtgttt ttttaaagtt 18000
tttttttgtt tttaaagaga aaaaaagttt ataatgatat atgatttttt taaaaggtcg 18060
tgatagttta ttacgttatt tttttcgttt ttgtttttaa cgtcgtttaa aaatattatg 18120
ttttcgttaa agattaaacg ttttgtatag gtagagttta tttttaagta gtttaggttt 18180
tgtttttttt ttttagtgag ttttattttt tttggtattt attgggcgga tgtttagttt 18240
ggatagaatt tcgaaacggg ggtagtacga gagcgattgg agatttttaa aagttagagg 18300
tttgagagag ggtggacgta gttagtagaa gatggtgtag aagttagttg agaacgattt 18360
tttagagtaa agagattttt ttttggtttt ttttgttttg ggggttttga aaggaattta 18420
taaaatggtt tttatttttta ggaggaggac ggattgattt ttttttgtta ttggtttaaa 18480
aagttttagg gcggcggttt tgggtttcgt gttgaaatcg gattgtattg tagttttttt 18540
ggatttgacg tttggttttg cgtttcgata aggggcgggt attttttttcg gtttttttta 18600 ggaacgtatt aattgttaaa tagttttggt ttagtggatg ggttgaaagt gttcgattta 18660
agtcgttggt gtgtatagat tttttttttt tgggaggtgg gttttatggt tcgttgtggt 18720
atttttagtc gcgatatata tttttatacg cggtagtagt tcggttttaa tttttttcga 18780
aggatttggg ttaattttgg cggttttggc ggtcgtagat tttttttcgt cgtttcgttt 18840
tcgcgttttt tatttaatta gcgaatgttt gcggagtata tattacgtgg atttttaatg 18900
tattttttga aagtaaataa tatagttttt ttcgtcgtta tgaagggatt ttaattttaa 18960
tatggatatt agcgagatta gtttagatcg tttttagtaa aacgtaaaat ggtggtgcgt 19020
ggggtggtga ttaaggtttt gagttttgtt agaaagaagg ggatgtgtag agaaaggtgg 19080
agaattttag ttgtggttag cgcggaaggg ataggtgttt gtcgaagggg gtatgaggtt 19140
tgaggaaaaa gtaacgaaat aggggtaagg agagtttttt attttttttt tttcgttcga 19200
ttttcgttat tttatttttt tttttttttt tttatttttc gcgttaatta aatttgtagt 19260
ttatttgaaa ggtgtttcgt cgcgttgtgg tttttttattt ttaggggaaa ttgtattagt 19320
tgttcgaaag tagttagttt ttgcggattt ttgttcgtaa aagtggtttt tataggtcgc 19380
gtttttcgtt gttgattcgg tatataaagt tttttaaggt tggttcggtt gttatttttt 19440
atcgttcgtt gttaatatat gtagtagttg ttagagcggt tcgggggaaa aggaaatgta 19500
taacgaaagt ttattcgtga gtaggaatat attaatggaa taatttgatg ttttttttaat 19560 tttatgtaaa aagttttgtc gtttttttaa tattgattga atgggtaatt aatggttttt 19620
tatttaggcg aatattttgt aatttaagat aggtaaaaga taataagttt aaggtagaag 19680
ataaaaggtt taattgtagc ggcgtttgtt cgttttttat tttttagggt ttttgattag 19740
gaaagttttt ttttagagga gaaaaaggta ggagtgggag aatatatatt tattatttcg 19800
gggttagatt ttatcgtagt atttgattat ttagtttagt tttttgttat tttgtttttt 19860
tatttttagt tttttttttt gtattttttt tttttttttaa ttttttttagg atgatttttt 19920 attattatcg ttattatggt tttaataatt ttttttttta aattttatat tttttatttt 19980
agtaattaat gaggttgttt tttgatttag gaggagattt ttttttttta gaatttaatg 20040
cgtagagttt ttgagaatta aagtagttgg taggggagga agaaattaat agaaagggag 20100
agagtatata gaattgtgtg tgtatgttaa agagcgatta ggaatgatag agttaatttt 20160
tttgtgagga tttgacggga agagtgttta agattttatt agtatgtttt taataggttg 20220
atattttaat ttaaattttt agaagtaata tattatttgg gttattataa tgaggtgggt 20280
tttttttttt ttgttagttg atagttttta aaatattatt tcgttaggga aataaaagtt 20340
ttattttaga ttataggtgg gtatttttgg atttaggtga tttatggtta ttatgataat 20400
taatgttgaa tgttagttat tagtatgttt gggagagaga aaatagaaag aagggagagt 20460
aaaagaaata gaaaagggag atggatataa gttggagagg gaagaaaaga gaaaaagagg 20520
aagatagatg agtgtttaat ttaattgttg tttaaaaaag tggcgggggg gtgggatttt 20580
atttagtttt ttgttatttt tttttttttt gatttggata tttatgttta attttatatt 20640
ttattttttt tttttttttt ttaaatatat gtgttatatt atttttttta ttttatttag 20700
ttcggtaagt agttgttttt tggagattta gtgatattta ggaaaattgt ggtagtaata 20760
tgtaaatgtg aggaagtatt aatagtatgt tcgttgagtg attttagtaa atgttttttt 20820
ttttaatttt tttttttttt tttttttagg ttattgtgag gtggtaattt ttattgttat 20880
ttgaatattg tttttttagg tagttatttt aaattttaaa tggttgagta gttagagttg 20940
tgggttggaa aaatgggtat tatttgtagg gatttagaga gggtggttgt tgtttaatat 21000
atttatagat ttttaattta gaaaataatt tttttttttt gataagttag agttttttaa 21060
attttattta ggaaatgggg aaaaggatag ttatagtgaa gtttttaatt tttgggttat 21120
ttggttttat agttatgagg ggtggtgggt agtggattgt ttttagtttg gtttgtatgt 21180
agagaaaagt tagatattgg agggggtggg gtatttttcg ggtaggatgt aaggttttta 21240
tttgattttt gcgttttatt aggagtttat atatttacgt ttattacgtg gttttaagtt 21300
gagtttaggc gggtttcgtt tttgagttag tttgggtagg gtaggatttt tattcgttta 21360
aggtttaata gtttagggag atgtttaatt aagttatttt ttgggtgaat tttgaagata 21420
gatttttttt aaaagttaga gattatttgg ttgagtttta ggttagattg atacggagag 21480
tttggcggta tagtttaatc gtttattgtt atggttagag ggattttgta taattaatat 21540
tgaagagtgt gaaattaaat aagattttaa gattggtaat cggtggtaaa tattagtata 21600
aaatacggtt gattttatgt tatatatttt tttttttag ggtttttttt tgaaagaata 21660
agtaagaaat tttaatcgag ataattttg atgtttttta gatttaaaat tttacgtcgg 21720
tattgggttt tttttttttg ttttacgtga gttatgtagt atttttagtt tttttattag 21780
gattttatta atgtttttcg tattggaaat ttttgtgtta gaggttgaat ttatagtaat 21840
ttttaaaatt aattaagaag aatttagtta gaggttatag taatgttgga attataaaat 21900
gtataagatt tatttttttt tggttttttt tttatttatg ttgtttatgt ttgtgtattt 21960
ataagtttta tgtatattaa atttttaaaa ttaattatta ttatgttata gagtttttat 22020
tggatagtgt tttttagttt ttattatata tttttttttt tttatgtaga tttattatgt 22080
tggtgttttg ttatataggg ggtttgagaa gaatgttatt taatcgtcgt tgttgtgagt 22140
gtgtaaagtg attaggagat taggagaatg ttgaaatttt tgttggaaaa atgtaaagaa 22200
aatttttatt ttgagttagt tgtttataga gttagtgtgt gtgtgcgtgt gtgtgtttgt 22260
aatataaaat ggatgtgaat atatatatat aaatagatat ggttttgttt ttattttaat 22320

-continued

```
ttgaattatt tagataattg tttttattta ttatttgatt ttaatgggtt tatataaatt  22380
aggatatttt atttttttag gtatttaggt tgttgttgat ttttagtgtt tttaatattt  22440
cgtatacgtt ggtattatga ggagtagtta cgtgtttttg ggttttttaa ttattttgga  22500
ggttgattga ggtttttttat atatgtatat ttgtcgtgat gaaagtttta tcggtagagt  22560
ggagttatta gagtttttat taaaattttg tgggtttatg agagatgggt ttagaaattt  22620
atatggtttt gtggggtttt tcggtttttt aaaataaggt attaatattt aagtttttaa  22680
aaatatttgt agttttgggg tttgaatttt gaaaaataag gagtgagggg ttgtgtatat  22740
taattatagt ggagattttt tttatttttt aatgtgatgg agttttttta tgaaatgaag  22800
ttttaagggg tatggtattg tggggattat agttattttg aggtttaaaa gaagaaattg  22860
gaatatgatt agtaaatata tttagtagaa aagagttgga tttttattga tttagttata  22920
ggttatcggt tggtagtgta atgggaggaa atatttattt tatatatata ttttatgatt  22980
ttgggggaat tagaggaaat ttaataagaa aacggttaga aatatttaaa atttttattt  23040
aaaagattta agtaaattag agttttatta gattaaaaat tattataaat gtaagagtat  23100
tgtttttagt gaaacgttgt ggggtttgag aaggagattt ttcgttaaat tttcgggata  23160
aaatgcgtta tttaagtatt agataatgag tagaatgtaa attaatttaa ttttttttat  23220
taataggttg ttagtgtaat gtgtataatt tagtgataag attgtaggat ttaatatagt  23280
tggatgtatg agttttagtt aatgtagatt tgttatatga ggatgtgttt tattttgagt  23340
aggtgtttgt atgtgtggaa tggggtaaag tggaataaaa ggttaaaagt agaaatgttg  23400
atttaaagtt tattatgaag aaattttttt tttgtagtta aattattttt aaagtgggat  23460
gatattggtg aagaaagatt gaaaaataat ttttatgtgc gtttttggat tgtaagttta  23520
aaatggggag gagttgtaga tagggtttgg gggtggttag ggtaaaggag agatatataa  23580
gttgtaaata tatttgtagt ttgttttatt tattttgttt tatatcgaat aagtttttta  23640
attttgtgaa taaggataag gagggagtgt tttaaagata ttttatgttg gtattgtaaa  23700
ttattgattg taatgttaaa taaatatata tttagagatg ataatattaa ttttatagta  23760
aaataatcgt ttatgtagaa atttagagga gattagtttg tttttttttag ttgatttatg  23820
ttgggggata aaaggatttt taaaaattat tttgaatatg tttggatttt tttttttaat  23880
ttttttggaa attaaatttg tttggaaata gtgttataaa gagttgatgt ttttaaaggt  23940
gatttttttt gttttatata aataaggttt tgtttttgtt agttgagcgt agttttaggt  24000
ttttcgtttt tagtttatat atattttttt tgtttgtttg gattttaatg gtttaagata  24060
gttttgagtt tattgggaaa agaaaatgat tgttaaaaat tatttttgaa attggttatt  24120
tggtaatatt tttaattgta tggaaattta ttaaggtata ttttatatat aattagttta  24180
aggttgttga ttttataggt tttatggatt taaatttgat tgataataaa gtaaataaga  24240
gagtcgaatt taaagcgtgg ttttttcggg ttaggacgag tttaatatag tgtataagga  24300
atttgaaaga tttaggatat gtgttttaat taacgttaag tagaatggat aagtttttag  24360
tattttgaaa acgttgggtt agggtttttt ttttattgtg tgttttttgt ttggggatta  24420
ataagtatta tagagaacgt gatttgaggc gattttttat ttttgtataa atttagagtg  24480
aattattaaa tagttgttcg tttaaagtta aggtaatttt tttttgacgg gtttatttgt  24540
ttttcgattt ttaatttatt agtttgtttt tttagggttt tgtttttttt gtaattaaag  24600
ttttttttaga ttagcgtagt atttatttga taggttgttt ggaaaattta agatcggaga  24660
ggtgatttgt tgttgttttt taaatttttt agttttaagt aacgtgtttt tttttttatat  24720
```

-continued

```
ggggtggggg attggaaatg gatgtagtga gatataaaga gtgggtgttt tgttgatttt 24780
tgtatttttt tttttttgat tattttattt ttttttttta agttttcgat ttttagtttt 24840
attttttat ttttgggttc gtattaaaag tcggatcgtt ttgggttggg taggagttga 24900
attttcggga gtttgtttgt gtagatttag tgcgtacggc gaggtagtag ttcggtttcg 24960
tattgttgat aggtgtaggt aggatagttt ttttatcgcg gttcggggcg ttttgattgg 25020
tgcggagtta cgttagtcgt attcggagaa gggtttggga ggaggcggag gcggagaggg 25080
ttggggaggg tcgcggcgga gtgacgtttc ggtattagga agttcgtttt tggttttaag 25140
atgttaggtt aatagggaag cgcggagtcg tagatttggt tcgtcgttcg tttgggtgtt 25200
tggagttgag ttgcggtaag gttcggtttt tgttcgatcg ttcgaggggt gtgcgtgtgc 25260
gcgttgcgga gggtgcgttt agagggtcgc gtcgtggttg tagcggttgt tgtcgtcgta 25320
ggggatttaa tattatttat ttgtttttgt tatttttgat atttttttgt tagggttgtc 25380
gcgtgggggg ggggcgggta gagcgcggtc ggcgttagtt tttttattg gaggggtttt 25440
tgggggaggg agggagagaa gaagggggtt tttgtttatt tttgtttcgt tttggagttt 25500
ggaagtttgt tttttaaaga cgttttgagt ggtgtttttt tgtttatatt ttatgttttc 25560
gtttgttcgt tgatttttcg ttttcggatt ttttcgtttg agtttttcgg aggagacggg 25620
ggtagtttgg tttgagaatt cggcgggggt tgcgtttttt ggtttttttc gtagcgggga 25680
aatttcgcgt ttagagcgcg attcggagcg ggtagcggcg gttacggggg ttcggcgggg 25740
tagtagttaa ggattagtag agcgtcgcgt tttttcgttt atgaattgta tgaaaggttc 25800
gttttatttg gagtatcgag tagcggggat taagttgtcg gtcgtttttt tatttttttg 25860
ttattatttt tagtcgttag ttatggtttc ggttttggtt ttcggttagt ttcggtcgtt 25920
ggattttttt aagtataggt tggaggtgta tattattttc gatattttta gttcggaggt 25980
cgtaggtaag gcgtcgcgtc gttttgtaga tattttcgtt tagttgtttt gcgttattcg 26040
tttttttcg ttttaaggaa gttagttttt tcgggggggag gcgtggtggg agtggtcgtt 26100
cgtttggttt ttcgtagaat tttcgggagt cggaattttg attatttcgt atttttttag 26160
ttttttttcg atcggttcgg tttttggggc gttaagggcg cgagtaattt tgtcgttttt 26220
tttattcgta ttttggtttt ttttttgttt tttgggttat aaaaatttta gtattttgat 26280
tcgaggattt ttagaggtcg tcgattttttg tttttgtttt tttttcggtt tttagttttc 26340
gaggagtttt attcgttagg aaattgtttg aaattattta gaaatgtttt tcgcgaagag 26400
gtattttttt ttttttttttg ggaaagggtc ggcgaatttc ggtgtttaat cgaattttta 26460
tatttttttt tagttttttt aaatcgtatg gaaatttgag tttttttgcga gggggagggg 26520
ggtttgtaaa ttacgcgcgt gtgcgcgttt taggagattt ggtgtgtttg cgtagaggtg 26580
tataaatata tttgaaagta taggttataa aagtgaatgt gtcgttgtag tgagataaat 26640
atgtaaataa aacgtgcggc gttgggggag gggaggaaat ggggcgcgga tatttatatt 26700
tgcgtttgta tattttatag gcgtagcgtt tttcgcggtt cggagtcgtc gcgcgtattt 26760
tttttcggcg ttaggtagtt tagttttttt acggtttttg tcgtcggttt agttggcgtt 26820
cgcgttgtag gtgggtatgt tgacgggaaa gtgtgtgtgt ttcgttttta gagaaagata 26880
aaagttagta ggggaagaat gaggacgtgg gcgtcgagga ttcgtttaag aagaagcggt 26940
aaaggcggta gcggatttat tttattagtt agtagtttta ggagttggag gttatttttt 27000
agaggaatcg ttattcggat atgtttatac gcgaagaaat cgttgtgtgg attaatttta 27060
```

```
cggaagttcg agttcgggta ggagttagta cggagtttgg gagggatggg gggaggatgt  27120
tgtggaggta taggttaagt agattaggag agaatgtgga aggtagcgtc gtttgggagg  27180
gcgtcggtgg ggcgtagttt tgtaaaggta gaaggtttcg cggcggtttg gttgcgagat  27240
tatagttttt ttttcgaggt cgataggatt gtcgttttgg tttaggtttt tagagcggta  27300
tcggtttatt gtttcgttat ttcgcgattt tacgagttgg gttgtatggg taattttttg  27360
tataggatat tgtgtttttg gtttgtagtt gttagagtag agttaataaa atttttatta  27420
ggttaagagt cgcgaatagg ttttaatttg tgagttttta ataaggaaaa ttcgttagag  27480
atacggaaga gttggttttt tttgggaaat ttttgtttcg gttttggttt agtttttttt  27540
tttttgggtt cgcgtttttt atattttttt tacggttgtt tcggttattt aggttttttt  27600
tatatatttt atttttttagt tttgtgattt tcgggagtaa agttttaata tataattatt  27660
agttttttta gaaggagaaa gaaaaaaaga agaaagattt ttttgtttgg tttatttatt  27720
ttttttttagg agttgaattt tggaaattga aatttatatt ttttttttta aattataatt  27780
atagttttgt aaaaagggtt tattttaatt ttgtagtaaa tttgtatttt atggattggt  27840
aaaaatgagt ttaaataaat aatttaatag taacgttttg gtttatgttg gtcggtggaa  27900
gattttaaat ttgttaggat tttggaagta gaaaatagaa ttaagtaaat taagcggtat  27960
ttagaggttt tgttgttaaa aaaaaaaaat taagtgtttt gggtagaaaa aataaagttt  28020
tcggttagag tagagtaaat aaaaagaaga aaataacgat aaaaagaata aagattaaaa  28080
tgttttttta aattagaggg aatgaagata ttttttgggt ggtatttgtg taaggtatga  28140
ggttatgttg gtggataaaa ggtcgggaag aagttgaaaa tggttttagt ttaattgttt  28200
agagttagag ttgggttttg ggcggcgtgg ttttgagtaa ggttagtttt ttattagttt  28260
ttttgtatat taagggaacg ggttttttac gtattttttt cgtttgagta aagtttagat  28320
ggtttagggt agaaatggta agtaattaaa gatagagttt atgggttttt tgggattttt  28380
cgaaaacgtt tttttatttc gttcgttatt tcgtagtttt attttagtgt tttgtagtcg  28440
cggcgttggg ttttttttgt agttgttttt ttttttaggg cggttgtttg tcgagttaag  28500
tgggagtgag gcgtgttttt tatagtagtc gggtgtaaag aggaaggggg ataaaaagga  28560
aattaagaat gaaaggaaaa agagaaaaag cggattatac ggttgggttc ggcggagatg  28620
tgtaatgtga aatattattg gtgttagttc ggatatttta ggttaggttt ttttttaata  28680
tataaaagtc gtcgtttggg gcgataggga ggttcgatgt ggattgggat cggggttgcg  28740
gttgggttat cggatacggg tggaagtcgg tcggtttggg tggtcgtttg taaagttaaa  28800
cgattcggtt gggtttggcg cgcggatagg tttgtggtgg gtttagggta aagaagaggt  28860
agagcgaaag aagggggaat ttttaaaatt atttttttcg ggttttcgga gtttaatatg  28920
ttaagttttt ggagttaacg agttgacgaa gaggtggttt tttgtttttt atttggttgt  28980
tttgttaggc gagaaagagt gttggcggtt tagtttttgt taagggagta cgtattaggg  29040
ggtgggggac gatagtggag gttagggaag gaagggagga attgcgtggg agaaagagcg  29100
atttttagt gttttttttag ttttttttttt ttattcgtgg gtttgtggtt ttggaatgga  29160
agtaagtttg taaggtgttt cgggaagggt tggaaaagtt tgttgtttcg cgtttgtttt  29220
atattaagtg tttttggatt tggagaaacg tttggttgag tgattaaatc gttcgtaggt  29280
ttttatgcgt tcggttgagg tttgtggcgt agtttcgagt tttagttcgt aggttagagt  29340
agattaggtt ttttgcgttt ggtggagatt cgggttagta attgaaagtt ggttttggta  29400
ttttggtgtg tagggcggtg tagtgaagcg aggttagggt gtgtgagtgc gttagcgtgt  29460
```

-continued

```
gtgtcggggg aaggcggggg ttggttttcg atggaagttt tagtaatttg tattgtggta  29520
tttgtttgtt tttttgtttt aatcgttttt aggtttggtt taagaatcgt cgggttaaat  29580
ggagaaagag ggagcgtaat tagtaggtcg agttatgtaa gaatggtttc gggtcgtagt  29640
ttaatgggtt tatgtagttt tacgacgata tgtatttagg ttattttat aataattggg   29700
tcgttaaggg ttttatattc gttttttat ttattaagag tttttttttt tttaatttta  29760
tgaacgttaa tttttgtta ttatagagta tgttttttttt atttaatttt atttcgttta  29820
tgagtatgtc gtttagtatg gtgtttttag tagtgatagg cgtttcgggt tttagtttta  29880
atagtttgaa taatttgaat aatttgagta gttcgtcgtt gaatttcgcg gtgtcgacgt  29940
ttgtttgttt ttacgcgtcg tcgatttttt cgtatgttta tagggatacg tgtaattcga  30000
gtttggttag tttgagattg aaagtaaagt agtattttag tttcggttac gttagcgtgt  30060
agaattcggt ttttaatttg agtgtttgtt agtatgtagt ggatcggttc gtgtgagtcg  30120
tatttatagc gtcgggattt taggattttg tcggatgggg taatttcgtt tttgaaagat  30180
tgggaattat gttagaaggt cgtgggtatt aaagaaaggg agagaaagag aagttatata  30240
gagaaaagga aattattgaa ttaaagagag agttttttg attttaaagg gatgttttta   30300
gtgtttgata ttttttatta taagtatttt taatagttgt aaggatatat atataaataa  30360
atgtttgatt ggatatgata ttttaatatt attataagtt tgttattttt taagtttagt  30420
attgttaata tttaaatgat tgaaaggatg tatatatatc gaaatgttaa attaatttta  30480
taaaagtagt tgttagtaat attataatag tgtttttaaa ggttaggttt taaaataaag  30540
tatgttatat agaagcgatt aggatttttc gtttgcgagt aagggagtgt atatattaaa  30600
tgttatattg tatgttttta atatattatt attattataa aaaatgtgtg aatattagtt  30660
ttagaatagt tttttggtg gatgtaatga tgtttttgaa attgttatgt ataatttatt   30720
ttgtgtataa tatttcgtat aatattattg ttttattttt tagtaaatat gaaataaatg  30780
tgttttattt tatgggagta aaatatattg tatataaatt ggtttggatt tttttttttt  30840
tttttgtta ttaatttggt taggatattt tagttattgt tttttaaata aattagtttt   30900
ttttgtttgt ttagttaaat atataaggta gtagttttta tttaaatttg gtagaaataa  30960
atgatagtta tttattagaa attaaaaaga aaaaaaaagg tattttcggg ggggaaaagg  31020
gttataaaat ttaattttgt ttttttaatt ttttttggt ttaaatttag aggattttat   31080
tatggttagt aaataatatg aaaaagaaaa aagaagaaag aaatttagta agtttattag  31140
tttaaaatga tttttaagtt tatttttta cggggaaatt tatattttta gtaaattgtt   31200
ttggagaaat atttgtgtat gtatatatgt atagtttata tgtatttttt ttaggaggaa  31260
tatatttata ataaatttat agggaaatat ttttagttta aaatatttag gtttttacgt  31320
ttatttttag gtttaagtag agagattttt tatgttatat tgtattatta tttttaaatt  31380
ttttggagat attaaaagaa ataaagatga tttttaataa ttatagtttt ttagtttttt  31440
aaagaattta ggggttgaga ggttagagtg gagtttttg agttttgtcg agtaatatgt   31500
agttgaggta aaggttatgt tttcggtgtt ttgttttaaa taatattgat ttattaattt  31560
taaatttgtt tgtttttgaa attatatagg attatagttt gtaaattgta ggataatgaa  31620
gtaaattaag atgaattata gttttggttt tttttgttat tttttgatat ttaaataggg  31680
aatgagttcg gtgtgagtgt ttaaatgaat tttaagtatt cgattttttt ttattcgcga  31740
tttttagttt taaaaaaatg tgaaatttga ttttataata aatagaaata aatattattt  31800
```

agttttagag aatttatttt tatggcgtta ggagggtcgt tgtggaggtg gggggaggga 31860
tgtgttgaga ttttttgtta tgtttgttaa tttttcgtat aattaaagtg ggcgagaata 31920
aatattacgt tggggaattt agagtaaaaa gtaatcgtcg attttttgga gtcgataata 31980
ttattgtttt ttcgttttag t 32001

<210> SEQ ID NO 5
<211> LENGTH: 12001
<212> TYPE: DNA
<213> ORGANISM: Homo sapiens

<400> SEQUENCE: 5
tatggattgc gtgattatta aatttggtat tttagggggt atattttttt tgagtaattt 60
ttataaatat gtttgtttgt aggatattta gatttttttgg tttggtagta aagtaatata 120
agaataattt tgaatttgat gtttattttt gttttttttt taattttagg agtttttttga 180 ggtttggatt aatttattga ttaggaaata gtatttggaa aggttaaata aaatattatt 240
tttagggaaa tagtatttgg aaaggttaaa taaaatatat ttttttagtt tttttaaatt 300
ttttagaaga tatattttttt aaaaaataaa ttaagttagt aatatttaaa ttaaattttt 360
gttttgttta taatataaaa gatgataaaa aaattgttgg gaaggtgaga aattaatttt 420
atttataatt agaagtaaag tttttattta aaaatgtaat attatttaaa tttaatttgg 480
gaaataaaaa ggatttaaaa aatagtttgt taaagttaat ttgtaaataa gtgcgttttt 540
ttttttttta agttgtattt taggtttaga gtatatgtgt aggtttgtta tgtaggtaaa 600
tttgttatag ggatttgttg tatagattat tttgttattt aggtattaag tttcgtattt 660
aatagttatt tttttgatt ttttttttt ttttattcgt tattttttaa taggttttag 720
tgtttgttgt ttttttttt gtatttatga gtttttttta tttagttttt atttataagt 780
gagaatatgc gttatttggt tttttggttt tgatttagtt tgttaaggat aatggttttt 840
agttttattt atatttttgt aaaaggtatg attttatttt tttttaatt attttatttt 900 ttttattatt ttttttttt tttttaattt tgaattttat tatgttagtt taattatttt 960 ttttttttt ttttttttg tttatttgta tatagttaaa agatgttatg aatttttttt 1020
tttaatttag tatatgttta ttaaagattt aaaaatatta tttatattat ttagaattta 1080
gtttaagaaa ttattaaaaa ataaagttat tagaaagtaa ttgaattatt ttgttgagtt 1140
ataattttag atttcgattt tgtttttttt ttattttagg taggttattt ttttttttt 1200 tttaaattgt ttttttgta tttaataata tatttttgtg gatttagaaa gggtggagta 1260
tgaggaaaag gaatatgata tatgtatttt agaggaaaat aataaataaa tattttagga 1320
tggaaaatat tatttttatt tttattgagt tttttagagt ttatttgatt tgtgtaaatt 1380
agaaattagt agaatgatat taatgaatta atgaaaagta gaatgagtta ttagttgtaa 1440
taaaaagaat aaagaatttt aagaatatag ttttaattat gtatggttgc ggggagagaa 1500
aaataataaa atgtttttag tgaatatatt tttgagagaa gaaaggaaat atttaaggag 1560
aggataaaaa gagtaaatat taaaaatagg agtaagaatt ttattgtttt ttttagttga 1620
taaataaaaa ttgtatatat ttattgtgga taatatgata ttttgaggat tacgattatt 1680
tttgatttat aaattatatt taagaaaaag aaatttttaa aaagtttggg aatatatgaa 1740
gttgaaagaa tattaatatt tagataagga tagtatatga taaattattt ttgttttaat 1800
attttttttt aggaaattta aatatttttt agtgaagtat tagtttttttg aaattaagta 1860 tgagaaaaaa aattaaattt atttgtggaa aaaaagatat agttaaataa aaaagcggtt 1920

-continued

```
gttataattt taagagtggt atgaataaaa tgattaatat ttttttaagt gatagtataa   1980
atattaaaag ttttaataag tggaagtggt tttgttatga taaaaggtgt ggtatttgta   2040
taatttttag ataagaataa agttatgacg ttaagatagt agtagtattg tttgttatac   2100
gtgatatttg aaaaatatga taattatttt aatttgttta agtagtattt atggtgaggg   2160
tgaaatttta ttaatattgg ttaatttatg gtgttttaaa aaattagtaa ggagataaat   2220
tgatggatta aaagataaat tatttatagg tagataaata gaaggataga tagagttata   2280
attaaatatg tatttttattt aggtagaaag ataataatta gtttttaaga agtgatgtgt   2340
ttgttagaaa agttttgaat atagaatttt ttgattttgt ttttaattta gttttttttag   2400
gtattacgtt gtataattag gtgtaatttt ttaaaagttt ttatgataga atttttttatt   2460
tgttaaatta ggttaataat atttttattt tttttttaggg taaagatgtg aaatatttgg   2520
agaattttgg aaaatatgtt ttttattaat tagagttttt tgatgtgata ttattttttt   2580
tagtatttgg agtttagtta atagatatat agtgtagttg tgaaattatg aagtatgaga   2640
atgtattatt aagggatcgt aggaggtttt ttattgaaaa gtgtagttgg ttatattttt   2700
ggaagtaatt taaatatagg ttgagggaga ggagtatttt ttagattttt tttagatttt   2760
atttttttatg aattttaatt tttttttttt atttagaaaa aataatgaga tttatagcgt   2820
agagatagaa aataaggttt tgtgtgtttt taaattttat ttttaaaaat attatagtat   2880
tttggacgag atagttttga atttttgtaa tagtataggt atgagagttt ttattagaaa   2940
ataggagatt ggattgattt ttttattttt tttttatgtt ttttaaaatt gaaaagttat   3000
atatataaat tatatttatt tattttttttt ggaaaaggtt aaaatgaatt taattttgga   3060
ttattttttaa taatgggata aatttgaatt gagaataatt tttagaatta gttttgtttt   3120
tttgtgataa aatggatttg tagaaagtta tttggtgttt tttttttagtt aatattttat   3180
tataaataac gggtatgtaa tttagtattg ttttttttatag gttatgtttt tggaattatt   3240
atttttgtat tttatttgtt tgttgatatt tttttattta agatgttttt tttagtataa   3300
gaagttattt ttttttaaaat tttaaatgat tttattataa taatagagtt gttaattaga   3360
tttaggtaag taatgataat aaaaatttga tttttattta gagtgtagta tggtttaata   3420
taataattag agttttaata ggtttttttta gattttattt ttatttaatt tgtatgtttt   3480
tgtaatatag atgtttttat tattcggttt ttattttttat ttttttttgt ttttggaata   3540
aaattattta aatttaattt agagatttta tttttttttg gaattattgg gaaatagttt   3600
tagtaaatta tattttttgag attttatatt aggtttagtt taaattgatt atttaagtat   3660
taattttttt gtggtttagg aatattttttg agtttatttt tttttttttta aattgtttag   3720
gataaatatc ggagtttggt tttttttgttt ttttatttaa ttattttttcg tttttttttt   3780
tttagtattt aaaatatttt tgattttttt tatttttttaa gaaatatatt tgttttttttg   3840
tttttgtatt atttttttgt ttatgaaata ttttataggt aagttttata tttttttttt   3900
ttagaggttt ttggtttttt ggttttagtt gttattggtt tagtgtatta gttaatattt   3960
tggattttgg agttatataa atttagattt aaatttttat tatgttattt attgtttacg   4020
tgatttgaag taatatttta tttattgtgg ttttttagtag ttataagttt gtgttttaat   4080
tagttgggtg attttgggtt agtgatataa ttatggtaaa ttttattgtt ttttatttgta   4140
aaatgatagt atttattttg tagtgttggt ataaggaata agtgtgattg ttaatataaa   4200
agtgtttagt ataatagtta aattaattaa gtattttgta aatattagtt tttattatta   4260
```

-continued

```
ttattaattt aaatgattag atgtattttg tgtatattag gtttttgag tttattttgt   4320
ttttaataaa tattattatt tttagtatgt ggtttatatt atattttatt agttagagga   4380
tatgtgaagt ttagagtgga aagttagggt agtaggaagt attgttatat tttatatagt   4440
taaagttatt taaatatgtt tgaatttgag ttttgttgag tttttatttg tttttatttt   4500
ttttgtgtgt tttagtttat taataaagta ggtttaatat aaatatatta aaagtttaaa   4560
tattgagatt atgataatga atatgagggt tatgattata aaatattatt gaattagaga   4620
tttgttacga aattatatgg tgaagattat aagggaggaa tttgtatata tatcgagtgt   4680
tttgggattt taaagtggga agagttagtg ttttaattaa agagaaattc ggggtaggga   4740
attaattata atattagtta ttttattgaa tttaggtttg ttttagttga cgtagttgtt   4800
aatttttaat gttttttttt tttttaattg tttttaattt atttttttag aaattgaaag   4860
tttattaaag aggatatttt tttagagagt tgttttagtt attataagtt tttgttagaa   4920
atttaagaa agtttataag gtatttttat aaggtggtat tgagtaagtt agaagtattt   4980
taagtattaa ttattatgta aataagggtt ttatttttag attttgttgt ttgtggtggt   5040
ggtgatgttg gtgttttttt tggaatttag tttaattttt aaaaaaagtaa aaggagtata   5100
aatagtaata taaattatta ttatttatat taattaaaat agaagttttg aatgagtaag   5160
gagttagagg aggtaaaaat tgggaatttc gtatattaaa aggtttttat aatttgaaaa   5220
ttaagattat gttggttaaa taggttgttt taaaattagt atagtaatta aatttgtttg   5280
taatgaatgt agatttaaat agtgatgtta gatttgataa ggatttgtaa attttaaaag   5340
agtgtaaaaa gattatagaa gaataatatt atatttttgt atttatagaa atggttagtt   5400
taagagatgt atttagttta gggtggttgt aagttttatt ttttgaattt gttattagaa   5460
gttaaaagaa attttgtata attgtttttg atggaaatat aaattggttg atgtaaatga   5520
aatatataaa gtagttggtg ttttatttat ttttataatt ataaatgaaa ttaaatgatt   5580
aaaaattata gattttgggg attttttttt tattgaggag tttatggaat ttgttttttt   5640
tagtattaat aattgtgttg atttattttt ttttgtttaa ttttgtatat attaaaatta   5700
ggtggttacg aataaaattt agaaatataa tttatatttt aataaaatga ttttaaaatt   5760
attttatttt ttattgtggt tttatttgtt gttttataat gtaggttttt ttgggttttt   5820
gtttagaatg attttgttaa tgtagatgat agttagagtt gaatggggaa tttagaaatt   5880
ggggattcgg gtttttgatg taatttatat gttaatttat tttattagtt ttttttttat   5940
ttatagtttg gtaaagaata tgggtggagt tgttttgggt ttatttgtat atatgtttaa   6000
attgttttga aaaaggaagg gtaagaaaga gtggtattta agttggaatt aggtaggtat   6060
tttagattaa gagacgaatt ggaaagggaa tatttgttag atattttggg tttgaaggta   6120
gtttgtgtaa gtttttatat ttttgagtgt gtgtatatag tggagagggt ggagtttgtt   6180
atttttaaat ttgaaaagat tgagagattt tagagggttt agatgtgtta aaggttagag   6240
ggattaatat ataggtttta ttacggaaag gcggggaaaa ggttcgaata gaaaattgtt   6300
gtagaaggga agttattgag aggtaaggga gtttttgaat aattaaaaag ttaagaataa   6360
gtaaaaggaa ggaggtcggg tgggggataa aaaaaagtag ttgatgtggt aattaagaat   6420
ttggtgggag tttgggtagg ttattttttt ttttagatta gagttttatt agaaattttt   6480
ttaagtgttt ttttgcgtcg ttaaagatga taatagtaaa ttaataagtg tttgaaatga   6540
aaggggatgt tgattagttt ttaggttata gatttttcgt cgttagtttt ttttgaattt   6600
ttatagcgtg tttttgtatc gttttttttta agaagagtta ttttttattt ttatttttag   6660
```

gacgaaggta agtgtttagt tagtatattt attaaatgtt agttttggtt ttagtttttc 6720
gtttgcgcgg aaagtttatt gttatagcgc gtttagtttg tcggaggggt agatagaaaa 6780
agtaagtttg gtttggcgat ttgcggggtt acgtattttt agggttggtt cggagttttt 6840
tagagtttaa cgtttttggg ttagaattgt aaggtttcgg ttcgagtaaa gggtttgagt 6900
tatcgtagtc gtgggagcgt tttttttatt tgaatgtatt tatttataaa taagtataaa 6960
atttttttaa tagtagagga gaaagatttt tgttttaaaa ttaaagttgg gaattatcgg 7020
aaatttcgtt ttgagtgcga gatattggtt tgttattttt ttaattttta tatttttttt 7080
gtaatatgtt ttgatttaat aatttttttta gcgtttagta ttgttcggac gttttaattg 7140
ggtaatttat tagtgagtta atataggtat ttatatattt ttttagttta agtggttaag 7200
tattaatttc gaaatgatta taaaatatcg gaatcggtaa cgtatagtaa ttttaattta 7260
tatgtaaatt aattggttta ttttaaatgt ttttttaaaa aaaataatta ttgtattgta 7320
gtatcggagg tatggattaa atttttagaa tagataattc ggaaataaga tttggattag 7380
gaagataatt tagaatagtt aataaattaa taatgtttga ggtagttaaa tatcgttagt 7440
tattggtatt tatatattcg tttgttgtta gataaggagt tggggaaatt gtttgttagg 7500
gttgagatta taatttagag tgaagaaagt aaatggtagt atatagttcg ttatagcggg 7560
ttttgaaata atattgtatt ttttttaaat tttgattttt gggtgatagg gagttggcgg 7620
aggttatttt atatttgttt acggttttgt tttaatttga ttacgaaatt gttgtttttt 7680
ttgagttttt taatttgatt attattttaa cggttttgtt atttgtttta atatattggg 7740
gggaggagtg taattgagat ttttattaaa aattatttga atttatttag ttagtattgt 7800
tttatttaag tttagtttta tgggttgtat ttaatttttt gtgtttttta tatattaaaa 7860
ttagattatt aaaatgtcgg taggaaaggg tgaaggaaat ggtttaatgt tttagtttat 7920
tggaagatta ttatttttag atatagttta aaattttgag gaaataaaaa ggatatacgt 7980
tttgggggga aaatgtttta atattttaga atgggggtat tatttttttt attttagaga 8040
attcgtattg gagttgttta tgtaaaaatg taatattttt gaaatttata gatacgtaag 8100
gttagtgttt tttttttttt aggtttttag tttaggcgat ttagttttaa aggagttagt 8160
atttttgatg ttataatttt gtttatattt gtagggtaga gaattgtttg ttttgtttgg 8220
acgttttttt tatttttttt taatttgaag taatcggaat ttaaatatag tcgttaaggt 8280
tcgttttttt tttattgttt tgataaggga aaaatttgaa atttacgttt taaattagtt 8340
cggtggtttg tagtttttta gtattttgtt tttacgattg tatgtttaat gtatttttttg 8400 gtgattttgg gtattaatta gttgtttaat aggagtatga ttaaaaatgt aaaagaagga 8460
ttaggagcgt gaaacgtatg tttagttttt tttatatatt cgaggaggga atgagaatta 8520
ttttgtattt tttattttt taggagttat ttgtattttt tattagttgt ttattttagt 8580
tgtattggcg ttgggtaagg cgaggattta aaagtttagc gtagtgtttg cggcggtcgg 8640
gattggggtt aattagtttt tggcgggcga gattttagat agaagggggg cgagaggaac 8700
gtgagttttt cgagtttttt ttttttagtt ttggtttgta aatttttgaa atttgaaagg 8760
ggagggagtt gtacgcgcgt atttttgcgt ttttttagcg taattttttt tttttttttt 8820
gtgttttttc gcggattttt gaattttttt gtttttggtt tttttatttt tttttaattt 8880
ttttatgaga ttgtttattt tcgttattag ttgaaggtaa ggtcgttttg ttacgagcgt 8940
tttttaattt ttataaaatg aaaagaaaaa aagggaggat tattagttta ttatttagag 9000

-continued gaatggggag gttgtaaaaa tcgtcgatgg gtagaggtga agatgttttt ttcggattgt 9060
atttttcggt gttttgtaat tagagtttag ttgtgggatt tgttgaagaa atttgatttt 9120
tttgtttcgg cgagatttta aaaattagaa atagaaattt ttagagttag agaggaaata 9180
taattaaata gtacgtgggt attttttttt ttattttttt tttttaaat aatattgttt 9240 tgagttttta ttgggtaaag agagaaagtt tgagttttta cggatgttac gtggaggtta 9300
gaaatggttt aaaatgtaga tttttaatta gttttttcg tggttgaaga ggttaatttt 9360
ttttataaaa tgagtttatt tgtcgattgt tagttatttt aaagtgaagg gatttagtat 9420
ttaaaataaa ttgagtaagt ttgtttgttt gtttttattg ttaatttaaa tgaatttaaa 9480
atacggagta atttaagaaa atatataata tgttttagat agtttttaaa agtagggaaa 9540
gtttagtatt tatatagtga ttagggttag ttttaagcgt taagtttttt taaacgtatt 9600
tattttatgt atatttttc gagttattat atatttttaa aattgcgagt attggtatat 9660
tgatttagga agagtaatat aatttttaga gggaatttta tttttaatta gggattaaag 9720
agatgttttt ttaatagcgg gtttgagttt tgtttttaag taggaattaa tattggtggg 9780
aaaattcgaa tttaggagta atggttgtgt ttcggtattt tttaaaaata tatattaata 9840
ggatgttttt gagattgaaa aaatattgtt ttatatgttt ggtagaagtt tttatatttg 9900 gtttttagg cgaattatat ttatagtttt tttatttaga ggtaggatag agttaaaata 9960
ttttgtttat tattaaaata tatatttttg tttaagttaa gaaattagaa aattagggtt 10020
tagaagtaag gtatattttt cgagtgagaa tatgttttgt aattttatat attttttgtt 10080
ttgtaggagt aaatgtggat ttgagggaaa ttttttttt tatttttatt tttatttcgt 10140
gtaatttaat attattttcg ttaggaattt taatttcgtt attttaaaaa atgagatatt 10200
cgtgatttag ggtgaatttg ttgaatgtag gtatagtaga ggaaatttta gattttatga 10260
gcgtttgagt tttgtttagt gtaaattttt cgtgaatatt gggttagtgc gtggtcgtgt 10320
ttatttgtgc gtcgatattt ttagtatgtt tggtttattc gttttgattt cgggcgcggt 10380
gttttagtta agttgggttt agcgtttcgg ttttttttag ttgataagtt tagttcgttc 10440
gttttcggtt gtggtttttt tattttttt tattagttta ttttattttt ttagattttt 10500
ttttatttat tttttttat ttttatcgcg tttattttta ttttcgtttt ttatcggttt 10560 tttattttt tttttcgta gttttttttt gttgtgattt ttttttttaa ttttgtaggt 10620
ttgaaagaag gttatatacg tacgtttata tttatatttt atacgtttcg ttttaaataa 10680
ttttatgaat attgtttttt gtttcgtttt ttgggttatt ttttttgtcg ttttttttta 10740
gttcgttttg atttgttttt taaaagtacg tttttgtttt ttcgttgttt tggcgttttt 10800
tttttgattt attagggttg tcgggttggc gtagattgtt tttttttttt ttttatttta 10860 ttttttttt tggttttttt ttttatagtg ggagttcgtg tttttgtttt tcggttggtt 10920
tttaagtgtt tcgttaggtt ttttttttt tcgtttttc ggtttcggtt ttcgattttt 10980
cggttcgttg gtatttgttt ttttttttg tttcgttttt cgtcgttttt gttcgttttt 11040
ttcggcgttc gttcgggcgt tgtgttcgtt tttggatcgt tagtcgcgta gtcgggttcg 11100
gtcggtcgtt cgcgcgttat tgtgtagtgg agtttggtgg aatttttgtt gacgttacgt 11160 tatttttat acggagtagg agtagaggga agagagaggg atgagaggga gggagaggag 11220
agagagtgcg agatcgagcg agaaagttgg agaggagtag aaagaaattg ttagtggcgg 11280
ttagatttcg gaggttttag tgtattcgtg gatttttcg gaatttggta tttttaggag 11340
ttttgtagtt tttttaggtt cggttttcgg gcgtttgtcg tgtagtcgga ggttcggttc 11400
gttggaaatc gtttcgggaa gtagtgggac gcggagatag tagttttttt tcggtagtcg 11460
gtaagtggag gttatttatt tcgtagggat gtgagataat gcgagtttgg aaatttgttt 11520
tatttcggag aatttttatc gtaggtgatt tgtggttttt ggggttaagt ttcgtttaag 11580
gtaacgtagt cggtaaatag attttgtaaa gttttgtttt tttcgttttt cgttatagat 11640
attaataatt tatagggtgt tgaagtcgag agggaagtta gatcgtggtt ggtatttaaa 11700
acgaggtatt ttttttaaa tttcggtgtt aatattgtag gaataaattt tcgggttaag 11760
gattagtatt tttaagataa agggttgggt ataaagtttt agttattgga agattagttt 11820 ttttttatt gttatttatt gggaaaaaaa agaaaagaaa aagattttat tttaattggt 11880
agttagtgat tttttaggtt taagcgaatt atttgggagt taggtttgga tgttaagttt 11940
ttattatttt tttggattgt aattttttta aattgattat tagttaattt taatttggta 12000
t 12001

<210> SEQ ID NO 6
<211> LENGTH: 4001
<212> TYPE: DNA
<213> ORGANISM: Homo sapiens

<400> SEQUENCE: 6
ttttcgtttt tagtttatat atattttttt tgtttgtttg gattttaatg gtttaagata 60
gttttgagtt tattgggaaa agaaaatgat tgttaaaaat tatttttgaa attggttatt 120
tggtaatatt tttaattgta tggaaattta ttaaggtata ttttatatat aattagttta 180
aggttgttga ttttataggt tttatggatt taaatttgat tgataataaa gtaaataaga 240
gagtcgaatt taaagcgtgg ttttttcggg ttaggacgag tttaatatag tgtataagga 300
atttgaaaga tttaggatat gtgttttaat taacgttaag tagaatggat aagtttttag 360
tattttgaaa acgttgggtt agggtttttt ttttattgtg tgttttttgt ttggggatta 420
ataagtatta tagagaacgt gatttgaggc gatttttat ttttgtataa atttagagtg 480
aattattaaa tagttgttcg tttaaagtta aggtaatttt tttttgacgg gtttatttgt 540
ttttcgattt ttaatttatt agtttgtttt tttagggttt tgtttttttt gtaattaaag 600
tttttttaga ttagcgtagt atttatttga taggttgttt ggaaaattta agatcggaga 660
ggtgatttgt tgttgttttt taaatttttt agttttaagt aacgtgtttt ttttttatat 720
ggggtggggg attggaaatg gatgtagtga gatataaaga gtgggtgttt tgttgatttt 780
tgtatttttt ttttttgat tattttattt ttttttttta agttttcgat ttttagtttt 840
atttttttat ttttgggttc gtattaaaag tcggatcgtt ttgggttggg taggagttga 900
attttcggga gtttgtttgt gtagatttag tgcgtacggc gaggtagtag ttcggtttcg 960
tattgttgat aggtgtaggt aggatagttt ttttatcgcg gttcggggcg ttttgattgg 1020
tgcggagtta cgttagtcgt attcggagaa gggtttggga ggaggcggag gcggagaggg 1080
ttggggaggg tcgcggcgga gtgacgtttc ggtattagga agttcgtttt tggttttaag 1140
atgttaggtt aatagggaag cgcggagtcg tagatttggt tcgtcgttcg tttgggtgtt 1200
tggagttgag ttgcggtaag gttcggtttt tgttcgatcg ttcgaggggt gtgcgtgtgc 1260
gcgttgcgga gggtgcgttt agagggtcgc gtcgtggttg tagcggttgt tgtcgtcgta 1320
ggggatttaa tattatttat ttgtttttgt tatttttgat atttttttgt tagggttgtc 1380
gcgtgggggg ggggcgggta gagcgcggtc ggcgttagtt ttttttattg gaggggtttt 1440

-continued

```
tgggggaggg agggagagaa gaagggggtt tttgtttatt tttgtttcgt tttggagttt   1500
ggaagtttgt tttttaaaga cgttttgagt ggtgtttttt tgtttatatt ttatgttttc   1560
gtttgttcgt tgatttttcg ttttcggatt ttttcgtttg agtttttcgg aggagacggg   1620
ggtagtttgg tttgagaatt cggcgggggt tgcgtttttt ggttttttttc gtagcgggga   1680
aatttcgcgt ttagagcgcg attcggagcg ggtagcggcg gttacggggg ttcggcgggg   1740
tagtagttaa ggattagtag agcgtcgcgt tttttcgttt atgaattgta tgaaaggttc   1800
gttttatttg gagtatcgag tagcggggat taagttgtcg gtcgtttttt tattttttttg   1860
ttattatttt tagtcgttag ttatggtttc ggttttggtt ttcggttagt ttcggtcgtt   1920
ggattttttt aagtataggt tggaggtgta tattattttc gatattttta gttcggaggt   1980
cgtaggtaag gcgtcgcgtc gttttgtaga tattttcgtt tagttgtttt gcgttattcg   2040
ttttttttcg ttttaaggaa gttagttttt tcggggggag gcgtggtggg agtggtcgtt   2100
cgtttggttt ttcgtagaat tttcgggagt cggaattttg attatttcgt atttttttag   2160
ttttttttcg atcggttcgg tttttggggc gttaagggcg cgagtaattt tgtcgttttt   2220
tttattcgta ttttggtttt ttttttgttt tttgggttat aaaaatttta gtattttgat   2280
tcgaggattt ttagaggtcg tcgatttttg tttttgtttt tttttcggtt tttagttttc   2340
gaggagtttt attcgttagg aaattgtttg aaattattta gaaatgtttt tcgcgaagag   2400
gtattttttt tttttttttg ggaaagggtc ggcgaatttc ggtgtttaat cgaattttta   2460
tattttttttt tagttttttt aaatcgtatg gaaatttgag tttttttgcga gggggagggg   2520
ggtttgtaaa ttacgcgcgt gtgcgcgttt taggagattt ggtgtgtttg cgtagaggtg   2580
tataaatata tttgaaagta taggttataa aagtgaatgt gtcgttgtag tgagataaat   2640
atgtaaataa aacgtgcggc gttgggggag gggaggaaat ggggcgcgga tatttatatt   2700
tgcgtttgta tattttatag gcgtagcgtt tttcgcggtt cggagtcgtc gcgcgtattt   2760
tttttcggcg ttaggtagtt tagttttttt acggttttttg tcgtcggttt agttggcgtt   2820
cgcgttgtag gtgggtatgt tgacgggaaa gtgtgtgtgt ttcgttttta gagaaagata   2880
aaagttagta ggggaagaat gaggacgtgg gcgtcgagga ttcgtttaag aagaagcggt   2940
aaaggcggta gcggatttat tttattagtt agtagtttta ggagttggag gttatttttt   3000
agaggaatcg ttattcggat atgtttatac gcgaagaaat cgttgtgtgg attaatttta   3060
cggaagttcg agttcgggta ggagttagta cggagtttgg gagggatggg gggaggatgt   3120
tgtggaggta taggttaagt agattaggag agaatgtgga aggtagcgtc gtttgggagg   3180
gcgtcggtgg ggcgtagttt tgtaaaggta gaaggtttcg cggcggtttg gttgcgagat   3240
tatagttttt ttttcgaggt cgataggatt gtcgttttgg tttaggtttt tagagcggta   3300
tcggtttatt gtttcgttat ttcgcgattt tacgagttgg gttgtatggg taatttttttg   3360
tataggatat tgtgtttttg gtttgtagtt gttagagtag agttaataaa atttttatta   3420
ggttaagagt cgcgaatagg ttttaatttg tgagttttta ataaggaaaa ttcgttagag   3480
atacggaaga gttggttttt tttgggaaat ttttgtttcg gttttggttt agtttttttt   3540
tttttgggtt cgcgtttttt atattttttt tacggttgtt tcggttattt aggttttttt   3600
tatatatttt atttttagt tttgtgattt tcgggagtaa agttttaata tataattatt   3660
agtttttttta gaaggagaaa gaaaaaaaga agaaagattt ttttgtttgg tttatttatt   3720
ttttttagg agttgaattt tggaaattga aatttatatt tttttttta aattataatt   3780
atagttttgt aaaaagggtt tattttaatt ttgtagtaaa tttgtatttt atggattggt   3840
```

aaaaatgagt ttaaataaat aatttaatag taacgttttg gtttatgttg gtcggtggaa 3900
gattttaaat ttgttaggat tttggaagta gaaaatagaa ttaagtaaat taagcggtat 3960
ttagaggttt tgttgttaaa aaaaaaaaat taagtgtttt g 4001

<210> SEQ ID NO 7
<211> LENGTH: 32001
<212> TYPE: DNA
<213> ORGANISM: Homo sapiens

<400> SEQUENCE: 7
attaaggcga aaaaataatg atattgtcgg ttttagaaaa tcggcggtta ttttttgttt 60
taagtttttt agcgtggtgt ttgttttcgt ttattttggt tgtgcggggg gttgataagt 120
ataataaaag attttagtat attttttttt ttatttttat aacgattttt ttagcgttat 180
gaggatgaat tttttgggat taagtggtat ttgtttttat ttgttatgaa attaaatttt 240
atattttttt aaagttgaaa atcgcggata aagaaggatc gggtgtttaa agtttattta 300
aatatttata tcgaatttat tttttgttta gatgttagag gatggtaggg agggttaggg 360
ttgtaattta ttttgatttg ttttattgtt ttgtagtttg taaattataa ttttgtataa 420
ttttaggaat aagtaggttt agaattaatg ggttaatatt atttaaaata aaatatcggg 480
agtatgattt ttgttttaat tatatattgt tcgataagat ttaggaaatt ttattttaat 540
tttttaattt ttgagttttt tgagaaattg aagggttgta gttattagaa attatttttg 600
ttttttttaa tgtttttaaa ggatttggaa atagtaatgt aatataatat gaaggatttt 660
tttatttaag tttgaagata aacgtggaag tttaaatatt ttgaattgga gatgtttttt 720
tgtaaattta ttatagatgt atttttttg agagaaatgt atataaatta tatatgtata 780
tatgtataaa tattttttta gaataatttg ttagaggtgt aggttttttc gtaaaggagt 840
aaatttgaga gttattttaa gttgatggat ttgttaaatt tttttttttt tttttttttt 900
ttatattatt tgttagttat aatggaattt tttaggttta agttaaagaa aaattggaga 960
gataaaatta gattttgtag tttttttttt tttcgggaat gttttttttt tttttttag 1020 tttttgatga atggttatta tttattttta ttaaatttaa ataaggattg ttgttttgta 1080
tgtttaatta ggtaggtaga gggaattggt ttgtttagga agtagtgatt gagatgtttt 1140
ggttaagtta gtgatagagg aggggagaaa gaatttagat taatttgtat gtagtatatt 1200
ttatttttat gaaataaaat atatttgttt tatatttgtt gaaaagtaaa ataataatat 1260
tgtacgaaat gttatatata gggtaggttg tatatagtag ttttagaaat attattgtat 1320
ttattagaga aattatttta aaattgatat ttatatattt tttataataa taataatatg 1380
ttagaaatat atagtgtggt atttagtata tatatttttt tgttcgtaag cgaaaaattt 1440
taatcgtttt tgtataatat gttttatttt aaagtttaat ttttaaaaat attgttgtga 1500
tattattaat aattgttttt ataaaattaa tttgatattt cgatatatat atattttttt 1560
agttatttaa atgttaataa tgttaaattt aaaaaataat aagtttatag taatgttaaa 1620
atgttatatt tagttaaata tttgtttgtg tatgtgtttt tgtaattgtt agaaatattt 1680
gtagtgaaag atgttagata ttgaggatat ttttttgaaa ttaaaggagt tttttttttg 1740
atttagtggt tttttttttt ttatatagtt tttttttttt tttttttttt tagtgtttac 1800
gattttttag tataattttt agttttttaa gggcggagtt gttttattcg gtaaggtttt 1860
aggatttcgg cgttgtgggt gcggtttata cgggtcggtt tattgtatat tggtaagtat 1920

```
ttaggttgga ggtcgggttt tgtacgttgg cgtagtcgaa gttggagtgt tgttttgttt   1980
ttagttttag gttggttagg ttcgagttat acgtgttttt ataaatatac ggaggagtcg   2040
gcggcgcgta aggataggta ggcgtcggta tcgcggaatt tagcgacggg ttatttaggt   2100
tgtttaagtt atttaggttg ttgagattgg agttcgggac gtttgttatt gttgagggta   2160
ttatgttgga cgatatgttt atggacgaga tagagttggg tggggaaaat atgttttgtg   2220
atgatagggg gttgacgttt atagagttga agaaggggaa gtttttggtg gatagggagg   2280
cggatgtaag gtttttggcg gtttagttgt tgtaggaata gtttgggtat atgtcgtcgt   2340
agggttgtat gagtttattg aattgcggtt cgaagttatt tttgtatagt tcggtttgtt   2400
ggttgcgttt ttttttttt tatttggttc gacgattttt gaattaaatt tgggggcggt   2460
tggggtaagg gagtaaatag atgttatagt gtagattatt aaaattttta tcggaggtta   2520
attttcgttt tttttcgata tatacgttag cgtatttata tattttggtt tcgttttatt   2580
gtatcgtttt gtatattaag atattagggt tagtttttag ttattggttc gggtttttat   2640
taagcgtagg agatttggtt tgttttggtt tgcgagttgg gattcggagt tacgttataa   2700
attttagtcg aacgtatgga gatttgcgga cggtttgatt atttagttag gcgttttttt   2760
aggtttaaaa atatttaatg taaaataaac gcggggtagt aggtttttt aatttttttc   2820
ggggtatttt gtaaatttgt ttttatttta aagttataga tttacggatg aggagaaggg   2880
gttggaaggg tattagagga tcgttttttt ttttacgtaa ttttttttt ttttttttga   2940
tttttattgt cgtttttat tttttggtac gtgtttttt aatagggatt aggtcgttaa   3000
tattttttt cgtttagtaa aataattaaa taaagagtaa aagattattt tttcgttagt   3060
tcgttaattt taggagtttg gtatattaaa tttcgggaat tcggaaaggg tagttttgga   3120
gatttttttt tttttcgttt tgttttttt ttattttaag tttattatag gtttgttcgc   3180
gcgttaggtt tagtcgggtc gtttggtttt gtaggcggtt atttaggtcg gtcggttttt   3240
attcgtgttc ggtggtttag tcgtaatttc gattttaatt tatatcgggt tttttgtcg   3300
ttttagacgg cggtttttgt gtattggaga gaggtttggt ttgagatatt cgagttgata   3360
ttagtgatgt tttatattat atattttcgt cgggtttagt cgtgtaattc gttttttttt   3420
ttttttttt tatttttgat tttttttta ttttttttt tttttgtatt cgattgttat   3480
aaaaagtacg ttttattttt atttggttcg ataagtagtc gttttggaag gagaggtagt   3540
tgtaaggaga gtttagcgtc gcggttataa agtattaggg tggagttgcg gaatagcggg   3600
cggggtggga gggcgtttc gaaggatttt agaaaattta tagattttgt ttttaattat   3660
ttgttatttt tattttaggt tatttaaatt ttgtttaggc gagaagagta cgtgagaggt   3720
tcgtttttt gatgtgtaag agagttaatg aaagattgat tttgtttaaa attacgtcgt   3780
ttaggattta gttttggttt tggatagtta aattaaaatt atttttaatt ttttttcggt   3840
tttttattta ttagtatagt tttatgtttt gtataaatgt tatttagaga gtgtttttat   3900
ttttttgat ttgggagagt attttggttt ttattttttt tatcgttgtt ttttttttt   3960
tgtttgtttt gttttaatcg gggtttttat tttttttatt tagagtattt aatttttttt   4020
ttttaatagt aaagttttg gatgtcgttt gatttgtttg attttgtttt ttgttttag   4080
aattttaata aatttggaat tttttatcga ttagtataaa ttaggacgtt gttattgggt   4140
tatttatttg agtttatttt tgttaattta taaagtatag atttgttata aagttaaggt   4200
aagtttttt tataaaatta tgattataat ttagaagagg gggtgtgagt tttaattttt   4260
agagtttaat ttttgagaga agataaataa attaagtaga aaagtttttt tttttttttt   4320
```

```
ttttttttt ttaagaggat tagtagttgt gtattaaaat tttgttttcg gagattataa   4380
aattaggaaa tagggtgtgt gggagagatt tgaatggtcg aaataatcgt aaagaaggtg   4440
taagaagcgc gagtttagga gggaaaaagt tgggttaggg tcgggataaa ggttttttag   4500
ggagggttaa ttttttcgtg tttttggcgg gttttttttg ttaaaggttt ataggttgga   4560
gtttgttcgc ggtttttggt ttggtaggga ttttattagt tttgttttgg taattgtaag   4620
ttaggaatat aatgttttgt gtaggggatt gtttatgtag tttagttcgt gagatcgcgg   4680
gatggcgggg tagtgagtcg gtgtcgtttt gggagtttga gttagggcgg tagttttgtc   4740
ggtttcggag agggaattgt aatttcgtaa ttaggtcgtc gcgaggtttt ttgtttttgt   4800
aaagttgcgt tttatcggcg tttttttagg cggcgttgtt ttttatattt ttttttggtt   4860
tatttggttt gtatttttat aatatttttt ttttattttt tttagatttc gtgttggttt   4920
ttattcggat tcgggttttc gtaaggttgg tttatatagc gatttttttcg cgtgtggata   4980
tgttcgggta gcggtttttt tggaaagtgg tttttagttt ttggagttgt tggttggtaa   5040
agtgagttcg ttgtcgtttt tgtcgttttt ttttagacgg gttttcggcg tttacgtttt   5100
tattttttttt ttgttggttt ttattttttt ttgaaaacga aatatatata ttttttcgtt   5160
agtatgttta tttgtaacgc ggacgttaat tggatcggcg gtagaagtcg tggaagagtt   5220
gggttgtttg gcgtcggagg agggtgcgcg cggcggtttc gggtcgcgag gagcgttgcg   5280
tttgtggggt gtgtaggcgt aagtgtgggt gttcgcgttt tatttttttt ttttttttag   5340
cgtcgtacgt tttatttata tgtttatttt attgtagcgg tatatttatt tttatagttt   5400
gtgtttttaa gtatatttat atatttttgc gtagatatat taaatttttt gggacgcgta   5460
tacgcgcgtg gtttatagat ttttttttt ttcgtagaaa gtttagattt ttatgcggtt   5520
tgggaaggtt aggaaaagat gtggggattc ggttgggtat cgaagttcgt cggttttttt   5580
ttaaaaaaaa aaaaaaaatg ttttttcgcg aagggtattt ttgagtggtt ttaggtaatt   5640
ttttaacgag tggagttttt cgggagttga aagtcgagag gaaaataggg atagaggtcg   5700
gcggtttttg aaggttttcg aattaagatg ttgggatttt tgtgatttag gaaatagaag   5760
ggaggttagg gtacgaatag agagggcggt agaattgttc gcgtttttag cgttttagga   5820
gtcgggtcgg tcgagggaga attaaaggga tgcggggtag ttaaaatttc ggttttcgga   5880
agttttgcgg ggagttaggc gaacgattat ttttattacg ttttttttcg gaggggttga   5940
tttttttggg gcgagaggga gcgggtggcg tagagtagtt gagcgggaat gtttgtaggg   6000
cggcgcggcg ttttatttgc ggttttcggg ttggaggtgt cggagatggt gtgtattttt   6060
agtttgtgtt tggaggagtt tagcgatcgg ggttgatcgg gagttagaat cgaagttatg   6120
gttaacggtt ggggatggtg ataggaagat gaggagacgg tcgatagttt ggttttcgtt   6180
gttcggtgtt ttaagtgaag cgggtttttt atgtagttta tggacgaggg agcgcgacgt   6240
tttattagtt tttggttatt gtttcgtcga gttttcgtag tcgtcgttgt tcgtttcggg   6300
tcgcgtttta ggcgcggagt tttttcgttg cggggagagt taggggacgt aattttcgtc   6360
gagtttttaa gttaagttgt tttcgttttt ttcggaaggt ttaagcgaaa aagttcggag   6420
acggaaagtt agcgggtaaa cgaagatatg ggatgtgggt agaagggtat tatttagagc   6480
gtttttaggg agtaggtttt taagttttaa agcgaaataa gagtgggtaa agattttttt   6540
ttttttttt ttttttttt aagaattttt ttaataagga aagttaacgt cgatcgcgtt   6600
ttgttcgttt tttttttacg cggtagtttt gatagagaag tgttaagagt gatagggata   6660
```

-continued

```
ggtaggtgat attagatttt ttgcggcggt agtagtcgtt gtagttacga cgcggttttt   6720
tgagcgtatt tttcgtaacg cgtatacgta tatttttcgg gcggtcgaat aggagtcggg   6780
ttttgtcgta gtttagtttt aggtatttag gcgagcgacg gattagattt gcggtttcgc   6840
gtttttttgt tggtttaata ttttaaaatt agaggcgggt tttttggtgt cgagacgtta   6900
tttcgtcgcg gtttttttta gtttttttcg ttttcgtttt tttttagatt ttttttcggg   6960
tgcgattgac gtggtttcgt attaattagg acgtttcgag tcgcggtgga gggattgttt   7020
tgtttgtatt tattagtagt gcggggtcgg gttattgttt cgtcgtgcgt attgggttta   7080
tataggtaag ttttcgggaa tttagttttt gtttagttta aggcgattcg gtttttagta   7140
cgaatttaaa ggtgaagaga tgaggttagg agtcgaaggt ttgggagaag agagtggaat   7200
ggttaagaag agaaaggtat aaggattaat aagatattta tttttttgtgt tttattatat   7260
ttatttttaa tttttttattt tatataaaaa ggagatacgt tatttaaaat tagaaaattt   7320
gaaaaatagt aataaattat tttttcgatt ttaaattttt taaatagttt gttaagtgaa   7380
tgttgcgtta atttgaagaa gtttttaattg taaagaagat agagttttga aaaggtaggt   7440
taataaatta gaaatcgaga agtaaatgga ttcgttaaaa gaaaattatt ttgattttaa   7500
acgaataatt gtttggtggt ttattttgga tttatataag aataaaaagt cgttttagat   7560
tacgtttttt gtgatgttta ttagttttta gatagaaaat atataataga agagaaattt   7620
taatttagcg tttttaaaat gttgaaagtt tatttatttt atttaacgtt gattaagata   7680
tatattttag atttttttaaa tttttttgtat attgtattaa gttcgtttta attcgagaga   7740
gttacgtttt aaattcgatt tttttgttta ttttattatt aattagattt aaatttataa   7800
agtttgtaga attaataatt ttgagttaat tatatatgaa atatgtttta atgaattttt   7860
atataattaa gaatgttgtt aaataattaa ttttaaggat aatttttaat agttattttt   7920
tttttttagt gagtttaagg ttgttttgag ttattaaagt ttaagtaggt agaaggggtg   7980
tgtgtgagtt aagggcgaaa agtttagaat tgcgtttaat tagtaaaagt aaaattttat   8040
ttatataaaa taaaaaaaat tatttttgga gatattaatt ttttatagta ttgtttttaa   8100
gtaaatttaa tttttaaaga aattaaagaa agaaatttaa atatatttaa aataattttt   8160
gaaagttttt ttgtttttta gtataggtta gttggagagg ataaattaat ttttttttggg   8220
tttttgtatg ggcgattgtt ttattatgga gttagtgtta ttatttttga atgtgtattt   8280
gtttgatatt atagttaatg atttgtaatg ttagtatgaa gtatttttaa aatatttttt   8340
ttttgttttt gtttataaga ttgggaaatt tattcgatgt ggaataaagt ggatgaagta   8400
gattataaat atatttgtaa tttatgtgtt ttttttttgt tttgattatt tttaaatttt   8460
atttgtaatt ttttttttatt ttaaatttgt agtttaaaga cgtatatgag aattgttttt   8520
tagtttttttt ttattagtat tattttattt taagaataat ttagttgtaa gggaggaatt   8580
tttttatagt aagttttaaa ttagtatttt tgtttttaat tttttatttt attttatttt   8640
attttatata tatagatatt tgtttagagt aaaatatatt tttatgtgat aggtttgtat   8700
tagttgaggt ttatatattt agttatatta ggttttgtaa ttttattatt aaattatata   8760
tattatatta gtagtttgtt ggtaaagaag gttaaattaa tttatatttt gtttattatt   8820
tggtgtttaa atgacgtatt ttatttcgga gatttggcgg agaatttttt ttttagattt   8880
tatagcgttt tattgaagat aatgttttta tatttgtagt ggtttttaat ttgataagat   8940
tttaatttgt ttaagttttt taaataaggg ttttaaatgt ttttagtcgt tttttttattg   9000
aatttttttt aattttttta agattataaa gtatatgtgt aaagtaaata tttttttttta   9060
```

-continued

```
ttgtattgtt agtcgatgat ttataattaa gttaataaga atttagtttt tttttgttga   9120
atgtgtttat taattatatt ttagtttttt tttttaaatt ttagaatagt tgtggttttt   9180
ataatattat gtttttttaaa gttttatttt atgaagggat tttattatat taaagaatga   9240
aaaaaatttt tattgtagtt agtatatata gttttttatt ttttgttttt taagatttaa   9300
attttagagt tgtaaatatt tttggaagtt tgggtgttaa tgttttattt tagaaagtcg   9360
agaagtttta tagagttata tagattttta aatttatttt ttataaattt atagaatttt   9420
gataaaagtt ttggtggttt tattttatcg atggaatttt tattacgata aatatatatg   9480
tatgaaggat tttaattagt ttttaaagtg gttgaaaaat ttaagggtac gtgattgttt   9540
tttatagtgt taacgtgtgc gagatgttgg aagtattggg gattagtagt agtttagatg   9600
tttaaaaaga taaggtgttt taatttgtgt ggatttattg aagttaagtg gtgaataaag   9660
ataattattt agataattta gattaaagta aaagtaaaat tatatttatt tgtatatata   9720
tatttatatt tattttatat tatagatata tatacgtata tatatattgg ttttgtaaat   9780
aattgattta aagtgaggat ttttttgta tttttttagt aggagtttta atattttttt   9840
aatttttttaa ttattttata tatttatagt agcggcgatt gggtgatatt ttttttaggt   9900
tttttgtgtg gtaggatatt aatatgataa gtttgtatgg ggaaaaggag gtatgtggtg   9960
ggaattaaga aatattgttt agtgaaaatt ttgtggtatg gtggtggttg attttggaga  10020
tttaatgtat ataagatttg tgggtgtata ggtataggta gtatggatga gaaaggggtt  10080
agaagaaaat aaattttatg tattttgtga ttttagtatt attgtgattt ttggttaagt  10140
tttttttaat tggttttaga aattattatg agtttagttt ttaatataga aatttttaat  10200
acggagaata ttggtgggat tttggtaggg aaattagagg tgttgtatgg tttacgtggg  10260
gtaaagaagg aaagtttagt gtcggcgtga ggttttgagt ttgggagata ttaggggttg  10320
tttcgattgg ggttttttgt ttattttttt aaagaaagat tttagaggag ggaaatgtgt  10380
gatatggggt tagtcgtgtt ttgtgttggt atttgttatc gattattagt tttaaagttt  10440
tatttaattt tatattttt agtgttagtt gtgtaaagtt tttttggtta tggtagtgag  10500
cggttgggtt gtgtcgttaa atttttcgta ttaatttggt ttgggattta attaagtgat  10560
ttttgatttt tggaaagagt ttgtttttag agtttattta gaagatggtt taattagata  10620
tttttttgag ttgttaggtt ttagacgggt gggagttttg ttttgtttaa gttagtttaa  10680
ggacgaggtt cgtttggatt tagtttggag ttacgtgatg ggcgtgagtg tgtgagtttt  10740
tggtaaggcg tagaggttag atggagattt tgtattttgt tcgagaagtg ttttattttt  10800
tttaatattt ggttttttttt tgtatataaa ttaagttgaa aatagtttat tatttattat  10860
tttttatagt tatggaatta aataatttag aaattaaaag ttttattgta gttgtttttt  10920
tttttatttt ttaaatggaa tttaaaaagt tttggtttgt taaaagggga agattatttt  10980
ttgaattgga agtttgtaga tatattgagt aatagttatt ttttttgggt ttttgtaaat  11040
ggtatttatt tttttaattt atagttttag ttgtttaatt atttgagatt tggggtaatt  11100
atttgggggga atagtgttta gatggtagtg ggagttatta ttttatagtg gtttggggaa  11160
gagaagagaa agagattaga ggagggggta tttgttaaaa ttatttaacg aatatgttgt  11220
taatgttttt ttatatttgt atgttattgt tatagttttt ttaggtgtta ttgagttttt  11280
agaaagtaat tatttgtcga attaagtaaa ataaggagaa tggtatagta tatgtgtttg  11340
gagaagggga aggaagggtg gaatatgaaa ttgagtatag atatttaggt taggaaagaa  11400
```

-continued

```
ggaagtggta aggggttaaa tgaagtttta ttttttcgtt atttttttaa ataatagttg  11460
gattaaatat ttatttgttt tttttttttt tttttttttt ttttttttag tttatgttta  11520
tttttttttt ttatttttt tgtttttttt ttttttgtt tttttttttt tagatatgtt  11580
ggtagttaat atttagtatt agttgttatg gtgattataa attatttaaa tttaaaaata  11640
tttatttata atttgagatg aagtttttat tttttagcg aaataatatt ttaaaagttg  11700
ttagttgata aaaaaaaagg aatttatttt attgtagtaa tttaagtaat atattatttt  11760
taaaggttta aattaaaatg ttagtttgtt aaaaatatgt tggtagagtt ttggatattt  11820
ttttcgttag atttttataa agaagttgat tttgttattt ttggtcgttt tttaatatat  11880
atatataatt ttgtatgttt tttttttttt tattaatttt tttttttttt attaattatt  11940
ttagttttta aagattttac gtattgggtt ttaaaagaaa agaatttttt tttggattag  12000
aaaatagttt tattggttgt tgaagtgaaa gatgtggggt ttagggggaa aggttattag  12060
gattataatg gcggtggtgg taggaggtta ttttagagga gttaagaaga aaaaaaaatg  12120
tagggagaag gattggaggt ggaaagatag agtaatagaa aattgagttg ggtggttagg  12180
tgttgcggtg aagtttagtt tcgaaatgat aggtatatat ttttttattt ttgtttttt  12240
tttttttgag agaaaatttt tttagttaga gattttgggg ggtaggaggc gggtaaacgt  12300
cgttgtagtt gggtttttg tttttattt tgggtttgtt gtttttgtt tattttggat  12360
tatagggtat tcgtttagat gaagagttat taattattta tttagttaat attaggaaga  12420
cgataaagtt ttttatatag gattaagaag atattagatt gttttattag tatattttg  12480
tttacgaata agttttcgtt atatattttt tttttttcg agtcgtttta ataattgttg  12540
tatatattag tagcgggcgg tgaggaataa tagtcgaatt agttttaaga aattttgtgt  12600
atcgagttag tagcgaggaa cgcgatttgt gaagattatt tttgcgggta gggattcgta  12660
gggattgatt attttcggat aattggtata attttttttg ggggtgaaaa attataacgc  12720
ggcggggtat tttttaagtg agttgtagat ttgattggcg cggggggtgg gggaggggag  12780
gggagaatgg gatggcggag gtcgggcgga ggaaagaaaa tggaaaattt tttttatttt  12840
tatttcgttg tttttttttt aagttttatg tttttttcgg taagtatttg tttttttcgc  12900
gttagttata gttagagttt tttattttt tttatatatt tttttttttt tgataaggtt  12960
taggattttg gttattattt tacgtattat tattttgcgt tttgttagag acggtttggg  13020
ttgatttcgt tggtgtttat gttaggatta aaattttttt atgacggcga ggaaaattgt  13080
attatttgtt tttagggggt atattaggag tttacgtagt atatgtttcg taaatattcg  13140
ttgattgaat gagaggcgcg ggggcggggc ggcggagagg ggtttgcggt cgttaaggtc  13200
gttagggtta atttaggttt ttcgaagaag gttgggatcg agttgttgtc gcgtgtgaag  13260
gtgtgtgtcg cggttggggg tgttataacg ggttatggag tttatttttt agagggagga  13320
agtttgtgta tattagcgat ttgggtcgaa tatttttagt ttatttattg ggttaaagtt  13380
atttaataat taatgcgttt ttgggggagg tcgggggaag tattcgtttt ttgtcgggac  13440
gtaaagttag gcgttaggtt taaaggggtt gtagtgtagt tcgattttag tacggaattt  13500
agagtcgtcg ttttgaaatt ttttaagtta gtgatagagg agggttagtt cgtttttttt  13560
ttgagggtga agattatttt atgagttttt tttaggattt ttaaagtaag aaaagttaaa  13620
gaaaggtttt tttgttttag ggggtcgttt ttagttggtt tttatattat tttttgttag  13680
ttgcgtttat tttttttaa atttttggtt tttaggggtt tttagtcgtt ttcgtgttat  13740
tttcgtttcg ggttttatt taggttgggt attcgtttaa tggatattaa ggagaatggg  13800
```

```
atttattagg gaaggaaggt agagtttgga ttgtttagag gtggattttg tttatataga  13860
acgtttagtt tttaacgagg atatggtatt tttgggcggc gttgggggta gaggcggaga  13920
gggtagcgta atagattatt acggtttttt gaagaagtta tatgttattg tgaatttttt  13980
tttttttaa aagtaaagaa aaattttaaa aaaatataag aaataaattt ttttgtttta  14040
taagtaggtt gtggttagga ttttggatat tttataagtt aatttaaaat tagggaagga  14100
taggtgtttt attttttagt agtgttatag ttttgtttat tcgtgtgatt tttttttgtc  14160
gtttattagt tttttaaaag ttaattaaat taagattttt agtatttttt tttattatat  14220
gttttttttt aattaatggt attaaacgtg tttaggtagt aatttttttt ttcggttaaa  14280
aagtagaaaa agatatattg agtgtagggg aagagttttt tacgtgtatt aaaataatgc  14340
gggtttgaaa gtaatggtta agaaagtaat tatttattat ttttagtttt ttatgtgtta  14400
gttattaaaa gcgaacgatt aggggcgttt gcgcggtttg tgattggcgt aagtagaatt  14460
tttttgtttt tagtcgtttt ttgtttattt acgaggattt tattttatcg taggtttttt  14520
tatttgtttt tagaatgtat tttttatgtt taggaaattt ggggtaggga ttgggggaag  14580
gagatatttt gcgttttttt ggtttttagt ataataagaa atgttagttt cggtttggcg  14640
attgcgagtt cgtttcgcgc gaagcgagat tggggagttt ttttagtttg gtcggagtta  14700
gggttgagtt cgcgtaaagt atttttttta gaagttatcg ttgtttttga tttttaatta  14760
tattttaaat atattacggt ttaataattt atttttatta tcgattatta aatagaagaa  14820
gaatttaata taatttaaat gatagaaatt acgcgacgtt atttttgtat tgttttttatt  14880
taattttatg gggttaattt cggataagtg agcgtttaat tggtttagta gggcgattgg  14940
cggtgtagtg tagtgttcgg gcgtgaagta ttggatcgtt ttagacgttt tattttaata  15000
aatgattatt ttttttttaga tttacgggga aattttaatg taagattttt gttttttttt  15060
tagtaatacg gtttgttttt ttgatcgggg ttttaaatcg ttttttttta ttttatatta  15120
tatttgtatt tttatatttt aattcggaaa gagggggtta ggggtcgagg gttgtggggg  15180
gggggggtt ttatttgttt atattattaa aggttaatag ttttttaagg ttaggtattt  15240
atttattacg gagttaggaa aatagaggaa tagtaaattt gaggggtttt tttttatgta  15300
tttgaaaaga aaggtatttt tttttttttta tttttttatat ttttttttttc gttttataga  15360
ataagtttta atttaggaaa ggtttgtggc gtaggttgga gattttttaa tttttttatat  15420
aagtttgtag atttttttttg gtaatgtttt tcgatttttt tagagtgaaa ttagttaatt  15480
aagtaacgat atcgttaaaa tttaaggttt ggtaattagt attttaggta ggttcgcgtc  15540
gataggggta aatttttatt ttattttggg ttgttaagta tagtggttgt tttttagttt  15600
tttagggatg ttgtcggttt ttcgtttttt ttttaattag ttaaagtaaa ttttcgttaa  15660
tttaagtttt ttttgtttgt ttttcgcgat gaatcgcgta tttataagtt tgggtggggc  15720
gtggttgaga gtttgagtga ttgagtgggt tttggtggtg ttgcgcgtag cgggatataa  15780
cgagcgatag aggtcgttgt tggattattt ttttacgtta gtttagacgt cgaggtttgt  15840
tggagcgtgc gtaggggatt agattatagg gagcgagcga gagggagaga gaggtgttgg  15900
gttttaggag tgtagtataa tttggggaaa ggaattaacg tttttgggac ggttgttttt  15960
cgttttattt agaggcggag tgtttaagtt taagtagtag gcgcgttagg tttggcggtt  16020
tcgttttttt gcgtttcgtt cgaggtttag agtttcggag gcgggtgttt agcgcgcggt  16080
ttgcgttttt ttttcggttt tattattggc gttaggatgt tgtcgcggga agaatttgtt  16140
```

-continued

```
gttggttgtt ttttttcggt ttttaggaga gttcgtgaat tcgatttttt tgatttcgga  16200
gtttttggag aagagatatt taacggtcgt cggttgtacg tttgggttac gcgcgcgttc  16260
gttttacgtg cggagagagg cgtttcggat cgcggtcgaa aggagtcggg gacgggagga  16320
gggggagggg cgaggtaggt cggaggagaa agagggataa agagtaaaga tttagttaga  16380
ggaaagagtt gacggtattt tcgtttttcg gatttttttgg taattcgggg taggatggcg  16440
tatttttttt gcgtttttc ggttgtcggc ggttttagtc gggaggagta ggttgggggg  16500
tttcggtata tagcgcgtcg ttgtttttta gtttatcgtt tcgttatagg gagaggttat  16560
tggcgatttg gttttgattt ttttttgtt taggttggtt tttcggggaa gcgtttttcg  16620
ttggggtttc gtcgtagggt tagtgttttt ttgtcgtttt tacgtggcgc ggtttttcgt  16680
tcgatgattc gggtaggaga agggggtttt tatttaattg tatatacgtc gatattagtt  16740
tgcggtagtt ggtttttatt tttcgttatt tgtaaaatag aagagaagga aggttgtaag  16800
aagcggcggt cgtcgagtga gtagggttta gatgagatta cgttatatta gttgttaggc  16860
gtttattgtg tgttaggttt taggcgtgtt ttttcgattt gatagttttt ggttgtgtag  16920
tagtattttt agtttagttt cgggtttagg atatttattt attaagaggg gatttttttt  16980
tagagttgtc gtaaaagtgt ttagaggtta gaggattata aagttatagt gtgttgggga  17040
ggttgtggat ttatttttaa gaatttcggt gtcggggtta agaatttatt tgaacgtaat  17100
ggtagcggga gtgggtgggt ggagaggatt tttttttttg ggaagttgta tgtaaagatt  17160
atttttagt gtttgtttat tagttggagt tcggtaaata tttgtagaat attagcgtta  17220
acgtgttttt gttttagata gtagtttttt tcggtttttt gtaattttga aacgaacggg  17280
tttttggttt agggtgtttt aggagcgagt tgagttcggg ttttttattt attaggagtt  17340
atttttttat atttagttat attttttttt agagatatta attcggttat ttatttattt  17400
attataaata attattttaa agtatgattt aagatcgtag aggagagata ttgggtggat  17460
tgagcgagat tgaggagagt agggtaaacg tttttggagg gtttattgtt cgttaaggac  17520
ggagaaatag ttttggtata attgttattt agtttttttt tttttttttt cgggcgagtt  17580
aaattttttt tacgttttta attataacgt agcgagttaa gtatttaacg cgtttttttt  17640
tttttgttat aggtaagtcg ggagaggtgg gtttcgaggg gttttatcgg gtgggtagaa  17700
gagtcgcggt tgttttaaag ataagaaaag aaggtttagg gttttttagg ttttttcgat  17760
tttagcgttt gttttttttt acgttaatta gggtacgtcg acgatcggag ggtttatttc  17820
gcgcgggtgc ggggatcggg gtgggagtaa gcgttgtcgg gttggcggag gtatagaggc  17880
ggggtaggga gttgcgggtt tgtttttggt ttgagtatcg tttttttgcg tttcggtttt  17940
ttttgaaggg agttgggttt tggggagttt ttggttaagg tcgttgttta taggaggggt  18000
tgttcggcgt tgtggcgtgg ggatttaggg tggggacggt taggcggttt ttttattcgt  18060
tagcgagaac gcgggcgggg attttgtcga ttcgattttt gtgggttcgt gggtttagaa  18120
gtagtagttt ggcggtttta gatttagtga ttttgtagta aaattatagg attagttttt  18180
gattgagatg tttgttcgtg agatattata aaatttatta ttatagtttt ttattaattc  18240
gatatgaagt aatatagatg ggattttatt agtttagatt ttaaatgttt atttatgata  18300
atttcggagg aaatttgtat gttattatta tttcgataat tttttttttt tatatgtttg  18360
aattggttgt attattagtt ggtagtcgga gtattgtaga tggtaattgt aaatagtttt  18420
tatttattta tttttttaa agaatgaaat atataaaaga aaaagattgc gttgtttggt  18480
gtaaagttag ttaattatta tatattttt tttttatttt ttcgtgtttt agtgttgaag  18540
```

```
attaaataaa gtaatataaa ataaattttt aagaatttat agagttttat tttaaggatt  18600
gaaaagaagg ttaaggcgtg ttttttagtt tatttttata tgtttttgtg atttggagat  18660
ttattttgta gttaaaatga gttttgagat ttgtattttt atgttttatt taatgattag  18720
gtttattaga agaattgagt ttaaataatt ggggaagata atttttttaaa aagagatttt  18780
taattttcgt ttgttgattt ttaaatttgt tttattaaga taagtttttt gtgagaaatt  18840
tggttgttag atttcggaat tggttttaat ggttaatttt ataaattgag atgggagatt  18900
tttttgatg ggaggtagtt tttattttta aagtttatgt tttagttgga atgtatatgt  18960
taaggatttt tgttttggtt aatttgggtt ttatattgtg agtatataaa aagtattata  19020
cggttaacgg aggacgagga attatggtaa agtaggtagg taagttttaa gaaataaaat  19080
aatttgttaa aaaataattt ttgatgatta tcgtaagatt gaaagtgtag gaaaaatata  19140
gttcgaataa ttttagattt ttttatattt tttttttttt tatatatttt gttattttat  19200
aataaaattt ttaatggaaa gtttaaaaat aaatagtata ggaatatgtg ttttaaatga  19260
attaaattgt gaaattagtt agtaaattaa tttgtagtaa gtaattattt aaggaaatta  19320
aaatattgtt tagtttagtt ttgtatttta ttatgtgtat gcgtttttta taattaatta  19380
atataagtgt tttaggaata tttgaagata aatacgttta atttaaggaa taaagtattt  19440
aaataattta agtgtaattt tgttgagtta aagtaaaata ttttataaat gaagtggtta  19500
tttaattttt tagggaaagt ttggttattg aaatgttgta tgtttatgtt atattaataa  19560
aaatttttaa tttattttgt ttatgtgttt tgtttttttg atattattgg tatttgaatt  19620
ttagatggat ttttgttaaa atgatatttt gtgtgataaa agtattttta gttttgattg  19680
atagattaaa ataaatgtaa ggaaattttt ttaaattaga ttaatttttt ataaaaatat  19740
tttagaatgt atgaattttg atatttatat ttataatggt aaaagttttt ttcgtttagt  19800
ttagtaagat aatatttata taaaagagta aaaaaaaatt atattatttt atgatagttt  19860
gatttttaaa ttgtttaaga aagtaaagtg gttaaattgg aaaagaggaa tatatttcgg  19920
aggtttagaa tcgaaaattt ttttttaat ttttagttgg aaaataattt tttgtattta  19980
tttaaagtgt attttttgaa gtgttagatt ggagttgatt ggtgattaat ttaaaggagt  20040
tataatttaa agaaatggtg agagtttggt atttaggttt ggtttttagg taattcgttt  20100
gggtttgaga ggttattaat tgttagttaa gatggaattt tttttttttt tttttttttt  20160
taatggataa taatgggaag ggggttaatt ttttagtagt tgaaattttg tatttagttt  20220
tttattttga gaatgttaat ttttggttcg aggatttgtt tttgtagtgt tggtatcgag  20280
atttaaggga agatatttcg ttttaaatgt tagttacggt ttggtttttt tttcgatttt  20340
agtattttgt agattgttag tgtttgtggc gggggacgaa aggaataggg ttttgtaagg  20400
tttgtttgtc gattgcgtta ttttgggcga aatttagttt taaaagttat aaattattta  20460
cggtgaagat ttttcgaagt ggaataaatt tttagattcg tattatttta tatttttgcg  20520
ggatagatgg tttttattta tcggttatcg ggagagagtt gttgttttcg cgttttattg  20580
tttttcgggg cgatttttag cgagtcgagt tttcggttgt acggtaagcg ttcgaaagtc  20640
gggtttgaga ggattgtagg gtttttgagg gtgttaagtt tcgaaggagt ttacgggtgt  20700
attggggttt tcgaaattta gtcgttattg gtagtttttt tttgtttttt tttagttttt  20760
tcgttcggtt tcgtattttt tttttttttt ttttttttta tttttttttt ttttttttgt  20820
ttttatttcg tgtggggagt gacgtgacgt tagtagagat tttattaaat tttattgtat  20880
```

```
agtggcgcgc gggcggtcgg tcgagttcgg ttgcgcggtt ggcgatttag gagcgagtat  20940
agcgttcggg cgagcgtcgg ggggagcgag taggggcgac gagaaacgag gtaggggagg  21000
gaagtagatg ttagcgggtc gaagagtcgg gagtcggagt cgggagagcg aaaggagagg  21060
ggatttggcg gggtatttag gagttaatcg aggagtagga gtacggattt ttattgtgga  21120
aaggaggatt agaagggagg atgggatgga agagaagaaa aagtaatttg cgttaattcg  21180
gtagttttaa taaattaaag ggggagcgtt agggtagcgg ggagatagaa acgtattttt  21240
ggggagtaaa ttaggacggg ttgggaggaa gcgataggga aagtggttta agagacggaa  21300
taaaggataa tgtttatggg gttgtttggg acgaggcgtg tggagtgtgg gtgtgagcgt  21360
gcgtgtgtga ttttttttta ggtttgtaga gttgaggaaa gaggttatag taaagaggga  21420
ttgcggaggg aggaaagtga gagatcggta gagggcggga gtggaggtgg gcgcggtggg  21480
gatgggagag gatgagtgaa gagaaattta gaagaatgga gtgagttagt gggagagggt  21540
gggagggtta tagtcgggag cgaacgagtt aggtttgtta gttggggaag gtcgggacgt  21600
tgggtttagt ttagttggga tatcgcgttc gaggttaagg cgggtggatt aggtatgttg  21660
agagtgtcgg cgtataggtg ggtacggtta cgtattgatt tagtgtttac gaagggtttg  21720
tattggataa ggtttagacg tttatagagt ttagaatttt ttttgttgta tttatattta  21780
ataagtttat tttgggttac ggatatttta tttttaaaa tgacgaggtt aaggtttttg  21840
gcgaggatgg tattaaattg tacgggatag aagtgggggt gggggagaga gttttttttta  21900
agtttatatt tgtttttgta aagtaaagag tatgtgaaat tatagggtat atttttattc  21960
gaaaagtgtg ttttattttt gaattttgat tttttgattt tttgatttga gtaaagatgt  22020
gtattttggt agtgagtaga atattttggt tttgttttgt ttttgagtgg aaggattata  22080
aatataattc gtttggagga ttaggtgtga aggtttttgt taggtatatg ggataatgtt  22140
tttttaattt taagggtatt ttgttaatgt atgtttttgg aaagtgtcgg aatatagtta  22200
ttgtttttgg attcggattt ttttattaat attaattttt gtttgagagt aaaatttagg  22260
ttcgttatta aaaagatatt tttttggttt ttaattgaga ataaagtttt ttttaaaagt  22320
tgtattgttt tttttaaatt aatatattaa tattcgtaat tttagaaata tatagtgatt  22380
cgggagaatg tgtataaaat agatacgttt aaaaaagttt ggcgtttaaa attaatttta  22440
gttattatat aggtgttggg ttttttttat ttttgggggt tgtttggaat atgttatgtg  22500
tttttttgaa ttatttcgtg ttttgaattt atttgagtta gtagtaaaaa taggtaaata  22560
aatttgttta atttgttttg agtgttaaat tttttttattt tgaaatagtt aatagtcgat  22620
agatggattt attttatgga aagggttagt ttttttagtt acgaagaaaa ttgattagag  22680
atttatattt taagttattt ttaattttta cgtaatattc gtgaaaattt aaattttttt  22740
tttttattta gtggaaattt aaagtagtgt tatttaaggg gagagaaatg agggggaaaa  22800
tgtttacgtg ttgtttaatt gtattttttt tttgattttg agaattttta tttttggttt  22860
ttgaaatttc gtcgaggtaa gaaaattaaa ttttttttaat aagttttata attgaatttt  22920
agttatagga tatcggaaag tgtagttcga gaaagatatt tttatttttg tttatcgacg  22980
atttttgtag tttttttatt tttttgagta atgggttaat aatttttttt tttttttttt  23040
ttattttgta gagattaaga ggcgttcgta gtagaacggt tttgttttta gttggtggcg  23100
aggataggta attttatgga aaagttggaa gagaatgaga aaattaaaga tagaaagatt  23160
tagagattcg cggagagata tagggagagg gaagggagtt gcgttgaaaa gacgtaaaga  23220
tacgcgcgtg taattttttt tttttttagg ttttagaggt ttgtaaatta gggttgagag  23280
```

```
gaaggggttc gggaagttta cgtttttttc gttttttttt tgtttggagt ttcgttcgtt  23340
agaggttggt taattttagt ttcggtcgtc gtagatattg cgttgagttt ttgggttttc  23400
gttttgttta gcgttagtgt agttgaagtg agtagttggt gggaaatgta aatggttttt  23460
ggagaaatag aagatataga atgattttta ttttttttc gagtgtgtgg aaggagttgg  23520
atatacgttt tacgttttta attttttttt tatattttta gttatatttt tattaaataa  23580
ttaattaatg tttagaatta ttagggaata tattaggtat gtaatcgtag aagtagggtg  23640
ttggggggtt ataaattatc gagttgattt aagacgtgga ttttaggttt ttttttgtt  23700
aaagtagtaa aggaagagcg ggttttggcg attgtattta gatttcgatt attttaaatt  23760
agaagggggt ggagggagcg tttaagtaaa gtaagtaatt ttttgttttg tagatgtaaa  23820
taagattgta gtattaaagg tattagtttt tttagggtta gatcgtttgg attgggagtt  23880
tggggaaggg gagatattaa ttttacgtat ttgtgaattt taaggatgtt atatttttat  23940
ataaataatt ttagtgcgga tttttggaa tgggggagt aatattttta ttttagaata  24000
ttaaaatatt ttttttttaa agcgtatatt tttttattt ttttaaaatt ttgaattatg  24060
tttaaagata atagtttttt agtaaattgg agtattggat tatttttttt attttttttt  24120
atcgatattt tgatgatttg attttaatgt gtgggggta tagggaatta aatatagttt  24180
ataaaattaa gtttagatga aatagtgttg gttaagtggg tttagataat ttttaatgag  24240
aattttaatt atattttttt ttttaatatg ttgagataag tgatagaatc gttagaatgg  24300
taattaaatt ggaaagttta gggagaataa taatttcgtg attaaattgg ggtaaaatcg  24360
tggataaatg tggggtgatt ttcgttaatt ttttgttatt taagagttag gatttgggaa  24420
aggtatagta ttattttaga gttcgttgtg acgggttgtg tgttattatt tattttttt  24480
attttggatt atgattttaa ttttggtaag taattttttt agtttttat ttgataataa  24540
gcgagtatgt aaatattaat ggttagcgat gtttaattgt tttaaatatt attgatttgt  24600
tggttgtttt aaattgtttt tttagtttag gttttgtttt cgaattgttt attttagagg  24660
tttgatttat gttttcgatg ttataatata ataattgttt ttttaaaaaa ggtatttaag  24720
atgaattaat tgatttgtat ataaattaaa attattatgc gttgtcgatt tcggtgtttt  24780
ataattattt cgaaattagt atttaattat ttgagttaaa agaatatata aatgtttgta  24840
ttgatttatt aatgaattat ttaattaaaa cgttcgggta atgttgggcg ttggaaagat  24900
tgttaaatta agatatatta taggagggat atgaagatta gaaaggtaat agattaatat  24960
ttcgtattta aaacggagtt ttcggtgatt tttagtttta attttggagt aggggttttt  25020
tttttttgtt gttaaaaaga ttttgtgttt gtttgtgagt gagtgtattt aagtggaagg  25080
aacgttttta cggttacggt ggtttaggtt ttttgttcgg atcgggattt tatagtttta  25140
atttaggagc gttaaatttt ggaagatttc gggttagttt tggaggtgcg tggtttcgta  25200
agtcgttagg ttaagtttgt tttttttgtt tgttttttcg gtaggttggg cgcgttatgg  25260
tagtgagttt ttcgcgtaaa cggagagttg gaattaaagt tgatatttaa tagatatgtt  25320
aattgagtat ttattttcgt tttgagaata ggaataaaag gtagtttttt ttaagagagg  25380
cggtgtaaag gtacgttata ggagtttaga aaaggttggc ggcgggaaat ttgtagtttg  25440
ggggttagtt aatatttttt tttattttaa gtatttattg atttgttgtt gttatttttg  25500
gcgacgtaga aggatatttg aaagaatttt tgatggggtt ttgatttgag aaaggaggtg  25560
atttgtttag gtttttatta aatttttaat tattatatta attgtttttt tttattttt  25620
```

attcgatttt tttttttttg tttattttta attttttaat tatttagaaa ttttttttatt 25680
ttttagtggt tttttttttg tagtagtttt ttattcgaat ttttttttcg tttttcgtg 25740
gtagggtttg tatattgatt tttttgattt ttggtatatt tgggtttttt gaaatttttt 25800
aatttttttta gatttgagga tggtaggttt tattttttttt attgtgtgta tatatttaga 25860
gatatgaaaa tttatataga ttgtttttaa atttagggta tttaatagat gttttttttt 25920
tagttcgttt tttgatttga aatgtttgtt tgattttaat ttggatatta ttttttttttg 25980
tttttttttt tttaaagtag tttggatatg tgtgtaagtg agtttagaat agttttattt 26040
atattttttta ttaaattgta aataaaagaa gaattaatga agtagattgg tatatagatt 26100
gtattaagag ttcgaatttt tagtttttgg atttttttatt taattttggt tgttatttat 26160
attgatagag ttattttaag tagaggttta gagaaatttg tattgtggga taataggtaa 26220
agttatagta aaaagtggaa taattttaaa gttattttat tagaatgtaa attgtatttt 26280
tgggttttgt tcgtaattat ttagttttaa tatatataga gttagatagg aaaaaatagg 26340
ttaatatagt tattggtatt agagaagata aattttatgg gtttttttagt gaaaagaaga 26400
tttttaaagt ttataatttt tgattattta attttattta taattgtggg aatgaataag 26460
atattaattg ttttatgtat tttatttata ttaattaatt tgtgttttta ttaaaagtag 26520
ttatatagaa tttttttttaa tttttggtag taagtttaga aaatgaagtt tatagttatt 26580
ttgaattgga tatatttttt gagttgatta tttttgtaag tgtaggaata taatattgtt 26640
tttttatggt ttttttgtat ttttttaggg tttgtaagtt tttattaggt ttgatattat 26700
tgtttgggtt tatatttatt ataagtaaat ttgattatta tgttgatttt aaaatagttt 26760
atttggttag tataatttta gtttttaaat tataaaaatt ttttaatata cgaagttttt 26820
agtttttatt ttttttagtt ttttgtttat ttaaaatttt tattttaatt ggtgtaagta 26880
ataataattt gtattattat ttgtattttt tttattttttt tggagattgg gttggatttt 26940
agagagaata ttagtattat tattattata aataataaaa tttaaaagta aagtttttat 27000
ttgtatgata attggtattt ggaatgtttt tgatttattt aatgttattt tataaaggta 27060
ttttgtaaat tttttttggaa tttttagtaa gagtttgtag taattggaat aattttttgg 27120
gaagatattt tttttgatgg gtttttagtt tttggaggaa tagattgaga gtaattaggg 27180
agggagggga tattggaaat tggtagttac gttagttgaa ataagtttgg gtttagtaag 27240
gtgattgatg ttgtggttga tttttttattt cgagtttttt tttaattggg gtattgattt 27300
tttttatttt gggattttaa ggtattcggt gtgtatgtag atttttttttt tgtggttttt 27360
attatgtggt ttcgtagtag gtttttggtt taatgatatt ttatagttat agtttttata 27420
tttattatta tgattttaat gtttaggttt ttagtgtatt tatattaaat ttgttttatt 27480
agtaagttgg agtatatagg agagatgggg gtaagtaagg atttagtaga gtttaaattt 27540
agatatgttt aaatggtttt gattgtgtaa agtgtggtaa tgtttttttgt tgttttagtt 27600
ttttattttta agttttatat gtttttttggt taatgaagtg tgatataggt tatatgttag 27660
gaataatagt atttgttgag aataaagtga atttaggaaa tttggtatat ataaaatgta 27720
tttagttatt tgaattagta ataatggtaa aaattaatat ttatagagtg tttagttaat 27780
ttagttattg tattaaatat ttttgtattg ataattatat ttatttttta tgttaatatt 27840
ataaggtagg tattgttatt ttataaatga agatagtgag gtttgttatg attgtgttat 27900
tggtttaagg ttatttagtt ggttagagta taagtttata attgttggag gttatagtgg 27960
ataggatatt gttttaggtt acgtaggtag taagtggtat agtgggaatt tgaatttagg 28020

-continued

```
tttgtgtaat tttaaagttt aaaatgttaa ttagtatatt gaattaatgg taattggaat  28080
tagaagatta ggggtttttg ggggaaggaa atatagaatt tatttatgga atattttata  28140
aataaaagaa taatgtagag ataggaaagt aaatatattt tttgagggat ggagaaagtt  28200
agaaatgttt taaatgttaa agaggaggaa acgagaaatg attggatgag aaagtagaaa  28260
agttaaattt cggtatttgt tttgggtagt ttaggaagag aaaggtaagt ttagggatat  28320
ttttgagtta taggaaaatt aatgtttaga tggttagttt ggattaagtt taatatagga  28380
ttttaggaat atggtttatt agaattgttt tttagtaatt ttaagggaga ataaaatttt  28440
tgaattgggt ttaagtagtt ttattttaga agtaaagaga gatggaagta aggatcgagt  28500
aataagaata tttatattgt aagaatatgt aagttgagta ggagtgaaat ttagaaaaat  28560
ttgttaggat tttggttgtt gtgttaaatt atgttatatt ttaagtagaa attagatttt  28620
tattattatt atttgtttag gtttagttag taattttatt attgtagtaa agttatttga  28680
aattttaaga gaaatgattt tttgtgttga agaagatatt ttgggtggaa ggatgttagt  28740
agataaatgg agtgtaaaga tagtgatttt aaggatatag tttgtgggga gtaatattgg  28800
attatatatt cgttgtttgt ggtagaatgt tagttagggg agaatattag gtagtttttt  28860
ataagtttat tttattataa aaagatagga ttgattttaa aggttatttt taatttaggt  28920
ttgttttatt attgaaaatg atttaaaatt ggatttattt tggttttttt taggagggat  28980
agataaatat aatttgtata tatggttttt tagttttagg aagtatagga ggagaatgaa  29040
agaattaatt tagtttttttg ttttttggta aaaattttta tatttgtgtt gttgtaagaa  29100
tttaagatta tttcgtttag aatgttgtgg tatttttgaa agtaaggttt gagggtatat  29160
agagttttat tttttatttt tacgttgtgg attttattgt ttttttttaaa tgggaaagag  29220
aaattagaat ttatagaaag taaggtttgg aaaggattta gagggtattt ttttttttta  29280
gtttatgttt aaattatttt tagaaatata gttagttata tttttagta aagagttttt  29340
tacggttttt tggtaatgta tttttatgtt ttataatttt atagttatat tgtatattta  29400
ttgattaaat tttaagtatt gaagaaaatg atgttatatt aaaaagtttt aattagtagg  29460
gggtatgttt tttagagttt tttaaatatt ttatattttt attttaaaaa aagatgaaaa  29520
tattattagt ttaatttaat agatggaaaa ttttgttata gagattttta gagagttata  29580
tttggttatg tagcgtgatg tttgaaagaa ttaaattaaa aataaagtta ggaaatttta  29640
tgtttagggt tttttagta gatatattat tttttgggg ttggttatta tttttttgtt  29700
tgagtaaagt atatgtttga ttgtaatttt atttgttttt ttgtttgttt gtttgtgagt  29760
agtttatttt ttaatttatt aatttatttt tttgttagtt ttttaaaata ttataagtta  29820
attaatgttg ataaaatttt atttttatta tgagtgttat ttgagtagat tgagatggtt  29880
gttatatttt ttaaatatta cgtgtaataa atagtgttgt tattgtttta gcgttatgat  29940
tttgttttta tttggaaatt gtataaatat tatatttttt gttatgatag gattattttt  30000
atttattagg atttttgata tttgtgttgt tatttgggag aatgttgatt attttgttta  30060
tgttattttt gaggttataa taatcgtttt tttgtttagt tgtgtttttt tttttatagg  30120
tgaatttagt tttttttttt atgtttgatt ttaagaaatt ggtgttttat tgaaagatgt  30180
ttaaattttt tgagagaaaa tgttggagta agaataattt gttatgtatt gtttttattt  30240
gagtattaat gtttttttaa ttttatatgt ttttaaattt tttgagaatt tttttttttt  30300
gaatgtaatt tatgaattaa aagtgatcgt aatttttaaa atattatgtt gtttatagta  30360
```

aatatatata atttttattt gttaattaaa aaaagtaata gggtttttat ttttattttt 30420
gatatttgtt tttttattt tttttttaag tattttttt tttttttag agatgtattt 30480 attgagagta ttttgttatt tttttttt cgtagttatg tatgattaaa gttgtgtttt 30540
tgaaattttt tattttttt gttataattg ataatttatt ttgtttttta ttaatttatt 30600
aatgttattt tattggtttt tgatttatat aaattaaata gattttagaa aatttaataa 30660
aaataaaaat aatgtttttt attttgaaat atttatttat tgttttttt tagggtatat 30720 atattatatt tttttttt atattttatt ttttttgaat ttataagaat gtgttattga 30780
atatagagaa aataatttaa gaaaggaaaa ggaatgattt gtttaaaatg aggaaaaagt 30840
agagtcgagg tttaggattg tggtttaata agatgattta gttatttttt ggtagtttta 30900
ttttttggta atttttaag ttgagttttg gatgatgtaa ataatatttt tagattttta 30960
atgggtatat gttgaattaa aaagaaaaat ttatggtatt ttttaattat gtgtaaatga 31020
gtaaagaaaa aggaaagaaa aggagtggtt aaattgatat ggtagggttt aggattgggg 31080
gaagaagaaa gagtaataga gagagtggaa tagttaaaaa aagaatgaga ttatgttttt 31140
tgtagaaata tggatggagt tggaggttat tattttagt aaattaaatt aggattagaa 31200
aattaaataa cgtatgtttt tatttataag tgggagttaa atgaggagaa tttatagata 31260
taaagagagg aataatagat attggggttt attggaaggt ggcggatggg agaggggaga 31320
ggattagaaa aaataattat tgggtacgag gtttagtatt tgggtgataa aataatttgt 31380
ataataaatt tttgtgatag gtttatttat ataataaatt tgtatatgtg ttttgaattt 31440
gagatataat ttaaagaaaa agagagcgta tttgtttgta aattggtttt agtagattgt 31500
tttttgagtt tttttgttt tttaaattga atttaagtgg tattatattt ttaaatgaaa 31560
attttatttt taattatagg tgaagttaat tttttatttt tttaataatt tttttattat 31620
tttttgtatt gtaagtaagg taaagattta gtttaaatgt tgttagttta gtttattttt 31680
taaaaaatat attttttgag aggtttgaga aaattaagaa agtatatttt gtttagtttt 31740
tttaaatatt atttttttgg aaatagtatt ttgtttagtt tttttaaata ttattttta 31800 attagtgagt tagtttagat tttagagggt ttttggaatt agaaagaagg taaggatgaa 31860
tattaggttt aagattattt ttatgttgtt ttattattaa attagaaaat ttggatgttt 31920
tgtaggtagg tatgtttatg agagttattt aaaaaagata tgttttttga agtgttaagt 31980
ttagtgatta cgtagtttat g 32001

<210> SEQ ID NO 8
<211> LENGTH: 12001
<212> TYPE: DNA
<213> ORGANISM: Homo sapiens

<400> SEQUENCE: 8
gtgttagatt ggagttgatt ggtgattaat ttaaaggagt tataatttaa agaaatggtg 60
agagtttggt atttaggttt ggtttttagg taattcgttt gggtttgaga ggttattaat 120
tgttagttaa gatggaattt tttttttt tttttttt taatggataa taatgggaag 180
ggggttaatt ttttagtagt tgaaattttg tatttagttt tttattttga gaatgttaat 240
ttttggttcg aggatttgtt tttgtagtgt tggtatcgag atttaaggga agatatttcg 300
ttttaaatgt tagttacggt ttggtttttt tttcgatttt agtattttgt agattgttag 360
tgtttgtggc gggggacgaa aggaataggg ttttgtaagg tttgtttgtc gattgcgtta 420
ttttgggcga aatttagttt taaaagttat aaattattta cggtgaagat ttttcgaagt 480

```
ggaataaatt tttagattcg tattatttta tatttttgcg ggatagatgg tttttattta    540
tcggttatcg ggagagagtt gttgttttcg cgttttattg tttttcgggg cgatttttag    600
cgagtcgagt tttcggttgt acggtaagcg ttcgaaagtc gggtttgaga ggattgtagg    660
gtttttgagg gtgttaagtt tcgaaggagt ttacgggtgt attggggttt tcgaaattta    720
gtcgttattg gtagtttttt tttgtttttt tttagttttt tcgttcggtt tcgtattttt    780
ttttttttt ttttttttta ttttttttt tttttttgt ttttatttcg tgtggggagt    840
gacgtgacgt tagtagagat tttattaaat tttattgtat agtggcgcgc gggcggtcgg    900
tcgagttcgg ttgcgcggtt ggcgatttag gagcgagtat agcgttcggg cgagcgtcgg    960
ggggagcgag taggggcgac gagaaacgag gtaggggagg gaagtagatg ttagcgggtc   1020
gaagagtcgg gagtcggagt cgggagagcg aaaggagagg ggatttggcg gggtatttag   1080
gagttaatcg aggagtagga gtacggattt ttattgtgga aaggaggatt agaagggagg   1140
atgggatgga agagaagaaa aagtaatttg cgttaattcg gtagttttaa taaattaaag   1200
ggggagcgtt agggtagcgg ggagatagaa acgtattttt ggggagtaaa ttaggacggg   1260
ttgggaggaa gcgataggga aagtggttta agagacggaa taaaggataa tgtttatggg   1320
gttgtttggg acgaggcgtg tggagtgtgg gtgtgagcgt gcgtgtgtga ttttttttta   1380
ggtttgtaga gttgaggaaa gaggttatag taaagaggga ttgcggaggg aggaaagtga   1440
gagatcggta gagggcggga gtggaggtgg gcgcggtggg gatgggagag gatgagtgaa   1500
gagaaattta gaagaatgga gtgagttagt gggagagggt gggagggtta tagtcgggag   1560
cgaacgagtt aggtttgtta gttggggaag gtcgggacgt tgggtttagt ttagttggga   1620
tatcgcgttc gaggttaagg cgggtggatt aggtatgttg agagtgtcgg cgtataggtg   1680
ggtacggtta cgtattgatt tagtgtttac gaagggtttg tattggataa ggtttagacg   1740
tttatagagt ttagaatttt ttttgttgta tttatattta ataagtttat tttgggttac   1800
ggatatttta ttttttaaaa tgacgaggtt aaggttttttg gcgaggatgg tattaaattg   1860
tacgggatag aagtgggggt gggggagaga gtttttttta agtttatatt tgtttttgta   1920
aagtaaagag tatgtgaaat tatagggtat atttttattc gaaaagtgtg ttttattttt   1980
gaattttgat tttttgattt tttgatttga gtaaagatgt gtattttggt agtgagtaga   2040
atattttggt tttgttttgt ttttgagtgg aaggattata aatataattc gtttggagga   2100
ttaggtgtga aggtttttgt taggtatatg ggataatgtt tttttaattt taagggtatt   2160
ttgttaatgt atgtttttgg aaagtgtcgg aatatagtta ttgtttttgg attcggattt   2220
ttttattaat attaattttt gtttgagagt aaaatttagg ttcgttatta aaaagatatt   2280
tttttggttt ttaattgaga ataaagtttt ttttaaaagt tgtattgttt tttttaaatt   2340
aatatattaa tattcgtaat tttagaaata tatagtgatt cgggagaatg tgtataaaat   2400
agatacgttt aaaaaagttt ggcgtttaaa attaatttta gttattatat aggtgttggg   2460
tttttttat ttttgggggt tgtttggaat atgttatgtg ttttttttgaa ttatttcgtg   2520
ttttgaattt atttgagtta gtagtaaaaa taggtaaata aatttgttta atttgttttg   2580
agtgttaaat ttttttattt tgaaatagtt aatagtcgat agatggattt attttatgga   2640
aagggttagt ttttttagtt acgaagaaaa ttgattagag atttatattt taagttattt   2700
ttaattttta cgtaatattc gtgaaaattt aaattttttt tttttattta gtggaaattt   2760
aaagtagtgt tatttaaggg gagagaaatg agggggaaaa tgtttacgtg ttgtttaatt   2820
```

gtattttttt tttgattttg agaattttta tttttggttt ttgaaatttc gtcgaggtaa 2880
gaaaattaaa tttttttaat aagttttata attgaatttt agttatagga tatcggaaag 2940
tgtagttcga gaaagatatt tttattttttg tttatcgacg atttttgtag ttttttttatt 3000 tttttgagta atgggttaat aatttttttt tttttttttt ttattttgta gagattaaga 3060
ggcgttcgta gtagaacggt tttgttttta gttggtggcg aggataggta attttatgga 3120
aaagttggaa gagaatgaga aaattaaaga tagaaagatt tagagattcg cggagagata 3180
tagggagagg gaagggagtt gcgttgaaaa gacgtaaaga tacgcgcgtg taattttttt 3240
tttttttagg ttttagaggt ttgtaaatta gggttgagag gaaggggttc gggaagttta 3300
cgtttttttc gttttttttt tgtttggagt ttcgttcgtt agaggttggt taattttagt 3360
ttcggtcgtc gtagatattg cgttgagttt ttgggttttc gttttgttta gcgttagtgt 3420
agttgaagtg agtagttggt gggaaatgta aatggttttt ggagaaatag aagatataga 3480
atgattttta ttttttttttc gagtgtgtgg aaggagttgg atatacgttt tacgttttta 3540
attttttttt tatattttta gttatatttt tattaaataa ttaattaatg tttagaatta 3600
ttagggaata tattaggtat gtaatcgtag aagtagggtg ttggggggtt ataaattatc 3660
gagttgattt aagacgtgga ttttaggttt tttttttgtt aaagtagtaa aggaagagcg 3720
ggttttggcg attgtattta gatttcgatt attttaaatt agaagggggt ggagggagcg 3780
tttaagtaaa gtaagtaatt ttttgttttg tagatgtaaa taagattgta gtattaaagg 3840
tattagtttt tttagggtta gatcgtttgg attgggagtt tggggaaggg gagatattaa 3900
ttttacgtat ttgtgaattt taaggatgtt atatttttat ataaataatt ttagtgcgga 3960
ttttttggaa tggggggagt aatattttta ttttagaata ttaaaatatt ttttttttaa 4020
agcgtatatt ttttttattt ttttaaaatt ttgaattatg tttaaagata atagtttttt 4080
agtaaattgg agtattggat tatttttttt attttttttt atcgatattt tgatgatttg 4140
attttaatgt gtgggggggta tagggaatta aatatagttt ataaaattaa gtttagatga 4200
aatagtgttg gttaagtggg tttagataat ttttaatgag aattttaatt atattttttt 4260
ttttaatatg ttgagataag tgatagaatc gttagaatgg taattaaatt ggaaagttta 4320
gggagaataa taatttcgtg attaaattgg ggtaaaatcg tggataaatg tggggtgatt 4380
ttcgttaatt ttttgttatt taagagttag gatttgggaa aggtatagta ttattttaga 4440
gttcgttgtg acgggttgtg tgttattatt tattttttttt attttggatt atgattttaa 4500
ttttggtaag taattttttt agtttttttat ttgataataa gcgagtatgt aaatattaat 4560
ggttagcgat gtttaattgt tttaaatatt attgatttgt tggttgtttt aaattgtttt 4620
tttagtttag gttttgtttt cgaattgttt attttagagg tttgatttat gttttcgatg 4680
ttataatata ataattgttt ttttaaaaaa ggtatttaag atgaattaat tgatttgtat 4740
ataaattaaa attattatgc gttgtcgatt tcggtgtttt ataattattt cgaaattagt 4800
atttaattat ttgagttaaa agaatatata aatgtttgta ttgatttatt aatgaattat 4860
ttaattaaaa cgttcgggta atgttgggcg ttggaaagat tgttaaatta agatatatta 4920
taggagggat atgaagatta gaaaggtaat agattaatat ttcgtattta aaacggagtt 4980
ttcggtgatt tttagtttta attttggagt aggggttttt tttttttgtt gttaaaaaga 5040
ttttgtgttt gtttgtgagt gagtgtattt aagtggaagg aacgttttta cggttacggt 5100
ggtttaggtt ttttgttcgg atcgggattt tatagtttta atttaggagc gttaaatttt 5160
ggaagatttc gggttagttt tggaggtgcg tggtttcgta agtcgttagg ttaagtttgt 5220

-continued

```
ttttttgtt tgttttttcg gtaggttggg cgcgttatgg tagtgagttt ttcgcgtaaa   5280
cggagagttg gaattaaagt tgatatttaa tagatatgtt aattgagtat ttattttcgt   5340
tttgagaata ggaataaaag gtagtttttt ttaagagagg cggtgtaaag gtacgttata   5400
ggagtttaga aaaggttggc ggcgggaaat ttgtagtttg ggggttagtt aatattttt   5460
tttattttaa gtatttattg atttgttgtt gttattttttg gcgacgtaga aggatatttg   5520
aaagaatttt tgatggggtt ttgatttgag aaaggaggtg atttgtttag gtttttatta   5580
aatttttaat tattatatta attgtttttt tttattttt attcgatttt ttttttttg   5640
tttattttta atttttaat tatttagaaa tttttttatt ttttagtggt ttttttttg   5700
tagtagtttt ttattcgaat ttttttttcg ttttttcgtg gtagggtttg tatattgatt   5760
tttttgattt ttggtatatt tgggtttttt gaaatttttt aattttttta gatttgagga   5820
tggtaggttt tattttttt attgtgtgta tatatttaga gatatgaaaa tttatataga   5880
ttgtttttaa atttagggta tttaatagat gtttttttt tagttcgttt tttgatttga   5940
aatgtttgtt tgattttaat ttggatatta ttttttttg ttttttttt tttaaagtag   6000
tttggatatg tgtgtaagtg agtttagaat agttttattt atattttta ttaaattgta   6060
aataaaagaa gaattaatga agtagattgg tatatagatt gtattaagag ttcgaatttt   6120
tagtttttgg atttttattt taattttggt tgttatttat attgatagag ttattttaag   6180
tagaggttta gagaaatttg tattgtggga taataggtaa agttatagta aaaagtggaa   6240
taattttaaa gttattttat tagaatgtaa attgtatttt tgggttttgt tcgtaattat   6300
ttagttttaa tatatataga gttagatagg aaaaaatagg ttaatatagt tattggtatt   6360
agagaagata aattttatgg gtttttagt gaaaagaaga tttttaaagt ttataatttt   6420
tgattattta attttattta taattgtggg aatgaataag atattaattg ttttatgtat   6480
tttatttata ttaattaatt tgtgttttta ttaaaagtag ttatatagaa tttttttaa   6540
tttttggtag taagtttaga aaatgaagtt tatagttatt ttgaattgga tatattttt   6600
gagttgatta tttttgtaag tgtaggaata taatattgtt tttttatggt ttttttgtat   6660
tttttagggg tttgtaagtt tttattaggt ttgatattat tgtttgggtt tatatttatt   6720
ataagtaaat ttgattatta tgttgatttt aaaatagttt atttggttag tataatttta   6780
gtttttaaat tataaaaatt ttttaatata cgaagttttt agtttttatt tttttagtt   6840
ttttgtttat ttaaaatttt tattttaatt ggtgtaagta ataataattt gtattattat   6900
ttgtattttt tttatttttt tggagattgg gttggatttt agagagaata ttagtattat   6960
tattattata aataataaaa tttaaaagta aagtttttat ttgtatgata attggtattt   7020
ggaatgtttt tgatttattt aatgttattt tataaaggta ttttgtaaat tttttggaa   7080
tttttagtaa gagtttgtag taattggaat aatttttgg gaagatattt ttttgatgg   7140
gtttttagtt tttggaggaa tagattgaga gtaattaggg agggagggga tattggaaat   7200
tggtagttac gttagttgaa ataagtttgg gtttagtaag gtgattgatg ttgtggttga   7260
ttttttattt cgagtttttt tttaattggg gtattgattt tttttatttt gggattttaa   7320
ggtattcggt gtgtatgtag atttttttt tgtggttttt attatgtggt ttcgtagtag   7380
gtttttggtt taatgatatt ttatagttat agtttttata tttattatta tgattttaat   7440
gtttaggttt ttagtgtatt tatattaaat ttgttttatt agtaagttgg agtatatagg   7500
agagatgggg gtaagtaagg atttagtaga gtttaaattt agatatgttt aaatggtttt   7560
```

-continued

```
gattgtgtaa agtgtggtaa tgttttttgt tgttttagtt ttttatttta agttttatat   7620
gtttttttggt taatgaagtg tgatataggt tatatgttag gaataatagt atttgttgag   7680
aataaagtga atttaggaaa tttggtatat ataaaatgta tttagttatt tgaattagta   7740
ataatggtaa aaattaatat ttatagagtg tttagttaat ttagttattg tattaaatat   7800
ttttgtattg ataattatat ttattttta tgttaatatt ataaggtagg tattgttatt   7860
ttataaatga agatagtgag gtttgttatg attgtgttat tggtttaagg ttatttagtt   7920
ggttagagta taagtttata attgttggag gttatagtgg ataggatatt gttttaggtt   7980
acgtaggtag taagtggtat agtgggaatt tgaatttagg tttgtgtaat tttaaagttt   8040
aaaatgttaa ttagtatatt gaattaatgg taattggaat tagaagatta ggggtttttg   8100
ggggaaggaa atatagaatt tatttatgga atattttata aataaaagaa taatgtagag   8160
ataggaaagt aaatatattt tttgagggat ggagaaagtt agaaatgttt taaatgttaa   8220
agaggaggaa acgagaaatg attggatgag aaagtagaaa agttaaattt cggtatttgt   8280
tttgggtagt ttaggaagag aaaggtaagt ttagggatat ttttgagtta taggaaaatt   8340
aatgtttaga tggttagttt ggattaagtt taatatagga ttttaggaat atggtttatt   8400
agaattgttt tttagtaatt ttaagggaga ataaaatttt tgaattgggt ttaagtagtt   8460
ttattttaga agtaaagaga gatggaagta aggatcgagt aataagaata tttatattgt   8520
aagaatatgt aagttgagta ggagtgaaat ttagaaaaat ttgttaggat tttggttgtt   8580
gtgttaaatt atgttatatt ttaagtagaa attagatttt tattattatt atttgtttag   8640
gtttagttag taattttatt attgtagtaa agttatttga aattttaaga gaaatgattt   8700
tttgtgttga agaagatatt ttgggtggaa ggatgttagt agataaatgg agtgtaaaga   8760
tagtgatttt aaggatatag tttgtgggga gtaatattgg attatatatt cgttgtttgt   8820
ggtagaatgt tagttagggg agaatattag gtagtttttt ataagtttat tttattataa   8880
aaagatagga ttgattttaa aggttatttt taatttaggt ttgttttatt attgaaaatg   8940
atttaaaatt ggatttattt tggttttttt taggagggat agataaatat aatttgtata   9000
tatggttttt tagttttagg aagtatagga ggagaatgaa agaattaatt tagtttttttg   9060
tttttggta aaaattttta tatttgtgtt gttgtaagaa tttaagatta tttcgtttag   9120
aatgttgtgg tatttttgaa agtaaggttt gagggtatat agagttttat tttttatttt   9180
tacgttgtgg atttattgt ttttttaaa tgggaaagag aaattagaat ttatagaaag   9240
taaggtttgg aaaggattta gagggtattt tttttttta gtttatgttt aaattatttt   9300
tagaaatata gttagttata tttttagta aagagttttt tacggttttt tggtaatgta   9360
tttttatgtt ttataatttt atagttatat tgtatattta ttgattaaat tttaagtatt   9420
gaagaaaatg atgttatatt aaaaagtttt aattagtagg gggtatgttt tttagagttt   9480
tttaaatatt ttatattttt attttaaaaa aagatgaaaa tattattagt ttaatttaat   9540
agatggaaaa ttttgttata gagattttta gagagttata tttggttatg tagcgtgatg   9600
tttgaaagaa ttaaattaaa aataaagtta ggaaatttta tgtttagggt tttttagta   9660
gatatattat tttttggggg ttggttatta tttttttgtt tgagtaaagt atatgtttga   9720
ttgtaatttt atttgtttt ttgtttgttt gtttgtgagt agtttatttt ttaatttatt   9780
aatttatttt tttgttagtt ttttaaaata ttataagtta attaatgttg ataaaatttt   9840
atttttatta tgagtgttat ttgagtagat tgagatggtt gttatatttt ttaaatatta   9900
cgtgtaataa atagtgttgt tattgtttta gcgttatgat tttgttttta tttggaaatt   9960
```

gtataaatat tatatttttt gttatgatag gattattttt atttattagg atttttgata 10020
tttgtgttgt tatttgggag aatgttgatt attttgttta tgttattttt gaggttataa 10080
taatcgtttt tttgtttagt tgtgtttttt tttttatagg tgaatttagt tttttttttt 10140
atgtttgatt ttaagaaatt ggtgttttat tgaaagatgt ttaaattttt tgagagaaaa 10200
tgttggagta agaataattt gttatgtatt gtttttattt gagtattaat gtttttttaa 10260
ttttatatgt ttttaaattt tttgagaatt tttttttttt gaatgtaatt tatgaattaa 10320
aagtgatcgt aatttttaaa atattatgtt gtttatagta aatatatata atttttattt 10380
gttaattaaa aaaagtaata gggtttttat ttttattttt gatatttgtt tttttttattt 10440
ttttttaag tattttttt tttttttag agatgtattt attgagagta ttttgttatt 10500
ttttttttt cgtagttatg tatgattaaa gttgtgtttt tgaaattttt tattttttt 10560
gttataattg ataatttatt ttgtttttta ttaatttatt aatgttattt tattggtttt 10620
tgatttatat aaattaaata gattttagaa aatttaataa aaataaaaat aatgtttttt 10680
attttgaaat atttatttat tgtttttttt tagggtatat atattatatt tttttttttt 10740
atattttatt tttttgaat ttataagaat gtgttattga atatagagaa aataatttaa 10800
gaaaggaaaa ggaatgattt gtttaaaatg aggaaaaagt agagtcgagg tttaggattg 10860
tggtttaata agatgattta gttatttttt ggtagtttta ttttttggta attttttaag 10920
ttgagttttg gatgatgtaa ataatatttt tagattttta atgggtatat gttgaattaa 10980
aaagaaaaat ttatggtatt ttttaattat gtgtaaatga gtaaagaaaa aggaaagaaa 11040
aggagtggtt aaattgatat ggtagggttt aggattgggg gaagaagaaa gagtaataga 11100
gagagtggaa tagttaaaaa aagaatgaga ttatgttttt tgtagaaata tggatggagt 11160
tggaggttat tatttttagt aaattaaatt aggattagaa aattaaataa cgtatgtttt 11220
tatttataag tgggagttaa atgaggagaa tttatagata taaagagagg aataatagat 11280
attggggttt attggaaggt ggcggatggg agaggggaga ggattagaaa aaataattat 11340
tgggtacgag gtttagtatt tgggtgataa aataatttgt ataataaatt tttgtgatag 11400
gtttatttat ataataaatt tgtatatgtg ttttgaattt gagatataat ttaaagaaaa 11460
agagagcgta tttgtttgta aattggtttt agtagattgt tttttgagtt tttttttgttt 11520
tttaaattga atttaagtgg tattatattt ttaaatgaaa attttatttt taattatagg 11580
tgaagttaat tttttatttt tttaataatt tttttattat tttttgtatt gtaagtaagg 11640
taaagattta gtttaaatgt tgttagttta gtttattttt taaaaaatat attttttgag 11700
aggtttgaga aaattaagaa agtatatttt gtttagtttt tttaaatatt atttttttgg 11760
aaatagtatt ttgtttagtt tttttaaata ttattttttta attagtgagt tagtttagat 11820
tttagagggt ttttggaatt agaaagaagg taaggatgaa tattaggttt aagattattt 11880
ttatgttgtt ttattattaa attagaaaat ttggatgttt tgtaggtagg tatgtttatg 11940
agagttattt aaaaaagata tgttttttga agtgttaagt ttagtgatta cgtagtttat 12000
g 12001

<210> SEQ ID NO 9
<211> LENGTH: 4001
<212> TYPE: DNA
<213> ORGANISM: Homo sapiens

<400> SEQUENCE: 9

```
tagagtattt aatttttttt ttttaatagt aaagtttttg gatgtcgttt gatttgtttg     60
attttgtttt ttgtttttag aattttaata aatttggaat tttttatcga ttagtataaa    120
ttaggacgtt gttattgggt tatttatttg agtttatttt tgttaattta taaagtatag    180
atttgttata aagttaaggt aagttttttt tataaaatta tgattataat ttagaagagg    240
gggtgtgagt tttaattttt agagtttaat ttttgagaga agataaataa attaagtaga    300
aaagtttttt tttttttttt tttttttttt ttaagaggat tagtagttgt gtattaaaat    360
tttgttttcg gagattataa aattaggaaa tagggtgtgt gggagagatt tgaatggtcg    420
aaataatcgt aaagaaggtg taagaagcgc gagtttagga gggaaaaagt tgggttaggg    480
tcgggataaa ggtttttttag ggagggttaa tttttcgtg ttttggcgg gttttttttg    540
ttaaaggttt ataggttgga gtttgttcgc ggtttttggt ttggtaggga ttttattagt    600
tttgttttgg taattgtaag ttaggaatat aatgttttgt gtaggggatt gtttatgtag    660
tttagttcgt gagatcgcgg gatggcgggg tagtgagtcg gtgtcgtttt gggagtttga    720
gttagggcgg tagttttgtc ggtttcggag agggaattgt aatttcgtaa ttaggtcgtc    780
gcgaggtttt ttgtttttgt aaagttgcgt tttatcggcg tttttttagg cggcgttgtt    840
ttttatattt tttttggtt tatttggttt gtatttttat aatatttttt ttttattttt    900
tttagatttc gtgttggttt ttattcggat tcgggttttc gtaaggttgg tttatatagc    960
gattttttcg cgtgtggata tgttcgggta gcggtttttt tggaaagtgg tttttagttt   1020
ttggagttgt tggttggtaa agtgagttcg ttgtcgtttt tgtcgttttt ttttagacgg   1080
gttttcggcg tttacgtttt tatttttttt ttgttggttt ttattttttt ttgaaaacga   1140
aatatatata tttttttcgtt agtatgttta tttgtaacgc ggacgttaat tggatcggcg   1200
gtagaagtcg tggaagagtt gggttgtttg gcgtcggagg agggtgcgcg cggcggtttc   1260
gggtcgcgag gagcgttgcg tttgtggggt gtgtaggcgt aagtgtgggt gttcgcgttt   1320
tatttttttt tttttttag cgtcgtacgt tttatttata tgtttatttt attgtagcgg   1380
tatatttatt tttatagttt gtgtttttaa gtatatttat atatttttgc gtagatatat   1440
taaatttttt gggacgcgta tacgcgcgtg gtttatagat tttttttttt ttcgtagaaa   1500
gtttagattt ttatgcggtt tgggaaggtt aggaaaagat gtggggattc ggttgggtat   1560
cgaagttcgt cggttttttt ttaaaaaaaa aaaaaaaatg tttttcgcg aagggtattt   1620
ttgagtggtt ttaggtaatt ttttaacgag tggagttttt cgggagttga aagtcgagag   1680
gaaaataggg atagaggtcg gcggtttttg aaggttttcg aattaagatg ttgggatttt   1740
tgtgatttag gaaatagaag ggaggttagg gtacgaatag agagggcggt agaattgttc   1800
gcgtttttag cgttttagga gtcgggtcgg tcgagggaga attaaaggga tgcggggtag   1860
ttaaaatttc ggttttcgga agttttgcgg ggagttaggc gaacgattat ttttattacg   1920
ttttttttcg gaggggttga tttttttggg gcgagaggga gcgggtggcg tagagtagtt   1980
gagcgggaat gtttgtaggg cggcgcggcg ttttatttgc ggttttcggg ttggaggtgt   2040
cggagatggt gtgtattttt agtttgtgtt tggaggagtt tagcgatcgg ggttgatcgg   2100
gagttagaat cgaagttatg gttaacggtt ggggatggtg ataggaagat gaggagacgg   2160
tcgatagttt ggttttcgtt gttcggtgtt ttaagtgaag cgggtttttt atgtagttta   2220
tggacgaggg agcgcgacgt tttattagtt tttggttatt gtttcgtcga gttttcgtag   2280
tcgtcgttgt tcgtttcggg tcgcgtttta ggcgcggagt tttttcgttg cggggagagt   2340
taggggacgt aattttcgtc gagtttttaa gttaagttgt tttcgttttt ttcggaaggt   2400
```

```
ttaagcgaaa aagttcggag acggaaagtt agcgggtaaa cgaagatatg ggatgtgggt   2460
agaagggtat tatttagagc gtttttaggg agtaggtttt taagttttaa agcgaaataa   2520
gagtgggtaa agattttttt tttttttttt tttttttttt aagaattttt ttaataagga   2580
aagttaacgt cgatcgcgtt ttgttcgttt tttttttacg cggtagtttt gatagagaag   2640
tgttaagagt gatagggata ggtaggtgat attagatttt ttgcggcggt agtagtcgtt   2700
gtagttacga cgcggttttt tgagcgtatt tttcgtaacg cgtatacgta tatttttcgg   2760
gcggtcgaat aggagtcggg ttttgtcgta gtttagtttt aggtatttag gcgagcgacg   2820
gattagattt gcggtttcgc gttttttttgt tggtttaata ttttaaaatt agaggcgggt   2880
tttttggtgt cgagacgtta tttcgtcgcg gtttttttta gttttttttcg ttttcgtttt   2940
tttttagatt ttttttcggg tgcgattgac gtggtttcgt attaattagg acgtttcgag   3000
tcgcggtgga gggattgttt tgtttgtatt tattagtagt gcggggtcgg gttattgttt   3060
cgtcgtgcgt attgggttta tataggtaag ttttcgggaa tttagttttt gtttagttta   3120
aggcgattcg gtttttagta cgaatttaaa ggtgaagaga tgaggttagg agtcgaaggt   3180
ttgggagaag agagtggaat ggttaagaag agaaaggtat aaggattaat aagatattta   3240
tttttttgtgt tttattatat ttatttttaa tttttttattt tatataaaaa ggagatacgt   3300
tatttaaaat tagaaaattt gaaaaaatagt aataaattat tttttcgatt ttaaattttt   3360
taaatagttt gttaagtgaa tgttgcgtta atttgaagaa gttttaattg taaagaagat   3420
agagttttga aaaggtaggt taataaatta gaaatcgaga agtaaatgga ttcgttaaaa   3480
gaaaattatt ttgattttaa acgaataatt gtttggtggt ttattttgga tttatataag   3540
aataaaaagt cgttttagat tacgtttttt gtgatgttta ttagtttttta gatagaaaat   3600
atataataga agagaaattt taatttagcg tttttaaaat gttgaaagtt tatttatttt   3660
atttaacgtt gattaagata tatattttag atttttttaaa tttttttgtat attgtattaa   3720
gttcgtttta attcgagaga gttacgtttt aaattcgatt tttttgttta ttttattatt   3780
aattagattt aaatttataa agtttgtaga attaataatt ttgagttaat tatatatgaa   3840
atatgtttta atgaattttt atataattaa gaatgttgtt aaataattaa ttttaaggat   3900
aatttttaat agttattttt ttttttttagt gagtttaagg ttgttttgag ttattaaagt   3960
ttaagtaggt agaaggggtg tgtgtgagtt aagggcgaaa a                        4001
```

<210> SEQ ID NO 10
<211> LENGTH: 32001
<212> TYPE: DNA
<213> ORGANISM: Homo sapiens

<400> SEQUENCE: 10

```
tatggattgt gtgattatta aatttggtat tttagggggt atattttttt tgagtaattt     60
ttataaatat gtttgtttgt aggatattta gatttttttgg tttggtagta aagtaatata   120
agaataattt tgaatttgat gtttattttt gtttttttttt taattttagg agttttttga   180
ggtttggatt aatttattga ttaggaaata gtatttggaa aggttaaata aaatattatt   240
tttagggaaa tagtatttgg aaaggttaaa taaaatatat ttttttagtt tttttaaatt   300
ttttagaaga tatatttttt aaaaaataaa ttaagttagt aatatttaaa ttaaattttt   360
gttttgttta taatataaaa gatgataaaa aaattgttgg gaaggtgaga aattaatttt   420
atttataatt agaagtaaag tttttattta aaaatgtaat attatttaaa tttaatttgg   480
```

-continued

```
gaaataaaaa ggatttaaaa aatagtttgt taaagttaat ttgtaaataa gtgtgttttt    540
ttttttttta agttgtattt taggtttaga gtatatgtgt aggtttgtta tgtaggtaaa    600
tttgttatag ggatttgttg tatagattat tttgttattt aggtattaag ttttgtattt    660
aatagttatt tttttgatt tttttttttt ttttatttgt tattttttaa taggttttag    720
tgtttgttgt ttttttttt gtatttatga gttttttta tttagttttt atttataagt    780
gagaatatgt gttatttggt tttttggttt tgatttagtt tgttaaggat aatggttttt    840
agttttattt atatttttgt aaaaggtatg attttatttt ttttttaatt attttatttt    900
ttttattatt ttttttttt tttttaattt tgaattttat tatgttagtt taattatttt    960
ttttttttt tttttttttg tttatttgta tatagttaaa agatgttatg aatttttttt   1020
tttaatttag tatatgttta ttaaagattt aaaaatatta tttatattat ttagaattta   1080
gtttaagaaa ttattaaaaa ataaagttat tagaaagtaa ttgaattatt ttgttgagtt   1140
ataattttag attttgattt tgtttttttt ttattttagg taggttattt ttttttttt   1200
tttaaattgt tttttttgta tttaataata tatttttgtg gatttagaaa gggtggagta   1260
tgaggaaaag gaatatgata tatgtatttt agaggaaaat aataaataaa tattttagga   1320
tggaaaatat tatttttatt tttattgagt tttttagagt ttatttgatt tgtgtaaatt   1380
agaaattagt agaatgatat taatgaatta atgaaaagta gaatgagtta ttagttgtaa   1440
taaaaagaat aaagaatttt aagaatatag ttttaattat gtatggttgt ggggagagaa   1500
aaataataaa atgtttttag tgaatatatt tttgagagaa gaaaggaaat atttaaggag   1560
aggataaaaa gagtaaatat taaaaatagg agtaagaatt ttattgtttt ttttagttga   1620
taaataaaaa ttgtatatat ttattgtgga taatatgata ttttgaggat tatgattatt   1680
tttgatttat aaattatatt taagaaaaag aaatttttaa aaagtttggg aatatatgaa   1740
gttgaaagaa tattaatatt tagataagga tagtatatga taaattattt ttgttttaat   1800
atttttttt aggaaattta aatatttttt agtgaagtat tagtttttttg aaattaagta   1860
tgagaaaaaa aattaaattt atttgtggaa aaaaagatat agttaaataa aaaagtggtt   1920
gttataattt taagagtggt atgaataaaa tgattaatat ttttttaagt gatagtataa   1980
atattaaaag ttttaataag tggaagtggt tttgttatga taaaaggtgt ggtatttgta   2040
taattttag ataagaataa agttatgatg ttaagatagt agtagtattg tttgttatat   2100
gtgatatttg aaaaatatga taattatttt aatttgttta agtagtattt atggtgaggg   2160
tgaaatttta ttaatattgg ttaatttatg gtgttttaaa aaattagtaa ggagataaat   2220
tgatggatta aaagataaat tatttatagg tagataaata gaaggataga tagagttata   2280
attaaatatg tatttttattt aggtagaaag ataataatta gtttttaaga agtgatgtgt   2340
ttgttagaaa agttttgaat atagaatttt ttgattttgt ttttaattta gttttttttag   2400
gtattatgtt gtataattag gtgtaatttt ttaaaagttt ttatgataga attttttatt   2460
tgttaaatta ggttaataat atttttattt tttttttaggg taaagatgtg aaatatttgg   2520
agaattttgg aaaatatgtt ttttattaat tagagttttt tgatgtgata ttattttttt   2580
tagtatttgg agtttagtta atagatatat agtgtagttg tgaaattatg aagtatgaga   2640
atgtattatt aagggattgt aggaggtttt ttattgaaaa gtgtagttgg ttatattttt   2700
ggaagtaatt taaatatagg ttgagggaga ggagtatttt ttagattttt tttagatttt   2760
atttttttatg aattttaatt ttttttttt atttagaaaa aataatgaga tttatagtgt   2820
agagatagaa aataaggttt tgtgtgtttt taaattttat ttttaaaaat attatagtat   2880
```

```
tttggatgag atagttttga atttttgtaa tagtataggt atgagagttt ttattagaaa   2940
ataggagatt ggattgattt ttttattttt tttttatgtt ttttaaaatt gaaaagttat   3000
atatataaat tatatttatt tattttttt ggaaaaggtt aaaatgaatt taattttgga   3060
ttatttttaa taatgggata aatttgaatt gagaataatt tttagaatta gttttgtttt   3120
tttgtgataa aatggatttg tagaaagtta tttggtgttt ttttttagtt aatattttat   3180
tataaataat gggtatgtaa tttagtattg ttttttatag gttatgtttt tggaattatt   3240
atttttgtat tttatttgtt tgttgatatt tttttattta agatgttttt tttagtataa   3300
gaagttattt tttttaaaat tttaaatgat tttattataa taatagagtt gttaattaga   3360
tttaggtaag taatgataat aaaaatttga tttttattta gagtgtagta tggtttaata   3420
taataattag agttttaata ggttttttta gattttattt ttatttaatt tgtatgtttt   3480
tgtaatatag atgtttttat tatttggttt ttatttttat tttttttgt ttttggaata   3540
aaattattta aatttaattt agagatttta ttttttttg gaattattgg gaaatagttt   3600
tagtaaatta tatttttgag attttatatt aggtttagtt taaattgatt atttaagtat   3660
taattttttt gtggtttagg aatattttg agtttatttt ttttttttta aattgtttag   3720
gataaatatt ggagtttggt tttttgttt ttttatttaa ttatttttg ttttttttt   3780
tttagtattt aaaatatttt tgattttttt tattttttaa gaaatatatt tgttttttg   3840
tttttgtatt attttttgt ttatgaaata ttttataggt aagttttata ttttttttt   3900
ttagaggttt ttggtttttt ggttttagtt gttattggtt tagtgtatta gttaatattt   3960
tggattttgg agttatataa atttagattt aaatttttat tatgttattt attgtttatg   4020
tgatttgaag taatatttta tttattgtgg tttttagtag ttataagttt gtgttttaat   4080
tagttgggtg attttgggtt agtgatataa ttatggtaaa ttttattgtt tttatttgta   4140
aaatgatagt atttatttg tagtgttggt ataaggaata agtgtgattg ttaatataaa   4200
agtgtttagt ataatagtta aattaattaa gtattttgta aatattagtt tttattatta   4260
ttattaattt aaatgattag atgtattttg tgtatattag gtttttgag tttattttgt   4320
ttttaataaa tattattatt tttagtatgt ggtttatatt atattttatt agttagagga   4380
tatgtgaagt ttagagtgga aagttagggt agtaggaagt attgttatat tttatatagt   4440
taaagttatt taaatatgtt tgaatttgag ttttgttgag tttttatttg tttttatttt   4500
ttttgtgtgt tttagtttat taataaagta ggtttaatat aaatatatta aaagtttaaa   4560
tattgagatt atgataatga atatgagggt tatgattata aaatattatt gaattagaga   4620
tttgttatga aattatatgg tgaagattat aagggaggaa tttgtatata tattgagtgt   4680
tttgggattt taaagtggga agagttagtg ttttaattaa agagaaattt ggggtaggga   4740
attaattata atattagtta ttttattgaa tttaggtttg ttttagttga tgtagttgtt   4800
aatttttaat gtttttttt tttttaattg tttttaattt atttttttag aaattgaaag   4860
tttattaaag aggatatttt tttagagagt tgttttagtt attataagtt tttgttagaa   4920
attttaagaa agtttataag gtatttttat aaggtggtat tgagtaagtt agaagtattt   4980
taagtattaa ttattatgta aataagggtt ttatttttag attttgttgt ttgtggtggt   5040
ggtgatgttg gtgtttttt tggaatttag tttaattttt aaaaaagtaa aaggagtata   5100
aatagtaata taaattatta ttatttatat taattaaaat agaagttttg aatgagtaag   5160
gagttagagg aggtaaaaat tgggaatttt gtatattaaa aggtttttat aatttgaaaa   5220
```

ttaagattat gttggttaaa taggttgttt taaaattagt atagtaatta aatttgtttg 5280
taatgaatgt agatttaaat agtgatgtta gatttgataa ggatttgtaa attttaaaag 5340
agtgtaaaaa gattatagaa gaataatatt atatttttgt atttatagaa atggttagtt 5400
taagagatgt atttagttta gggtggttgt aagttttatt ttttgaattt gttattagaa 5460
gttaaaagaa attttgtata attgtttttg atggaaatat aaattggttg atgtaaatga 5520
aatatataaa gtagttggtg ttttatttat ttttataatt ataaatgaaa ttaaatgatt 5580
aaaaattata gattttgggg attttttttt tattgaggag tttatggaat ttgttttttt 5640
tagtattaat aattgtgttg atttattttt ttttgtttaa ttttgtatat attaaaatta 5700
ggtggttatg aataaaattt agaaatataa tttatatttt aataaaatga ttttaaaatt 5760
attttatttt ttattgtggt tttatttgtt gttttataat gtaggttttt ttgggttttt 5820
gtttagaatg attttgttaa tgtagatgat agttagagtt gaatggggaa tttagaaatt 5880
ggggatttgg gtttttgatg taatttatat gttaatttat tttattagtt tttttttat 5940
ttatagtttg gtaaagaata tgggtggagt tgtttttgggt ttatttgtat atatgtttaa 6000
attgttttga aaaaggaagg gtaagaaaga gtggtattta agttggaatt aggtaggtat 6060
tttagattaa gagatgaatt ggaaagggaa tatttgttag atatttttggg tttgaaggta 6120
gtttgtgtaa gtttttatat ttttgagtgt gtgtatatag tggagagggt ggagtttgtt 6180
atttttaaat ttgaaaagat tgagagattt tagagggttt agatgtgtta aaggttagag 6240
ggattaatat ataggtttta ttatggaaag gtggggaaaa ggtttgaata gaaaattgtt 6300
gtagaaggga agttattgag aggtaaggga gtttttgaat aattaaaaag ttaagaataa 6360
gtaaaaggaa ggaggttggg tgggggataa aaaaaagtag ttgatgtggt aattaagaat 6420
ttggtgggag tttgggtagg ttattttttt ttttagatta gagttttatt agaaattttt 6480
ttaagtgttt ttttgtgttg ttaaagatga taatagtaaa ttaataagtg tttgaaatga 6540
aaggggatgt tgattagttt ttaggttata gatttttttgt tgttagtttt ttttgaattt 6600
ttatagtgtg tttttgtatt gttttttttta agaagagtta ttttttattt ttatttttag 6660
gatgaaggta agtgtttagt tagtatattt attaaatgtt agttttggtt ttagtttttt 6720
gtttgtgtgg aaagtttatt gttatagtgt gtttagtttg ttggaggggt agatagaaaa 6780
agtaagtttg gtttggtgat ttgtggggtt atgtattttt agggttggtt tggagttttt 6840
tagagtttaa tgtttttggg ttagaattgt aaggttttgg tttgagtaaa gggtttgagt 6900
tattgtagtt gtgggagtgt tttttttatt tgaatgtatt tatttataaa taagtataaa 6960
atttttttaa tagtagagga gaaagatttt tgttttaaaa ttaaagttgg gaattattgg 7020
aaattttgtt ttgagtgtga gatattggtt tgttattttt ttaattttta tatttttttt 7080
gtaatatgtt ttgatttaat aattttttta gtgtttagta ttgtttggat gttttaattg 7140
ggtaatttat tagtgagtta atataggtat ttatatattt ttttagttta agtggttaag 7200
tattaatttt gaaatgatta taaaatattg gaattggtaa tgtatagtaa ttttaattta 7260
tatgtaaatt aattggttta ttttaaatgt ttttttttaaa aaaataatta ttgtattgta 7320
gtattggagg tatggattaa atttttagaa tagataattt ggaaataaga tttggattag 7380
gaagataatt tagaatagtt aataaattaa taatgtttga ggtagttaaa tattgttagt 7440
tattggtatt tatatatttg tttgttgtta gataaggagt tggggaaatt gtttgttagg 7500
gttgagatta taatttagag tgaagaaagt aaatggtagt atatagtttg ttatagtggg 7560
ttttgaaata atattgtatt ttttttaaat tttgattttt gggtgatagg gagttggtgg 7620

-continued

```
aggttatttt atatttgttt atggttttgt tttaatttga ttatgaaatt gttgtttttt   7680
ttgagttttt taatttgatt attattttaa tggttttgtt atttgtttta atatattggg   7740
gggaggagtg taattgagat ttttattaaa aattatttga atttatttag ttagtattgt   7800
tttatttaag tttagtttta tgggttgtat ttaatttttt gtgtttttta tatattaaaa   7860
ttagattatt aaaatgttgg taggaaaggg tgaaggaaat ggtttaatgt tttagtttat   7920
tggaagatta ttatttttag atatagttta aaattttgag gaaataaaaa ggatatatgt   7980
tttgggggga aaatgtttta atattttaga atgggggtat tatttttttt attttagaga   8040
atttgtattg gagttgttta tgtaaaaatg taatattttt gaaatttata gatatgtaag   8100
gttagtgttt tttttttttt aggtttttag tttaggtgat ttagttttaa aggagttagt   8160
atttttgatg ttataatttt gtttatattt gtagggtaga gaattgtttg ttttgtttgg   8220
atgttttttt tatttttttt taatttgaag taattggaat ttaaatatag ttgttaaggt   8280
ttgttttttt tttattgttt tgataaggga aaaatttgaa atttatgttt taaattagtt   8340
tggtggtttg tagtttttta gtattttgtt tttatgattg tatgtttaat gtattttttg   8400
gtgattttgg gtattaatta gttgtttaat aggagtatga ttaaaaatgt aaaagaagga   8460
ttaggagtgt gaaatgtatg tttagttttt tttatatatt tgaggaggga atgagaatta   8520
ttttgtattt tttatttttt taggagttat ttgtattttt tattagttgt ttattttagt   8580
tgtattggtg ttgggtaagg tgaggattta aaagtttagt gtagtgtttg tggtggttgg   8640
gattggggtt aattagtttt tggtgggtga gattttagat agaagggggg tgagaggaat   8700
gtgagttttt tgagtttttt tttttagtt ttggtttgta aatttttgaa atttgaaagg   8760
ggagggagtt gtatgtgtgt atttttgtgt tttttagtg taattttttt tttttttttt   8820
gtgttttttt gtggattttt gaattttttt gtttttggtt tttttatttt tttttaattt   8880
ttttatgaga ttgtttattt ttgttattag ttgaaggtaa ggttgttttg ttatgagtgt   8940
tttttaattt ttataaaatg aaaagaaaaa aagggaggat tattagttta ttatttagag   9000
gaatggggag gttgtaaaaa ttgttgatgg gtagaggtga agatgttttt tttggattgt   9060
attttttggt gttttgtaat tagagtttag ttgtgggatt tgttgaagaa atttgatttt   9120
tttgttttgg tgagatttta aaaattagaa atagaaattt ttagagttag agaggaaata   9180
taattaaata gtatgtgggt attttttttt ttattttttt ttttttaaat aatattgttt   9240
tgagttttta ttgggtaaag agagaaagtt tgagttttta tggatgttat gtggaggtta   9300
gaaatggttt aaaatgtaga tttttaatta gttttttttg tggttgaaga ggttaatttt   9360
ttttataaaa tgagtttatt tgttgattgt tagttatttt aaagtgaagg gatttagtat   9420
ttaaaataaa ttgagtaagt ttgtttgttt gtttttattg ttaatttaaa tgaatttaaa   9480
atatggagta atttaagaaa atatataata tgttttagat agtttttaaa agtagggaaa   9540
gtttagtatt tatatagtga ttagggttag ttttaagtgt taagtttttt taaatgtatt   9600
tattttatgt atattttttt gagttattat atatttttaa aattgtgagt attggtatat   9660
tgatttagga agagtaatat aatttttaga gggaatttta tttttaatta gggattaaag   9720
agatgttttt ttaatagtgg gtttgagttt tgtttttaag taggaattaa tattggtggg   9780
aaaatttgaa tttaggagta atggttgtgt tttggtattt tttaaaaata tatattaata   9840
ggatgttttt gagattgaaa aaatattgtt ttatatgttt ggtagaagtt tttatatttg   9900
gtttttttagg tgaattatat ttatagtttt tttatttaga ggtaggatag agttaaaata   9960
```

-continued ttttgtttat tattaaaata tatatttttg tttaagttaa gaaattagaa aattagggtt 10020
tagaagtaag gtatattttt tgagtgagaa tatgttttgt aattttatat atttttgtt 10080
ttgtaggagt aaatgtggat ttgagggaaa tttttttttt tatttttatt tttattttgt 10140
gtaatttaat attattttg ttaggaattt taattttgtt attttaaaaa atgagatatt 10200
tgtgatttag ggtgaatttg ttgaatgtag gtatagtaga ggaaatttta gattttatga 10260
gtgtttgagt tttgtttagt gtaaattttt tgtgaatatt gggttagtgt gtggttgtgt 10320
ttatttgtgt gttgatattt ttagtatgtt tggtttattt gttttgattt tgggtgtggt 10380
gttttagtta agttgggttt agtgttttgg ttttttttag ttgataagtt tagtttgttt 10440
gtttttggtt gtggtttttt tatttttttt tattagttta ttttattttt ttagattttt 10500
ttttatttat ttttttttat ttttattgtg tttattttta tttttgtttt ttattggttt 10560
tttatttttt ttttttgta gtttttttt gttgtgattt ttttttttaa ttttgtaggt 10620
ttgaaagaag gttatatatg tatgtttata tttatatttt atatgttttg ttttaaataa 10680
ttttatgaat attgtttttt gttttgtttt ttgggttatt tttttgttg tttttttta 10740
gtttgttttg atttgttttt taaaagtatg tttttgtttt tttgttgttt tggtgttttt 10800
tttttgattt attagggttg ttgggttggt gtagattgtt tttttttttt ttttatttta 10860
ttttttttt tggtttttt ttttatagtg ggagtttgtg tttttgtttt ttggttggtt 10920
tttaagtgtt ttgttaggtt tttttttttt ttgttttttt ggttttggtt tttgattttt 10980
tggtttgttg gtatttgttt tttttttttg ttttgttttt tgttgttttt gtttgttttt 11040
tttggtgttt gtttgggtgt tgtgtttgtt tttggattgt tagttgtgta gttgggtttg 11100
gttggttgtt tgtgtgttat tgtgtagtgg agtttggtgg aatttttgtt gatgttatgt 11160
tattttttat atggagtagg agtagaggga agagagaggg atgagaggga gggagaggag 11220
agagagtgtg agattgagtg agaaagttgg agaggagtag aaagaaattg ttagtggtgg 11280
ttagattttg gaggttttag tgtatttgtg gatttttttg gaatttggta tttttaggag 11340
ttttgtagtt tttttaggtt tggtttttgg gtgtttgttg tgtagttgga ggtttggttt 11400
gttggaaatt gttttgggaa gtagtgggat gtggagatag tagttttttt ttggtagttg 11460
gtaagtggag gttatttatt ttgtagggat gtgagataat gtgagtttgg aaatttgttt 11520
tattttggag aatttttatt gtaggtgatt tgtggttttt ggggttaagt tttgtttaag 11580
gtaatgtagt tggtaaatag attttgtaaa gttttgtttt ttttgttttt tgttatagat 11640
attaataatt tatagggtgt tgaagttgag agggaagtta gattgtggtt ggtatttaaa 11700
atgaggtatt tttttttaaa ttttggtgtt aatattgtag gaataaattt ttgggttaag 11760
gattagtatt tttaagataa agggttgggt ataaagtttt agttattgga agattagttt 11820
ttttttattt gttatttatt gggaaaaaaa agaaaagaaa aagattttat tttaattggt 11880
agttagtgat tttttaggtt taagtgaatt atttgggagt taggtttgga tgttaagttt 11940
ttattatttt tttggattgt aatttttttta aattgattat tagttaattt taatttggta 12000
ttttaggaga tatattttaa atggatgtag agaattattt tttagttgga gattaagaaa 12060
aaaattttttg attttaaatt tttgaaatat gttttttttt tttagtttaa ttattttatt 12120
tttttaagta atttagaaat taaattatta taaggtggtg tgattttttt ttattttttt 12180
gtgtgagtat tgttttatta aattaaatgg aaaaaaattt tattattata aatgtaaata 12240
ttagaattta tatattttaa aatattttta tgaaaaatta atttgattta aagaaatttt 12300
tttgtatttg ttttagttta ttaattaaaa ttaaagatgt ttttattata taaaatatta 12360

-continued

```
ttttggtaga aatttattta aaatttaaat attaataata ttaagaaaat aaagtatata  12420
agtaaaataa attgaagatt tttgttgatg taatatgagt atataatatt ttaataatta  12480
aatttttttt aaaaaattaa atagttattt tatttgtgga atgttttatt ttaatttagt  12540
aaaattatat ttaaattatt taggtgtttt gtttttttaag ttaagtgtgt ttgtttttaa  12600
atgtttttaa agtatttata ttaattggtt gtaaagaatg tatatatatg gtaaaatata  12660
gaattgaatt gagtagtatt ttaatttttt taaataatta tttattataa attaatttat  12720
tggttaattt tataatttag tttatttaaa atatatgttt ttgtgttgtt tatttttaaa  12780
tttttttatta aagattttgt tatggggtaa taaagtgtat gaaaaggggg gaaatgtgaa  12840
aggatttggg attatttgaa ttgtattttt tttgtatttt tagttttgtg gtagttatta  12900
gaaattattt tttagtaaat tgttttattt tttagggttt gtttgtttgt tttgttatgg  12960
tttttttgttt tttgttagtt gtgtagtgtt ttttgtgtgt ttataaatata aaatttaagt  13020
tggttaaaat aagagttttt ggtatatata ttttaattag aatatgaatt ttgggggtga  13080
gaattatttt ttattaggaa aagtttttta ttttaatttg tgagattagt tattgaagtt  13140
agttttgaag tttggtagtt aaattttttta tagaagattt gttttgatag ggtaagttta  13200
aggattagta ggtgggaatt ggaggttttt ttttaaaaaa ttattttttt tagttattta  13260
gatttagttt ttttagtagg tttggttatt aaatgaagta taaaaatgta agttttaagg  13320
tttattttga ttgtaaaata aatttttaag ttataaggat atgtaggagt gagttaagga  13380
atatgttttg attttttttt tagtttttag agtggagttt tatgagtttt tgaagatttg  13440
ttttgtattg ttttgtttgg tttttagtat tgaagtatgg ggaagtgggg ggaagaatgt  13500
gtaataattg attgatttta tattaagtaa tgtaattttt tttttttgta tattttattt  13560
tttaaaaaaa ataaataaat aaaaattatt tgtagttatt atttgtagtg ttttggttat  13620
tagttaataa tgtagttagt ttagatatat aaaaaaaaaa gattattgaa atgatgatga  13680
tatgtaaatt ttttttgaaa ttattataag taaatatttg aagtttggat taataaaatt  13740
ttatttgtgt tattttatat tgagttagta gaaagttgtg ataatgaatt ttgtaatatt  13800
ttatgaatag atattttaat tagggattaa ttttgtgatt ttattgtaga attattaaat  13860
ttggagttgt taaattgtta tttttgggtt tatgggttta taaggattga attggtagag  13920
tttttgtttg tgtttttgtt agtgggtggg ggaattgttt ggttgttttt attttggatt  13980
tttatgttat agtgttgggt agtttttttt gtaggtagtg attttggtta gaggtttttt  14040
agggtttagt tttttttagg agaggttgag atgtagggaa atggtattta ggttagaggt  14100
aggtttgtag tttttttgttt tgtttttgtg tttttgttaa tttgataatg tttgttttta  14160
ttttgatttt tgtatttgtg tgaagtgggt tttttggttg ttggtgtatt ttggttagtg  14220
tggagagagg taggtgttga gattgaaggg gtttagggag ttttggattt tttttttttg  14280
tttttaaagt aattgtggtt tttttattta tttggtggag ttttttgaga tttattttttt  14340
ttggtttgtt tgtggtagag aagggggagt gtgttaaatg tttggtttgt tgtgttgtgg  14400
ttgaaaatgt gaaaaagatt tggtttgttt gggagagaaa gggggagaat tgggtagtag  14460
ttatattaga gttatttttt tgtttttggt gggtagtaaa ttttttaaga atgtttgttt  14520
tgtttttttt agttttgttt agtttattta gtgttttttt tttgtgattt taaattatat  14580
tttagggtaa ttatttgtag taagtaaata aatggttggg ttagtatttt taggagaaag  14640
tgtggttaaa tatggaaaag tggtttttga tggatgagag gtttgaattt agtttgtttt  14700
```

-continued

```
tgaaatattt taggttaaga gtttgtttgt tttagaatta tagaaaattg agggaaattg  14760
ttgtttagga taggggtatg ttggtgttga tgttttataa atgtttattg agttttaatt  14820
aatggataag tattgaaggg tggtttttgt atatagtttt ttaaagagaa aagttttttt  14880
tatttattta tttttgttgt tattgtgttt agatgagttt ttaattttgg tattgagatt  14940
tttgaaagta ggtttatagt ttttttagta tattgtggtt ttatagtttt ttaatttttg  15000
ggtatttttg tggtaatttt ggagggagat ttttttttga taaataaatg ttttgggttt  15060
gaggttaggt tggagatgtt gttgtatagt tagaggttgt taggttggaa aaatatgttt  15120
gaagtttagt atatagtagg tgtttaatag ttagtgtaat gtagttttat ttgagttttg  15180
tttatttgat ggttgttgtt ttttatagtt tttttttttt tttgttttgt agataatggg  15240
gaatggagat taattgttgt aaattggtgt tggtgtgtgt gtaattaggt aagaattttt  15300
ttttttgtt tgggttattg gatgggaggt tgtgttatgt gagggtggta agagggtatt  15360
ggttttgtgg tgaggtttta gtgaggggtg tttttttgag gggttagttt gggtaggaag  15420
gaaattagaa ttaaattgtt agtggttttt ttttgtggtg gggtggtgga ttaggaagta  15480
gtggtgtgtt gtgtattgaa gttttttagt ttattttttt tggttggaat tgttggtaat  15540
tggggaggtg tagaaagagt atgttatttt gttttgggtt gttagagggt ttgggggatg  15600
gggatgttgt tagttttttt ttttaattgg gtttttgttt tttgtttttt tttttttttt  15660
ggtttgtttt gttttttttt ttttttttgt ttttggtttt ttttggttgt ggtttgggat  15720
gttttttttt gtatgtgggg tgggtgtgtg tgtggtttag gtgtgtagtt ggtggttgtt  15780
gaatgttttt tttttaaaga ttttgaaatt aaaaaggttg agtttatgga tttttttgag  15840
agttgaaaag aggtagttag tagtaagttt tttttgtggt agtattttgg tgttaatggt  15900
aaggttggga gggaagtgta ggttgtgtgt tgggtatttg tttttgggat tttgggtttt  15960
gggtgaagtg taagaaggtg aggttgttag atttgatgtg tttgttgttt gaatttagat  16020
attttgtttt tgggtgggat gggaagtagt tgttttaggg atgttaattt tttttttttaa  16080
attatattgt atttttgaga tttaatattt tttttttttt tttgtttgtt ttttgtggtt  16140
tgattttttg tgtatgtttt agtaaatttt ggtgtttagg ttggtgtgga aaagtggttt  16200
aatagtgatt tttgttgttt gttatatttt gttgtgtgta gtattattag ggtttattta  16260
gttatttagg tttttagtta tgttttattt agatttgtgg gtgtgtggtt tattgtggga  16320
ggtaagtaag ggaaatttga gttggtgaag gtttgttttg gttggttggg ggaggggtgg  16380
ggggttgata atatttttga agagttggag ggtagttatt gtgtttagta gtttagggta  16440
gaatggaggt ttgtttttgt tgatgtgaat ttgtttgaag tattggttgt taggttttgg  16500
gttttggtga tgttgttgtt tgattggttg gttttatttt ggaggaattg agggatattg  16560
ttagaggagg tttataggtt tatgtaaaaa gttaaaaagt ttttaattta tgttataggt  16620
ttttttttgaa ttgaaatttg ttttatgggg tggagggggg ggtgtaaggg atggaggagg  16680
gaagatgttt ttttttttaa atatatggaa aaaaattttt taaatttatt gtttttttat  16740
tttttggtt ttgtagtaaa taagtgttta gttttaggag gttattgatt tttgataatg  16800
tgagtagata aagttttttt ttttttatag tttttggttt ttaatttttt ttttttggat  16860
taaagtgtaa gaatataaat gtaatatggg atggaggggg gtgatttggg attttggtta  16920
aaaaaataaa ttgtattatt aagaagaaaa taaaggtttt gtattggagt ttttttgtga  16980
atttgagaga aaatgattat ttgttgaaat gaagtgttta aagtgattta gtgttttatg  17040
tttggatatt gtattatatt gttagttgtt ttgttgggtt agttaaatgt ttatttgttt  17100
```

gggattaatt ttatggggtt aaatgggggt aatgtagaga taatgttgtg tgatttttgt 17160
tatttagatt gtgttaaatt tttttttgt ttgataattg gtagtaaaaa taaattatta 17220
gattgtagta tgtttgggat atggttaaaa attaagagta gtgatgattt ttggggagaa 17280
tgttttgtgt gggtttagtt ttggttttgg ttagattaga ggagtttttt aattttgttt 17340
tgtgtggggt gggtttgtag ttgttaagtt gaggttgata tttttattg tgttgggagt 17400
tagagagatg taaaatgttt ttttttttta gtttttattt taggtttttt agatatgggg 17460
aatgtatttt gaggataggt ggagaagttt atggtaggat ggggtttttg taggtgagta 17520
ggaaatggtt aagagtagag gagttttgtt tgtgttagtt ataagttgtg taggtgtttt 17580
tggttgtttg tttttgataa ttagtatata aagaattaga aataatgaat gattgttttt 17640
ttaattatta tttttaggtt tgtattgttt tagtgtatgt gaaaggtttt tttttttatat 17700
ttaatatgtt ttttttttatt ttttgattga aaagaaaaat tgttgtttaa atatgtttaa 17760
tgttattaat taagaaaagg tatgtaatgg gaagaaatgt tgaaaatttt gatttaattg 17820
gtttttaagg aattagtaga tgataaaaaa aaattatatg agtgggtaaa gttatagtat 17880
tgttgaagga tagagtattt atttttttttt gattttaagt taatttatgg aatatttaaa 17940
gttttggtta tagtttgttt gtaaaataaa aggatttatt ttttgtgttt ttttaaagtt 18000
ttttttgtt tttaaagaga aaaaaagttt ataatgatat atgatttttt taaaaggttg 18060
tgatagttta ttatgttatt ttttttgttt ttgtttttaa tgttgtttaa aaatattatg 18120
tttttgttaa agattaaatg ttttgtatag gtagagttta tttttaagta gtttaggttt 18180
tgtttttttt ttttagtgag ttttattttt tttggtattt attgggtgga tgtttagttt 18240
ggatagaatt ttgaaatggg ggtagtatga gagtgattgg agatttttaa aagttagagg 18300
tttgagagag ggtggatgta gttagtagaa gatggtgtag aagttagttg agaatgattt 18360
tttagagtaa agagattttt ttttggtttt ttttgttttg ggggttttga aaggaattta 18420
taaaatggtt tttattttta ggaggaggat ggattgattt ttttttgtta ttggtttaaa 18480
aagttttagg gtggtggttt tgggttttgt gttgaaattg gattgtattg tagtttttttt 18540
ggatttgatg tttggttttg tgttttgata aggggtgggt atttttttttg gtttttttta 18600
ggaatgtatt aattgttaaa tagttttggt ttagtggatg ggttgaaagt gtttgattta 18660
agttgttggt gtgtatagat tttttttttt tgggaggtgg gttttatggt ttgttgtggt 18720
atttttagtt gtgatatata tttttatatg tggtagtagt ttggttttaa ttttttttga 18780
aggatttggg ttaattttgg tggttttggt ggttgtagat ttttttttgt tgttttgttt 18840
ttgtgttttt tatttaatta gtgaatgttt gtggagtata tattatgtgg atttttaatg 18900
tattttttga aagtaaataa tatagttttt tttgttgtta tgaagggatt ttaattttaa 18960
tatggatatt agtgagatta gtttagattg tttttagtaa aatgtaaaat ggtggtgtgt 19020
ggggtggtga ttaaggtttt gagttttgtt agaaagaagg ggatgtgtag agaaaggtgg 19080
agaattttag ttgtggttag tgtggaaggg ataggtgttt gttgaagggg gtatgaggtt 19140
tgaggaaaaa gtaatgaaat aggggtaagg agagtttttt attttttttt ttttgtttga 19200
tttttgttat tttatttttt tttttttttt tttatttttt gtgttaatta aatttgtagt 19260
ttatttgaaa ggtgttttgt tgtgttgtgg tttttttattt ttaggggaaa ttgtattagt 19320
tgtttgaaag tagttagttt ttgtggattt ttgtttgtaa aagtggtttt tataggttgt 19380
gttttttgtt gttgatttgg tatataaagt tttttaaggt tggtttggtt gttatttttt 19440

-continued

```
attgtttgtt gttaatatat gtagtagttg ttagagtggt ttgggggaaa aggaaatgta  19500
taatgaaagt ttatttgtga gtaggaatat attaatggaa taatttgatg tttttttaat  19560
tttatgtaaa aagttttgtt gtttttttaa tattgattga atgggtaatt aatggttttt  19620
tatttaggtg aatattttgt aatttaagat aggtaaaaga taataagttt aaggtagaag  19680
ataaaaggtt taattgtagt ggtgtttgtt tgttttttat tttttagggt ttttgattag  19740
gaaagttttt ttttagagga gaaaaaggta ggagtgggag aatatatatt tattattttg  19800
gggttagatt ttattgtagt atttgattat ttagtttagt tttttgttat tttgtttttt  19860
tatttttagt tttttttttt gtattttttt ttttttttaa ttttttttagg atgatttttt  19920
attattattg ttattatggt tttaataatt ttttttttta aattttatat tttttatttt  19980
agtaattaat gaggttgttt tttgatttag gaggagattt ttttttttta gaatttaatg  20040
tgtagagttt ttgagaatta aagtagttgg taggggagga agaaattaat agaaagggag  20100
agagtatata gaattgtgtg tgtatgttaa agagtgatta ggaatgatag agttaatttt  20160
tttgtgagga tttgatggga agagtgttta agattttatt agtatgtttt taataggttg  20220
atattttaat ttaaattttt agaagtaata tattatttgg gttattataa tgaggtgggt  20280
tttttttttt ttgttagttg atagttttta aaatattatt ttgttaggga aataaaagtt  20340
ttattttaga ttataggtgg gtatttttgg atttaggtga tttatggtta ttatgataat  20400
taatgttgaa tgttagttat tagtatgttt gggagagaga aaatagaaag aagggagagt  20460
aaaagaaata gaaaagggag atggatataa gttggagagg gaagaaaaga gaaaaagagg  20520
aagatagatg agtgtttaat ttaattgttg tttaaaaaag tggtgggggg gtgggatttt  20580
atttagtttt ttgttatttt tttttttttt gatttggata tttatgttta attttatatt  20640
ttattttttt tttttttttt ttaaatatat gtgttatatt attttttttta ttttatttag  20700
tttggtaagt agttgttttt tggagattta gtgatattta ggaaaattgt ggtagtaata  20760
tgtaaatgtg aggaagtatt aatagtatgt ttgttgagtg attttagtaa atgttttttt  20820
ttttaatttt tttttttttt ttttttttagg ttattgtgag gtggtaattt ttattgttat  20880
ttgaatattg ttttttttagg tagttatttt aaattttaaa tggttgagta gttagagttg  20940
tgggttggaa aaatgggtat tatttgtagg gatttagaga gggtggttgt tgtttaatat  21000
atttatagat ttttaattta gaaaataatt tttttttttt gataagttag agtttttttaa  21060
attttattta ggaaatgggg aaaaggatag ttatagtgaa gtttttaatt tttgggttat  21120
ttggttttat agttatgagg ggtggtgggt agtggattgt ttttagtttg gtttgtatgt  21180
agagaaaagt tagatattgg agggggtggg gtattttttg ggtaggatgt aaggttttta  21240
tttgattttt gtgttttatt aggagtttat atatttatgt ttattatgtg gttttaagtt  21300
gagtttaggt gggttttgtt tttgagttag tttgggtagg gtaggatttt tatttgttta  21360
aggtttaata gtttagggag atgtttaatt aagttatttt ttgggtgaat tttgaagata  21420
gatttttttt aaaagttaga gattatttgg ttgagtttta ggttagattg atatggagag  21480
tttggtggta tagtttaatt gtttattgtt atggttagag ggattttgta taattaatat  21540
tgaagagtgt gaaattaaat aagattttaa gattggtaat tggtggtaaa tattagtata  21600
aaatatggtt gattttatgt tatatatttt tttttttttag ggtttttttt tgaaagaata  21660
agtaagaaat tttaattgag ataatttttg atgtttttta gatttaaaat tttatgttgg  21720
tattgggttt ttttttttttg ttttatgtga gttatgtagt atttttagtt tttttattag  21780
gattttatta atgtttttttg tattggaaat ttttgtgtta gaggttgaat ttatagtaat  21840
```

ttttaaaatt aattaagaag aatttagtta gaggttatag taatgttgga attataaaat 21900
gtataagatt tatttttttt tggttttttt tttatttatg ttgtttatgt ttgtgtattt 21960
ataagtttta tgtatattaa atttttaaaa ttaattatta ttatgttata gagtttttat 22020
tggatagtgt tttttagttt ttattatata tttttttttt tttatgtaga tttattatgt 22080
tggtgttttg ttatataggg ggtttgagaa gaatgttatt taattgttgt tgttgtgagt 22140
gtgtaaagtg attaggagat taggagaatg ttgaaatttt tgttggaaaa atgtaaagaa 22200
aatttttatt ttgagttagt tgtttataga gttagtgtgt gtgtgtgtgt gtgtgtttgt 22260
aatataaaat ggatgtgaat atatatatat aaatagatat ggttttgttt ttattttaat 22320
ttgaattatt tagataattg tttttattta ttatttgatt ttaatgggtt tatataaatt 22380
aggatatttt atttttttag gtatttaggt tgttgttgat ttttagtgtt tttaatattt 22440
tgtatatgtt ggtattatga ggagtagtta tgtgtttttg ggttttttaa ttattttgga 22500
ggttgattga ggtttttttat atatgtatat ttgttgtgat gaaagtttta ttggtagagt 22560
ggagttatta gagtttttat taaaattttg tgggtttatg agagatgggt ttagaaattt 22620
atatggtttt gtggggtttt ttggtttttt aaaataaggt attaatattt aagtttttaa 22680
aaatatttgt agttttgggg tttgaatttt gaaaaataag gagtgagggg ttgtgtatat 22740
taattatagt ggagattttt tttatttttt aatgtgatgg agttttttta tgaaatgaag 22800
ttttaagggg tatggtattg tggggattat agttattttg aggtttaaaa gaagaaattg 22860
gaatatgatt agtaaatata tttagtagaa aagagttgga tttttattga tttagttata 22920
ggttattggt tggtagtgta atgggaggaa atatttattt tatatatata ttttatgatt 22980
ttgggggaat tagaggaaat ttaataagaa aatggttaga aatatttaaa atttttattt 23040
aaaagattta agtaaattag agttttatta gattaaaaat tattataaat gtaagagtat 23100
tgtttttagt gaaatgttgt ggggtttgag aaggagattt tttgttaaat ttttgggata 23160
aaatgtgtta tttaagtatt agataatgag tagaatgtaa attaatttaa ttttttttat 23220
taataggttg ttagtgtaat gtgtataatt tagtgataag attgtaggat ttaatatagt 23280
tggatgtatg agttttagtt aatgtagatt tgttatatga ggatgtgttt tattttgagt 23340
aggtgtttgt atgtgtggaa tggggtaaag tggaataaaa ggttaaaagt agaaatgttg 23400
atttaaagtt tattatgaag aaattttttt tttgtagtta aattattttt aaagtgggat 23460
gatattggtg aagaaagatt gaaaaataat ttttatgtgt gtttttggat tgtaagttta 23520
aaatggggag gagttgtaga tagggtttgg gggtggttag ggtaaaggag agatatataa 23580
gttgtaaata tatttgtagt ttgttttatt tattttgttt tatattgaat aagtttttta 23640
attttgtgaa taaggataag gagggagtgt tttaaagata ttttatgttg gtattgtaaa 23700
ttattgattg taatgttaaa taaatatata tttagagatg ataatattaa ttttatagta 23760
aaataattgt ttatgtagaa atttagagga gattagtttg tttttttttag ttgatttatg 23820
ttgggggata aaaggatttt taaaaattat tttgaatatg tttggatttt ttttttttaat 23880
tttttggaa attaaatttg tttggaaata gtgttataaa gagttgatgt ttttaaaggt 23940
gatttttttt gttttatata aataaggttt tgtttttgtt agttgagtgt agttttaggt 24000
tttttgtttt tagtttatat atattttttt tgtttgtttg gattttaatg gtttaagata 24060
gttttgagtt tattgggaaa agaaaatgat tgttaaaaat tatttttgaa attggttatt 24120
tggtaatatt tttaattgta tggaaattta ttaaggtata ttttatatat aattagttta 24180

-continued

```
aggttgttga ttttataggt tttatggatt taaatttgat tgataataaa gtaaataaga  24240
gagttgaatt taaagtgtgg ttttttgggg ttaggatgag tttaatatag tgtataagga  24300
atttgaaaga tttaggatat gtgttttaat taatgttaag tagaatggat aagtttttag  24360
tattttgaaa atgttgggtt agggtttttt ttttattgtg tgttttttgt ttggggatta  24420
ataagtatta tagagaatgt gatttgaggt gattttttat ttttgtataa atttagagtg  24480
aattattaaa tagttgtttg tttaaagtta aggtaatttt tttttgatgg gtttatttgt  24540
tttttgattt ttaatttatt agtttgtttt tttagggttt tgttttttttt gtaattaaag  24600
tttttttaga ttagtgtagt atttatttga taggttgttt ggaaaattta agattggaga  24660
ggtgatttgt tgttgttttt taaatttttt agttttaagt aatgtgtttt tttttttatat  24720
ggggtggggg attggaaatg gatgtagtga gatataaaga gtgggtgttt tgttgatttt  24780
tgtatttttt tttttttgat tattttattt tttttttttta agtttttgat ttttagtttt  24840
atttttttat ttttgggttt gtattaaaag ttggattgtt ttgggttggg taggagttga  24900
atttttggga gtttgtttgt gtagatttag tgtgtatggt gaggtagtag tttggttttg  24960
tattgttgat aggtgtaggt aggatagttt ttttattgtg gtttggggtg ttttgattgg  25020
tgtggagtta tgttagttgt atttggagaa gggtttggga ggaggtggag gtggagaggg  25080
ttggggaggg ttgtggtgga gtgatgtttt ggtattagga agtttgtttt tggttttaag  25140
atgttaggtt aatagggaag tgtggagttg tagatttggt ttgttgtttg tttgggtgtt  25200
tggagttgag ttgtggtaag gtttggtttt tgtttgattg tttgaggggt gtgtgtgtgt  25260
gtgttgtgga gggtgtgttt agagggttgt gttgtggttg tagtggttgt tgttgttgta  25320
ggggatttaa tattatttat ttgtttttgt tatttttgat atttttttgt tagggttgtt  25380
gtgtgggggg ggggtgggta gagtgtggtt ggtgttagtt ttttttattg gaggggtttt  25440
tgggggaggg agggagagaa gaagggggtt tttgtttatt tttgttttgt tttggagttt  25500
ggaagtttgt tttttaaaga tgttttgagt ggtgtttttt tgtttatatt ttatgttttt  25560
gtttgtttgt tgatttttttg tttttggatt tttttgtttg agttttttgg aggagatggg  25620
ggtagtttgg tttgagaatt tggtgggggt tgtgtttttt ggtttttttt gtagtgggga  25680
aattttgtgt ttagagtgtg atttggagtg ggtagtggtg gttatggggg tttggtgggg  25740
tagtagttaa ggattagtag agtgttgtgt ttttttgttt atgaattgta tgaaaggttt  25800
gttttatttg gagtattgag tagtggggat taagttgttg gttgtttttt tatttttttg  25860
ttattatttt tagttgttag ttatggtttt ggttttggtt tttggttagt tttggttgtt  25920
ggattttttt aagtataggt tggaggtgta tattattttt gatattttta gtttggaggt  25980
tgtaggtaag gtgttgtgtt gttttgtaga tatttttgtt tagttgtttt gtgttatttg  26040
tttttttttg ttttaaggaa gttagttttt ttggggggag gtgtggtggg agtggttgtt  26100
tgtttggttt tttgtagaat ttttgggagt tggaattttg attattttgt atttttttag  26160
tttttttttg attggtttgg tttttggggt gttaagggtg tgagtaattt tgttgttttt  26220
tttatttgta ttttggtttt tttttttgttt tttgggttat aaaaatttta gtattttgat  26280
ttgaggattt ttagaggttg ttgatttttg tttttgtttt ttttttggtt tttagttttt  26340
gaggagtttt atttgttagg aaattgtttg aaattattta gaaatgtttt ttgtgaagag  26400
gtattttttt tttttttttg ggaaagggtt ggtgaatttt ggtgtttaat tgaattttta  26460
tattttttttt tagttttttt aaattgtatg gaaatttgag tttttttgtga gggggagggg  26520
ggtttgtaaa ttatgtgtgt gtgtgtgttt taggagattt ggtgtgtttg tgtagaggtg  26580
```

tataaatata tttgaaagta taggttataa aagtgaatgt gttgttgtag tgagataaat 26640
atgtaaataa aatgtgtggt gttgggggag gggaggaaat ggggtgtgga tatttatatt 26700
tgtgtttgta tattttatag gtgtagtgtt ttttgtggtt tggagttgtt gtgtgtattt 26760
ttttttggtg ttaggtagtt tagttttttt atggtttttg ttgttggttt agttggtgtt 26820
tgtgttgtag gtgggtatgt tgatgggaaa gtgtgtgtgt tttgttttta gagaaagata 26880
aaagttagta ggggaagaat gaggatgtgg gtgttgagga tttgtttaag aagaagtggt 26940
aaaggtggta gtggatttat tttattagtt agtagtttta ggagttggag gttatttttt 27000
agaggaattg ttatttggat atgtttatat gtgaagaaat tgttgtgtgg attaatttta 27060
tggaagtttg agtttgggta ggagttagta tggagtttgg gagggatggg gggaggatgt 27120
tgtggaggta taggttaagt agattaggag agaatgtgga aggtagtgtt gtttgggagg 27180
gtgttggtgg ggtgtagttt tgtaaaggta gaaggttttg tggtggtttg gttgtgagat 27240
tatagttttt tttttgaggt tgataggatt gttgttttgg tttaggtttt tagagtggta 27300
ttggtttatt gttttgttat tttgtgattt tatgagttgg gttgtatggg taattttttg 27360
tataggatat tgtgttttttg gtttgtagtt gttagagtag agttaataaa atttttatta 27420
ggttaagagt tgtgaatagg ttttaatttg tgagttttta ataaggaaaa tttgttagag 27480
atatggaaga gttggttttt tttgggaaat ttttgttttg gttttggttt agtttttttt 27540
tttttgggtt tgtgtttttt atattttttt tatggttgtt ttggttattt aggttttttt 27600
tatatatttt atttttagt tttgtgattt ttgggagtaa agttttaata tataattatt 27660
agtttttta gaaggagaaa gaaaaaaaga agaaagattt ttttgtttgg tttatttatt 27720
ttttttagg agttgaattt tggaaattga aatttatatt ttttttttta aattataatt 27780
atagttttgt aaaaagggtt tattttaatt ttgtagtaaa tttgtatttt atggattggt 27840
aaaaatgagt ttaaataaat aatttaatag taatgttttg gtttatgttg gttggtggaa 27900
gattttaaat ttgttaggat tttggaagta gaaaatagaa ttaagtaaat taagtggtat 27960
ttagaggttt tgttgttaaa aaaaaaaaat taagtgtttt gggtagaaaa aataaagttt 28020
ttggttagag tagagtaaat aaaaagaaga aaataatgat aaaaagaata aagattaaaa 28080
tgttttttta aattagaggg aatgaagata ttttttgggt ggtatttgtg taaggtatga 28140
ggttatgttg gtggataaaa ggttgggaag aagttgaaaa tggttttagt ttaattgttt 28200
agagttagag ttgggttttg ggtggtgtgg ttttgagtaa ggttagtttt ttattagttt 28260
ttttgtatat taagggaatg ggttttttat gtattttttt tgtttgagta aagtttagat 28320
ggtttagggt agaaatggta agtaattaaa gatagagttt atgggttttt tgggattttt 28380
tgaaaatgtt tttttatttt gtttgttatt ttgtagtttt attttagtgt tttgtagttg 28440
tggtgttggg ttttttttgt agttgttttt ttttttaggg tggttgtttg ttgagttaag 28500
tgggagtgag gtgtgttttt tatagtagtt gggtgtaaag aggaaggggg ataaaaagga 28560
aattaagaat gaaaggaaaa agagaaaaag tggattatat ggttgggttt ggtggagatg 28620
tgtaatgtga aatattattg gtgttagttt ggatatttta ggttaggttt tttttttaata 28680
tataaaagtt gttgtttggg gtgataggga ggtttgatgt ggattgggat tggggttgtg 28740
gttgggttat tggatatggg tggaagttgg ttggtttggg tggttgtttg taaagttaaa 28800
tgatttggtt gggtttggtg tgtggatagg tttgtggtgg gtttagggta aagaagaggt 28860
agagtgaaag aagggggaat ttttaaaatt atttttttttg ggtttttgga gtttaatatg 28920

```
ttaagttttt ggagttaatg agttgatgaa gaggtggttt tttgtttttt atttggttgt  28980
tttgttaggt gagaaagagt gttggtggtt tagtttttgt taagggagta tgtattaggg  29040
ggtgggggat gatagtggag gttagggaag gaagggagga attgtgtggg agaaagagtg  29100
atttttagt gtttttttag ttttttttt ttatttgtgg gtttgtggtt ttggaatgga  29160
agtaagtttg taaggtgttt tgggaagggt tggaaaagtt tgttgttttg tgtttgtttt  29220
atattaagtg tttttggatt tggagaaatg tttggttgag tgattaaatt gtttgtaggt  29280
ttttatgtgt ttggttgagg tttgtggtgt agttttgagt tttagtttgt aggttagagt  29340
agattaggtt ttttgtgttt ggtggagatt tgggttagta attgaaagtt ggttttggta  29400
ttttggtgtg tagggtggtg tagtgaagtg aggttagggt gtgtgagtgt gttagtgtgt  29460
gtgttggggg aaggtggggg ttggtttttg atggaagttt tagtaatttg tattgtggta  29520
tttgtttgtt tttttgtttt aattgttttt aggtttggtt taagaattgt tgggttaaat  29580
ggagaaagag ggagtgtaat tagtaggttg agttatgtaa gaatggtttt gggttgtagt  29640
ttaatgggtt tatgtagttt tatgatgata tgtatttagg ttattttat aataattggg  29700
ttgttaaggg ttttatattt gttttttat ttattaagag ttttttttt tttaatttta  29760
tgaatgttaa tttttgtta ttatagagta tgttttttt atttaatttt attttgttta  29820
tgagtatgtt gtttagtatg gtgtttttag tagtgatagg tgttttgggt tttagtttta  29880
atagtttgaa taatttgaat aatttgagta gtttgttgtt gaattttgtg gtgttgatgt  29940
ttgtttgttt ttatgtgttg ttgatttttt tgtatgttta tagggatatg tgtaatttga  30000
gtttggttag tttgagattg aaagtaaagt agtattttag ttttggttat gttagtgtgt  30060
agaatttggt ttttaatttg agtgtttgtt agtatgtagt ggattggttt gtgtgagttg  30120
tatttatagt gttgggattt taggattttg ttggatgggg taattttgtt tttgaaagat  30180
tgggaattat gttagaaggt tgtgggtatt aaagaaaggg agagaaagag aagttatata  30240
gagaaaagga aattattgaa ttaaagagag agttttttg attttaaagg gatgttttta  30300
gtgtttgata tttttatta taagtatttt taatagttgt aaggatatat atataaataa  30360
atgtttgatt ggatatgata ttttaatatt attataagtt tgttattttt taagtttagt  30420
attgttaata tttaaatgat tgaaaggatg tatatatatt gaaatgttaa attaatttta  30480
taaaagtagt tgttagtaat attataatag tgtttttaaa ggttaggttt taaaataaag  30540
tatgttatat agaagtgatt aggatttttt gtttgtgagt aagggagtgt atatattaaa  30600
tgttatattg tatgtttta atatattatt attattataa aaaatgtgtg aatattagtt  30660
ttagaatagt tttttggtg gatgtaatga tgtttttgaa attgttatgt ataatttatt  30720
ttgtgtataa tatttgtat aatattattg ttttatttt tagtaaatat gaaataaatg  30780
tgttttattt tatgggagta aaatatattg tatataaatt ggtttggatt ttttttttt  30840
ttttttgtta ttaatttggt taggatattt tagttattgt tttttaaata aattagtttt  30900
ttttgtttgt ttagttaaat atataaggta gtagtttta tttaaatttg gtagaaataa  30960
atgatagtta tttattagaa attaaaaaga aaaaaaaagg tatttttggg ggggaaaagg  31020
gttataaaat ttaattttgt tttttaatt tttttttggt ttaaatttag aggattttat  31080
tatggttagt aaataatatg aaaaagaaaa aagaagaaag aaatttagta agtttattag  31140
tttaaaatga tttttaagtt tattttttta tggggaaatt tatatttta gtaaattgtt  31200
ttggagaaat atttgtgtat gtatatatgt atagtttata tgtatttttt ttaggaggaa  31260
tatatttata ataaatttat agggaaatat ttttagttta aaatatttag gtttttatgt  31320
```

```
ttatttttag gtttaagtag agagattttt tatgttatat tgtattatta tttttaaatt  31380
ttttggagat attaaaagaa ataaagatga tttttaataa ttatagtttt ttagtttttt  31440
aaagaattta ggggttgaga ggttagagtg gagtttttttg agttttgttg agtaatatgt  31500
agttgaggta aaggttatgt ttttggtgtt ttgttttaaa taatattgat ttattaattt  31560
taaatttgtt tgtttttgaa attatatagg attatagttt gtaaattgta ggataatgaa  31620
gtaaattaag atgaattata gttttggttt tttttgttat tttttgatat ttaaataggg  31680
aatgagtttg gtgtgagtgt ttaaatgaat tttaagtatt tgattttttt ttatttgtga  31740
tttttagttt taaaaaaatg tgaaatttga ttttataata aatagaaata aatattattt  31800
agttttagag aatttatttt tatggtgtta ggagggttgt tgtggaggtg gggggaggga  31860
tgtgttgaga ttttttgtta tgtttgttaa ttttttgtat aattaaagtg ggtgagaata  31920
aatattatgt tggggaattt agagtaaaaa gtaattgttg attttttgga gttgataata  31980
ttattgtttt tttgttttag t                                             32001
```

<210> SEQ ID NO 11
<211> LENGTH: 12001
<212> TYPE: DNA
<213> ORGANISM: Homo sapiens

<400> SEQUENCE: 11

```
tatggattgt gtgattatta aatttggtat tttagggggt atattttttt tgagtaattt     60
ttataaatat gtttgtttgt aggatattta gatttttttgg tttggtagta aagtaatata    120
agaataattt tgaatttgat gtttattttt gttttttttt taattttagg agtttttttga    180
ggtttggatt aatttattga ttaggaaata gtatttggaa aggttaaata aaatattatt    240
tttagggaaa tagtatttgg aaaggttaaa taaaatatat ttttttagtt tttttaaatt    300
ttttagaaga tatatttttt aaaaaataaa ttaagttagt aatatttaaa ttaaattttt    360
gttttgttta taatataaaa gatgataaaa aaattgttgg gaaggtgaga aattaatttt    420
atttataatt agaagtaaag tttttattta aaaatgtaat attatttaaa tttaatttgg    480
gaaataaaaa ggatttaaaa aatagtttgt taaagttaat ttgtaaataa gtgtgttttt    540
ttttttttta agttgtattt taggtttaga gtatatgtgt aggtttgtta tgtaggtaaa    600
tttgttatag ggatttgttg tatagattat tttgttattt aggtattaag ttttgtattt    660
aatagttatt ttttttgatt tttttttttt ttttatttgt tattttttaa taggttttag    720
tgtttgttgt tttttttttt gtatttatga gttttttttta tttagttttt atttataagt    780
gagaatatgt gttatttggt tttttggttt tgatttagtt tgttaaggat aatggttttt    840
agttttattt atattttttgt aaaaggtatg attttatttt ttttttaatt attttatttt    900
ttttattatt tttttttttt tttttaattt tgaattttat tatgttagtt taattatttt    960
tttttttttt tttttttttg tttatttgta tatagttaaa agatgttatg aatttttttt   1020
tttaatttag tatatgttta ttaaagattt aaaaatatta tttatattat tttagaattta   1080
gtttaagaaa ttattaaaaa ataaagttat tagaaagtaa ttgaattatt ttgttgagtt   1140
ataattttag attttgattt tgtttttttt ttattttagg taggttattt tttttttttt   1200
tttaaattgt tttttttgta tttaataata tattttttgtg gatttagaaa gggtggagta   1260
tgaggaaaag gaatatgata tatgtatttt agaggaaaat aataaataaa tattttagga   1320
tggaaaatat tatttttatt tttattgagt tttttagagt ttatttgatt tgtgtaaatt   1380
```

-continued

```
agaaattagt agaatgatat taatgaatta atgaaaagta gaatgagtta ttagttgtaa   1440
taaaaagaat aaagaatttt aagaatatag ttttaattat gtatggttgt ggggagagaa   1500
aaataataaa atgtttttag tgaatatatt tttgagagaa gaaaggaaat atttaaggag   1560
aggataaaaa gagtaaatat taaaaatagg agtaagaatt ttattgtttt ttttagttga   1620
taaataaaaa ttgtatatat ttattgtgga taatatgata ttttgaggat tatgattatt   1680
tttgatttat aaattatatt taagaaaaag aaatttttaa aaagtttggg aatatatgaa   1740
gttgaaagaa tattaatatt tagataagga tagtatatga taaattattt ttgttttaat   1800
attttttttt aggaaattta aatatttttt agtgaagtat tagtttttttg aaattaagta   1860
tgagaaaaaa aattaaattt atttgtggaa aaaaagatat agttaaataa aaaagtggtt   1920
gttataattt taagagtggt atgaataaaa tgattaatat ttttttaagt gatagtataa   1980
atattaaaag ttttaataag tggaagtggt tttgttatga taaaaggtgt ggtatttgta   2040
taatttttag ataagaataa agttatgatg ttaagatagt agtagtattg tttgttatat   2100
gtgatatttg aaaaatatga taattatttt aatttgttta agtagtattt atggtgaggg   2160
tgaaatttta ttaatattgg ttaatttatg gtgttttaaa aaattagtaa ggagataaat   2220
tgatggatta aaagataaat tatttatagg tagataaata gaaggataga tagagttata   2280
attaaatatg tattttattt aggtagaaag ataataatta gtttttaaga agtgatgtgt   2340
ttgttagaaa agttttgaat atagaatttt ttgattttgt ttttaattta gtttttttag   2400
gtattatgtt gtataattag gtgtaatttt ttaaaagttt ttatgataga atttttttatt   2460
tgttaaatta ggttaataat atttttattt tttttaggg taaagatgtg aaatatttgg   2520
agaattttgg aaaatatgtt ttttattaat tagagttttt tgatgtgata ttattttttt   2580
tagtatttgg agtttagtta atagatatat agtgtagttg tgaaattatg aagtatgaga   2640
atgtattatt aagggattgt aggaggtttt ttattgaaaa gtgtagttgg ttatattttt   2700
ggaagtaatt taaatatagg ttgagggaga ggagtatttt ttagattttt tttagatttt   2760
atttttttatg aattttaatt tttttttttt atttagaaaa aataatgaga tttatagtgt   2820
agagatagaa aataaggttt tgtgtgtttt taaattttat ttttaaaaat attatagtat   2880
tttggatgag atagttttga atttttgtaa tagtataggt atgagagttt ttattagaaa   2940
ataggagatt ggattgattt ttttattttt tttttatgtt ttttaaaatt gaaaagttat   3000
atatataaat tatatttatt tatttttttt ggaaaaggtt aaaatgaatt taattttgga   3060
ttattttttaa taatgggata aatttgaatt gagaataatt tttagaatta gttttgtttt   3120
tttgtgataa aatggatttg tagaaagtta tttggtgttt ttttttagtt aatattttat   3180
tataaataat gggtatgtaa tttagtattg ttttttatag gttatgtttt tggaattatt   3240
atttttgtat tttatttgtt tgttgatatt tttttattta agatgttttt tttagtataa   3300
gaagttattt tttttaaaat tttaaatgat tttattataa taatagagtt gttaattaga   3360
tttaggtaag taatgataat aaaaatttga tttttattta gagtgtagta tggtttaata   3420
taataattag agttttaata ggtttttttta gattttattt ttatttaatt tgtatgtttt   3480
tgtaatatag atgtttttat tatttggttt ttatttttat ttttttttgt ttttggaata   3540
aaattattta aatttaattt agagatttta tttttttttg gaattattgg gaaatagttt   3600
tagtaaatta tatttttgag attttatatt aggtttagtt taaattgatt atttaagtat   3660
taattttttt gtggtttagg aatatttttg agtttatttt tttttttttta aattgtttag   3720
gataaatatt ggagtttggt tttttttgttt ttttatttaa ttattttttg tttttttttt   3780
```

tttagtattt aaaatatttt tgattttttt tatttttaa gaaatatatt tgttttttg 3840 tttttgtatt attttttgt ttatgaaata ttttataggt aagttttata ttttttttt 3900 ttagaggttt ttggtttttt ggttttagtt gttattggtt tagtgtatta gttaatattt 3960
tggattttgg agttatataa atttagattt aaatttttat tatgttattt attgtttatg 4020
tgatttgaag taatatttta tttattgtgg tttttagtag ttataagttt gtgttttaat 4080
tagttgggtg attttgggtt agtgatataa ttatggtaaa ttttattgtt tttatttgta 4140
aaatgatagt atttattttg tagtgttggt ataaggaata agtgtgattg ttaatataaa 4200
agtgtttagt ataatagtta aattaattaa gtattttgta aatattagtt tttattatta 4260
ttattaattt aaatgattag atgtattttg tgtatattag gtttttgag tttattttgt 4320 ttttaataaa tattattatt tttagtatgt ggtttatatt atattttatt agttagagga 4380
tatgtgaagt ttagagtgga aagttagggt agtaggaagt attgttatat tttatatagt 4440
taaagttatt taaatatgtt tgaatttgag ttttgttgag tttttatttg tttttatttt 4500
ttttgtgtgt tttagtttat taataaagta ggtttaatat aaatatatta aaagtttaaa 4560
tattgagatt atgataatga atatgagggt tatgattata aaatattatt gaattagaga 4620
tttgttatga aattatatgg tgaagattat aagggaggaa tttgtatata tattgagtgt 4680
tttgggattt taaagtggga agagttagtg ttttaattaa agagaaattt ggggtaggga 4740
attaattata atattagtta ttttattgaa tttaggtttg ttttagttga tgtagttgtt 4800
aatttttaat gtttttttt tttttaattg tttttaattt atttttttag aaattgaaag 4860
tttattaaag aggatatttt tttagagagt tgttttagtt attataagtt tttgttagaa 4920
attttaagaa agtttataag gtatttttat aaggtggtat tgagtaagtt agaagtattt 4980
taagtattaa ttattatgta aataagggtt ttatttttag attttgttgt ttgtggtggt 5040
ggtgatgttg gtgtttttt tggaatttag tttaattttt aaaaaagtaa aaggagtata 5100
aatagtaata taaattatta ttatttatat taattaaaat agaagttttg aatgagtaag 5160
gagttagagg aggtaaaaat tgggaatttt gtatattaaa aggtttttat aatttgaaaa 5220
ttaagattat gttggttaaa taggttgttt taaaattagt atagtaatta aatttgtttg 5280
taatgaatgt agatttaaat agtgatgtta gatttgataa ggatttgtaa attttaaaag 5340
agtgtaaaaa gattatagaa gaataatatt atatttttgt atttatagaa atggttagtt 5400
taagagatgt atttagttta gggtggttgt aagttttatt ttttgaattt gttattagaa 5460
gttaaaagaa attttgtata attgtttttg atggaaatat aaattggttg atgtaaatga 5520
aatatataaa gtagttggtg ttttatttat ttttataatt ataaatgaaa ttaaatgatt 5580
aaaaattata gattttgggg atttttttt tattgaggag tttatggaat ttgtttttt 5640 tagtattaat aattgtgttg atttatttt ttttgtttaa ttttgtatat attaaaatta 5700
ggtggttatg aataaaattt agaaatataa tttatatttt aataaaatga ttttaaaatt 5760
attttatttt ttattgtggt tttatttgtt gttttataat gtaggttttt ttgggttttt 5820
gtttagaatg attttgttaa tgtagatgat agttagagtt gaatggggaa tttagaaatt 5880
ggggatttgg gtttttgatg taatttatat gttaatttat tttattagtt ttttttttat 5940
ttatagtttg gtaaagaata tgggtggagt tgttttgggt ttatttgtat atatgtttaa 6000
attgttttga aaaaggaagg gtaagaaaga gtggtattta agttggaatt aggtaggtat 6060
tttagattaa gagatgaatt ggaaagggaa tatttgttag atattttggg tttgaaggta 6120
gtttgtgtaa gtttttatat ttttgagtgt gtgtatatag tggagagggt ggagtttgtt 6180
atttttaaat ttgaaaagat tgagagattt tagagggttt agatgtgtta aaggttagag 6240
ggattaatat ataggtttta ttatggaaag gtggggaaaa ggtttgaata gaaaattgtt 6300
gtagaaggga agttattgag aggtaaggga gtttttgaat aattaaaaag ttaagaataa 6360
gtaaaaggaa ggaggttggg tgggggataa aaaaaagtag ttgatgtggt aattaagaat 6420
ttggtgggag tttgggtagg ttattttttt ttttagatta gagttttatt agaaattttt 6480
ttaagtgttt ttttgtgttg ttaaagatga taatagtaaa ttaataagtg tttgaaatga 6540
aaggggatgt tgattagttt ttaggttata gatttttttgt tgttagtttt ttttgaattt 6600
ttatagtgtg tttttgtatt gtttttttta agaagagtta ttttttattt ttatttttag 6660
gatgaaggta agtgtttagt tagtatattt attaaatgtt agttttggtt ttagtttttt 6720
gtttgtgtgg aaagtttatt gttatagtgt gtttagtttg ttggaggggt agatagaaaa 6780
agtaagtttg gtttggtgat ttgtggggtt atgtattttt agggttggtt tggagttttt 6840
tagagtttaa tgtttttggg ttagaattgt aaggttttgg tttgagtaaa gggtttgagt 6900
tattgtagtt gtgggagtgt tttttttatt tgaatgtatt tatttataaa taagtataaa 6960
atttttttaa tagtagagga gaaagatttt tgttttaaaa ttaaagttgg gaattattgg 7020
aaattttgtt ttgagtgtga gatattggtt tgttattttt ttaattttta tatttttttt 7080
gtaatatgtt ttgatttaat aattttttta gtgtttagta ttgtttggat gttttaattg 7140
ggtaatttat tagtgagtta atataggtat ttatatattt ttttagttta agtggttaag 7200
tattaatttt gaaatgatta taaaatattg gaattggtaa tgtatagtaa ttttaattta 7260
tatgtaaatt aattggttta ttttaaatgt ttttttttaaa aaaataatta ttgtattgta 7320
gtattggagg tatggattaa atttttagaa tagataattt ggaaataaga tttggattag 7380
gaagataatt tagaatagtt aataaattaa taatgtttga ggtagttaaa tattgttagt 7440
tattggtatt tatatatttg tttgttgtta gataaggagt tggggaaatt gtttgttagg 7500
gttgagatta taatttagag tgaagaaagt aaatggtagt atatagtttg ttatagtggg 7560
ttttgaaata atattgtatt ttttttaaat tttgattttt gggtgatagg gagttggtgg 7620
aggttatttt atatttgttt atggttttgt tttaatttga ttatgaaatt gttgtttttt 7680
ttgagttttt taatttgatt attattttaa tggttttgtt atttgtttta atatattggg 7740
gggaggagtg taattgagat ttttattaaa aattatttga atttatttag ttagtattgt 7800
tttatttaag tttagtttta tgggttgtat ttaatttttt gtgtttttta tatattaaaa 7860
ttagattatt aaaatgttgg taggaaaggg tgaaggaaat ggtttaatgt tttagtttat 7920
tggaagatta ttatttttag atatagttta aaattttgag gaaataaaaa ggatatatgt 7980
tttgggggga aaatgtttta atattttaga atgggggtat tattttttttt attttagaga 8040
atttgtattg gagttgttta tgtaaaaatg taatattttt gaaatttata gatatgtaag 8100
gttagtgttt tttttttttt aggtttttag tttaggtgat ttagttttaa aggagttagt 8160
atttttgatg ttataatttt gtttatattt gtagggtaga gaattgtttg ttttgtttgg 8220
atgttttttt tatttttttt taatttgaag taattggaat ttaaatatag ttgttaaggt 8280
ttgttttttt tttattgttt tgataaggga aaaatttgaa atttatgttt taaattagtt 8340
tggtggtttg tagtttttta gtattttgtt tttatgattg tatgtttaat gtattttttg 8400
gtgattttgg gtattaatta gttgtttaat aggagtatga ttaaaaatgt aaaagaagga 8460
ttaggagtgt gaaatgtatg tttagttttt tttatatatt tgaggaggga atgagaatta 8520

-continued

```
ttttgtattt tttatttttt taggagttat ttgtattttt tattagttgt ttattttagt   8580
tgtattggtg ttgggtaagg tgaggattta aaagtttagt gtagtgtttg tggtggttgg   8640
gattggggtt aattagtttt tggtgggtga gattttagat agaagggggg tgagaggaat   8700
gtgagttttt tgagtttttt ttttttagtt ttggtttgta aatttttgaa atttgaaagg   8760
ggagggagtt gtatgtgtgt atttttgtgt ttttttagtg taattttttt tttttttttt   8820
gtgttttttt gtggattttt gaattttttt gtttttggtt tttttatttt tttttaattt   8880
ttttatgaga ttgtttattt ttgttattag ttgaaggtaa ggttgttttg ttatgagtgt   8940
tttttaattt ttataaaatg aaaagaaaaa aagggaggat tattagttta ttatttagag   9000
gaatggggag gttgtaaaaa ttgttgatgg gtagaggtga agatgttttt tttggattgt   9060
atttttggt gttttgtaat tagagtttag ttgtgggatt tgttgaagaa atttgatttt   9120
tttgttttgg tgagatttta aaaattagaa atagaaattt ttagagttag agaggaaata   9180
taattaaata gtatgtgggt attttttttt ttattttttt tttttaaat aatattgttt   9240
tgagttttta ttgggtaaag agagaaagtt tgagttttta tggatgttat gtggaggtta   9300
gaaatggttt aaaatgtaga tttttaatta gttttttttg tggttgaaga ggttaatttt   9360
ttttataaaa tgagtttatt tgttgattgt tagttatttt aaagtgaagg gatttagtat   9420
ttaaaataaa ttgagtaagt ttgtttgttt gtttttattg ttaatttaaa tgaatttaaa   9480
atatggagta atttaagaaa atatataata tgttttagat agtttttaaa agtagggaaa   9540
gtttagtatt tatatagtga ttagggttag ttttaagtgt taagtttttt taaatgtatt   9600
tattttatgt atattttttt gagttattat atatttttaa aattgtgagt attggtatat   9660
tgatttagga agagtaatat aatttttaga gggaatttta tttttaatta gggattaaag   9720
agatgttttt ttaatagtgg gtttgagttt tgtttttaag taggaattaa tattggtggg   9780
aaaatttgaa tttaggagta atggttgtgt tttggtattt tttaaaaata tatattaata   9840
ggatgttttt gagattgaaa aaatattgtt ttatatgttt ggtagaagtt tttatatttg   9900
gtttttttagg tgaattatat ttatagtttt tttatttaga ggtaggatag agttaaaata   9960
ttttgtttat tattaaaata tatatttttg tttaagttaa gaaattagaa aattagggtt  10020
tagaagtaag gtatattttt tgagtgagaa tatgttttgt aattttatat atttttttgtt  10080
ttgtaggagt aaatgtggat ttgagggaaa tttttttttt tatttttatt tttattttgt  10140
gtaatttaat attattttttg ttaggaattt taattttgtt attttaaaaa atgagatatt  10200
tgtgatttag ggtgaatttg ttgaatgtag gtatagtaga ggaaatttta gattttatga  10260
gtgtttgagt tttgtttagt gtaaattttt tgtgaatatt gggttagtgt gtggttgtgt  10320
ttatttgtgt gttgatattt ttagtatgtt tggtttattt gttttgattt tgggtgtggt  10380
gttttagtta agttgggttt agtgttttgg tttttttttag ttgataagtt tagtttgttt  10440
gtttttggtt gtggtttttt tatttttttt tattagttta ttttattttt ttagattttt  10500
ttttatttat ttttttttat ttttattgtg tttattttta tttttgtttt ttattggttt  10560
tttattttttt ttttttttgta gttttttttt gttgtgattt tttttttttaa ttttgtaggt  10620
ttgaaagaag gttatatatg tatgtttata tttatatttt atatgttttg ttttaaataa  10680
ttttatgaat attgtttttt gttttgtttt ttgggttatt tttttgttg tttttttttta  10740
gtttgttttg atttgttttt taaaagtatg tttttgtttt tttgttgttt tggtgttttt  10800
tttttgattt attagggttg ttgggttggt gtagattgtt tttttttttt ttttatttta  10860
```

ttttttttt tggtttttt ttttatagtg ggagtttgtg tttttgtttt ttggttggtt 10920
tttaagtgtt ttgttaggtt ttttttttt ttgtttttt ggttttggtt tttgattttt 10980
tggtttgttg gtatttgttt tttttttttg ttttgttttt tgttgttttt gtttgttttt 11040
tttggtgttt gtttgggtgt tgtgtttgtt tttggattgt tagttgtgta gttgggtttg 11100
gttggttgtt tgtgtgttat tgtgtagtgg agtttggtgg aatttttgtt gatgttatgt 11160
tattttttat atggagtagg agtagaggga agagagaggg atgagaggga gggagaggag 11220
agagagtgtg agattgagtg agaaagttgg agaggagtag aaagaaattg ttagtggtgg 11280
ttagattttg gaggttttag tgtatttgtg gatttttttg gaatttggta tttttaggag 11340
ttttgtagtt tttttaggtt tggtttttgg gtgtttgttg tgtagttgga ggtttggttt 11400
gttggaaatt gttttgggaa gtagtgggat gtggagatag tagttttttt ttggtagttg 11460
gtaagtggag gttatttatt ttgtagggat gtgagataat gtgagtttgg aaatttgttt 11520
tattttggag aatttttatt gtaggtgatt tgtggttttt ggggttaagt tttgtttaag 11580
gtaatgtagt tggtaaatag attttgtaaa gttttgtttt ttttgttttt tgttatagat 11640
attaataatt tatagggtgt tgaagttgag agggaagtta gattgtggtt ggtatttaaa 11700
atgaggtatt ttttttaaa ttttggtgtt aatattgtag gaataaattt ttgggttaag 11760
gattagtatt tttaagataa agggttgggt ataaagtttt agttattgga agattagttt 11820
tttttttatt gttatttatt gggaaaaaaa agaaaagaaa aagattttat tttaattggt 11880
agttagtgat tttttaggtt taagtgaatt atttgggagt taggtttgga tgttaagttt 11940
ttattatttt tttggattgt aattttttta aattgattat tagttaattt taatttggta 12000
t 12001

<210> SEQ ID NO 12
<211> LENGTH: 4001
<212> TYPE: DNA
<213> ORGANISM: Homo sapiens

<400> SEQUENCE: 12
tttttgtttt tagtttatat atatttttttt tgtttgtttg gattttaatg gtttaagata 60
gttttgagtt tattgggaaa agaaaatgat tgttaaaaat tatttttgaa attggttatt 120
tggtaatatt tttaattgta tggaaattta ttaaggtata ttttatatat aattagttta 180
aggttgttga ttttataggt tttatggatt taaatttgat tgataataaa gtaaataaga 240
gagttgaatt taaagtgtgg ttttttttggg ttaggatgag tttaatatag tgtataagga 300
atttgaaaga tttaggatat gtgttttaat taatgttaag tagaatggat aagtttttag 360
tattttgaaa atgttgggtt agggtttttt ttttattgtg tgttttttgt ttggggatta 420
ataagtatta tagagaatgt gatttgaggt gattttttat ttttgtataa atttagagtg 480
aattattaaa tagttgtttg tttaaagtta aggtaatttt tttttgatgg gtttatttgt 540
tttttgattt ttaatttatt agtttgtttt tttagggttt tgttttttttt gtaattaaag 600 ttttttttaga ttagtgtagt atttatttga taggttgttt ggaaaattta agattggaga 660
ggtgatttgt tgttgttttt taaatttttt agttttaagt aatgtgtttt tttttttatat 720 ggggtggggg attggaaatg gatgtagtga gatataaaga gtgggtgttt tgttgatttt 780
tgtatttttt tttttttgat tattttattt ttttttttta agtttttgat ttttagtttt 840
atttttttat ttttgggttt gtattaaaag ttggattgtt ttgggttggg taggagttga 900
atttttggga gtttgtttgt gtagatttag tgtgtatggt gaggtagtag tttggttttg 960

-continued

```
tattgttgat aggtgtaggt aggatagttt ttttattgtg gtttggggtg ttttgattgg   1020
tgtggagtta tgttagttgt atttggagaa gggtttggga ggaggtggag gtggagaggg   1080
ttggggaggg ttgtggtgga gtgatgtttt ggtattagga agtttgtttt tggttttaag   1140
atgttaggtt aatagggaag tgtggagttg tagatttggt ttgttgtttg tttgggtgtt   1200
tggagttgag ttgtggtaag gtttggtttt tgtttgattg tttgaggggt gtgtgtgtgt   1260
gtgttgtgga gggtgtgttt agagggttgt gttgtggttg tagtggttgt tgttgttgta   1320
ggggatttaa tattatttat ttgtttttgt tatttttgat atttttttgt tagggttgtt   1380
gtgtgggggg ggggtgggta gagtgtggtt ggtgttagtt ttttttattg gaggggtttt   1440
tgggggaggg agggagagaa gaagggggtt tttgtttatt tttgttttgt tttggagttt   1500
ggaagtttgt tttttaaaga tgttttgagt ggtgtttttt tgtttatatt ttatgttttt   1560
gtttgtttgt tgatttttttg tttttggatt tttttgtttg agttttttgg aggagatggg  1620
ggtagtttgg tttgagaatt tggtgggggt tgtgtttttt ggtttttttt gtagtgggga   1680
aattttgtgt ttagagtgtg atttggagtg ggtagtggtg gttatggggg tttggtgggg   1740
tagtagttaa ggattagtag agtgttgtgt tttttttgttt atgaattgta tgaaaggttt  1800
gttttatttg gagtattgag tagtggggat taagttgttg gttgtttttt tattttttttg  1860
ttattatttt tagttgttag ttatggtttt ggttttggtt tttggttagt tttggttgtt   1920
ggattttttt aagtataggt tggaggtgta tattattttt gatattttta gtttggaggt   1980
tgtaggtaag gtgttgtgtt gttttgtaga tatttttgtt tagttgtttt gtgttatttg   2040
ttttttttttg ttttaaggaa gttagttttt ttggggggag gtgtggtggg agtggttgtt  2100
tgtttggttt tttgtagaat ttttgggagt tggaatttttg attattttgt atttttttag  2160
ttttttttttg attggtttgg tttttggggt gttaagggtg tgagtaattt tgttgttttt  2220
tttatttgta ttttggtttt tttttttgttt tttgggttat aaaaatttta gtattttgat  2280
ttgaggattt ttagaggttg ttgatttttg tttttgtttt ttttttggtt tttagttttt   2340
gaggagtttt atttgttagg aaattgtttg aaattattta gaaatgtttt ttgtgaagag   2400
gtattttttt tttttttttg ggaaagggtt ggtgaatttt ggtgtttaat tgaattttta   2460
tatttttttt tagttttttt aaattgtatg gaaatttgag tttttgtga gggggagggg    2520
ggtttgtaaa ttatgtgtgt gtgtgtgttt taggagattt ggtgtgtttg tgtagaggtg   2580
tataaatata tttgaaagta taggttataa aagtgaatgt gttgttgtag tgagataaat   2640
atgtaaataa aatgtgtggt gttgggggag gggaggaaat ggggtgtgga tatttatatt   2700
tgtgtttgta tattttatag gtgtagtgtt ttttgtggtt tggagttgtt gtgtgtattt   2760
ttttttggtg ttaggtagtt tagtttttttt atggttttttg ttgttggttt agttggtgtt 2820
tgtgttgtag gtgggtatgt tgatgggaaa gtgtgtgtgt tttgtttttta gagaaagata  2880
aaagttagta ggggaagaat gaggatgtgg gtgttgagga tttgtttaag aagaagtggt   2940
aaaggtggta gtggatttat tttattagtt agtagtttta ggagttggag gttatttttt   3000
agaggaattg ttatttggat atgtttatat gtgaagaaat tgttgtgtgg attaatttta   3060
tggaagtttg agtttgggta ggagttagta tggagtttgg gagggatggg gggaggatgt   3120
tgtggaggta taggttaagt agattaggag agaatgtgga aggtagtgtt gtttgggagg   3180
gtgttggtgg ggtgtagttt tgtaaaggta gaaggttttg tggtggtttg gttgtgagat   3240
tatagttttt tttttgaggt tgataggatt gttgttttgg tttaggtttt tagagtggta   3300
```

ttggtttatt gttttgttat tttgtgattt tatgagttgg gttgtatggg taatttttttg 3360 tataggatat tgtgtttttg gtttgtagtt gttagagtag agttaataaa atttttatta 3420
ggttaagagt tgtgaatagg ttttaatttg tgagttttta ataaggaaaa tttgttagag 3480
atatggaaga gttggttttt tttgggaaat ttttgttttg gttttggttt agtttttttt 3540
tttttgggtt tgtgtttttt atattttttt tatggttgtt ttggttattt aggtttttttt 3600 tatatatttt atttttagt tttgtgattt ttgggagtaa agttttaata tataattatt 3660 agtttttta gaaggagaaa gaaaaaaaga agaaagattt ttttgtttgg tttatttatt 3720
tttttttagg agttgaattt tggaaattga aatttatatt ttttttttta aattataatt 3780
atagttttgt aaaaagggtt tattttaatt ttgtagtaaa tttgtatttt atggattggt 3840
aaaaatgagt ttaaataaat aatttaatag taatgttttg gtttatgttg gttggtggaa 3900
gattttaaat ttgttaggat tttggaagta gaaaatagaa ttaagtaaat taagtggtat 3960
ttagaggttt tgttgttaaa aaaaaaaaat taagtgtttt g 4001

<210> SEQ ID NO 13
<211> LENGTH: 32001
<212> TYPE: DNA
<213> ORGANISM: Homo sapiens

<400> SEQUENCE: 13
attaaggtga aaaaataatg atattgttgg ttttagaaaa ttggtggtta tttttttgttt 60 taagtttttt agtgtggtgt ttgtttttgt ttattttggt tgtgtggggg gttgataagt 120
ataataaaag atttagtat attttttttt ttattttat aatgattttt ttagtgttat 180
gaggatgaat tttttgggat taagtggtat ttgtttttat ttgttatgaa attaaatttt 240
atattttttt aaagttgaaa attgtggata aagaaggatt gggtgtttaa agtttattta 300
aatatttata ttgaatttat tttttgttta gatgttagag gatggtaggg agggttaggg 360
ttgtaattta ttttgatttg ttttattgtt ttgtagtttg taaattataa ttttgtataa 420
ttttaggaat aagtaggttt agaattaatg ggttaatatt atttaaaata aaatattggg 480
agtatgattt ttgttttaat tatatattgt ttgataagat ttaggaaatt ttattttaat 540
tttttaattt ttgagttttt tgagaaattg aagggttgta gttattagaa attatttttg 600 tttttttaa tgtttttaaa ggatttggaa atagtaatgt aatataatat gaaggatttt 660
tttatttaag tttgaagata aatgtggaag tttaaatatt ttgaattgga gatgtttttt 720
tgtaaattta ttatagatgt atttttttg agagaaatgt atataaatta tatatgtata 780
tatgtataaa tattttttta gaataatttg ttagaggtgt aggtttttt gtaaaggagt 840 aaatttgaga gttattttaa gttgatggat ttgttaaatt tttttttttt tttttttttt 900
ttatattatt tgttagttat aatggaattt tttaggttta agttaaagaa aaattggaga 960
gataaaatta gattttgtag tttttttttt ttttgggaat gttttttttt tttttttag 1020 tttttgatga atggttatta tttattttta ttaaatttaa ataaggattg ttgttttgta 1080
tgtttaatta ggtaggtaga gggaattggt ttgtttagga agtagtgatt gagatgtttt 1140
ggttaagtta gtgatagagg aggggagaaa gaatttagat taatttgtat gtagtatatt 1200
ttatttttat gaaataaaat atatttgttt tatatttgtt gaaaagtaaa ataataatat 1260
tgtatgaaat gttatatata gggtaggttg tatatagtag ttttagaaat attattgtat 1320
ttattagaga aattatttta aaattgatat ttatatattt tttataataa taataatatg 1380
ttagaaatat atagtgtggt atttagtata tatatttttt tgtttgtaag tgaaaaattt 1440

-continued

```
taattgtttt tgtataatat gttttatttt aaagtttaat ttttaaaaat attgttgtga   1500
tattattaat aattgttttt ataaaattaa tttgatattt tgatatatat atattttttt   1560
agttatttaa atgttaataa tgttaaattt aaaaaataat aagtttatag taatgttaaa   1620
atgttatatt tagttaaata tttgtttgtg tatgtgtttt tgtaattgtt agaaatattt   1680
gtagtgaaag atgttagata ttgaggatat ttttttgaaa ttaaaggagt tttttttttg   1740
atttagtggt tttttttttt ttatatagtt tttttttttt tttttttttt tagtgtttat   1800
gatttttag tataattttt agtttttaa gggtggagtt gttttatttg gtaaggtttt    1860
aggattttgg tgttgtgggt gtggtttata tgggttggtt tattgtatat tggtaagtat   1920
ttaggttgga ggttgggttt tgtatgttgg tgtagttgaa gttggagtgt tgttttgttt   1980
ttagttttag gttggttagg tttgagttat atgtgttttt ataaatatat ggaggagttg   2040
gtggtgtgta aggataggta ggtgttggta ttgtggaatt tagtgatggg ttatttaggt   2100
tgtttaagtt atttaggttg ttgagattgg agtttgggat gtttgttatt gttgagggta   2160
ttatgttgga tgatatgttt atggatgaga tagagttggg tggggaaaat atgttttgtg   2220
atgatagggg gttgatgttt atagagttga agaaggggaa gtttttggtg gatagggagg   2280
tggatgtaag gtttttggtg gtttagttgt tgtaggaata gtttgggtat atgttgttgt   2340
agggttgtat gagtttattg aattgtggtt tgaagttatt tttgtatagt ttggtttgtt   2400
ggttgtgttt tttttttttt tatttggttt gatgattttt gaattaaatt tgggggtggt   2460
tggggtaagg gagtaaatag atgttatagt gtagattatt aaaattttta ttggaggtta   2520
attttgttt tttttgata tatatgttag tgtatttata tattttggtt ttgttttatt     2580
gtattgtttt gtatattaag atattagggt tagtttttag ttattggttt gggtttttat   2640
taagtgtagg agatttggtt tgttttggtt tgtgagttgg gatttggagt tatgttataa   2700
attttagttg aatgtatgga gatttgtgga tggtttgatt atttagttag gtgtttttt    2760
aggtttaaaa atatttaatg taaaataaat gtggggtagt aggtttttt aattttttt     2820
ggggtatttt gtaaatttgt ttttattttta aagttataga tttatggatg aggagaaggg  2880
gttggaaggg tattagagga ttgtttttt ttttatgtaa tttttttttt ttttttttga    2940
tttttattgt tgtttttat tttttggtat gtgtttttt aatagggatt aggttgttaa     3000
tattttttt tgtttagtaa aataattaaa taaagagtaa aagattattt ttttgttagt    3060
ttgttaattt taggagtttg gtatattaaa ttttgggaat ttggaaaggg tagttttgga   3120
gatttttttt ttttttgttt tgtttttttt ttattttaag tttattatag gtttgtttgt   3180
gtgttaggtt tagttgggtt gtttggtttt gtaggtggtt atttaggttg gttggttttt   3240
atttgtgttt ggtggtttag ttgtaatttt gattttaatt tatattgggt tttttgttg    3300
ttttagatgg tggtttttgt gtattggaga gaggtttggt ttgagatatt tgagttgata   3360
ttagtgatgt tttatattat atatttttgt tgggtttagt tgtgtaattt gtttttttt    3420
tttttttttt tattttttgat ttttttttta tttttttttt tttttgtatt tgattgttat  3480
aaaaagtatg ttttattttt atttggtttg ataagtagtt gttttggaag gagaggtagt   3540
tgtaaggaga gtttagtgtt gtggttataa agtattaggg tggagttgtg gaatagtggg   3600
tggggtggga gggtgttttt gaaggatttt agaaaattta tagattttgt ttttaattat   3660
ttgttatttt tattttaggt tatttaaatt ttgtttaggt gagaagagta tgtgagaggt   3720
ttgtttttt gatgtgtaag agagttaatg aaagattgat tttgtttaaa attatgttgt    3780
```

-continued

```
ttaggattta gttttggttt tggatagtta aattaaaatt atttttaatt ttttttggt   3840
tttttattta ttagtatagt tttatgtttt gtataaatgt tatttagaga gtgtttttat   3900
ttttttgat ttgggagagt attttggttt ttattttttt tattgttgtt tttttttttt   3960
tgtttgtttt gttttaattg gggtttttat ttttttatt tagagtattt aattttttttt   4020
ttttaatagt aaagtttttg gatgttgttt gatttgtttg attttgtttt ttgtttttag   4080
aattttaata aatttggaat tttttattga ttagtataaa ttaggatgtt gttattgggt   4140
tatttatttg agtttatttt tgttaattta taaagtatag atttgttata aagttaaggt   4200
aagttttttt tataaaatta tgattataat ttagaagagg gggtgtgagt tttaattttt   4260
agagtttaat ttttgagaga agataaataa attaagtaga aaagtttttt tttttttttt   4320
tttttttttt ttaagaggat tagtagttgt gtattaaaat tttgtttttg gagattataa   4380
aattaggaaa tagggtgtgt gggagagatt tgaatggttg aaataattgt aaagaaggtg   4440
taagaagtgt gagtttagga gggaaaaagt tgggttaggg ttgggataaa ggtttttag   4500
ggagggttaa ttttttgtg tttttggtgg gtttttttg ttaaaggttt ataggttgga   4560
gtttgtttgt ggtttttggt ttggtaggga ttttattagt tttgttttgg taattgtaag   4620
ttaggaatat aatgttttgt gtaggggatt gtttatgtag tttagtttgt gagattgtgg   4680
gatggtgggg tagtgagttg gtgttgtttt gggagtttga gttagggtgg tagttttgtt   4740
ggttttggag agggaattgt aattttgtaa ttaggttgtt gtgaggtttt ttgtttttgt   4800
aaagttgtgt tttattggtg tttttttagg tggtgttgtt ttttatattt tttttggtt   4860
tatttggttt gtatttttat aatattttt ttttattttt tttagatttt gtgttggttt   4920
ttatttggat ttgggttttt gtaaggttgg tttatatagt gatttttttg tgtgtggata   4980
tgtttgggta gtggtttttt tggaaagtgg tttttagttt ttggagttgt tggttggtaa   5040
agtgagtttg ttgttgtttt tgttgttttt ttttagatgg gtttttggtg tttatgtttt   5100
tatttttttt ttgttggttt ttattttttt ttgaaaatga aatatatata ttttttgtt   5160
agtatgttta tttgtaatgt ggatgttaat tggattggtg gtagaagttg tggaagagtt   5220
gggttgtttg gtgttggagg agggtgtgtg tggtggtttt gggttgtgag gagtgttgtg   5280
tttgtggggt gtgtaggtgt aagtgtgggt gtttgtgttt tatttttttt ttttttttag   5340
tgttgtatgt tttatttata tgtttatttt attgtagtgg tatatttatt tttatagttt   5400
gtgtttttaa gtatatttat atatttttgt gtagatatat taaatttttt gggatgtgta   5460
tatgtgtgtg gtttatagat tttttttttt tttgtagaaa gtttagattt ttatgtggtt   5520
tgggaaggtt aggaaaagat gtggggattt ggttgggtat tgaagtttgt tggtttttttt   5580
ttaaaaaaaa aaaaaaaatg ttttttgtg aagggtattt ttgagtggtt ttaggtaatt   5640
ttttaatgag tggagttttt tgggagttga aagttgagag gaaaataggg atagaggttg   5700
gtggtttttg aaggtttttg aattaagatg ttgggatttt tgtgatttag gaaatagaag   5760
ggaggttagg gtatgaatag agagggtggt agaattgttt gtgtttttag tgttttagga   5820
gttgggttgg ttgagggaga attaaaggga tgtggggtag ttaaaatttt ggtttttgga   5880
agttttgtgg ggagttaggt gaatgattat ttttattatg ttttttttg gaggggttga   5940
tttttttggg gtgagaggga gtgggtggtg tagagtagtt gagtgggaat gtttgtaggg   6000
tggtgtggtg ttttatttgt ggtttttggg ttggaggtgt tggagatggt gtgtattttt   6060
agtttgtgtt tggaggagtt tagtgattgg ggttgattgg gagttagaat tgaagttatg   6120
gttaatggtt ggggatggtg ataggaagat gaggagatgg ttgatagttt ggtttttgtt   6180
```

-continued gtttggtgtt ttaagtgaag tgggtttttt atgtagttta tggatgaggg agtgtgatgt 6240
tttattagtt tttggttatt gttttgttga gtttttgtag ttgttgttgt ttgttttggg 6300
ttgtgtttta ggtgtggagt tttttttgttg tggggagagt taggggatgt aatttttgtt 6360
gagtttttaa gttaagttgt ttttgttttt tttggaaggt ttaagtgaaa aagtttggag 6420
atggaaagtt agtgggtaaa tgaagatatg ggatgtgggt agaagggtat tatttagagt 6480
gtttttaggg agtaggtttt taagttttaa agtgaaataa gagtgggtaa agattttttt 6540
tttttttttt tttttttttt aagaattttt ttaataagga aagttaatgt tgattgtgtt 6600
ttgtttgttt tttttttatg tggtagtttt gatagagaag tgttaagagt gatagggata 6660
ggtaggtgat attagatttt ttgtggtggt agtagttgtt gtagttatga tgtggttttt 6720
tgagtgtatt ttttgtaatg tgtatatgta tattttttgg gtggttgaat aggagttggg 6780
ttttgttgta gtttagtttt aggtatttag gtgagtgatg gattagattt gtggttttgt 6840
gtttttttgt tggtttaata ttttaaaatt agaggtgggt tttttggtgt tgagatgtta 6900
ttttgttgtg gtttttttta gtttttttttg tttttgtttt tttttagatt tttttttggg 6960
tgtgattgat gtggttttgt attaattagg atgttttgag ttgtggtgga gggattgttt 7020
tgtttgtatt tattagtagt gtggggttgg gttattgttt tgttgtgtgt attgggttta 7080
tataggtaag tttttgggaa tttagttttt gtttagttta aggtgatttg gtttttagta 7140
tgaatttaaa ggtgaagaga tgaggttagg agttgaaggt ttgggagaag agagtggaat 7200
ggttaagaag agaaaggtat aaggattaat aagatattta ttttttgtgt tttattatat 7260
ttatttttaa ttttttattt tatataaaaa ggagatatgt tatttaaaat tagaaaattt 7320
gaaaaatagt aataaattat ttttttgatt ttaaattttt taaatagttt gttaagtgaa 7380
tgttgtgtta atttgaagaa gttttaattg taaagaagat agagttttga aaaggtaggt 7440
taataaatta gaaattgaga agtaaatgga tttgttaaaa gaaaattatt ttgattttaa 7500
atgaataatt gtttggtggt ttattttgga tttatataag aataaaaagt tgttttagat 7560
tatgtttttt gtgatgttta ttagttttta gatagaaaat atataataga agagaaattt 7620
taatttagtg tttttaaaat gttgaaagtt tatttatttt atttaatgtt gattaagata 7680
tatattttag atttttttaaa tttttttgtat attgtattaa gtttgtttta atttgagaga 7740
gttatgtttt aaatttgatt tttttgttta ttttattatt aattagattt aaatttataa 7800
agtttgtaga attaataatt ttgagttaat tatatatgaa atatgtttta atgaattttt 7860
atataattaa gaatgttgtt aaataattaa ttttaaggat aatttttaat agttattttt 7920
tttttttagt gagtttaagg ttgttttgag ttattaaagt ttaagtaggt agaaggggtg 7980
tgtgtgagtt aagggtgaaa agtttagaat tgtgtttaat tagtaaaagt aaaattttat 8040
ttatataaaa taaaaaaaat tatttttgga gatattaatt ttttatagta ttgtttttaa 8100
gtaaatttaa tttttaaaga aattaaagaa agaaatttaa atatatttaa aataattttt 8160
gaaagttttt ttgtttttta gtataggtta gttggagagg ataaattaat tttttttggg 8220
tttttgtatg ggtgattgtt ttattatgga gttagtgtta ttatttttga atgtgtattt 8280
gtttgatatt atagttaatg atttgtaatg ttagtatgaa gtatttttaa aatatttttt 8340
ttttgttttt gtttataaga ttgggaaatt tatttgatgt ggaataaagt ggatgaagta 8400
gattataaat atatttgtaa tttatgtgtt tttttttttgt tttgattatt tttaaatttt 8460
atttgtaatt tttttttatt ttaaatttgt agtttaaaga tgtatatgag aattgttttt 8520
tagttttttt ttattagtat tattttattt taagaataat ttagttgtaa gggaggaatt 8580
tttttatagt aagttttaaa ttagtatttt tgtttttaat tttttatttt attttatttt 8640
attttatata tatagatatt tgtttagagt aaaatatatt tttatgtgat aggtttgtat 8700
tagttgaggt ttatatattt agttatatta ggttttgtaa ttttattatt aaattatata 8760
tattatatta gtagtttgtt ggtaaagaag gttaaattaa tttatatttt gtttattatt 8820
tggtgtttaa atgatgtatt ttattttgga gatttggtgg agaatttttt ttttagattt 8880
tatagtgttt tattgaagat aatgttttta tatttgtagt ggtttttaat ttgataagat 8940
tttaatttgt ttaagttttt taaataaggg ttttaaatgt ttttagttgt tttttttattg 9000 aattttttttt aattttttta agattataaa gtatatgtgt aaagtaaata ttttttttta 9060
ttgtattgtt agttgatgat ttataattaa gttaataaga atttagtttt tttttgttga 9120
atgtgtttat taattatatt ttagtttttt tttttaaatt ttagaatagt tgtggttttt 9180
ataatattat gtttttttaaa gttttatttt atgaagggat tttattatat taaagaatga 9240
aaaaaatttt tattgtagtt agtatatata gtttttttatt ttttgttttt taagatttaa 9300
attttagagt tgtaaatatt tttggaagtt tgggtgttaa tgttttattt tagaaagttg 9360
agaagtttta tagagttata tagattttta aatttatttt ttataaattt atagaatttt 9420
gataaaagtt ttggtggttt tattttattg atggaatttt tattatgata aatatatatg 9480
tatgaaggat tttaattagt ttttaaagtg gttgaaaaat ttaagggtat gtgattgttt 9540
tttatagtgt taatgtgtgt gagatgttgg aagtattggg gattagtagt agtttagatg 9600
tttaaaaaga taaggtgttt taatttgtgt ggatttattg aagttaagtg gtgaataaag 9660
ataattattt agataattta gattaaagta aaagtaaaat tatatttatt tgtatatata 9720
tatttatatt tattttatat tatagatata tatatgtata tatatattgg ttttgtaaat 9780
aattgattta aagtgaggat ttttttttgta tttttttagt aggagtttta atattttttt 9840
aattttttaa ttattttata tatttatagt agtggtgatt gggtgatatt ttttttaggt 9900
tttttgtgtg gtaggatatt aatatgataa gtttgtatgg ggaaaaggag gtatgtggtg 9960
ggaattaaga aatattgttt agtgaaaatt ttgtggtatg gtggtggttg attttggaga 10020
tttaatgtat ataagatttg tgggtgtata ggtataggta gtatggatga gaaaggggtt 10080
agaagaaaat aaattttatg tattttgtga ttttagtatt attgtgattt ttggttaagt 10140
tttttttaat tggttttaga aattattatg agtttagttt ttaatataga aatttttaat 10200
atggagaata ttggtgggat tttggtaggg aaattagagg tgttgtatgg tttatgtggg 10260
gtaaagaagg aaagtttagt gttggtgtga ggttttgagt ttgggagata ttaggggttg 10320
ttttgattgg ggttttttgt ttattttttt aaagaaagat tttagaggag ggaaatgtgt 10380
gatatggggt tagttgtgtt ttgtgttggt atttgttatt gattattagt tttaaagttt 10440
tatttaattt tatatttttt agtgttagtt gtgtaaagtt tttttggtta tggtagtgag 10500
tggttgggtt gtgttgttaa atttttttgta ttaatttggt ttgggattta attaagtgat 10560
ttttgatttt tggaaagagt ttgtttttag agtttattta gaagatggtt taattagata 10620 ttttttttgag ttgttaggtt ttagatgggt gggagttttg ttttgtttaa gttagtttaa 10680
ggatgaggtt tgtttggatt tagtttggag ttatgtgatg ggtgtgagtg tgtgagtttt 10740
tggtaaggtg tagaggttag atggagattt tgtattttgt ttgagaagtg ttttattttt 10800
tttaatattt ggtttttttt tgtatataaa ttaagttgaa aatagtttat tatttattat 10860
tttttatagt tatggaatta aataatttag aaattaaaag ttttattgta gttgtttttt 10920
tttttatttt ttaaatggaa tttaaaaagt tttggtttgt taaaagggga agattatttt 10980
ttgaattgga agtttgtaga tatattgagt aatagttatt ttttttgggt ttttgtaaat 11040
ggtatttatt tttttaattt atagttttag ttgtttaatt atttgagatt tggggtaatt 11100
atttggggga atagtgttta gatggtagtg ggagttatta ttttatagtg gtttggggaa 11160
gagaagagaa agagattaga ggagggggta tttgttaaaa ttatttaatg aatatgttgt 11220
taatgttttt ttatatttgt atgttattgt tatagttttt ttaggtgtta ttgagttttt 11280
agaaagtaat tatttgttga attaagtaaa ataaggagaa tggtatagta tatgtgtttg 11340
gagaagggga aggaagggtg gaatatgaaa ttgagtatag atatttaggt taggaaagaa 11400
ggaagtggta aggggttaaa tgaagtttta tttttttgtt attttttaa ataatagttg 11460
gattaaatat ttatttgttt ttttttttt ttttttttt tttttttag tttatgttta 11520
ttttttttt ttattttttt tgttttttt ttttttgtt ttttttttt tagatatgtt 11580
ggtagttaat atttagtatt agttgttatg gtgattataa attatttaaa tttaaaaata 11640
tttatttata atttgagatg aagtttttat tttttagtg aaataatatt ttaaaagttg 11700
ttagttgata aaaaaaaagg aatttatttt attgtagtaa tttaagtaat atattatttt 11760
taaaggttta aattaaaatg ttagtttgtt aaaaatatgt tggtagagtt ttggatattt 11820
tttttgttag atttttataa agaagttgat tttgttattt ttggttgttt tttaatatat 11880
atatataatt ttgtatgttt ttttttttt tattaatttt ttttttttt attaattatt 11940
ttagtttttta aagattttat gtattgggtt ttaaaagaaa agaatttttt tttggattag 12000
aaaatagttt tattggttgt tgaagtgaaa gatgtggggt ttagggggaa aggttattag 12060
gattataatg gtggtggtgg taggaggtta ttttagagga gttaagaaga aaaaaaaatg 12120
tagggagaag gattggaggt ggaaagatag agtaatagaa aattgagttg ggtggttagg 12180
tgttgtggtg aagtttagtt ttgaaatgat aggtatatat ttttttattt ttgttttttt 12240
tttttttgag agaaaatttt tttagttaga gattttgggg ggtaggaggt gggtaaatgt 12300
tgttgtagtt gggttttttg ttttttattt tgggtttgtt gtttttttgtt tattttggat 12360
tatagggtat ttgtttagat gaagagttat taattattta tttagttaat attaggaaga 12420
tgataaagtt ttttatatag gattaagaag atattagatt gttttattag tatatttttg 12480
tttatgaata agtttttgtt atatattttt tttttttttg agttgtttta ataattgttg 12540
tatatattag tagtgggtgg tgaggaataa tagttgaatt agttttaaga aattttgtgt 12600
attgagttag tagtgaggaa tgtgatttgt gaagattatt tttgtgggta gggatttgta 12660
gggattgatt atttttggat aattggtata atttttttttg ggggtgaaaa attataatgt 12720
ggtggggtat tttttaagtg agttgtagat ttgattggtg tggggggtgg gggaggggag 12780
gggagaatgg gatggtggag gttgggtgga ggaaagaaaa tggaaaattt tttttatttt 12840
tattttgttg ttttttttt aagttttatg tttttttgg taagtatttg tttttttttgt 12900
gttagttata gttagagttt tttatttttt tttatatatt ttttttttt tgataaggtt 12960
taggattttg gttattattt tatgtattat tattttgtgt tttgttagag atggtttggg 13020
ttgattttgt tggtgtttat gttaggatta aaattttttt atgatggtga ggaaaattgt 13080
attatttgtt tttagggggt atattaggag tttatgtagt atatgttttg taaatatttg 13140
ttgattgaat gagaggtgtg ggggtggggt ggtggagagg ggtttgtggt tgttaaggtt 13200
gttagggtta atttaggttt tttgaagaag gttgggattg agttgttgtt gtgtgtgaag 13260
gtgtgtgttg tggttggggg tgttataatg ggttatggag tttatttttt agagggagga 13320
agtttgtgta tattagtgat ttgggttgaa tatttttagt ttatttattg ggttaaagtt 13380
atttaataat taatgtgttt ttgggggagg ttgggggaag tatttgtttt ttgttgggat 13440
gtaaagttag gtgttaggtt taaaggggtt gtagtgtagt ttgattttag tatggaattt 13500
agagttgttg ttttgaaatt ttttaagtta gtgatagagg agggttagtt tgtttttttt 13560
ttgagggtga agattatttt atgagttttt tttaggattt ttaaagtaag aaaagttaaa 13620
gaaaggtttt tttgttttag ggggttgttt ttagttggtt tttatattat tttttgttag 13680
ttgtgtttat ttttttttaa atttttggtt tttaggggtt tttagttgtt tttgtgttat 13740
ttttgttttg gggttttatt taggttgggt atttgtttaa tggatattaa ggagaatggg 13800
atttattagg gaaggaaggt agagtttgga ttgtttagag gtggattttg tttatataga 13860
atgtttagtt tttaatgagg atatggtatt tttgggtggt gttgggggta gaggtggaga 13920
gggtagtgta atagattatt atggtttttt gaagaagtta tatgttattg tgaatttttt 13980 tttttttaa aagtaaagaa aaattttaaa aaaatataag aaataaattt ttttgtttta 14040
taagtaggtt gtggttagga ttttggatat tttataagtt aatttaaaat tagggaagga 14100
taggtgtttt atttttttagt agtgttatag ttttgtttat ttgtgtgatt tttttttgtt 14160
gtttattagt tttttaaaag ttaattaaat taagattttt agtatttttt tttattatat 14220
gttttttttt aattaatggt attaaatgtg tttaggtagt aatttttttt tttggttaaa 14280
aagtagaaaa agatatattg agtgtagggg aagagttttt tatgtgtatt aaaataatgt 14340
gggtttgaaa gtaatggtta agaaagtaat tatttattat ttttagtttt ttatgtgtta 14400
gttattaaaa gtgaatgatt aggggtgttt gtgtggtttg tgattggtgt aagtagaatt 14460
tttttgtttt tagttgtttt ttgtttattt atgaggattt tattttattg taggtttttt 14520
tatttgtttt tagaatgtat tttttatgtt taggaaattt ggggtaggga ttgggggaag 14580
gagatatttt gtgttttttt ggtttttagt ataataagaa atgttagttt tggtttggtg 14640
attgtgagtt tgttttgtgt gaagtgagat tggggagttt ttttagtttg gttggagtta 14700
gggttgagtt tgtgtaaagt attttttttta gaagttattg ttgtttttga tttttaatta 14760
tattttaaat atattatggt ttaataattt atttttatta ttgattatta aatagaagaa 14820
gaatttaata taatttaaat gatagaaatt atgtgatgtt atttttgtat tgtttttatt 14880
taattttatg gggttaattt tggataagtg agtgtttaat tggtttagta gggtgattgg 14940
tggtgtagtg tagtgtttgg gtgtgaagta ttggattgtt ttagatgttt tattttaata 15000
aatgattatt ttttttttaga tttatgggga aattttaatg taagattttt gttttttttt 15060
tagtaatatg gtttgttttt ttgattgggg ttttaaattg ttttttttta ttttatatta 15120
tatttgtatt tttatatttt aatttggaaa gagggggtta ggggttgagg gttgtggggg 15180 gggggggtt ttatttgttt atattattaa aggttaatag ttttttaagg ttaggtattt 15240
atttattatg gagttaggaa aatagaggaa tagtaaattt gaggggtttt tttttatgta 15300
tttgaaaaga aaggtatttt ttttttttta tttttatat ttttttttt gttttataga 15360 ataagtttta atttaggaaa ggtttgtggt gtaggttgga gatttttttaa tttttatat 15420 aagtttgtag atttttttttg gtaatgtttt ttgatttttt tagagtgaaa ttagttaatt 15480
aagtaatgat attgttaaaa tttaaggttt ggtaattagt attttaggta ggtttgtgtt 15540
gataggggta aatttttatt ttattttggg ttgttaagta tagtggttgt tttttagttt 15600
tttagggatg ttgttggttt tttgtttttt ttttaattag ttaaagtaaa tttttgttaa 15660

```
tttaagtttt ttttgtttgt tttttgtgat gaattgtgta tttataagtt tgggtggggt  15720
gtggttgaga gtttgagtga ttgagtgggt tttggtggtg ttgtgtgtag tgggatataa  15780
tgagtgatag aggttgttgt tggattattt ttttatgtta gtttagatgt tgaggtttgt  15840
tggagtgtgt gtaggggatt agattatagg gagtgagtga gagggagaga gaggtgttgg  15900
gttttaggag tgtagtataa tttggggaaa ggaattaatg tttttgggat ggttgttttt  15960
tgttttattt agaggtggag tgtttaagtt taagtagtag gtgtgttagg tttggtggtt  16020
ttgttttttt gtgttttgtt tgaggtttag agttttggag gtgggtgttt agtgtgtggt  16080
ttgtgttttt tttttggttt tattattggt gttaggatgt tgttgtggga agaatttgtt  16140
gttggttgtt tttttttggt ttttaggaga gtttgtgaat ttgatttttt tgattttgga  16200
gtttttggag aagagatatt taatggttgt tggttgtatg tttgggttat gtgtgtgttt  16260
gttttatgtg tggagagagg tgttttggat tgtggttgaa aggagttggg gatgggagga  16320
gggggagggg tgaggtaggt tggaggagaa agagggataa agagtaaaga tttagttaga  16380
ggaaagagtt gatggtattt ttgttttttg gatttttttgg taatttgggg taggatggtg  16440
tatttttttt gtgttttttt ggttgttggt ggttttagtt gggaggagta ggttgggggg  16500
ttttggtata tagtgtgttg ttgtttttta gtttattgtt ttgttatagg gagaggttat  16560
tggtgatttg gttttgattt tttttttgtt taggttggtt ttttggggaa gtgtttttttg  16620
ttggggtttt gttgtagggt tagtgttttt ttgttgtttt tatgtggtgt ggttttttgt  16680
ttgatgattt gggtaggaga aggggggtttt tatttaattg tatatatgtt gatattagtt  16740
tgtggtagtt ggtttttatt ttttgttatt tgtaaaatag aagagaagga aggttgtaag  16800
aagtggtggt tgttgagtga gtagggttta gatgagatta tgttatatta gttgttaggt  16860
gtttattgtg tgttaggttt taggtgtgtt tttttgattt gatagttttt ggttgtgtag  16920
tagtattttt agtttagttt tgggtttagg atatttattt attaagaggg gatttttttt  16980
tagagttgtt gtaaaagtgt ttagaggtta gaggattata aagttatagt gtgttgggga  17040
ggttgtggat ttatttttaa gaattttggt gttggggtta agaatttatt tgaatgtaat  17100
ggtagtggga gtgggtgggt ggagaggatt tttttttttg ggaagttgta tgtaaagatt  17160
atttttagt gtttgtttat tagttggagt ttggtaaata tttgtagaat attagtgtta  17220
atgtgttttt gttttagata gtagtttttt ttggtttttt gtaattttga aatgaatggg  17280
tttttggttt agggtgtttt aggagtgagt tgagtttggg ttttttattt attaggagtt  17340
atttttttat atttagttat attttttttt agagatatta atttggttat ttatttattt  17400
attataaata attattttaa agtatgattt aagattgtag aggagagata ttgggtggat  17460
tgagtgagat tgaggagagt agggtaaatg tttttggagg gtttattgtt tgttaaggat  17520
ggagaaatag ttttggtata attgttattt agtttttttt tttttttttt tgggtgagtt  17580
aaattttttt tatgttttta attataatgt agtgagttaa gtatttaatg tgtttttttt  17640
tttttgttat aggtaagttg ggagaggtgg gttttgaggg gttttattgg gtgggtagaa  17700
gagttgtggt tgttttaaag ataagaaaag aaggtttagg gttttttagg tttttttgat  17760
tttagtgttt gttttttttt atgttaatta gggtatgttg atgattggag ggtttatttt  17820
gtgtgggtgt ggggattggg gtgggagtaa gtgttgttgg gttggtggag gtatagaggt  17880
ggggtaggga gttgtgggtt tgtttttggt ttgagtattg ttttttttgtg ttttggtttt  17940
ttttgaaggg agttgggttt tggggagttt ttggttaagg ttgttgttta taggaggggt  18000
```

-continued

```
tgtttggtgt tgtggtgtgg ggatttaggg tggggatggt taggtggttt ttttatttgt  18060
tagtgagaat gtgggtgggg attttgttga tttgattttt gtgggtttgt gggtttagaa  18120
gtagtagttt ggtggtttta gatttagtga ttttgtagta aaattatagg attagttttt  18180
gattgagatg tttgtttgtg agatattata aaatttatta ttatagtttt ttattaattt  18240
gatatgaagt aatatagatg ggattttatt agtttagatt ttaaatgttt atttatgata  18300
attttggagg aaatttgtat gttattatta ttttgataat tttttttttt tatatgtttg  18360
aattggttgt attattagtt ggtagttgga gtattgtaga tggtaattgt aaatagtttt  18420
tatttattta tttttttaa agaatgaaat atataaaaga aaaagattgt gttgtttggt  18480
gtaaagttag ttaattatta tatatttttt tttttatttt tttgtgtttt agtgttgaag  18540
attaaataaa gtaatataaa ataaattttt aagaatttat agagttttat tttaaggatt  18600
gaaaagaagg ttaaggtgtg ttttttagtt tatttttata tgtttttgtg atttggagat  18660
ttattttgta gttaaaatga gttttgagat ttgtattttt atgttttatt taatgattag  18720
gtttattaga agaattgagt ttaaataatt ggggaagata attttttaaa aagagatttt  18780
taatttttgt ttgttgattt ttaaatttgt tttattaaga taagtttttt gtgagaaatt  18840
tggttgttag attttggaat tggttttaat ggttaatttt ataaattgag atgggagatt  18900
ttttttgatg ggaggtagtt tttattttta aagtttatgt tttagttgga atgtatatgt  18960
taaggatttt tgttttggtt aatttgggtt ttatattgtg agtatataaa aagtattata  19020
tggttaatgg aggatgagga attatggtaa agtaggtagg taagttttaa gaaataaaat  19080
aatttgttaa aaaataattt ttgatgatta ttgtaagatt gaaagtgtag gaaaaatata  19140
gtttgaataa ttttagattt ttttatattt tttttttttt tatatatttt gttattttat  19200
aataaaattt ttaatggaaa gtttaaaaat aaatagtata ggaatatgtg ttttaaatga  19260
attaaattgt gaaattagtt agtaaattaa tttgtagtaa gtaattattt aaggaaatta  19320
aaatattgtt tagtttagtt ttgtatttta ttatgtgtat gtgtttttta taattaatta  19380
atataagtgt tttaggaata tttgaagata aatatgttta atttaaggaa taaagtattt  19440
aaataattta agtgtaattt tgttgagtta aagtaaaata ttttataaat gaagtggtta  19500
tttaattttt tagggaaagt ttggttattg aaatgttgta tgtttatgtt atattaataa  19560
aaatttttaa tttattttgt ttatgtgttt tgtttttttg atattattgg tatttgaatt  19620
ttagatggat ttttgttaaa atgatatttt gtgtgataaa agtattttta gttttgattg  19680
atagattaaa ataaatgtaa ggaaattttt ttaaattaga ttaatttttt ataaaaatat  19740
tttagaatgt atgaattttg atatttatat ttataatggt aaaagttttt tttgtttagt  19800
ttagtaagat aatatttata taaaagagta aaaaaaaatt atattatttt atgatagttt  19860
gatttttaaa ttgtttaaga aagtaaagtg gttaaattgg aaaagaggaa tatattttgg  19920
aggtttagaa ttgaaaattt ttttttttaat ttttagttgg aaaataattt tttgtattta  19980
tttaaagtgt atttttttgaa gtgttagatt ggagttgatt ggtgattaat ttaaaggagt  20040
tataatttaa agaaatggtg agagtttggt atttaggttt ggtttttagg taatttgttt  20100
gggtttgaga ggttattaat tgttagttaa gatggaattt tttttttttt tttttttttt  20160
taatggataa taatgggaag gggggttaatt ttttagtagt tgaaattttg tatttagttt  20220
tttattttga gaatgttaat ttttggtttg aggatttgtt tttgtagtgt tggtattgag  20280
atttaaggga agatattttg ttttaaatgt tagttatggt ttggtttttt ttttgatttt  20340
agtattttgt agattgttag tgtttgtggt gggggatgaa aggaataggg ttttgtaagg  20400
```

tttgtttgtt gattgtgtta ttttgggtga aatttagttt taaaagttat aaattattta 20460
tggtgaagat tttttgaagt ggaataaatt tttagatttg tattatttta tatttttgtg 20520
ggatagatgg tttttattta ttggttattg ggagagagtt gttgtttttg tgttttattg 20580
ttttttgggg tgatttttag tgagttgagt ttttggttgt atggtaagtg tttgaaagtt 20640
gggtttgaga ggattgtagg gtttttgagg gtgttaagtt ttgaaggagt ttatgggtgt 20700
attggggttt ttgaaattta gttgttattg gtagtttttt tttgtttttt tttagttttt 20760
ttgtttggtt ttgtattttt tttttttttt ttttttttta tttttttttt ttttttttgt 20820
ttttattttg tgtggggagt gatgtgatgt tagtagagat tttattaaat tttattgtat 20880
agtggtgtgt gggtggttgg ttgagtttgg ttgtgtggtt ggtgatttag gagtgagtat 20940
agtgtttggg tgagtgttgg ggggagtgag taggggtgat gagaaatgag gtaggggagg 21000
gaagtagatg ttagtgggtt gaagagttgg gagttggagt tgggagagtg aaaggagagg 21060
ggatttggtg gggtatttag gagttaattg aggagtagga gtatggattt ttattgtgga 21120
aaggaggatt agaagggagg atgggatgga agagaagaaa aagtaatttg tgttaatttg 21180
gtagttttaa taaattaaag ggggagtgtt agggtagtgg ggagatagaa atgtattttt 21240
ggggagtaaa ttaggatggg ttgggaggaa gtgataggga aagtggttta agagatggaa 21300
taaaggataa tgtttatggg gttgtttggg atgaggtgtg tggagtgtgg gtgtgagtgt 21360
gtgtgtgtga ttttttttta ggtttgtaga gttgaggaaa gaggttatag taaagaggga 21420
ttgtggaggg aggaaagtga gagattggta gagggtggga gtggaggtgg gtgtggtggg 21480
gatgggagag gatgagtgaa gagaaattta gaagaatgga gtgagttagt gggagagggt 21540
gggagggtta tagttgggag tgaatgagtt aggtttgtta gttggggaag gttgggatgt 21600
tgggtttagt ttagttggga tattgtgttt gaggttaagg tgggtggatt aggtatgttg 21660
agagtgttgg tgtataggtg ggtatggtta tgtattgatt tagtgtttat gaagggtttg 21720
tattggataa ggtttagatg tttatagagt ttagaatttt ttttgttgta tttatattta 21780
ataagtttat tttgggttat ggatatttta ttttttaaaa tgatgaggtt aaggtttttg 21840
gtgaggatgg tattaaattg tatgggatag aagtgggggt gggggagaga gttttttttta 21900
agtttatatt tgtttttgta aagtaaagag tatgtgaaat tatagggtat atttttattt 21960
gaaaagtgtg ttttattttt gaattttgat tttttgattt tttgatttga gtaaagatgt 22020
gtattttggt agtgagtaga atattttggt tttgttttgt ttttgagtgg aaggattata 22080
aatataattt gtttggagga ttaggtgtga aggtttttgt taggtatatg ggataatgtt 22140
tttttaattt taagggtatt ttgttaatgt atgtttttgg aaagtgttgg aatatagtta 22200
ttgtttttgg atttggattt ttttattaat attaattttt gtttgagagt aaaatttagg 22260
tttgttatta aaaagatatt tttttggttt ttaattgaga ataaagtttt ttttaaaagt 22320
tgtattgttt tttttaaatt aatatattaa tatttgtaat tttagaaata tatagtgatt 22380
tgggagaatg tgtataaaat agatatgttt aaaaaagttt ggtgtttaaa attaatttta 22440
gttattatat aggtgttggg tttttttttat ttttgggggt tgtttggaat atgttatgtg 22500
ttttttttgaa ttattttgtg ttttgaattt atttgagtta gtagtaaaaa taggtaaata 22560
aatttgttta atttgttttg agtgttaaat ttttttattt tgaaatagtt aatagttgat 22620
agatggattt attttatgga aagggttagt ttttttagtt atgaagaaaa ttgattagag 22680
atttatattt taagttattt ttaattttta tgtaatattt gtgaaaattt aaattttttt 22740

-continued

```
tttttattta gtggaaattt aaagtagtgt tatttaaggg gagagaaatg agggggaaaa  22800
tgtttatgtg ttgtttaatt gtattttttt tttgattttg agaattttta tttttggttt  22860
ttgaaatttt gttgaggtaa gaaaattaaa tttttttaat aagttttata attgaatttt  22920
agttatagga tattggaaag tgtagtttga gaaagatatt tttatttttg tttattgatg  22980
atttttgtag ttttttttatt tttttgagta atgggttaat aatttttttt tttttttttt  23040
ttattttgta gagattaaga ggtgtttgta gtagaatggt tttgttttta gttggtggtg  23100
aggataggta attttatgga aaagttggaa gagaatgaga aaattaaaga tagaaagatt  23160
tagagatttg tggagagata tagggagagg gaagggagtt gtgttgaaaa gatgtaaaga  23220
tatgtgtgtg taattttttt ttttttttagg ttttagaggt ttgtaaatta gggttgagag  23280
gaaggggttt gggaagttta tgtttttttt gttttttttt tgtttggagt tttgtttgtt  23340
agaggttggt taattttagt tttggttgtt gtagatattg tgttgagttt ttgggttttt  23400
gttttgttta gtgttagtgt agttgaagtg agtagttggt gggaaatgta aatggttttt  23460
ggagaaatag aagatataga atgattttta tttttttttt gagtgtgtgg aaggagttgg  23520
atatatgttt tatgttttta attttttttt tatattttta gttatatttt tattaaataa  23580
ttaattaatg tttagaatta ttagggaata tattaggtat gtaattgtag aagtagggtg  23640
ttgggggggtt ataaattatt gagttgattt aagatgtgga ttttaggttt tttttttgtt  23700
aaagtagtaa aggaagagtg ggttttggtg attgtattta gattttgatt attttaaatt  23760
agaaggggggt ggagggagtg tttaagtaaa gtaagtaatt ttttgttttg tagatgtaaa  23820
taagattgta gtattaaagg tattagtttt tttagggtta gattgtttgg attgggagtt  23880
tggggaaggg gagatattaa ttttatgtat ttgtgaattt taaggatgtt atatttttat  23940
ataaataatt ttagtgtgga ttttttggaa tggggggagt aatattttta ttttagaata  24000
ttaaaatatt ttttttttaa agtgtatatt ttttttattt ttttaaaatt ttgaattatg  24060
tttaaagata atagtttttt agtaaattgg agtattggat tatttttttt attttttttt  24120
attgatattt tgatgatttg attttaatgt gtgggggggta tagggaatta aatatagttt  24180
ataaaattaa gtttagatga aatagtgttg gttaagtggg tttagataat ttttaatgag  24240
aattttaatt atattttttt ttttaatatg ttgagataag tgatagaatt gttagaatgg  24300
taattaaatt ggaaagttta gggagaataa taattttgtg attaaattgg ggtaaaattg  24360
tggataaatg tggggtgatt tttgttaatt ttttgttatt taagagttag gatttgggaa  24420
aggtatagta ttattttaga gtttgttgtg atgggttgtg tgttattatt tatttttttt  24480
attttggatt atgattttaa ttttggtaag taattttttt agtttttttat ttgataataa  24540
gtgagtatgt aaatattaat ggttagtgat gtttaattgt tttaaatatt attgatttgt  24600
tggttgtttt aaattgtttt tttagtttag gttttgtttt tgaattgttt attttagagg  24660
tttgatttat gtttttgatg ttataatata ataattgttt ttttaaaaaa ggtatttaag  24720
atgaattaat tgatttgtat ataaattaaa attattatgt gttgttgatt ttggtgtttt  24780
ataattattt tgaaattagt atttaattat ttgagttaaa agaatatata aatgtttgta  24840
ttgatttatt aatgaattat ttaattaaaa tgtttgggta atgttgggtg ttggaaagat  24900
tgttaaatta agatatatta taggagggat atgaagatta gaaaggtaat agattaatat  24960
tttgtattta aaatggagtt tttggtgatt tttagtttta attttggagt aggggttttt  25020
tttttttgtt gttaaaaaga ttttgtgttt gtttgtgagt gagtgtattt aagtggaagg  25080
aatgtttttta tggttatggt ggtttaggtt ttttgtttgg attgggattt tatagtttta  25140
```

```
atttaggagt gttaaatttt ggaagatttt gggttagttt tggaggtgtg tggttttgta  25200
agttgttagg ttaagtttgt ttttttgtt tgtttttttg gtaggttggg tgtgttatgg  25260
tagtgagttt tttgtgtaaa tggagagttg gaattaaagt tgatatttaa tagatatgtt  25320
aattgagtat ttatttttgt tttgagaata ggaataaaag gtagtttttt ttaagagagg  25380
tggtgtaaag gtatgttata ggagtttaga aaaggttggt ggtgggaaat ttgtagtttg  25440
ggggttagtt aatatttttt tttattttaa gtatttattg atttgttgtt gttatttttg  25500
gtgatgtaga aggatatttg aaagaatttt tgatggggtt ttgatttgag aaaggaggtg  25560
atttgtttag gtttttatta aatttttaat tattatatta attgtttttt tttatttttt  25620
atttgatttt tttttttttg tttattttta atttttaat tatttagaaa ttttttttatt  25680
ttttagtggt tttttttttg tagtagtttt ttatttgaat tttttttttg tttttttgtg  25740
gtagggtttg tatattgatt tttttgattt ttggtatatt tgggtttttt gaaatttttt  25800
aattttttta gatttgagga tggtaggttt tatttttttt attgtgtgta tatatttaga  25860
gatatgaaaa tttatataga ttgtttttaa atttagggta tttaatagat gttttttttt  25920
tagtttgttt tttgatttga aatgtttgtt tgattttaat ttggatatta tttttttttg  25980
ttttttttt tttaaagtag tttggatatg tgtgtaagtg agtttagaat agttttattt  26040
atattttta ttaaattgta aataaaagaa gaattaatga agtagattgg tatatagatt  26100
gtattaagag tttgaatttt tagtttttgg atttttttatt taattttggt tgttatttat  26160
attgatagag ttattttaag tagaggttta gagaaatttg tattgtggga taataggtaa  26220
agttatagta aaaagtggaa taattttaaa gttattttat tagaatgtaa attgtatttt  26280
tgggttttgt ttgtaattat ttagttttaa tatatataga gttagatagg aaaaaatagg  26340
ttaatatagt tattggtatt agagaagata aattttatgg gtttttttagt gaaaagaaga  26400
tttttaaagt ttataatttt tgattattta attttattta taattgtggg aatgaataag  26460
atattaattg ttttatgtat tttatttata ttaattaatt tgtgttttta ttaaaagtag  26520
ttatatagaa tttttttttaa tttttggtag taagtttaga aaatgaagtt tatagttatt  26580
ttgaattgga tatattttt gagttgatta tttttgtaag tgtaggaata taatattgtt  26640
tttttatggt tttttgtat ttttttaggg tttgtaagtt tttattaggt ttgatattat  26700
tgtttgggtt tatatttatt ataagtaaat ttgattatta tgttgatttt aaaatagttt  26760
atttggttag tataatttta gtttttaaat tataaaaatt ttttaatata tgaagttttt  26820
agtttttatt ttttttagtt ttttgtttat ttaaaatttt tattttaatt ggtgtaagta  26880
ataataattt gtattattat ttgtattttt tttattttt tggagattgg gttggatttt  26940
agagagaata ttagtattat tattattata aataataaaa tttaaaagta aagtttttat  27000
ttgtatgata attggtattt ggaatgtttt tgatttattt aatgttattt tataaaggta  27060
ttttgtaaat ttttttggaa tttttagtaa gagtttgtag taattggaat aatttttttgg  27120
gaagatattt tttttgatgg gtttttagtt tttggaggaa tagattgaga gtaattaggg  27180
agggagggga tattggaaat tggtagttat gttagttgaa ataagtttgg gtttagtaag  27240
gtgattgatg ttgtggttga ttttttattt tgagtttttt tttaattggg gtattgattt  27300
ttttttattt gggattttaa ggtatttggt gtgtatgtag attttttttt tgtggttttt  27360
attatgtggt tttgtagtag gtttttggtt taatgatatt tttatagttat agtttttata  27420
tttattatta tgattttaat gtttaggttt ttagtgtatt tatattaaat ttgttttatt  27480
```

```
agtaagttgg agtatatagg agagatgggg gtaagtaagg atttagtaga gtttaaattt  27540
agatatgttt aaatggtttt gattgtgtaa agtgtggtaa tgtttttgt tgttttagtt  27600
ttttatttta agttttatat gtttttggt taatgaagtg tgatataggt tatatgttag  27660
gaataatagt atttgttgag aataaagtga atttaggaaa tttggtatat ataaaatgta  27720
tttagttatt tgaattagta ataatggtaa aaattaatat ttatagagtg tttagttaat  27780
ttagttattg tattaaatat ttttgtattg ataattatat ttattttta tgttaatatt  27840
ataaggtagg tattgttatt ttataaatga agatagtgag gtttgttatg attgtgttat  27900
tggtttaagg ttatttagtt ggttagagta taagtttata attgttggag gttatagtgg  27960
ataggatatt gttttaggtt atgtaggtag taagtggtat agtgggaatt tgaatttagg  28020
tttgtgtaat tttaaagttt aaaatgttaa ttagtatatt gaattaatgg taattggaat  28080
tagaagatta ggggttttg ggggaaggaa atatagaatt tatttatgga atattttata  28140
aataaaagaa taatgtagag ataggaaagt aaatatattt tttgagggat ggagaaagtt  28200
agaaatgttt taaatgttaa agaggaggaa atgagaaatg attggatgag aaagtagaaa  28260
agttaaattt tggtatttgt tttgggtagt ttaggaagag aaaggtaagt ttagggatat  28320
ttttgagtta taggaaaatt aatgtttaga tggttagttt ggattaagtt taatatagga  28380
ttttaggaat atggtttatt agaattgttt tttagtaatt ttaagggaga ataaaatttt  28440
tgaattgggt ttaagtagtt ttattttaga agtaaagaga gatggaagta aggattgagt  28500
aataagaata tttatattgt aagaatatgt aagttgagta ggagtgaaat ttagaaaaat  28560
ttgttaggat tttggttgtt gtgttaaatt atgttatatt ttaagtagaa attagatttt  28620
tattattatt atttgtttag gtttagttag taattttatt attgtagtaa agttatttga  28680
aattttaaga gaaatgattt tttgtgttga agaagatatt ttgggtggaa ggatgttagt  28740
agataaatgg agtgtaaaga tagtgatttt aaggatatag tttgtgggga gtaatattgg  28800
attatatatt tgttgtttgt ggtagaatgt tagttagggg agaatattag gtagtttttt  28860
ataagtttat tttattataa aaagatagga ttgattttaa aggttatttt taatttaggt  28920
ttgttttatt attgaaaatg atttaaaatt ggatttattt tggtttttt taggagggat  28980
agataaatat aatttgtata tatggttttt tagttttagg aagtatagga ggagaatgaa  29040
agaattaatt tagtttttg tttttggta aaaattttta tatttgtgtt gttgtaagaa  29100
tttaagatta ttttgtttag aatgttgtgg tatttttgaa agtaaggttt gagggtatat  29160
agagttttat tttttatttt tatgttgtgg attttattgt ttttttaaa tgggaaagag  29220
aaattagaat ttatagaaag taaggtttgg aaaggattta gagggtattt ttttttttta  29280
gtttatgttt aaattatttt tagaaatata gttagttata tttttagta aagagttttt  29340
tatggttttt tggtaatgta tttttatgtt ttataatttt atagttatat tgtatattta  29400
ttgattaaat tttaagtatt gaagaaaatg atgttatatt aaaaagtttt aattagtagg  29460
gggtatgttt tttagagttt tttaaatatt ttatattttt attttaaaaa aagatgaaaa  29520
tattattagt ttaatttaat agatggaaaa ttttgttata gagattttta gagagttata  29580
tttggttatg tagtgtgatg tttgaaagaa ttaaattaaa aataaagtta ggaaatttta  29640
tgtttagggt ttttttagta gatatattat tttttggggg ttggttatta tttttttgtt  29700
tgagtaaagt atatgtttga ttgtaatttt atttgttttt ttgtttgttt gtttgtgagt  29760
agtttatttt ttaatttatt aatttatttt tttgttagtt ttttaaaata ttataagtta  29820
attaatgttg ataaaatttt atttttatta tgagtgttat ttgagtagat tgagatggtt  29880
```

```
gttatatttt ttaaatatta tgtgtaataa atagtgttgt tattgtttta gtgttatgat  29940
tttgttttta tttggaaatt gtataaatat tatatttttt gttatgatag gattattttt  30000
atttattagg atttttgata tttgtgttgt tatttgggag aatgttgatt attttgttta  30060
tgttattttt gaggttataa taattgtttt tttgtttagt tgtgtttttt tttttatagg  30120
tgaatttagt tttttttttt atgtttgatt ttaagaaatt ggtgttttat tgaaagatgt  30180
ttaaattttt tgagagaaaa tgttggagta agaataattt gttatgtatt gtttttattt  30240
gagtattaat gttttttaa ttttatatgt ttttaaattt tttgagaatt tttttttttt  30300
gaatgtaatt tatgaattaa aagtgattgt aatttttaaa atattatgtt gtttatagta  30360
aatatatata atttttattt gttaattaaa aaaagtaata gggtttttat ttttattttt  30420
gatatttgtt tttttttattt tttttttaag tatttttttt ttttttttag agatgtattt  30480
attgagagta ttttgttatt tttttttttt tgtagttatg tatgattaaa gttgtgtttt  30540
tgaaattttt tatttttttt gttataattg ataatttatt ttgtttttta ttaatttatt  30600
aatgttattt tattggtttt tgatttatat aaattaaata gattttagaa aatttaataa  30660
aaataaaaat aatgtttttt attttgaaat atttatttat tgtttttttt tagggtatat  30720
atattatatt tttttttttt atattttatt ttttttgaat ttataagaat gtgttattga  30780
atatagagaa aataatttaa gaaaggaaaa ggaatgattt gtttaaaatg aggaaaaagt  30840
agagttgagg tttaggattg tggtttaata agatgattta gttatttttt ggtagtttta  30900
ttttttggta atttttaag ttgagttttg gatgatgtaa ataatatttt tagattttta  30960
atgggtatat gttgaattaa aaagaaaaat ttatggtatt ttttaattat gtgtaaatga  31020
gtaaagaaaa aggaaagaaa aggagtggtt aaattgatat ggtagggttt aggattgggg  31080
gaagaagaaa gagtaataga gagagtggaa tagttaaaaa aagaatgaga ttatgttttt  31140
tgtagaaata tggatggagt tggaggttat tatttttagt aaattaaatt aggattagaa  31200
aattaaataa tgtatgtttt tatttataag tgggagttaa atgaggagaa tttatagata  31260
taaagagagg aataatagat attggggttt attggaaggt ggtggatggg agaggggaga  31320
ggattagaaa aaataattat tgggtatgag gtttagtatt tgggtgataa aataatttgt  31380
ataataaatt tttgtgatag gtttatttat ataataaatt tgtatatgtg ttttgaattt  31440
gagatataat ttaaagaaaa agagagtgta tttgtttgta aattggtttt agtagattgt  31500
tttttgagtt ttttttgttt tttaaattga atttaagtgg tattatattt ttaaatgaaa  31560
atttttatttt taattatagg tgaagttaat tttttatttt tttaataatt tttttattat  31620
tttttgtatt gtaagtaagg taaagattta gtttaaatgt tgttagttta gtttattttt  31680
taaaaaatat attttttgag aggtttgaga aaattaagaa agtatatttt gtttagtttt  31740
tttaaatatt atttttttgg aaatagtatt ttgtttagtt tttttaaata ttattttttta  31800
attagtgagt tagtttagat tttagagggt ttttggaatt agaaagaagg taaggatgaa  31860
tattaggttt aagattattt ttatgttgtt ttattattaa attagaaaat ttggatgttt  31920
tgtaggtagg tatgtttatg agagttattt aaaaaagata tgttttttga agtgttaagt  31980
ttagtgatta tgtagtttat g                                           32001
```

<210> SEQ ID NO 14
<211> LENGTH: 12001
<212> TYPE: DNA
<213> ORGANISM: Homo sapiens

<400> SEQUENCE: 14

```
gtgttagatt ggagttgatt ggtgattaat ttaaaggagt tataatttaa agaaatggtg     60
agagtttggt atttaggttt ggtttttagg taatttgttt gggtttgaga ggttattaat    120
tgttagttaa gatggaattt tttttttttt tttttttttt taatggataa taatgggaag    180
ggggttaatt ttttagtagt tgaaattttg tatttagttt tttattttga gaatgttaat    240
ttttggtttg aggatttgtt tttgtagtgt tggtattgag atttaaggga agatattttg    300
ttttaaatgt tagttatggt ttggtttttt ttttgatttt agtattttgt agattgttag    360
tgtttgtggt gggggatgaa aggaataggg ttttgtaagg tttgtttgtt gattgtgtta    420
ttttgggtga aatttagttt taaaagttat aaattattta tggtgaagat tttttgaagt    480
ggaataaatt tttagatttg tattatttta tatttttgtg ggatagatgg tttttattta    540
ttggttattg ggagagagtt gttgtttttg tgttttattg ttttttgggg tgatttttag    600
tgagttgagt ttttggttgt atggtaagtg tttgaaagtt gggtttgaga ggattgtagg    660
gtttttgagg gtgttaagtt ttgaaggagt ttatgggtgt attggggttt ttgaaattta    720
gttgttattg gtagtttttt tttgtttttt tttagttttt ttgtttggtt ttgtattttt    780
tttttttttt ttttttttta tttttttttt ttttttttgt ttttattttg tgtggggagt    840
gatgtgatgt tagtagagat tttattaaat tttattgtat agtggtgtgt gggtggttgg    900
ttgagtttgg ttgtgtggtt ggtgatttag gagtgagtat agtgtttggg tgagtgttgg    960
ggggagtgag taggggtgat gagaaatgag gtaggggagg gaagtagatg ttagtgggtt   1020
gaagagttgg gagttggagt tgggagagtg aaaggagagg ggatttggtg gggtatttag   1080
gagttaattg aggagtagga gtatggattt ttattgtgga aaggaggatt agaagggagg   1140
atgggatgga agagaagaaa aagtaatttg tgttaatttg gtagttttaa taaattaaag   1200
ggggagtgtt agggtagtgg ggagatagaa atgtattttt ggggagtaaa ttaggatggg   1260
ttgggaggaa gtgataggga aagtggttta agagatggaa taaaggataa tgtttatggg   1320
gttgtttggg atgaggtgtg tggagtgtgg gtgtgagtgt gtgtgtgtga ttttttttta   1380
ggtttgtaga gttgaggaaa gaggttatag taaagaggga ttgtggaggg aggaaagtga   1440
gagattggta gagggtggga gtggaggtgg gtgtggtggg gatgggagag gatgagtgaa   1500
gagaaattta gaagaatgga gtgagttagt gggagagggt gggagggtta tagttgggag   1560
tgaatgagtt aggtttgtta gttggggaag gttgggatgt tgggtttagt ttagttggga   1620
tattgtgttt gaggttaagg tgggtggatt aggtatgttg agagtgttgg tgtataggtg   1680
ggtatggtta tgtattgatt tagtgtttat gaagggtttg tattggataa ggtttagatg   1740
tttatagagt ttagaatttt ttttgttgta tttatattta ataagtttat tttgggttat   1800
ggatatttta ttttttaaaa tgatgaggtt aaggttttttg gtgaggatgg tattaaattg   1860
tatgggatag aagtgggggt gggggagaga gttttttttta agtttatatt tgtttttgta   1920
aagtaaagag tatgtgaaat tatagggtat atttttattt gaaaagtgtg ttttattttt   1980
gaattttgat tttttgattt tttgatttga gtaaagatgt gtattttggt agtgagtaga   2040
atattttggt tttgttttgt ttttgagtgg aaggattata aatataattt gtttggagga   2100
ttaggtgtga aggtttttgt taggtatatg ggataatgtt tttttaattt taagggtatt   2160
ttgttaatgt atgtttttgg aaagtgttgg aatatagtta ttgtttttgg atttggattt   2220
ttttattaat attaattttt gtttgagagt aaaatttagg tttgttatta aaaagatatt   2280
tttttggttt ttaattgaga ataaagtttt ttttaaaagt tgtattgttt tttttaaatt   2340
```

-continued aatatattaa tatttgtaat tttagaaata tatagtgatt tgggagaatg tgtataaaat 2400
agatatgttt aaaaaagttt ggtgtttaaa attaatttta gttattatat aggtgttggg 2460
ttttttttat ttttgggggt tgtttggaat atgttatgtg ttttttgaa ttattttgtg 2520
ttttgaattt atttgagtta gtagtaaaaa taggtaaata aatttgttta atttgttttg 2580
agtgttaaat ttttttattt tgaaatagtt aatagttgat agatggattt attttatgga 2640
aagggttagt ttttttagtt atgaagaaaa ttgattagag atttatattt taagttattt 2700
ttaattttta tgtaatattt gtgaaaattt aaattttttt tttttattta gtggaaattt 2760
aaagtagtgt tatttaaggg gagagaaatg agggggaaaa tgtttatgtg ttgtttaatt 2820
gtattttttt tttgattttg agaattttta tttttggttt ttgaaatttt gttgaggtaa 2880
gaaaattaaa ttttttaat aagttttata attgaatttt agttatagga tattggaaag 2940
tgtagtttga gaaagatatt tttattttg tttattgatg atttttgtag tttttttatt 3000
tttttgagta atgggttaat aatttttttt tttttttttt ttattttgta gagattaaga 3060
ggtgtttgta gtagaatggt tttgttttta gttggtggtg aggataggta attttatgga 3120
aaagttggaa gagaatgaga aaattaaaga tagaaagatt tagagatttg tggagagata 3180
tagggagagg gaagggagtt gtgttgaaaa gatgtaaaga tatgtgtgtg taattttttt 3240
tttttttagg ttttagaggt ttgtaaatta gggttgagag gaaggggttt gggaagttta 3300
tgtttttttt gttttttttt tgtttggagt tttgtttgtt agaggttggt taattttagt 3360
tttggttgtt gtagatattg tgttgagttt ttgggttttt gttttgttta gtgttagtgt 3420
agttgaagtg agtagttggt gggaaatgta aatggttttt ggagaaatag aagatataga 3480
atgattttta tttttttttt gagtgtgtgg aaggagttgg atatatgttt tatgttttta 3540
attttttttt tatattttta gttatatttt tattaaataa ttaattaatg tttagaatta 3600
ttagggaata tattaggtat gtaattgtag aagtagggtg ttggggggtt ataaattatt 3660
gagttgattt aagatgtgga ttttaggttt tttttttgtt aaagtagtaa aggaagagtg 3720
ggttttggtg attgtattta gattttgatt attttaaatt agaagggggt ggagggagtg 3780
tttaagtaaa gtaagtaatt ttttgttttg tagatgtaaa taagattgta gtattaaagg 3840
tattagtttt tttagggtta gattgtttgg attgggagtt tggggaaggg gagatattaa 3900
ttttatgtat ttgtgaattt taaggatgtt atatttttat ataaataatt ttagtgtgga 3960
ttttttggaa tgggggggagt aatattttta ttttagaata ttaaaatatt tttttttaa 4020
agtgtatatt tttttattt ttttaaaatt ttgaattatg tttaaagata atagtttttt 4080
agtaaattgg agtattggat tatttttttt attttttttt attgatattt tgatgatttg 4140
atttaatgt gtgggggggta tagggaatta aatatagttt ataaaattaa gtttagatga 4200
aatagtgttg gttaagtggg tttagataat ttttaatgag aattttaatt atattttttt 4260
ttttaatatg ttgagataag tgatagaatt gttagaatgg taattaaatt ggaaagttta 4320
gggagaataa taattttgtg attaaattgg ggtaaaattg tggataaatg tggggtgatt 4380
tttgttaatt ttttgttatt taagagttag gatttgggaa aggtatagta ttattttaga 4440
gtttgttgtg atgggttgtg tgttattatt tattttttttt attttggatt atgattttaa 4500
ttttggtaag taattttttt agtttttat ttgataataa gtgagtatgt aaatattaat 4560
ggttagtgat gtttaattgt tttaaatatt attgatttgt tggttgtttt aaattgtttt 4620
tttagtttag gttttgtttt tgaattgttt attttagagg tttgatttat gtttttgatg 4680

-continued

```
ttataatata ataattgttt ttttaaaaaa ggtatttaag atgaattaat tgatttgtat   4740
ataaattaaa attattatgt gttgttgatt ttggtgtttt ataattattt tgaaattagt   4800
atttaattat ttgagttaaa agaatatata aatgtttgta ttgatttatt aatgaattat   4860
ttaattaaaa tgtttgggta atgttgggtg ttggaaagat tgttaaatta agatatatta   4920
taggagggat atgaagatta gaaaggtaat agattaatat tttgtattta aaatggagtt   4980
tttggtgatt tttagtttta attttggagt aggggttttt tttttttgtt gttaaaaaga   5040
ttttgtgttt gtttgtgagt gagtgtattt aagtggaagg aatgttttta tggttatggt   5100
ggtttaggtt ttttgtttgg attgggattt tatagtttta atttaggagt gttaaatttt   5160
ggaagatttt gggttagttt tggaggtgtg tggttttgta agttgttagg ttaagtttgt   5220
tttttttgtt tgtttttttg gtaggttggg tgtgttatgg tagtgagttt tttgtgtaaa   5280
tggagagttg gaattaaagt tgatatttaa tagatatgtt aattgagtat ttatttttgt   5340
tttgagaata ggaataaaag gtagtttttt ttaagagagg tggtgtaaag gtatgttata   5400
ggagtttaga aaaggttggt ggtgggaaat ttgtagtttg ggggttagtt aatatttttt   5460
tttattttaa gtatttattg atttgttgtt gttatttttg gtgatgtaga aggatatttg   5520
aaagaatttt tgatggggtt ttgatttgag aaaggaggtg atttgtttag gtttttatta   5580
aatttttaat tattatatta attgtttttt tttatttttt atttgatttt tttttttttg   5640
tttattttta atttttaat tatttagaaa tttttttatt ttttagtggt tttttttttg   5700
tagtagtttt ttatttgaat tttttttttg tttttttgtg gtagggtttg tatattgatt   5760
tttttgattt ttggtatatt tgggtttttt gaaatttttt aatttttta gatttgagga   5820
tggtaggttt tatttttttt attgtgtgta tatatttaga gatatgaaaa tttatataga   5880
ttgtttttaa atttagggta tttaatagat gttttttttt tagtttgttt tttgatttga   5940
aatgtttgtt tgattttaat ttggatatta tttttttttg tttttttttt tttaaagtag   6000
tttggatatg tgtgtaagtg agtttagaat agttttattt atatttttta ttaaattgta   6060
aataaaagaa gaattaatga agtagattgg tatatagatt gtattaagag tttgaatttt   6120
tagtttttgg atttttattt taattttggt tgttatttat attgatagag ttattttaag   6180
tagaggttta gagaaatttg tattgtggga taataggtaa agttatagta aaaagtggaa   6240
taattttaaa gttattttat tagaatgtaa attgtatttt tgggttttgt ttgtaattat   6300
ttagttttaa tatatataga gttagatagg aaaaaatagg ttaatatagt tattggtatt   6360
agagaagata aattttatgg gtttttttagt gaaaagaaga tttttaaagt tttataatttt   6420
tgattattta attttattta taattgtggg aatgaataag atattaattg ttttatgtat   6480
tttatttata ttaattaatt tgtgttttta ttaaaagtag ttatatagaa ttttttttaa   6540
tttttggtag taagtttaga aaatgaagtt tatagttatt ttgaattgga tatatttttt   6600
gagttgatta tttttgtaag tgtaggaata taatattgtt tttttatggt ttttttgtat   6660
tttttaggg tttgtaagtt tttattaggt ttgatattat tgtttgggtt tatatttatt   6720
ataagtaaat ttgattatta tgttgatttt aaaatagttt atttggttag tataatttta   6780
gtttttaaat tataaaaatt ttttaatata tgaagttttt agtttttatt ttttttagtt   6840
ttttgtttat ttaaaatttt tattttaatt ggtgtaagta ataataattt gtattattat   6900
ttgtattttt tttatttttt tggagattgg gttggatttt agagagaata ttagtattat   6960
tattattata aataataaaa tttaaaagta aagtttttat ttgtatgata attggtattt   7020
ggaatgtttt tgatttattt aatgttattt tataaaggta ttttgtaaat ttttttggaa   7080
```

```
tttttagtaa gagtttgtag taattggaat aattttttgg gaagatattt tttttgatgg   7140
gtttttagtt tttggaggaa tagattgaga gtaattaggg agggagggga tattggaaat   7200
tggtagttat gttagttgaa ataagtttgg gtttagtaag gtgattgatg ttgtggttga   7260
tttttattt tgagtttttt tttaattggg gtattgattt tttttatttt gggattttaa   7320
ggtatttggt gtgtatgtag attttttttt tgtggttttt attatgtggt tttgtagtag   7380
gtttttggtt taatgatatt ttatagttat agtttttata tttattatta tgattttaat   7440
gtttaggttt ttagtgtatt tatattaaat ttgttttatt agtaagttgg agtatatagg   7500
agagatgggg gtaagtaagg atttagtaga gtttaaattt agatatgttt aaatggtttt   7560
gattgtgtaa agtgtggtaa tgttttttgt tgttttagtt ttttatttta agttttatat   7620
gtttttggt taatgaagtg tgatataggt tatatgttag gaataatagt atttgttgag   7680
aataaagtga atttaggaaa tttggtatat ataaaatgta tttagttatt tgaattagta   7740
ataatggtaa aaattaatat ttatagagtg tttagttaat ttagttattg tattaaatat   7800
ttttgtattg ataattatat ttattttta tgttaatatt ataaggtagg tattgttatt   7860
ttataaatga agatagtgag gtttgttatg attgtgttat tggtttaagg ttatttagtt   7920
ggttagagta taagtttata attgttggag gttatagtgg ataggatatt gttttaggtt   7980
atgtaggtag taagtggtat agtgggaatt tgaatttagg tttgtgtaat tttaaagttt   8040
aaaatgttaa ttagtatatt gaattaatgg taattggaat tagaagatta ggggtttttg   8100
ggggaaggaa atatagaatt tatttatgga atattttata aataaaagaa taatgtagag   8160
ataggaaagt aaatatattt tttgagggat ggagaaagtt agaaatgttt taaatgttaa   8220
agaggaggaa atgagaaatg attggatgag aaagtagaaa agttaaattt tggtatttgt   8280
tttgggtagt ttaggaagag aaaggtaagt ttagggatat ttttgagtta taggaaaatt   8340
aatgtttaga tggttagttt ggattaagtt taatatagga ttttaggaat atggtttatt   8400
agaattgttt tttagtaatt ttaagggaga ataaaatttt tgaattgggt ttaagtagtt   8460
ttattttaga agtaaagaga gatggaagta aggattgagt aataagaata tttatattgt   8520
aagaatatgt aagttgagta ggagtgaaat ttagaaaaat ttgttaggat tttggttgtt   8580
gtgttaaatt atgttatatt ttaagtagaa attagatttt tattattatt atttgtttag   8640
gtttagttag taattttatt attgtagtaa agttatttga aattttaaga gaaatgattt   8700
tttgtgttga agaagatatt ttgggtggaa ggatgttagt agataaatgg agtgtaaaga   8760
tagtgatttt aaggatatag tttgtgggga gtaatattgg attatatatt tgttgtttgt   8820
ggtagaatgt tagttagggg agaatattag gtagtttttt ataagtttat tttattataa   8880
aaagatagga ttgattttaa aggttatttt taatttaggt ttgttttatt attgaaaatg   8940
atttaaaatt ggatttattt tggttttttt taggagggat agataaatat aatttgtata   9000
tatggttttt tagttttagg aagtatagga ggagaatgaa agaattaatt tagtttttg   9060
ttttttggta aaaattttta tatttgtgtt gttgtaagaa tttaagatta ttttgtttag   9120
aatgttgtgg tatttttgaa agtaaggttt gagggtatat agagttttat tttttatttt   9180
tatgttgtgg attttattgt ttttttaaa tgggaaagag aaattagaat ttatagaaag   9240
taaggtttgg aaaggattta gagggtattt ttttttttta gtttatgttt aaattatttt   9300
tagaaatata gttagttata ttttttagta aagagttttt tatggttttt tggtaatgta   9360
tttttatgtt ttataatttt atagttatat tgtatattta ttgattaaat tttaagtatt   9420
```

-continued

```
gaagaaaatg atgttatatt aaaaagtttt aattagtagg gggtatgttt tttagagttt   9480
tttaaatatt ttatattttt attttaaaaa aagatgaaaa tattattagt ttaatttaat   9540
agatggaaaa ttttgttata gagattttta gagagttata tttggttatg tagtgtgatg   9600
tttgaaagaa ttaaattaaa aataaagtta ggaaatttta tgtttagggt ttttttagta   9660
gatatattat tttttgggg ttggttatta tttttttgtt tgagtaaagt atatgtttga   9720
ttgtaatttt atttgttttt ttgtttgttt gtttgtgagt agtttatttt ttaatttatt   9780
aatttatttt tttgttagtt ttttaaaata ttataagtta attaatgttg ataaaatttt   9840
atttttatta tgagtgttat ttgagtagat tgagatggtt gttatatttt ttaaatatta   9900
tgtgtaataa atagtgttgt tattgtttta gtgttatgat tttgtttttta tttggaaatt   9960
gtataaatat tatattttt gttatgatag gattattttt atttattagg atttttgata  10020
tttgtgttgt tatttgggag aatgttgatt attttgttta tgttattttt gaggttataa  10080
taattgtttt tttgtttagt tgtgtttttt tttttatagg tgaatttagt tttttttttt  10140
atgtttgatt ttaagaaatt ggtgttttat tgaaagatgt ttaaattttt tgagagaaaa  10200
tgttggagta agaataattt gttatgtatt gtttttattt gagtattaat gtttttttaa  10260
ttttatatgt ttttaaattt tttgagaatt tttttttttt gaatgtaatt tatgaattaa  10320
aagtgattgt aatttttaaa atattatgtt gtttatagta aatatatata atttttattt  10380
gttaattaaa aaaagtaata gggtttttat ttttattttt gatatttgtt tttttttattt  10440
tttttttaag tatttttttt ttttttttag agatgtattt attgagagta ttttgttatt  10500
tttttttttt tgtagttatg tatgattaaa gttgtgtttt tgaaattttt tattttttttt  10560
gttataattg ataatttatt ttgtttttta ttaatttatt aatgttattt tattggtttt  10620
tgatttatat aaattaaata gattttagaa aatttaataa aaataaaaat aatgtttttt  10680
attttgaaat atttatttat tgtttttttt tagggtatat atattatatt tttttttttt  10740
atattttatt tttttgaat ttataagaat gtgttattga atatagagaa aataatttaa  10800
gaaaggaaaa ggaatgattt gtttaaaatg aggaaaaagt agagttgagg tttaggattg  10860
tggtttaata agatgattta gttatttttt ggtagtttta tttttggta atttttttaag  10920
ttgagttttg gatgatgtaa ataatatttt tagattttta atgggtatat gttgaattaa  10980
aaagaaaaat ttatggtatt ttttaattat gtgtaaatga gtaaagaaaa aggaaagaaa  11040
aggagtggtt aaattgatat ggtagggttt aggattgggg gaagaagaaa gagtaataga  11100
gagagtggaa tagttaaaaa aagaatgaga ttatgttttt tgtagaaata tggatggagt  11160
tggaggttat tatttttagt aaattaaatt aggattagaa aattaaataa tgtatgtttt  11220
tatttataag tgggagttaa atgaggagaa tttatagata taaagagagg aataatagat  11280
attggggttt attggaaggt ggtggatggg agaggggaga ggattagaaa aaataattat  11340
tgggtatgag gtttagtatt tgggtgataa aataatttgt ataataaatt tttgtgatag  11400
gtttatttat ataataaatt tgtatatgtg ttttgaattt gagatataat ttaaagaaaa  11460
agagagtgta tttgtttgta aattggtttt agtagattgt tttttgagtt ttttttgttt  11520
tttaaattga atttaagtgg tattatattt ttaaatgaaa attttatttt taattatagg  11580
tgaagttaat tttttatttt tttaataatt tttttattat tttttgtatt gtaagtaagg  11640
taaagattta gtttaaatgt tgttagttta gtttattttt taaaaaaatat attttttgag  11700
aggtttgaga aaattaagaa agtatatttt gtttagtttt tttaaatatt atttttttgg  11760
aaatagtatt ttgtttagtt tttttaaata ttattttttta attagtgagt tagtttagat  11820
```

tttagagggt ttttggaatt agaaagaagg taaggatgaa tattaggttt aagattattt 11880
ttatgttgtt ttattattaa attagaaaat ttggatgttt tgtaggtagg tatgtttatg 11940
agagttattt aaaaaagata tgtttttttga agtgttaagt ttagtgatta tgtagtttat 12000
g 12001

<210> SEQ ID NO 15
<211> LENGTH: 4001
<212> TYPE: DNA
<213> ORGANISM: Homo sapiens

<400> SEQUENCE: 15
tagagtattt aatttttttt ttttaatagt aaagtttttg gatgttgttt gatttgtttg 60
attttgtttt ttgtttttag aattttaata aatttggaat tttttattga ttagtataaa 120
ttaggatgtt gttattgggt tatttatttg agtttatttt tgttaattta taaagtatag 180
atttgttata aagttaaggt aagttttttt tataaaatta tgattataat ttagaagagg 240
gggtgtgagt tttaattttt agagtttaat ttttgagaga agataaataa attaagtaga 300
aaagtttttt tttttttttt tttttttttt ttaagaggat tagtagttgt gtattaaaat 360
tttgtttttg gagattataa aattaggaaa tagggtgtgt gggagagatt tgaatggttg 420
aaataattgt aaagaaggtg taagaagtgt gagtttagga gggaaaaagt tgggttaggg 480
ttgggataaa ggtttttttag ggagggttaa tttttttgtg tttttggtgg gttttttttg 540
ttaaaggttt ataggttgga gtttgtttgt ggtttttggt ttggtaggga ttttattagt 600
tttgttttgg taattgtaag ttaggaatat aatgttttgt gtaggggatt gtttatgtag 660
tttagtttgt gagattgtgg gatggtgggg tagtgagttg gtgttgtttt gggagtttga 720
gttagggtgg tagttttgtt ggttttggag agggaattgt aattttgtaa ttaggttgtt 780
gtgaggtttt ttgtttttgt aaagttgtgt tttattggtg tttttttagg tggtgttgtt 840
ttttatattt ttttttggtt tatttggttt gtatttttat aatatttttt ttttattttt 900
tttagatttt gtgttggttt ttatttggat ttgggttttt gtaaggttgg tttatatagt 960
gatttttttg tgtgtggata tgtttgggta gtggtttttt tggaaagtgg tttttagttt 1020
ttggagttgt tggttggtaa agtgagtttg ttgttgtttt tgttgttttt ttttagatgg 1080
gtttttggtg tttatgtttt tatttttttt ttgttggttt ttattttttt ttgaaaatga 1140
aatatatata tttttttgtt agtatgttta tttgtaatgt ggatgttaat tggattggtg 1200
gtagaagttg tggaagagtt gggttgtttg gtgttggagg agggtgtgtg tggtggtttt 1260
gggttgtgag gagtgttgtg tttgtggggt gtgtaggtgt aagtgtgggt gtttgtgttt 1320
tatttttttt ttttttttag tgttgtatgt tttatttata tgtttatttt attgtagtgg 1380
tatatttatt tttatagttt gtgtttttaa gtatatttat atatttttgt gtagatatat 1440
taaatttttt gggatgtgta tatgtgtgtg gtttatagat tttttttttt tttgtagaaa 1500
gtttagattt ttatgtggtt tgggaaggtt aggaaaagat gtggggattt ggttgggtat 1560
tgaagtttgt tggttttttt ttaaaaaaaa aaaaaaaatg tttttttgtg aagggtattt 1620
ttgagtggtt ttaggtaatt ttttaatgag tggagttttt tgggagttga aagttgagag 1680
gaaaataggg atagaggttg gtggtttttg aaggtttttg aattaagatg ttgggatttt 1740
tgtgatttag gaaatagaag ggaggttagg gtatgaatag agagggtggt agaattgttt 1800
gtgtttttag tgttttagga gttgggttgg ttgagggaga attaaaggga tgtggggtag 1860

-continued

```
ttaaaatttt ggtttttgga agttttgtgg ggagttaggt gaatgattat ttttattatg   1920
ttttttttttg gaggggttga tttttttggg gtgagaggga gtgggtggtg tagagtagtt   1980
gagtgggaat gtttgtaggg tggtgtggtg ttttatttgt ggtttttggg ttggaggtgt   2040
tggagatggt gtgtattttt agtttgtgtt tggaggagtt tagtgattgg ggttgattgg   2100
gagttagaat tgaagttatg gttaatggtt ggggatggtg ataggaagat gaggagatgg   2160
ttgatagttt ggtttttgtt gtttggtgtt ttaagtgaag tgggtttttt atgtagttta   2220
tggatgaggg agtgtgatgt tttattagtt tttggttatt gttttgttga gtttttgtag   2280
ttgttgttgt ttgttttggg ttgtgtttta ggtgtggagt ttttttgttg tggggagagt   2340
taggggatgt aatttttgtt gagtttttaa gttaagttgt ttttgttttt tttggaaggt   2400
ttaagtgaaa aagtttggag atggaaagtt agtgggtaaa tgaagatatg ggatgtgggt   2460
agaagggtat tatttagagt gtttttaggg agtaggtttt taagttttaa agtgaaataa   2520
gagtgggtaa agattttttt tttttttttt tttttttttt aagaattttt ttaataagga   2580
aagttaatgt tgattgtgtt ttgtttgttt ttttttatg tggtagtttt gatagagaag   2640
tgttaagagt gatagggata ggtaggtgat attagatttt ttgtggtggt agtagttgtt   2700
gtagttatga tgtggttttt tgagtgtatt ttttgtaatg tgtatatgta tattttttgg   2760
gtggttgaat aggagttggg ttttgttgta gtttagtttt aggtatttag gtgagtgatg   2820
gattagattt gtggttttgt gtttttttgt tggtttaata ttttaaaatt agaggtgggt   2880
tttttggtgt tgagatgtta ttttgttgtg gtttttttta gtttttttttg tttttgtttt   2940
tttttagatt tttttttggg tgtgattgat gtggttttgt attaattagg atgttttgag   3000
ttgtggtgga gggattgttt tgtttgtatt tattagtagt gtggggttgg gttattgttt   3060
tgttgtgtgt attgggttta tataggtaag tttttgggaa tttagttttt gtttagttta   3120
aggtgatttg gtttttagta tgaatttaaa ggtgaagaga tgaggttagg agttgaaggt   3180
ttgggagaag agagtggaat ggttaagaag agaaaggtat aaggattaat aagatattta   3240
ttttttgtgt tttattatat ttatttttaa tttttttattt tatataaaaa ggagatatgt   3300
tatttaaaat tagaaaattt gaaaaatagt aataaattat ttttttgatt ttaaattttt   3360
taaatagttt gttaagtgaa tgttgtgtta atttgaagaa gttttaattg taaagaagat   3420
agagttttga aaaggtaggt taataaatta gaaattgaga agtaaatgga tttgttaaaa   3480
gaaaattatt ttgattttaa atgaataatt gtttggtggt ttattttgga tttatataag   3540
aataaaaagt tgttttagat tatgtttttt gtgatgttta ttagttttta gatagaaaat   3600
atataataga agagaaattt taatttagtg tttttaaaat gttgaaagtt tatttatttt   3660
atttaatgtt gattaagata tatattttag atttttttaaa tttttttgtat attgtattaa   3720
gtttgtttta atttgagaga gttatgtttt aaatttgatt tttttgttta ttttattatt   3780
aattagattt aaatttataa agtttgtaga attaataatt ttgagttaat tatatatgaa   3840
atatgtttta atgaattttt atataattaa gaatgttgtt aaataattaa ttttaaggat   3900
aatttttaat agttattttt tttttttagt gagtttaagg ttgttttgag ttattaaagt   3960
ttaagtaggt agaaggggtg tgtgtgagtt aagggtgaaa a                         4001
```

<210> SEQ ID NO 16
<211> LENGTH: 408
<212> TYPE: DNA
<213> ORGANISM: Homo sapiens

<400> SEQUENCE: 16

```
tcctcaactc tgcaggcctg aaagaaggtc acacacgcac gctcacaccc acactccaca     60

cgcctcgtcc caaacaaccc catgaacatt gtcctttgtt ccgtctcttg ggccactttc    120

cctgtcgctt cctcccagcc cgtcctgatt tgctccccaa aagtacgttt ctgtctcccc    180

gctgccctgg cgctccccct ttgatttatt agggctgccg ggttggcgca gattgctttt    240

tcttctcttc catcccatcc tcccttctgg tcctcctttc cacagtggga gtccgtgctc    300

ctgctcctcg gttggctcct aagtgccccg ccaggtcccc tctcctttcg ctctcccggc    360

tccggctccc gactcttcgg cccgctggca tctgcttccc tcccctgc                 408


<210> SEQ ID NO 17
<211> LENGTH: 144
<212> TYPE: DNA
<213> ORGANISM: Homo sapiens

<400> SEQUENCE: 17

ttctggtcct cctttccaca gtgggagtcc gtgctcctgc tcctcggttg gctcctaagt     60

gccccgccag gtcccctctc ctttcgctct cccggctccg gctcccgact cttcggcccg    120

ctggcatctg cttccctccc ctgc                                           144


<210> SEQ ID NO 18
<211> LENGTH: 162
<212> TYPE: DNA
<213> ORGANISM: Homo sapiens

<400> SEQUENCE: 18

tggcatctgc ttccctcccc tgcctcgttt ctcgtcgccc ctgctcgctc cccccggcgc     60

tcgcccgggc gctgtgctcg ctcctggatc gccagccgcg cagcgggctc gccggcgccc    120

gcgcgccact gtgcagtgga gtttggtgga atctctgctg ac                       162


<210> SEQ ID NO 19
<211> LENGTH: 408
<212> TYPE: DNA
<213> ORGANISM: Homo sapiens

<400> SEQUENCE: 19

tttttaattt tgtaggtttg aaagaaggtt atatacgtac gtttatattt atattttata     60

cgtttcgttt taaataattt tatgaatatt gtttttgtt tcgtttttg ggttattttt    120

tttgtcgttt tttttagtt cgttttgatt tgtttttaa aagtacgttt ttgttttttc    180

gttgttttgg cgtttttttt ttgatttatt agggttgtcg ggttggcgta gattgttttt    240

ttttttttt tattttattt tttttttgg ttttttttt tatagtggga gttcgtgttt    300

ttgtttttcg gttggttttt aagtgtttcg ttaggttttt tttttttcg tttttcggt    360

ttcggttttc gatttttcgg ttcgttggta tttgtttttt tttttgt                  408


<210> SEQ ID NO 20
<211> LENGTH: 144
<212> TYPE: DNA
<213> ORGANISM: Homo sapiens

<400> SEQUENCE: 20

ttttggtttt ttttttata gtgggagttc gtgtttttgt ttttcggttg gtttttaagt     60

gtttcgttag gttttttttt ttttcgtttt ttcggtttcg gttttcgatt tttcggttcg    120

ttggtatttg ttttttttt ttgt                                            144
```

<210> SEQ ID NO 21
<211> LENGTH: 162
<212> TYPE: DNA
<213> ORGANISM: Homo sapiens

<400> SEQUENCE: 21
tggtatttgt tttttttttt tgtttcgttt ttcgtcgttt ttgttcgttt ttttcggcgt 60
tcgttcgggc gttgtgttcg tttttggatc gttagtcgcg tagcgggttc gtcggcgttc 120
gcgcgttatt gtgtagtgga gtttggtgga atttttgttg at 162

<210> SEQ ID NO 22
<211> LENGTH: 408
<212> TYPE: DNA
<213> ORGANISM: Homo sapiens

<400> SEQUENCE: 22
acaaaaaaaa aaaacaaata ccaacgaacc gaaaaatcga aaaccgaaac cgaaaaaacg 60
aaaaaaaaaa aaacctaacg aaacacttaa aaaccaaccg aaaaacaaaa acacgaactc 120
ccactataaa aaaaaaaacc aaaaaaaaaa ataaaataaa aaaaaaaaaa aaacaatcta 180
cgccaacccg acaaccctaa taaatcaaaa aaaaaaacgcc aaaacaacga aaaaacaaaa 240
acgtactttt aaaaaacaaa tcaaaacgaa ctaaaaaaaa acgacaaaaa aaataaccca 300
aaaaacgaaa caaaaaacaa tattcataaa attatttaaa acgaaacgta taaaatataa 360
atataaacgt acgtatataa ccttctttca aacctacaaa attaaaaa 408

<210> SEQ ID NO 23
<211> LENGTH: 144
<212> TYPE: DNA
<213> ORGANISM: Homo sapiens

<400> SEQUENCE: 23
acaaaaaaaa aaaacaaata ccaacgaacc gaaaaatcga aaaccgaaac cgaaaaaacg 60
aaaaaaaaaa aaacctaacg aaacacttaa aaaccaaccg aaaaacaaaa acacgaactc 120
ccactataaa aaaaaaaacc aaaa 144

<210> SEQ ID NO 24
<211> LENGTH: 162
<212> TYPE: DNA
<213> ORGANISM: Homo sapiens

<400> SEQUENCE: 24
atcaacaaaa attccaccaa actccactac acaataacgc gcgaacgccg acgaacccgc 60
tacgcgacta acgatccaaa aacgaacaca acgcccgaac gaacgccgaa aaaaacgaac 120
aaaaacgacg aaaaacgaaa caaaaaaaaa aaacaaatac ca 162

<210> SEQ ID NO 25
<211> LENGTH: 408
<212> TYPE: DNA
<213> ORGANISM: Homo sapiens

<400> SEQUENCE: 25
tttttaattt tgtaggtttg aaagaaggtt atatatgtat gtttatattt atattttata 60
tgttttgttt taaataattt tatgaatatt gttttttgtt ttgtttttttg ggttattttt 120 tttgttgttt ttttttagtt tgttttgatt tgttttttaa aagtatgttt ttgttttttt 180
gttgttttgg tgtttttttt ttgatttatt agggttgttg ggttggtgta gattgttttt 240
tttttttttt tattttattt tttttttgg tttttttttt tatagtggga gtttgtgttt 300 ttgtttttttg gttggttttt aagtgttttg ttaggttttt tttttttttg ttttttttggt 360 tttggttttt gattttttgg tttgttggta tttgtttttt tttttgt 408

<210> SEQ ID NO 26
<211> LENGTH: 144
<212> TYPE: DNA
<213> ORGANISM: Homo sapiens

<400> SEQUENCE: 26
ttttggtttt tttttttata gtgggagttt gtgtttttgt tttttggttg gtttttaagt 60
gttttgttag gttttttttt tttttgtttt tttggttttg gtttttgatt ttttggtttg 120
ttggtatttg tttttttttt ttgt 144

<210> SEQ ID NO 27
<211> LENGTH: 162
<212> TYPE: DNA
<213> ORGANISM: Homo sapiens

<400> SEQUENCE: 27
tggtatttgt tttttttttt tgttttgttt tttgttgttt ttgtttgttt tttttggtgt 60
ttgtttgggt gttgtgtttg tttttggatt gttagttgtg tagtgggttt gttggtgttt 120
gtgtgttatt gtgtagtgga gtttggtgga atttttgttg at 162

<210> SEQ ID NO 28
<211> LENGTH: 408
<212> TYPE: DNA
<213> ORGANISM: Homo sapiens

<400> SEQUENCE: 28
acaaaaaaaa aaaacaaata ccaacaaacc aaaaaatcaa aaaccaaaac caaaaaaaca 60
aaaaaaaaaa aaacctaaca aaacacttaa aaaccaacca aaaaacaaaa acacaaactc 120
ccactataaa aaaaaaaacc aaaaaaaaaa ataaaataaa aaaaaaaaaa aaacaatcta 180
caccaaccca acaaccctaa taaatcaaaa aaaaaacacc aaaacaacaa aaaaacaaaa 240
acatactttt aaaaaacaaa tcaaaacaaa ctaaaaaaaa acaacaaaaa aaataaccca 300
aaaaacaaaa caaaaaacaa tattcataaa attatttaaa acaaaacata taaaatataa 360
atataaacat acatatataa ccttctttca aacctacaaa attaaaaa 408

<210> SEQ ID NO 29
<211> LENGTH: 144
<212> TYPE: DNA
<213> ORGANISM: Homo sapiens

<400> SEQUENCE: 29
acaaaaaaaa aaaacaaata ccaacaaacc aaaaaatcaa aaaccaaaac caaaaaaaca 60
aaaaaaaaaa aaacctaaca aaacacttaa aaaccaacca aaaaacaaaa acacaaactc 120
ccactataaa aaaaaaaacc aaaa 144

<210> SEQ ID NO 30
<211> LENGTH: 162
<212> TYPE: DNA
<213> ORGANISM: Homo sapiens

<400> SEQUENCE: 30
atcaacaaaa attccaccaa actccactac acaataacac acaaacacca acaaacccac 60
tacacaacta acaatccaaa aacaaacaca acacccaaac aaacaccaaa aaaaacaaac 120
aaaaacaaca aaaaacaaaa caaaaaaaaa aaacaaatac ca 162

<210> SEQ ID NO 31
<211> LENGTH: 22
<212> TYPE: DNA
<213> ORGANISM: Homo sapiens

<400> SEQUENCE: 31
gtaggggagg gaagtagatg tt 22

<210> SEQ ID NO 32
<211> LENGTH: 24
<212> TYPE: DNA
<213> ORGANISM: Homo sapiens

<400> SEQUENCE: 32
ttctaatcct cctttccaca ataa 24

<210> SEQ ID NO 33
<211> LENGTH: 20
<212> TYPE: DNA
<213> ORGANISM: Homo sapiens

<400> SEQUENCE: 33
agtcggagtc gggagagcga 20

<210> SEQ ID NO 34
<211> LENGTH: 27
<212> TYPE: DNA
<213> ORGANISM: Homo sapiens

<400> SEQUENCE: 34
agttggagtt gggagagtga aaggaga 27

<210> SEQ ID NO 35
<211> LENGTH: 144
<212> TYPE: DNA
<213> ORGANISM: Homo sapiens

<400> SEQUENCE: 35
gcaggggagg gaagcagatg ccagcgggcc gaagagtcgg gagccggagc cgggagagcg 60
aaaggagagg ggacctggcg gggcacttag gagccaaccg aggagcagga gcacggactc 120
ccactgtgga aaggaggacc agaa 144

<210> SEQ ID NO 36
<211> LENGTH: 144
<212> TYPE: DNA
<213> ORGANISM: Homo sapiens

<400> SEQUENCE: 36
gtaggggagg gaagtagatg ttagcgggtc gaagagtcgg gagtcggagt cgggagagcg 60
aaaggagagg ggatttggcg gggtatttag gagttaatcg aggagtagga gtacggattt 120
ttattgtgga aaggaggatt agaa 144

<210> SEQ ID NO 37
<211> LENGTH: 144
<212> TYPE: DNA
<213> ORGANISM: Homo sapiens

<400> SEQUENCE: 37
gtaggggagg gaagtagatg ttagtgggtt gaagagttgg gagttggagt tgggagagtg 60
aaaggagagg ggatttggtg gggtatttag gagttaattg aggagtagga gtatggattt 120
ttattgtgga aaggaggatt agaa 144

<210> SEQ ID NO 38
<211> LENGTH: 21
<212> TYPE: DNA
<213> ORGANISM: Homo sapiens

<400> SEQUENCE: 38
gtaggggagg gaagtagatg t 21

<210> SEQ ID NO 39
<211> LENGTH: 22
<212> TYPE: DNA
<213> ORGANISM: Homo sapiens

<400> SEQUENCE: 39
gagtgatagg gataggtagg tg 22

<210> SEQ ID NO 40
<211> LENGTH: 23
<212> TYPE: DNA
<213> ORGANISM: Homo sapiens

<400> SEQUENCE: 40
tcctcaactc tacaaaccta aaa 23

<210> SEQ ID NO 41
<211> LENGTH: 27
<212> TYPE: DNA
<213> ORGANISM: Homo sapiens

<400> SEQUENCE: 41
ccttaaacta aacaaaaact aaattcc 27

<210> SEQ ID NO 42
<211> LENGTH: 408
<212> TYPE: DNA
<213> ORGANISM: Homo sapiens

<400> SEQUENCE: 42
gcaggggagg gaagcagatg ccagcgggcc gaagagtcgg gagccggagc cgggagagcg 60
aaaggagagg ggacctggcg gggcacttag gagccaaccg aggagcagga gcacggactc 120
ccactgtgga aaggaggacc agaagggagg atgggatgga agagaagaaa aagcaatctg 180
cgccaacccg gcagccctaa taaatcaaag ggggagcgcc agggcagcgg ggagacagaa 240
acgtactttt ggggagcaaa tcaggacggg ctgggaggaa gcgacaggga aagtggccca 300
agagacggaa caaaggacaa tgttcatggg gttgtttggg acgaggcgtg tggagtgtgg 360
gtgtgagcgt gcgtgtgtga ccttctttca ggcctgcaga gttgagga 408

<210> SEQ ID NO 43
<211> LENGTH: 477
<212> TYPE: DNA
<213> ORGANISM: Homo sapiens

<400> SEQUENCE: 43

```
gagtgacagg gacaggtagg tgatattaga tcccctgcgg cggcagcagc cgctgcagcc     60

acgacgcggc cctctgagcg caccctccgc aacgcgcaca cgcacacccc tcgggcggtc    120

gaacaggagc cgggccttgc cgcagctcag ctccaggcac ccaggcgagc gacggaccag    180

atctgcggct ccgcgcttcc ctgttggcct aacatcttaa aaccagaggc gggcttcctg    240

gtgccgagac gtcactccgc cgcggccctc cccagccctc tccgcctccg cctcctccca    300

gacccttctc cgggtgcgac tgacgtggct ccgcaccaat caggacgccc cgagccgcgg    360

tggagggact gtcctgcctg cacctatcag cagtgcgggg ccgggctact gcctcgccgt    420

gcgcactggg tctacacagg caagctcccg ggaattcagc tcctgcccag cccaagg       477


<210> SEQ ID NO 44
<211> LENGTH: 408
<212> TYPE: DNA
<213> ORGANISM: Homo sapiens

<400> SEQUENCE: 44

gtaggggagg gaagtagatg ttagcgggtc gaagagtcgg gagtcggagt cgggagagcg     60

aaaggagagg ggatttggcg gggtatttag gagttaatcg aggagtagga gtacggattt    120

ttattgtgga aaggaggatt agaagggagg atgggatgga agagaagaaa aagtaatttg    180

cgttaattcg gtagttttaa taaattaaag ggggagcgtt agggtagcgg ggagatagaa    240

acgtattttt ggggagtaaa ttaggacggg ttgggaggaa gcgataggga aagtggttta    300

agagacggaa taaaggataa tgtttatggg gttgtttggg acgaggcgtg tggagtgtgg    360

gtgtgagcgt gcgtgtgtga ttttttttta ggtttgtaga gttgagga                 408


<210> SEQ ID NO 45
<211> LENGTH: 477
<212> TYPE: DNA
<213> ORGANISM: Homo sapiens

<400> SEQUENCE: 45

gagtgatagg gataggtagg tgatattaga tttttttgcgg cggtagtagt cgttgtagtt     60

acgacgcggt tttttgagcg tatttttcgt aacgcgtata cgtatatttt tcgggcggtc    120

gaataggagt cgggttttgt cgtagtttag ttttaggtat ttaggcgagc gacggattag    180

atttgcggtt tcgcgttttt ttgttggttt aatattttaa aattagaggc gggtttttttg    240

gtgtcgagac gttatttcgt cgcggttttt tttagttttt ttcgttttcg ttttttttta    300

gatttttttt cgggtgcgat tgacgtggtt tcgtattaat taggacgttt cgagtcgcgg    360

tggagggatt gttttgtttg tatttattag tagtgcgggg tcgggttatt gtttcgtcgt    420

gcgtattggg tttatatagg taagttttcg ggaatttagt ttttgtttag tttaagg       477


<210> SEQ ID NO 46
<211> LENGTH: 408
<212> TYPE: DNA
<213> ORGANISM: Homo sapiens

<400> SEQUENCE: 46

tttttaattt tgtaggtttg aaagaaggtt atatacgtac gtttatattt atattttata     60

cgtttcgttt taaataattt tatgaatatt gtttttttgtt tcgtttttttg ggttattttt    120

tttgtcgttt ttttttagtt cgttttgatt tgttttttaa aagtacgttt ttgttttttc    180

gttgttttgg cgtttttttt ttgatttatt agggttgtcg ggttggcgta gattgttttt    240

tttttttttt tattttattt tttttttgg ttttttttt tatagtggga gttcgtgttt    300
```

ttgtttttcg gttggttttt aagtgtttcg ttaggttttt tttttttcg ttttttcggt 360 ttcggttttc gatttttcgg ttcgttggta tttgtttttt tttttgt 408

<210> SEQ ID NO 47
<211> LENGTH: 477
<212> TYPE: DNA
<213> ORGANISM: Homo sapiens

<400> SEQUENCE: 47
ttttgggttg ggtaggagtt gaattttcgg gagtttgttt gtgtagattt agtgcgtacg 60
gcgaggtagt agttcggttt cgtattgttg ataggtgtag gtaggatagt ttttttatcg 120
cggttcgggg cgttttgatt ggtgcggagt tacgttagtc gtattcggag aagggtttgg 180
gaggaggcgg aggcggagag ggttggggag ggtcgcggcg gagtgacgtt tcggtattag 240
gaagttcgtt tttggtttta agatgttagg ttaataggga agcgcggagt cgtagatttg 300
gttcgtcgtt cgtttgggtg tttggagttg agttgcggta aggttcggtt tttgttcgat 360
cgttcgaggg gtgtgcgtgt gcgcgttgcg gagggtgcgt ttagagggtc gcgtcgtggt 420
tgtagcggtt gttgtcgtcg taggggattt aatattattt atttgttttt gttattt 477

<210> SEQ ID NO 48
<211> LENGTH: 408
<212> TYPE: DNA
<213> ORGANISM: Homo sapiens

<400> SEQUENCE: 48
gtaggggagg gaagtagatg ttagtgggtt gaagagttgg gagttggagt tgggagagtg 60
aaaggagagg ggatttggtg gggtatttag gagttaattg aggagtagga gtatggattt 120
ttattgtgga aaggaggatt agaagggagg atgggatgga agagaagaaa aagtaatttg 180
tgttaatttg gtagttttaa taaattaaag ggggagtgtt agggtagtgg ggagatagaa 240
atgtattttt ggggagtaaa ttaggatggg ttgggaggaa gtgataggga aagtggttta 300
agagatggaa taaaggataa tgtttatggg gttgtttggg atgaggtgtg tggagtgtgg 360
gtgtgagtgt gtgtgtgtga ttttttttta ggtttgtaga gttgagga 408

<210> SEQ ID NO 49
<211> LENGTH: 477
<212> TYPE: DNA
<213> ORGANISM: Homo sapiens

<400> SEQUENCE: 49
gagtgatagg gataggtagg tgatattaga tttttttgtgg tggtagtagt tgttgtagtt 60
atgatgtggt tttttgagtg tattttttgt aatgtgtata tgtatatttt ttgggtggtt 120
gaataggagt tgggttttgt tgtagtttag ttttaggtat ttaggtgagt gatggattag 180
atttgtggtt ttgtgttttt ttgttggttt aatattttaa aattagaggt gggtttttttg 240 gtgttgagat gttattttgt tgtggttttt tttagttttt tttgtttttg ttttttttta 300 gattttttttt tgggtgtgat tgatgtggtt ttgtattaat taggatgttt tgagttgtgg 360
tggagggatt gttttgtttg tatttattag tagtgtgggg ttgggttatt gttttgttgt 420
gtgtattggg tttatatagg taagtttttg ggaatttagt ttttgtttag tttaagg 477

<210> SEQ ID NO 50
<211> LENGTH: 408
<212> TYPE: DNA

<213> ORGANISM: Homo sapiens

<400> SEQUENCE: 50
tttttaattt tgtaggtttg aaagaaggtt atatatgtat gtttatattt atattttata 60
tgttttgttt taaataattt tatgaatatt gtttttttgtt ttgttttttg ggttattttt 120
tttgttgttt tttttagtt tgttttgatt tgttttttaa aagtatgttt ttgttttttt 180
gttgttttgg tgtttttttt ttgatttatt agggttgttg ggttggtgta gattgttttt 240
tttttttttt tattttattt tttttttgg tttttttttt tatagtggga gtttgtgttt 300 ttgtttttttg gttggttttt aagtgttttg ttaggttttt tttttttttg tttttttggt 360
tttggttttt gattttttgg tttgttggta tttgtttttt ttttttgt 408

<210> SEQ ID NO 51
<211> LENGTH: 477
<212> TYPE: DNA
<213> ORGANISM: Homo sapiens

<400> SEQUENCE: 51
ttttgggttg ggtaggagtt gaatttttgg gagtttgttt gtgtagattt agtgtgtatg 60
gtgaggtagt agtttggttt tgtattgttg ataggtgtag gtaggatagt ttttttattg 120
tggtttgggg tgttttgatt ggtgtggagt tatgttagtt gtatttggag aagggtttgg 180
gaggaggtgg aggtggagag ggttggggag ggttgtggtg gagtgatgtt ttggtattag 240
gaagtttgtt tttggtttta agatgttagg ttaataggga agtgtggagt tgtagatttg 300
gtttgttgtt tgtttgggtg tttggagttg agttgtggta aggtttggtt tttgtttgat 360
tgtttgaggg gtgtgtgtgt gtgtgttgtg gagggtgtgt ttagagggtt gtgttgtggt 420
tgtagtggtt gttgttgttg taggggattt aatattattt atttgttttt gttattt 477

<210> SEQ ID NO 52
<211> LENGTH: 16
<212> TYPE: DNA
<213> ORGANISM: Homo sapiens

<400> SEQUENCE: 52
agtagtgcgg ggtcgg 16

<210> SEQ ID NO 53
<211> LENGTH: 17
<212> TYPE: DNA
<213> ORGANISM: Homo sapiens

<400> SEQUENCE: 53
agtagtgtgg ggttggg 17

<210> SEQ ID NO 54
<211> LENGTH: 17
<212> TYPE: DNA
<213> ORGANISM: Homo sapiens

<400> SEQUENCE: 54
tgtagttacg acgcggt 17

<210> SEQ ID NO 55
<211> LENGTH: 22
<212> TYPE: DNA
<213> ORGANISM: Homo sapiens

<400> SEQUENCE: 55
gttgtagtta tgatgtggtt tt 22

<210> SEQ ID NO 56
<211> LENGTH: 16
<212> TYPE: DNA
<213> ORGANISM: Homo sapiens

<400> SEQUENCE: 56
tttcgggcgg tcgaat 16

<210> SEQ ID NO 57
<211> LENGTH: 20
<212> TYPE: DNA
<213> ORGANISM: Homo sapiens

<400> SEQUENCE: 57
ttttgggtgg ttgaatagga 20

<210> SEQ ID NO 58
<211> LENGTH: 16
<212> TYPE: DNA
<213> ORGANISM: Homo sapiens

<400> SEQUENCE: 58
taggcgagcg acggat 16

<210> SEQ ID NO 59
<211> LENGTH: 21
<212> TYPE: DNA
<213> ORGANISM: Homo sapiens

<400> SEQUENCE: 59
taggtgagtg atggattaga t 21

<210> SEQ ID NO 60
<211> LENGTH: 19
<212> TYPE: DNA
<213> ORGANISM: Homo sapiens

<400> SEQUENCE: 60
tgtcgagacg ttatttcgt 19

<210> SEQ ID NO 61
<211> LENGTH: 22
<212> TYPE: DNA
<213> ORGANISM: Homo sapiens

<400> SEQUENCE: 61
tggtgttgag atgttatttt gt 22

<210> SEQ ID NO 62
<211> LENGTH: 18
<212> TYPE: DNA
<213> ORGANISM: Homo sapiens

<400> SEQUENCE: 62
agttgggaga gtgaaagg 18

<210> SEQ ID NO 63
<211> LENGTH: 16
<212> TYPE: DNA
<213> ORGANISM: Homo sapiens

<400> SEQUENCE: 63
gagtcgggag agcgaa 16

<210> SEQ ID NO 64
<211> LENGTH: 19
<212> TYPE: DNA
<213> ORGANISM: Homo sapiens

<400> SEQUENCE: 64
tttgcgttaa ttcggtagt 19

<210> SEQ ID NO 65
<211> LENGTH: 23
<212> TYPE: DNA
<213> ORGANISM: Homo sapiens

<400> SEQUENCE: 65
tttgtgttaa tttggtagtt tta 23

<210> SEQ ID NO 66
<211> LENGTH: 18
<212> TYPE: DNA
<213> ORGANISM: Homo sapiens

<400> SEQUENCE: 66
agcgttaggg tagcgggg 18

<210> SEQ ID NO 67
<211> LENGTH: 18
<212> TYPE: DNA
<213> ORGANISM: Homo sapiens

<400> SEQUENCE: 67
ggagtgttag ggtagtgg 18

<210> SEQ ID NO 68
<211> LENGTH: 17
<212> TYPE: DNA
<213> ORGANISM: Homo sapiens

<400> SEQUENCE: 68
gggatgaggt gtgtgga 17

<210> SEQ ID NO 69
<211> LENGTH: 16
<212> TYPE: DNA
<213> ORGANISM: Homo sapiens

<400> SEQUENCE: 69
ttgggacgag gcgtgt 16

<210> SEQ ID NO 70
<211> LENGTH: 18
<212> TYPE: DNA
<213> ORGANISM: Homo sapiens

<400> SEQUENCE: 70
agcgggtcga agagtcgg 18

<210> SEQ ID NO 71
<211> LENGTH: 18
<212> TYPE: DNA
<213> ORGANISM: Homo sapiens

<400> SEQUENCE: 71
agtgggttga agagttgg 18